US008916743B2

(12) United States Patent
Ohmori et al.

(10) Patent No.: US 8,916,743 B2
(45) Date of Patent: Dec. 23, 2014

(54) METHOD FOR ASSESSMENT OF POTENTIAL FOR DEVELOPMENT OF DRAVET SYNDROME AND USE THEREOF

(71) Applicant: National University Corporation Okayama University, Okayama-shi, Okayama (JP)

(72) Inventors: Iori Ohmori, Okayama (JP); Mamoru Ouchida, Okayama (JP)

(73) Assignee: National University Corporation Okayama University, Okayama (JP)

( * ) Notice: Subject to any disclaimer, the term of this patent is extended or adjusted under 35 U.S.C. 154(b) by 0 days.

(21) Appl. No.: 14/312,191

(22) Filed: Jun. 23, 2014

(65) Prior Publication Data

US 2014/0304843 A1 Oct. 9, 2014

Related U.S. Application Data

(62) Division of application No. 13/574,977, filed as application No. PCT/JP2011/051636 on Jan. 27, 2011.

(30) Foreign Application Priority Data

Jan. 29, 2010 (JP) ................................ 2010-018705

(51) Int. Cl.
*G01N 33/53* (2006.01)
*C12N 15/00* (2006.01)
*A61K 49/00* (2006.01)
*A01K 67/027* (2006.01)
*G01N 33/50* (2006.01)

(52) U.S. Cl.
CPC ......... *A61K 49/0008* (2013.01); *A01K 67/0275* (2013.01); *A01K 67/027* (2013.01); *G01N 33/5008* (2013.01); *A01K 2227/10* (2013.01); *A01K 2267/0306* (2013.01)
USPC ..................................... 800/3; 800/9; 800/21

(58) Field of Classification Search
CPC .................. A61K 2267/0306; G01N 33/5008; G01N 33/6872; A01K 2227/10
See application file for complete search history.

(56) References Cited

U.S. PATENT DOCUMENTS

| | | | |
|---|---|---|---|
| 6,582,908 B2 | 6/2003 | Fodor et al. |
| 2004/0229257 A1 | 11/2004 | Petrou et al. |
| 2010/0088778 A1 | 4/2010 | Mulley et al. |
| 2010/0203548 A1 | 8/2010 | Petrou et al. |

FOREIGN PATENT DOCUMENTS

| | | |
|---|---|---|
| JP | 2004-73058 | 3/2004 |
| JP | 2004-329153 | 11/2004 |
| JP | 2006-524490 | 11/2006 |
| JP | 2008-173193 | 7/2008 |
| JP | 2008-546376 | 12/2008 |
| JP | 2009-112251 | 5/2009 |
| JP | 2009-131247 | 6/2009 |
| WO | 2006/019978 | 2/2006 |

OTHER PUBLICATIONS

Sugawara, T., et al., "Frequent mutations of SCN1A in severe myoclonic epilepsy in infancy," Neurology 58: pp. 1122-1124 (2002).
Ohmori, Iori, et al., "Significant correlation of the SCN1A mutations and severe myoclonic epilepsy in infancy," Biochemical and Biophysical Research Communications 295 (2002) pp. 17-23.
Escayg, A., et al., "A Novel SCN1A Mutation Associated with Generalized Epilepsy with Febrile Seizures Plus—and Prevalence of Variants in Patients with Epilepsy," Am. J. Hum. Genet. 68:866-873 (2001).
Imoto, K., et al., "Neurological disorders associated with voltage-gated Na+ and Ca2+ channels," Igaku no Ayumi (Development in Medical Science), vol. 201, No. 13, pp. 1128-1132 (Jun. 29, 2002).
Tsunemi, T. & Mizusawa, H.: "Polyglutamine disease—centering Spinocerebellar ataxia type 6—", Igaku no Ayumi (Development in Medical Science), vol. 201 No. 13 pp. 1133-1137 (Jun. 29, 2002).
Ohmori, Iori, et al., "A CACNB4 mutation shows that altered Cav2.1 function may be a genetic modifier of severe myoclonic epilepsy in infancy," Neurobiology of Disease 32: 349-354 (2008).
Tokuda, Satoko, et al., "The ataxic groggy rat has a missense mutation in the P/Q-type voltage-gated Ca2+ channel α1A subunit gene and exhibits absence seizures," Brain Research 1133: 168-177 (2007).
Tanaka, Kenta, et al., "Increased Ca2+ channel currents in cerebellar Purkinje cells of the ataxic groggy rat," Neuroscience Letters 426: 75-80 (2007).
Ohmori, I., et al., "A CACNB4 mutation showing altered Cav2.1 function in a patient with Dravet syndrome", Journal of Okayama Medical Association, vol. 121, Dec. 2009, pp. 149-156.
Journal of Okayama Medical Association vol. 121 No. 2, Printed Jul. 21, 2009, Issued Aug. 3, 2009, p. 140.
U.S. Office Action from U.S. Appl. No. 13/574,977 dated May 14, 2013.
U.S. Office Action from U.S. Appl. No. 13/574,977 dated Sep. 24, 2013.
U.S. Office Action from U.S. Appl. No. 13/574,977 dated Apr. 1, 2014.
U.S. Office Action from U.S. Appl. No. 13/574,977 dated Jun. 5, 2014.

*Primary Examiner* — Ruixiang Li
(74) *Attorney, Agent, or Firm* — Casimir Jones SC

(57) ABSTRACT

Provided is a method of assessing a potential for development of Dravet syndrome with high accuracy, and use thereof. The method according to the present invention of assessing a potential for development of Dravet syndrome includes, with use of a sample taken from a subject, detecting whether or not a mutation is on α-subunit type 1 of voltage-gated sodium ion channel $Na_V1.1$, and detecting whether or not a mutation is on α-subunit type 1 of voltage-gated calcium ion channel $Ca_V2.1$.

9 Claims, 14 Drawing Sheets

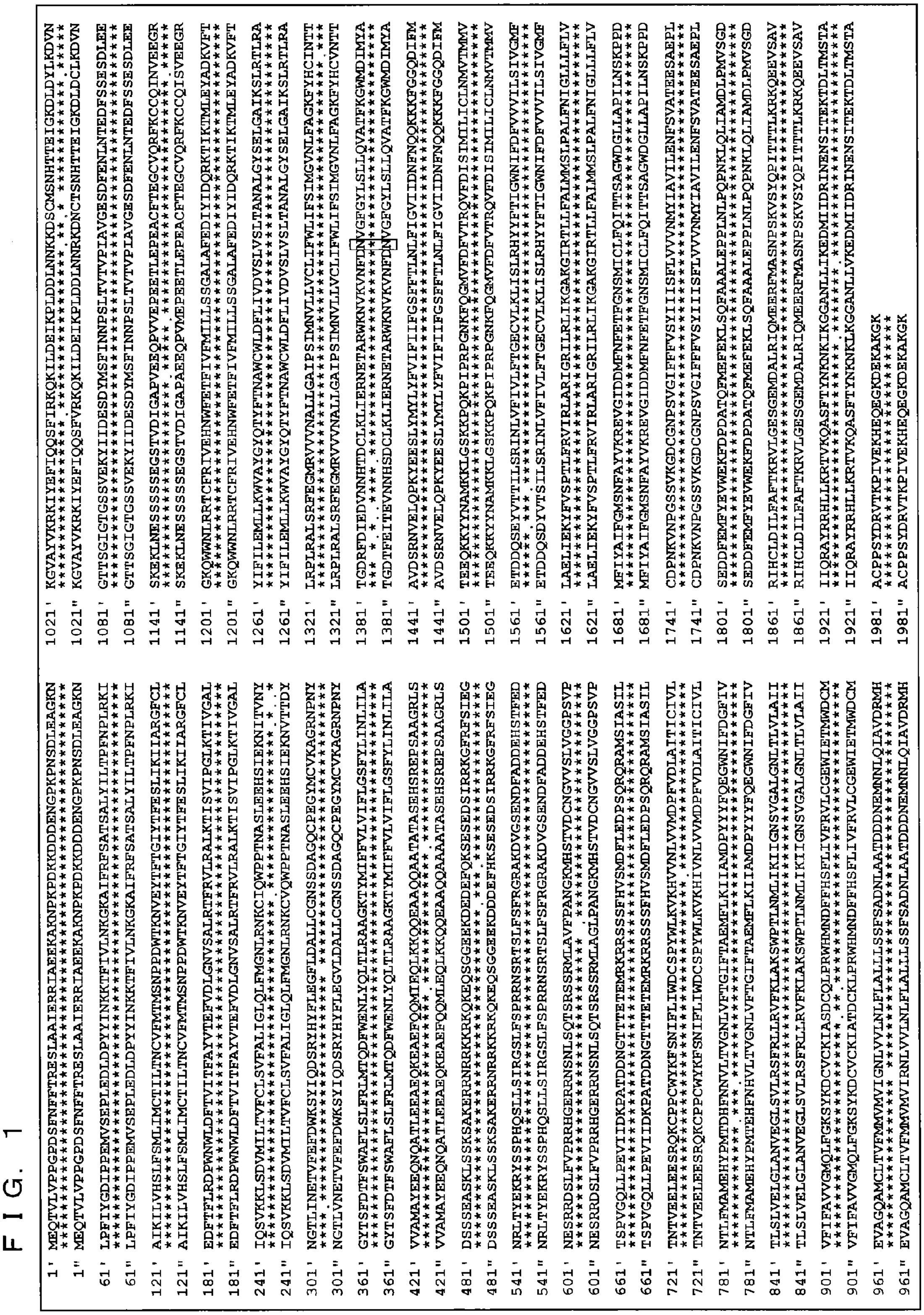

FIG. 1

```
   1' MEQTVLVPPGPDSFNFFTRESLAAIERRIAEEKAKNPKPDKDDENGPKPNSDLEAGKN         1021' KGVAYVRKIYEFIQQSFIRKQKILDEIKPLDDLNNKKDSCMSNHTTEIGKDLDYLKDVN
   1" MEQTVLVPPGPDSFNFFTRESLAAIERRIAEEKAKNPKPDKDDENGPKPNSDLEAGKN         1021" KGVAYVRKIYEFIQQSFVRKQKILDEIKPLDDLNNRKDNCTSNHTTEIGKDLDCLKDVN

  61' LPFIYGDIPPENVSEPLEDLDPYYINKKTFIVLNKGKAIFRFSATSALYILTPFNPLRKI       1081' GTTSGIGTGSSVEKYIIDESDYMSFINNPSLTVTVPIAVGESDFENLNTEDFSSESDLEE
  61" LPFIYGDIPPENVSEPLEDLDPYYINKKTFIVLNKGKAIFRFSATSALYILTPFNPLRKI       1081" GTTSGIGTGSSVEKYIIDESDYMSFINNPSLTVTVPIAVGESDFENLNTEDFSSESDLEE

 121' AIKILVHSLFSMLIMCTILTNCVEMTMSNPPDWTKNVEYTFTGIYTFFSLIKLIARGFCL       1141' SKEKLNESSSSSEGSTVDIGAFVEEQPVVEPEETLEPEACFTEGCVQRFKCCQINVEEGR
 121" AIKILVHSLFSMLIMCTILTNCVEMTMSNPPDWTKNVEYTFTGIYTFFSLIKLIARGFCL       1141" SKEKLNESSSSSEGSTVDIGAPAEEQPVMEPEETLEPEACFTEGCVQRFKCCQISVEEGR

 181' EDFTFLRDPWNMLDFTVITFAYVTEFVDLGNVSALRTFRVLRALKTISVIPGLKTIVGAL       1201' GKQWWNLRRTCFRIVEHNWFETFIVFMILLSSGALAFEDIYIDQRKTIKTMLEYADKVFI
 181" EDFTFLRDPWNMLDFTVITFAYVTEFVDLGNVSALRTFRVLRALKTISVIPGLKTIVGAL       1201" GKQWWNLRRTCFRIVEHNWFETFIVFMILLSSGALAFEDIYIDQRKTIKTMLEYADKVFT

 241' IQSVKKLSDVMLTVFCLSVFALIGLQLFMGNLRNKCIQWPPTNASLEEHSIEKNITVNY       1261' YIFILEMLLKWVAYGYQTYFTNAWCWLDFLIVDVSLVSLTANALGYSELGAIKSLRTLRA
 241" IQSVKKLSDVMLTVFCLSVFALIGLQLFMGNLRNKCVQWPPTNASLEEHSIEKNVTTDY       1261" YIFILEMLLKWVAYGYQTYFTNAWCWLDFLIVDVSLVSLTANALGYSELGAIKSLRTLRA

 301' NGTLINETVFEEDWKSYIQDSRYHYFLEGFLDALLCGNSSDAGQCPEGYMCVKAGRNPNY     1321' LRPLRALSREFGMRVVVNALLGAIPSIMNVLLVCLIFWLIFSIMGVNLFAGKFYHCINTT
 301" NGTLVNETVFEEFDWKSYIQDSRYHYFLEGVLDALLCGNSSDAGQCPEGYMCVKAGRNPNY     1321" LRPLRALSREFGMRVVVNALLGAIPSIMNVLLVCLIFWLIFSIMGVNLFAGKFYHCVNTT

 361' GYTSFDTFSWAFLSLFRLMTQDFWENLYQLTLRAAGKTYMIFFVLVIFLGSFYLINLIIA     1381' TGDRFDIEDVNNHTDCLKLIERNETARWKNVKVNFDN VGFGYLSLLQVATFKGWMDIMYA
 361" GYTSFDTFSWAFLSLFRLMTQDFWENLYQLTLRAAGKTYMIFFVLVIFLGSFYLINLIIA     1381" TGDTFEITEVNNHSDCLKLIERNETARWKNVKVNFDN VGFGYLSLLQVATFKGWMDIMYA

 421' VVAMAYEEQNQATLEEEAEQKEAEFQQMEQLKKQQEEAAQQAATATAESHSREPSAAGRLS   1441' AVDSRNVELQPKYEESLXMYLYFVIFIIFGSFFTLNLFTGVIIDNFNQQKKFGQDIFM
 421" VVAMAYEEQNQATLEEEAEQKEAEFQQMEQLKKQQEEAAQQAAAATAESHSREPSAAGRLS   1441" AVDSRNVELQPKYEESLXMYLYFVIFIIFGSFFTLNLFIGVIIDNFNQQKKFGQDIFM

 481' DSSSEASKLSSKSAKERNRRKRKQKEQSGGEEKDEDEFQKSESEDSIRRKGFRFSIEG     1501' TEEQKKYNAMKKLGSKKPQKFIPRPGNKFQGMVFDFVTRQVFDISIMLLCLNMVTMMV
 481" DSSSEASKLSSKSAKERNRRKRKQKEQSGGEEKDEDEFHKSESEDSIRRKGFRFSIEG     1501" TEEQKKYNAMKKLGSKKPQKFIPRPGNKFQGMVFDFVTRQVFDISIMLLCLNMVTMMV

 541' NFLTYEKRYSSPHQSLLSIRGSLFSPRRNSRTSLFSFRGRAKDVGSENDFADDEHSTFED   1561' ETDDQSEYVTTILSRINLVFIVLFTGECVLKLISLRHYFTIGWNIFDFVVILSIVGMF
 541" NFLTYEKRYSSPHQSLLSIRGSLFSPRRNSRTSLFSFRGRAKDVGSENDFADDEHSTFED   1561" ETDDQSDIVTSLLSRINLVFIVLFTGECVLKLISLRHYFTIGWNIFDFVVILSIVGMF

 601' NESRRDSLFVPRRHGERRNSNLSQTSRSSRMLAVFPANGKMHSTVDCNGVVSLVGGPSVP   1621' LAELIEKIFVSPTLFRVIRLARIGRILRLIKGAKGIRTLLFALMMSLPALFNIGLLLFLV
 601" NESRRDSLFVPRRHGERRNSNLSQTSRSSRMLAGIPANGKMHSTVDCNGVVSLVGGPSVP   1621" LAELIEKIFVSPTLFRVIRLARIGRILRLIKGAKGIRTLLFALMMSLPALFNIGLLLFLV

 661' TSPVGQLLPEVIIDKPAIDNGTTETEMRKRSSSSFHVSMDFLEDPSQRQRAMSIASTL     1681' MFIYAIFGMSNFAYVKREVGIDDMFNFETFGNSMICLFQITTSAGWDGLLAPILNSKPD
 661" TSPVGQLLPEVIIDKPAIDNGTTETEMRKRSSSSFHVSMDFLEDPSQRQRAMSIASTL     1681" MFIYAIFGMSNFAYVKREVGIDDMFNFETFGNSMICLFQITTSAGWDGLLAPILNSKPD

 721' TNTVEELEESRQKCPPCWYKFSNIFLIWDCSPYWLKVKHVNLVVMDPFVDLATTICIVL    1741' CDPNKVNPGSSVKGDCGNPSVGIFFFVSYIIISFLVVVNMYIAVILENFSVATEESAEPL
 721" TNTVEELEESRQKCPPCWYKFSNIFLIWDCSPYWLKVKHVNLVVMDPFVDLATTICIVL    1741" CDPNKVNPGSSVKGDCGNPSVGIFFFVSYIIISFLVVVNMYIAVILENFSVATEESAEPL

 781' NTLFMAMEHYPMTDHFNVLITVGNLVFTGIFTAEMFLKIIAMDPYYIYQEGWNIFDGFIV   1801' SEDDFEMFYEVWEKFDPDATQFMEFEKLSQFAAALEPPLNLPQPNKLQLIAMDLPMVSGD
 781" NTLFMAMEHYPMTEHFNVLTVGNLVFTGIFTAEMFLKIIAMDPYYIFQEGWNIFDGFIV    1801" SEDDFEMFYEVWEKFDPDATQFMEFEKLSQFAAALEPPLNLPQPNKLQLIAMDLPMVSGD

 841' TLSLVELGLANVEGLSVLRSFRLLRVFKLAKSWPTLNMLIKIIGNSVGALGNLTLVLAII  1861' RIHCLDILFAFTKRVLGESGEMDALRIQMEERFMASNPSKVSYQPITTTLKRKQEEVSAV
 841" TLSLVELGLANVEGLSVLRSFRLLRVFKLAKSWPTLNMLIKIIGNSVGALGNLTLVLAII  1861" RIHCLDILFAFTKRVLGESGEMDALRIQMEERFMASNPSKVSYQPITTTLKRKQEEVSAV

 901' VFIFAVVGMQLFGKSYKDCVCKIASDCCLPRWHMNDFFHSFLIVFRVLCGEWIETMWDCM  1921' IIQRAYRRHLLKRTVKQASFTYNKNKIKGGANLLIKEDMIIDRINENSITEKTDLTMSTA
 901" VFIFAVVGMQLFGKSYKDCVCKIATDCKLPRWHMNDFFHSFLIVFRVLCGEWIETMWDCM  1921" IIQRAYRRHLLKRTVKQASFTYNKNKLKGGANLLVKEDMIIDRINENSITEKTDLTMSTA

 961' EVAGQAMCLTVFMMVIGNLVVLNLFLALLLSSFSADNLAATDDDNEMNNLQIAVDRMH    1981' ACPPSYDRVTKPIVEKHEQEGKDEKAKGK
 961" EVAGQAMCLTVFMMVIRNLVVLNLFLALLLSSFSADNLAATDDDNEMNNLQIAVDRMH    1981" ACPPSYDRVTKPIVEKHEQEGKDEKAKGK
```

P ; Scn1a$^{Mut/Mut}$Cacna1a$^{WT/WT}$ × Scn1a$^{WT/WT}$Cacna1a$^{Mut/Mut}$
(Scn1A-mutated rat) (Cacna1a-mutated rat)

F1; Scn1a$^{Mut/WT}$Cacna1a$^{Mut/WT}$ (b)

F1; Scn1a$^{Mut/WT}$Cacna1a$^{Mut/WT}$ × Scn1a$^{Mut/WT}$Cacna1a$^{Mut/WT}$

| | | | |
|---|---|---|---|
| F2; Scn1a$^{WT/WT}$Cacna1a$^{WT/WT}$ | Scn1a wild-type (homo) + Cacna1a wild-type (homo) | Control | (1) |
| Scn1a$^{Mut/WT}$Cacna1a$^{WT/WT}$ | | | |
| Scn1a$^{Mut/Mut}$Cacna1a$^{WT/WT}$ | Scn1a mutant (homo) + Cacna1a wild-type (homo) | | (2) |
| Scn1a$^{WT/WT}$Cacna1a$^{Mut/WT}$ | Scn1a wild-type (homo) + Cacna1a mutant (hetero) | Control | (4) |
| Scn1a$^{Mut/WT}$Cacna1a$^{Mut/WT}$ | | | |
| Scn1a$^{Mut/Mut}$Cacna1a$^{Mut/WT}$ | Scn1a mutant (homo) + Cacna1a mutant (hetero) | | (3) |
| Scn1a$^{WT/WT}$Cacna1a$^{Mut/Mut}$ | | | |
| Scn1a$^{Mut/WT}$Cacna1a$^{Mut/Mut}$ | | | |
| Scn1a$^{Mut/Mut}$Cacna1a$^{Mut/Mut}$ | | | |

FIG. 11

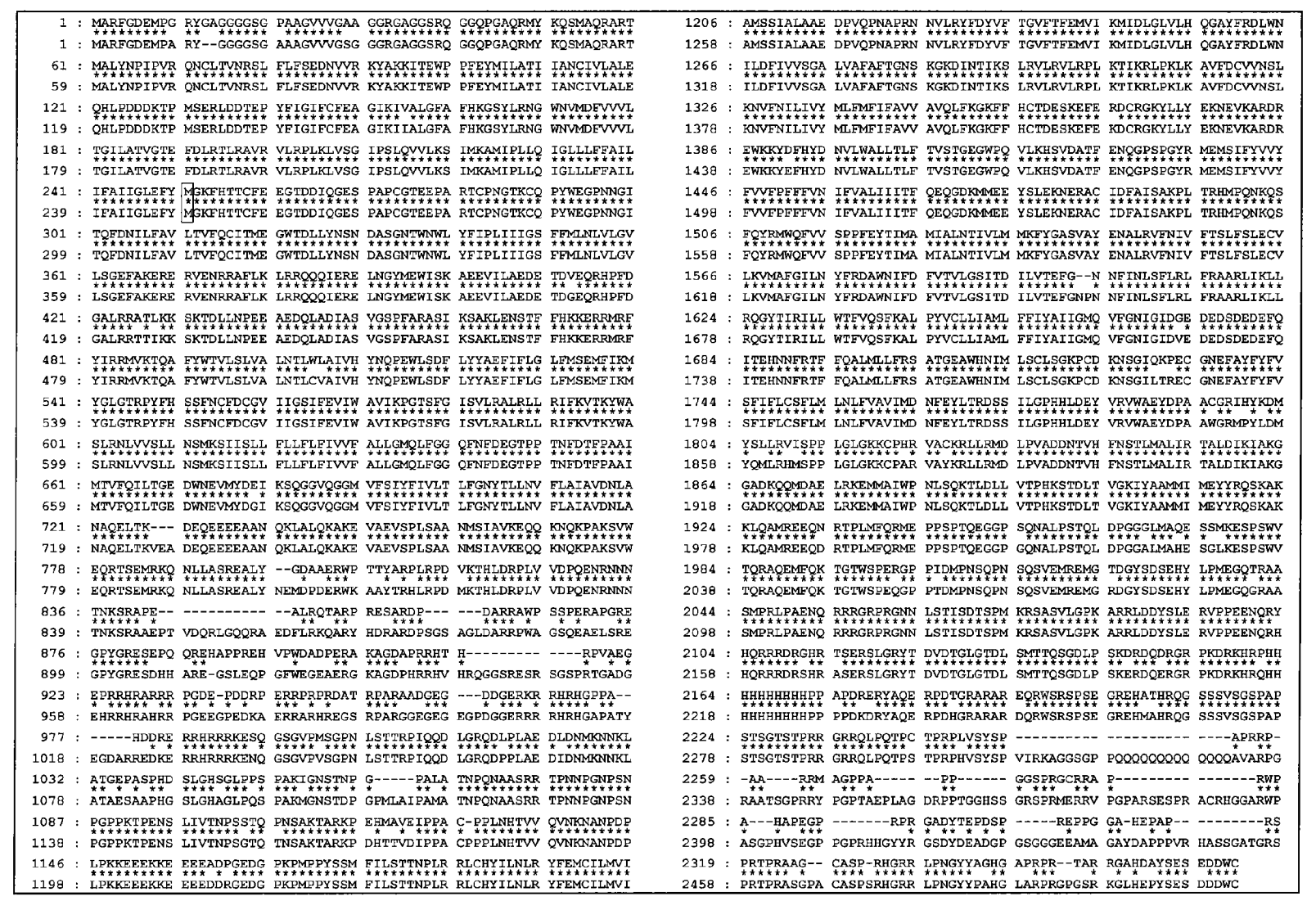

```
   1 : MARFGDEMPG RYGAGGGGSG PAAGVVVGAA GGRGAGGSRQ GGQPGAQRMY KQSMAQRART
   1 : MARFGDEMPA RY--GGGGSG AAAGVVVGSG GGRGAGGSRQ GGQPGAQRMY KQSMAQRART

  61 : MALYNPIPVR QNCLTVNRSL FLFSEDNVVR KYAKKITEWP PFEYMILATI IANCIVLALE
  59 : MALYNPIPVR QNCLTVNRSL FLFSEDNVVR KYAKKITEWP PFEYMILATI IANCIVLALE

 121 : QHLPDDDKTP MSERLDDTEP YFIGIFCFEA GIKIVALGFA FHKGSYLRNG WNVMDFVVVL
 119 : QHLPDDDKTP MSERLDDTEP YFIGIFCFEA GIKIIALGFA FHKGSYLRNG WNVMDFVVVL

 181 : TGILATVGTE FDLRTLRAVR VLRPLKLVSG IPSLQVVLKS IMKAMIPLLQ IGLLLFFAIL
 179 : TGILATVGTE FDLRTLRAVR VLRPLKLVSG IPSLQVVLKS IMKAMIPLLQ IGLLLFFAIL

 241 : IFAIIGLEFY MGKFHTTCFE EGTDDIQGES PAPCGTEEPA RTCPNGTKCQ PYWEGPNNGI
 239 : IFAIIGLEFY MGKFHTTCFE EGTDDIQGES PAPCGTEEPA RTCPNGTKCQ PYWEGPNNGI

 301 : TQFDNILFAV LTVFQCITME GWTDLLYNSN DASGNTWNWL YFIPLIIIGS FFMLNLVLGV
 299 : TQFDNILFAV LTVFQCITME GWTDLLYNSN DASGNTWNWL YFIPLIIIGS FFMLNLVLGV

 361 : LSGEFAKERE RVENRRAFLK LRRQQQIERE LNGYMEWISK AEEVILAEDE TDVEQRHPFD
 359 : LSGEFAKERE RVENRRAFLK LRRQQQIERE LNGYMEWISK AEEVILAEDE TDGEQRHPFD

 421 : GALRRATLKK SKTDLLNPEE AEDQLADIAS VGSPFARASI KSAKLENSTF FHKKERRMRF
 419 : GALRRTTIKK SKTDLLNPEE AEDQLADIAS VGSPFARASI KSAKLENSTF FHKKERRMRF

 481 : YIRRMVKTQA FYWTVLSLVA LNTLWLAIVH YNQPEWLSDF LYYAEFIFLG LFMSEMFIKM
 479 : YIRRMVKTQA FYWTVLSLVA LNTLCVAIVH YNQPEWLSDF LYYAEFIFLG LFMSEMFIKM

 541 : YGLGTRPYFH SSFNCFDCGV IIGSIFEVIW AVIKPGTSFG ISVLRALRLL RIFKVTKYWA
 539 : YGLGTRPYFH SSFNCFDCGV IIGSIFEVIW AVIKPGTSFG ISVLRALRLL RIFKVTKYWA

 601 : SLRNLVVSLL NSMKSIISLL FLLFLFIVVF ALLGMQLFGG QFNFDEGTPP TNFDTFPAAI
 599 : SLRNLVVSLL NSMKSIISLL FLLFLFIVVF ALLGMQLFGG QFNFDEGTPP TNFDTFPAAI

 661 : MTVFQILTGE DWNEVMYDEI KSQGGVQGGM VFSIYFIVLT LFGNYTLLNV FLAIAVDNLA
 659 : MTVFQILTGE DWNEVMYDGI KSQGGVQGGM VFSIYFIVLT LFGNYTLLNV FLAIAVDNLA

 721 : NAQELTK--- DEQEEEEAAN QKLALQKAKE VAEVSPLSAA NMSIAVKEQQ KNQKPAKSVW
 719 : NAQELTKVEA DEQEEEEAAN QKLALQKAKE VAEVSPLSAA NMSIAVKEQQ KNQKPAKSVW

 778 : EQRTSEMRKQ NLLASREALY --GDAAERWP TTYARPLRPD VKTHLDRPLV VDPQENRNNN
 779 : EQRTSEMRKQ NLLASREALY NEMDPDERWK AAYTRHLRPD MKTHLDRPLV VDPQENRNNN

 836 : TNKSRAPE-- ---------- --ALRQTARP RESARDP--- ---DARRAWP SSPERAPGRE
 839 : TNKSRAAEPT VDQRLGQQRA EDFLRKQARY HDRARDPSGS AGLDARRPWA GSQEAELSRE

 876 : GPYGRESEPQ QREHAPPREH VPWDADPERA KAGDAPRRHT H--------- ----RPVAEG
 899 : GPYGRESDHH ARE-GSLEQP GFWEGEAERG KAGDPHRRHV HRQGGSRESR SGSPRTGADG

 923 : EPRRHRARRR PGDE-PDDRP ERRPRPRDAT RPARAADGEG ---DDGERKR RHRHGPPA--
 958 : EHRRHRAHRR PGEEGPEDKA ERRARHREGS RPARGGEGEG EGPDGGERRR RHRHGAPATY

 977 : -----HDDRE RRHRRRKESQ GSGVPMSGPN LSTTRPIQQD LGRQDLPLAE DLDNMKNNKL
1018 : EGDARREDKE RRHRRRKENQ GSGVPVSGPN LSTTRPIQQD LGRQDPPLAE DIDNMKNNKL

1032 : ATGEPASPHD SLGHSGLPPS PAKIGNSTNP G-----PALA TNPQNAASRR TPNNPGNPSN
1078 : ATAESAAPHG SLGHAGLPQS PAKMGNSTDP GPMLAIPAMA TNPQNAASRR TPNNPGNPSN

1087 : PGPPKTPENS LIVTNPSSTQ PNSAKTARKP EHMAVEIPPA C-PPLNHTVV QVNKNANPDP
1138 : PGPPKTPENS LIVTNPSGTQ TNSAKTARKP DHTTVDIPPA CPPPLNHTVV QVNKNANPDP

1146 : LPKKEEEKKE EEEADPGEDG PKPMPPYSSM FILSTTNPLR RLCHYILNLR YFEMCILMVI
1198 : LPKKEEEKKE EEEDDRGEDG PKPMPPYSSM FILSTTNPLR RLCHYILNLR YFEMCILMVI

1206 : AMSSIALAAE DPVQPNAPRN NVLRYFDYVF TGVFTFEMVI KMIDLGLVLH QGAYFRDLWN
1258 : AMSSIALAAE DPVQPNAPRN NVLRYFDYVF TGVFTFEMVI KMIDLGLVLH QGAYFRDLWN

1266 : ILDFIVVSGA LVAFAFTGNS KGKDINTIKS LRVLRVLRPL KTIKRLPKLK AVFDCVVNSL
1318 : ILDFIVVSGA LVAFAFTGNS KGKDINTIKS LRVLRVLRPL KTIKRLPKLK AVFDCVVNSL

1326 : KNVFNILIVY MLFMFIFAVV AVQLFKGKFF HCTDESKEFE RDCRGKYLLY EKNEVKARDR
1378 : KNVFNILIVY MLFMFIFAVV AVQLFKGKFF HCTDESKEFE KDCRGKYLLY EKNEVKARDR

1386 : EWKKYDFHYD NVLWALLTLF TVSTGEGWPQ VLKHSVDATF ENQGPSPGYR MEMSIFYVVY
1438 : EWKKYEFHYD NVLWALLTLF TVSTGEGWPQ VLKHSVDATF ENQGPSPGYR MEMSIFYVVY

1446 : FVVFPFFFVN IFVALIIITF QEQGDKMMEE YSLEKNERAC IDFAISAKPL TRHMPQNKQS
1498 : FVVFPFFFVN IFVALIIITF QEQGDKMMEE YSLEKNERAC IDFAISAKPL TRHMPQNKQS

1506 : FQYRMWQFVV SPPFEYTIMA MIALNTIVLM MKFYGASVAY ENALRVFNIV FTSLFSLECV
1558 : FQYRMWQFVV SPPFEYTIMA MIALNTIVLM MKFYGASVAY ENALRVFNIV FTSLFSLECV

1566 : LKVMAFGILN YFRDAWNIFD FVTVLGSITD ILVTEFG--N NFINLSFLRL FRAARLIKLL
1618 : LKVMAFGILN YFRDAWNIFD FVTVLGSITD ILVTEFGNPN NFINLSFLRL FRAARLIKLL

1624 : RQGYTIRILL WTFVQSFKAL PYVCLLIAML FFIYAIIGMQ VFGNIGIDGE DEDSDEDEFQ
1678 : RQGYTIRILL WTFVQSFKAL PYVCLLIAML FFIYAIIGMQ VFGNIGIDVE DEDSDEDEFQ

1684 : ITEHNNFRTF FQALMLLFRS ATGEAWHNIM LSCLSGKPCD KNSGIQKPEC GNEFAYFYFV
1738 : ITEHNNFRTF FQALMLLFRS ATGEAWHNIM LSCLSGKPCD KNSGILTREC GNEFAYFYFV

1744 : SFIFLCSFLM LNLFVAVIMD NFEYLTRDSS ILGPHHLDEY VRVWAEYDPA ACGRIHYKDM
1798 : SFIFLCSFLM LNLFVAVIMD NFEYLTRDSS ILGPHHLDEY VRVWAEYDPA AWGRMPYLDM

1804 : YSLLRVISPP LGLGKKCPHR VACKRLLRMD LPVADDNTVH FNSTLMALIR TALDIKIAKG
1858 : YQMLRHMSPP LGLGKKCPAR VAYKRLLRMD LPVADDNTVH FNSTLMALIR TALDIKIAKG

1864 : GADKQQMDAE LRKEMMAIWP NLSQKTLDLL VTPHKSTDLT VGKIYAAMMI MEYYRQSKAK
1918 : GADKQQMDAE LRKEMMAIWP NLSQKTLDLL VTPHKSTDLT VGKIYAAMMI MEYYRQSKAK

1924 : KLQAMREEQN RTPLMFQRME PPSPTQEGGP SQNALPSTQL DPGGGLMAQE SSMKESPSWV
1978 : KLQAMREEQD RTPLMFQRME PPSPTQEGGP GQNALPSTQL DPGGALMAHE SGLKESPSWV

1984 : TQRAQEMFQK TGTWSPERGP PIDMPNSQPN SQSVEMREMG TDGYSDSEHY LPMEGQTRAA
2038 : TQRAQEMFQK TGTWSPEQGP PTDMPNSQPN SQSVEMREMG RDGYSDSEHY LPMEGQGRAA

2044 : SMPRLPAENQ RRRGRPRGNN LSTISDTSPM KRSASVLGPK ARRLDDYSLE RVPPEENQRY
2098 : SMPRLPAENQ RRRGRPRGNN LSTISDTSPM KRSASVLGPK ARRLDDYSLE RVPPEENQRH

2104 : HQRRRDRGHR TSERSLGRYT DVDTGLGTDL SMTTQSGDLP SKDRDQDRGR PKDRKHRPHH
2158 : HQRRRDRSHR ASERSLGRYT DVDTGLGTDL SMTTQSGDLP SKERDQERGR PKDRKHRQHH

2164 : HHHHHHHHPP APDRERYAQE RPDTGRARAR EQRWSRSPSE GREHATHRQG SSSVSGSPAP
2218 : HHHHHHHHPP PPDKDRYAQE RPDHGRARAR DQRWSRSPSE GREHMAHRQG SSSVSGSPAP

2224 : STSGTSTPRR GRRQLPQTPC TPRPLVSYSP ---------- ---------- ----APRRP-
2278 : STSGTSTPRR GRRQLPQTPS TPRPHVSYSP VIRKAGGSGP PQQQQQQQQQ QQQQAVARPG

2259 : -AA----RRM AGPPA----- --PP------ GGSPRGCRRA P--------- -------RWP
2338 : RAATSGPRRY PGPTAEPLAG DRPPTGGHSS GRSPRMERRV PGPARSESPR ACRHGGARWP

2285 : A---HAPEGP -------RPR GADYTEPDSP -----REPPG GA-HEPAP-- --------RS
2398 : ASGPHVSEGP PGPRHHGYYR GSDYDEADGP GSGGGEEAMA GAYDAPPPVR HASSGATGRS

2319 : PRTPRAAG-- CASP-RHGRR LPNGYYAGHG APRPR--TAR RGAHDAYSES EDDWC
2458 : PRTPRASGPA CASPSRHGRR LPNGYYPAHG LARPRGPGSR KGLHEPYSES DDDWC
```

METHOD FOR ASSESSMENT OF POTENTIAL FOR DEVELOPMENT OF DRAVET SYNDROME AND USE THEREOF

CROSS-REFERENCE TO RELATED APPLICATIONS

This application is a divisional of U.S. application Ser. No. 13/574,977, filed Oct. 10, 2012, which is a national stage of International (PCT) Patent Application Serial No. PCT/JP2011/051636, filed Jan. 27, 2011, which claims the benefit of and priority to JP Patent Application No. 2010-018705 filed Jan. 29, 2010, the contents of each of which are hereby incorporated by reference for all purposes.

TECHNICAL FIELD

The present invention relates to a method for assessing a potential for development of Dravet syndrome, and use thereof.

BACKGROUND ART

Febrile seizure is a disease that has a high incidence rate of approximately 8% in infants. A main symptom of febrile seizure is known as a continuation of generalized convulsions for 1 to 5 minutes while suffering a fever at or over 38° C. caused by a viral or bacterial infection such as a cold, or microbism. Most cases of febrile seizure that have an onset of between 6 months after birth and around 5 years old cure by the time when the patient turns 6 years old. In many cases, febrile seizure does not require active treatment. Therefore, febrile seizure is considered, in principle, as a benign disease.

However, among patients whose onset of febrile seizure was under the age of one, other than the patients of the benign disease which cease as a regular febrile seizure, there are some patients who suffer from convulsions continuously even after turning 6 years old, and there are some patients who are patients of Dravet syndrome (previously called "Severe Myoclonic Epilepsy in Infancy; SMEI"), which are patients of an intractable epilepsy disease.

The patients of Dravet syndrome are triggered in the onset of convulsions under the age of one. An average age of the onset of convulsions for patients of Dravet syndrome is 4 months to 6 months after birth. An incipient seizure of convulsion for a patient of Dravet syndrome is generally a systemic or a unilateral tonic-clonic or clonic convulsion, and during infancy, may lead to status epilepticus. Moreover, this convulsion seizure is easily induced by fever or bathing.

Conventionally, febrile seizure was diagnosed and treated by a general pediatrician or a family doctor, and Dravet syndrome is also diagnosed based on clinical symptoms characteristic of Dravet syndrome such as convulsion seizure or the like. However, by the time the patients of Dravet syndrome turn two to three years old, that is around when the clinical symptoms of Dravet syndrome have all appeared, these patients would have suffered repetitive convulsions many times and would often have had experienced critical conditions such as status epilepticus or the like. Hence, it is necessary to develop a diagnosis method that enables detection of Dravet syndrome in its possible earliest stage by a general pediatrician or family doctor, who is engaged in primary medical care. Detection of Dravet syndrome at an earlier stage would allow for the patent to see an epilepsy specialist in advance, which would allow for preventing the patient from reaching a critical condition.

Recently, it has been reported that 30% to 80% of Dravet syndrome patients find missense mutation (mutation causing a substitution of an amino acid) and nonsense mutation (mutation causing protein synthesis to stop in an incomplete state) on a SCN1A gene that encodes a voltage-gated sodium ion channel $Na_V1.1$ α-subunit type 1 (see Non Patent Literature 1 and 2). From such a point in view, attempts have been made to examine abnormalities in the SCN1A gene to diagnose Dravet syndrome on the basis of genes.

For example, Patent Literatures 1 to 4 disclose that mutation of the SCN1A gene is related to SMEI. Moreover, Patent Literatures 1 to 4 disclose that SMEI can be diagnosed by use of the mutation of the SCN1A gene as an indicator.

More specifically, Patent Literature 1 discloses the diagnosis of SMEI by assessing a plurality of mutations on the SCN1A gene that relate to SMEI, as a whole.

Patent Literature 2 discloses the diagnosis of SMEI performed by detecting a presence of a mutation that frequently occurs on the SCN1A gene of a nerve that is affected by SMEI.

Patent Literatures 3 and 4 disclose a method of diagnosing epilepsy syndromes including SMEI and syndromes associated with SMEI, by detecting a change in the SCN1A gene and confirming whether that change is known as being related to SMEI or a syndrome associated with SMEI or is known as not being related to SMEI or a syndrome associated with SMEI.

CITATION LIST

Patent Literature

Patent Literature 1

Japanese Patent Application Publication, Tokukai, No. 2004-329153 A (Publication Date: Nov. 25, 2004)

Patent Literature 2

Japanese Patent Application Publication, Tokukai, No. 2004-73058 A (Publication Date: Mar. 11, 2004)

Patent Literature 3

Published Japanese Translations of PCT International Publication, Tokuhyo, No. 2008-546376 A (Publication Date: Dec. 25, 2008)

Patent Literature 4

Published Japanese Translations of PCT International Publication, Tokuhyo, No. 2006-524490 A (Publication Date: Nov. 2, 2006)

Non Patent Literature

Non Patent Literature 1

Sugawara T, Mazaki-Miyazaki E, Fukushima K, Shimomura J, Fujiwara T, Hamano S, Inoue Y, Yamakawa K. 2002. Frequent mutations of SCN1A in severe myoclonic epilepsy in infancy. Neurology 58: 1122-1124.

Non Patent Literature 2

Ohmori I, Ouchida M, Ohtsuka Y, Oka E, Shimizu K. 2002. Significant correlation of the SCN1A mutations and severe myoclonic epilepsy in infancy. Biochem Biophys Res Commun 295: 17-23.

Non Patent Literature 3

Escayg A, Heils A, MacDonald B T, Haug K, Sander T, and Meisler M H. 2001. A novel SCN1A mutation associated with generalized epilepsy with febrile seizures plus- and prevalence of variants in patients with epilepsy. Am J Hum Genet. 68: 866-873.

SUMMARY OF INVENTION

Technical Problem

As described above, the mutation on the SCN1A gene is found in an extremely large number of Dravet syndrome patients (30% to 80%). However, it is becoming revealed that the presence of a mutation on the SCN1A gene does not necessarily mean that the symptoms of Dravet syndrome would appear.

For example, Non Patent Literature 3 reports that not just the patients of the intractable Dravet syndrome, but also patients of febrile seizure and patients with a certain kind of benign epilepsy (e.g. GEFS+ (Generalized epilepsy with febrile seizure plus)) have a mutation on the SCN1A gene.

As such, the mutation on the SCN1A gene is not a phenomenon specific to Dravet syndrome. Hence, the conventional methods of examining just the abnormalities on the SCN1A gene as described in Patent Literatures 1 to 4 can be said as insufficient for specifically diagnosing Dravet syndrome.

Therefore, in order to distinguish between the patients with benign febrile seizure and the patients with Dravet syndrome and to allow for the patients with Dravet syndrome to receive appropriate treatment by a specialist, further development is required in techniques for more accurately diagnosing Dravet syndrome.

The present invention is accomplished in view of the foregoing problems, and an object thereof is to provide a method of (specifically) assessing with high accuracy a potential for development of Dravet syndrome.

Solution to Problem

Patients of GEFS+ and the patients of Dravet syndrome are common in a point that the SCN1A gene has a mutation. Meanwhile, the inventors performed diligent study based on their unique point of view of focusing on the difference in malignancy between the diseases; they considered that the development of Dravet syndrome is related to not just the mutation on the SCN1A gene but also another factor, and that another cause is related to the worsening and intractableness of Dravet syndrome. As a result, the inventors uniquely found out that many Dravet syndrome patients have a mutation on the SCN1A gene and further a mutation on the CACNA1A gene that encodes a P/Q type voltage-gated calcium ion channel $Ca_V2.1$ α1 subunit.

Furthermore, based on this finding, the inventors produced a rat having both the mutations on the SCN1A gene and the CACNA1A gene, and demonstrated that the rat having both the mutations on the SCN1A gene and the CACNA1A gene experienced more serious convulsion seizures as compared to rats having just the mutation on the SCN1A gene.

Based on these results of analyzing genes and animal testing results, it was found that the potential for development of Dravet syndrome can be assessed with high accuracy by detecting mutations for both α-subunit type 1 of voltage-gated sodium ion channel $Na_V1.1$ and α-subunit type 1 of voltage-gated calcium ion channel $Ca_V2.1$, and accomplished the present invention.

Namely, the present invention includes the following inventions.

An assessment method according to the present invention is a method of assessing a potential for development of Dravet syndrome, the method including:

with use of a sample taken from a subject, detecting whether or not a mutation is on α-subunit type 1 of voltage-gated sodium ion channel $Na_V1.1$; and detecting whether or not a mutation is on α-subunit type 1 of voltage-gated calcium ion channel $Ca_V2.1$. It is preferable that the assessment method according to the present invention is a method of obtaining data for assessing potential for development of Dravet syndrome.

A kit according to the present invention is a kit for assessing a potential for development of Dravet syndrome, the kit comprising:

a polynucleotide being used for determining a mutation on α-subunit type 1 of voltage-gated sodium ion channel $Na_V1.1$; and a polynucleotide being used for determining a mutation on α-subunit type 1 of voltage-gated calcium ion channel $Ca_V2.1$. The kit according to the present invention may be a kit for obtaining data for assessing a potential for development of Dravet syndrome.

A model animal of Dravet syndrome according to the present invention has a mutation on both α-subunit type 1 of voltage-gated sodium ion channel $Na_V1.1$ and α-subunit type 1 of voltage-gated calcium ion channel $Ca_V2.1$.

A production method according to the present invention of a model animal of Dravet syndrome is a method of producing the model animal of Dravet syndrome described above, which method includes:

introducing a mutation on a α-subunit type 1 of the voltage-gated sodium ion channel $Na_V1.1$; and introducing a mutation on a α-subunit type 1 of the voltage-gated calcium ion channel $Ca_V2.1$.

A cell according to the present invention has a mutation on both α-subunit type 1 of voltage-gated sodium ion channel $Na_V1.1$ and α-subunit type 1 of voltage-gated calcium ion channel $Ca_V2.1$.

A method of producing a cell according to the present invention is a method of producing the cell described above, which method includes:

introducing a mutation on a α-subunit type 1 of the voltage-gated sodium ion channel $Na_V1.1$; and introducing a mutation on a α-subunit type 1 of the voltage-gated calcium ion channel $Ca_V2.1$.

A screening method according to the present invention of a drug for treating Dravet syndrome includes:

administering a candidate agent to the model animal of Dravet syndrome according to the present invention; and assessing whether or not the administering of the candidate agent has made Dravet syndrome improve or cure in the model animal of Dravet syndrome.

A screening method according to the present invention of a drug for treating Dravet syndrome includes:

administering a candidate agent to the cell according to the present invention; and assessing whether or not the administering of the candidate agent has made activity of the voltage-gated sodium ion channel $Na_V1.1$ and/or activity of the voltage-gated calcium ion channel $Ca_V2.1$ change in the cell.

For a fuller understanding of the nature and advantages of the invention, reference should be made to the ensuing detailed description taken in conjunction with the accompanying drawings.

Advantageous Effects of Invention

The method according to the present invention of assessing a potential for development of Dravet syndrome allows for obtaining data for assessing the potential for development of Dravet syndrome, by detecting mutations for both α-subunit type 1 of voltage-gated sodium ion channel $Na_V1.1$ and α-subunit type 1 of voltage-gated calcium ion channel $Ca_V2.1$.

Patients of GEFS+, being a benign epilepsy, inherit the mutation of the SCN1A gene within the family. In comparison, in patients of Dravet syndrome, approximately 90% of the mutations on SCN1A gene are de novo mutation, i.e. are anew mutations in which a mutation arises even though their parents have no mutation. As such, although the GEFS+ patients and the Dravet syndrome patients are common in that a mutation is on the SCN1A gene, the cause for the difference in malignancy of the disease was unknown. However, it was clarified by the present inventors for the first time, that the presence of mutations on both the SCN1A gene and the CACNA1A gene is related to the worsening and intractableness of Dravet syndrome.

As described above, reports have already been made that a mutation on α-subunit type 1 of voltage-gated sodium ion channel $Na_V1.1$ (hereinafter, referred to as "sodium ion channel α1 subunit") is related to the development of Dravet syndrome. However, no reports have been made whatsoever that Dravet syndrome is related to a mutation on α-subunit type 1 of voltage-gated calcium ion channel $Ca_V2.1$ (hereinafter, referred to as "calcium ion channel α1 subunit").

Reports have been made that a mutation on α subunit other than the α1 subunit of voltage-gated calcium ion channel $Ca_V2.1$ is associated with Dravet syndrome (see Iori Ohmori et. Al., Neurobiology of Disease 32 (2008) 349-354). More specifically, this literature (Iori Ohmori et. Al.) discloses that a mutation on β4 subunit of voltage-gated calcium ion channel $Ca_V2.1$ (hereinafter, simply referred to as "calcium ion channel β4 subunit") is associated with Dravet syndrome.

However, the foregoing literature strongly teaches regarding Dravet syndrome that a mutation on the "calcium ion channel β4 subunit" is important together with the mutation on the "α-subunit of sodium ion channel $Na_V1.1$". This description in the literature hinders a motivation to arrive at a point that a mutation suitable for detecting Dravet syndrome is present in the calcium ion channel α1 subunit.

In the first place, a skilled person would not arrive at considering, just because a relationship of a mutation on a specific subunit with a disease is known for a specific channel, that other subunits would also have a mutation related to that disease. At least, the finding that the voltage-gated sodium ion channel $Na_V1.1$ is related to Dravet syndrome is only known regarding the mutation on the "α1 subunit"; this does not give motivation for analyzing mutations on other subunits.

As to a mutation on the calcium ion channel α1 subunit, reports have been made stating a relationship with (1) epixodic ataxia type 2 (characterized in paroxysmal cerebellar ataxia), (2) familial hemiplegic migraine type 1 (e.g. hemiplegia, hemianopsia, dysphagia, throbbing headache), and (3) spinocerebellar ataxia type 6 (e.g. ataxic gait, limb ataxia, cerebellar dysarthria, nystagmus) (see Keiji IMOTO et al., "Igaku no Ayumi" (Development in Medical Science), Vol. 201, No. 13 (Issued Jun. 29, 2002); Taiji TSUNEMI et al., "Igaku no Ayumi" (Development in Medical Science), Vol. 201, No. 13 (Issued Jun. 29, 2002)). However, the diseases of (1) to (3) all show no symptoms of epilepsy, and neither are diseases related to Dravet syndrome. At least, although the finding regarding the mutation on the calcium ion channel α1 subunit is known as related to the diseases of (1) to (3), it is not one that gives motivation for analyzing a mutation on the calcium ion channel α1 subunit in Dravet syndrome, which disease is completely unrelated to the diseases of (1) to (3).

The assessment method according to the present invention detects a mutation on α-subunit type 1 of the voltage-gated sodium ion channel $Na_V1.1$ and on α-subunit type 1 of the voltage-gated calcium ion channel $Ca_V2.1$. Hence, it is possible to detect Dravet syndrome with high accuracy. Consequently, the assessment method of the present invention brings about an effect that it is possible to improve reliability of a potential for detecting Dravet syndrome as compared to the conventional method by detecting a mutation on the SCN1A gene. Furthermore, detection of a mutation on α-subunit type 1 of the voltage-gated sodium ion channel $Na_V1.1$ and a mutation on α-subunit type 1 of the voltage-gated calcium ion channel $Ca_V2.1$ is possible even with an infant under the age of one. Hence, according to the assessment method of the present invention, an effect is brought about that data for assessing the potential for development in Dravet syndrome can be obtained from a patient in an early stage of development or in a stage prior to the onset of the intractable disease, in particular of an infant under the age of one.

Moreover, as shown in Examples later described, an effect is brought about that by detecting a mutation on both α-subunit type 1 of the voltage-gated sodium ion channel $Na_V1.1$ and α-subunit type 1 of the voltage-gated calcium ion channel $Ca_V2.1$, the detection sensitivity of Dravet syndrome patients dramatically improve.

Furthermore, with use of the kit according to the present invention, it is possible to easily detect the mutation on both α-subunit type 1 of the voltage-gated sodium ion channel $Na_V1.1$ and α-subunit type 1 of the voltage-gated calcium ion channel $Ca_V2.1$. Hence, the kit according to the present invention is useful for a general pediatrician to screen, at an early stage of disease of under the age of one, a patient of Dravet syndrome that requires treatment by a specialist, among benign febrile epilepsy.

By using the assessment method and kit according to the present invention, it is possible to detect the patients of Dravet syndrome with high accuracy at the point in time of an age under one, which is an age difficult to detect until now. Moreover, by sending a blood sample to an examination center and examining its abnormal genes, it is possible to detect a Dravet syndrome patient with high accuracy even in a private hospital at a remote location or the like.

Moreover, the Dravet syndrome model animal and cell according to the present invention can be usefully used for resolving a development mechanism of the intractable Dravet syndrome, and for development and the like of medicament for Dravet syndrome.

BRIEF DESCRIPTION OF DRAWINGS

FIG. 1 is a view illustrating an amino acid sequence of a protein encoded by a human SCN1A gene and an amino acid sequence of a protein encoded by a rat SCN1A gene.

FIG. 5 is a view illustrating genotypes of parent rats (P), first filial generation (F1) rats, and second filial generation (F2) rats. Illustrated in (a) is a view showing genotypes of the parent rats (P) and the F1 rats. Illustrated in (b) are genotypes of the F1 rats and the F2 rats.

FIG. 11 is a view illustrating an amino acid sequence of a protein encoded by a human CACNA1A gene and an amino acid sequence of a protein encoded by a rat Cacna1a gene.

DESCRIPTION OF EMBODIMENTS

Figure 2:
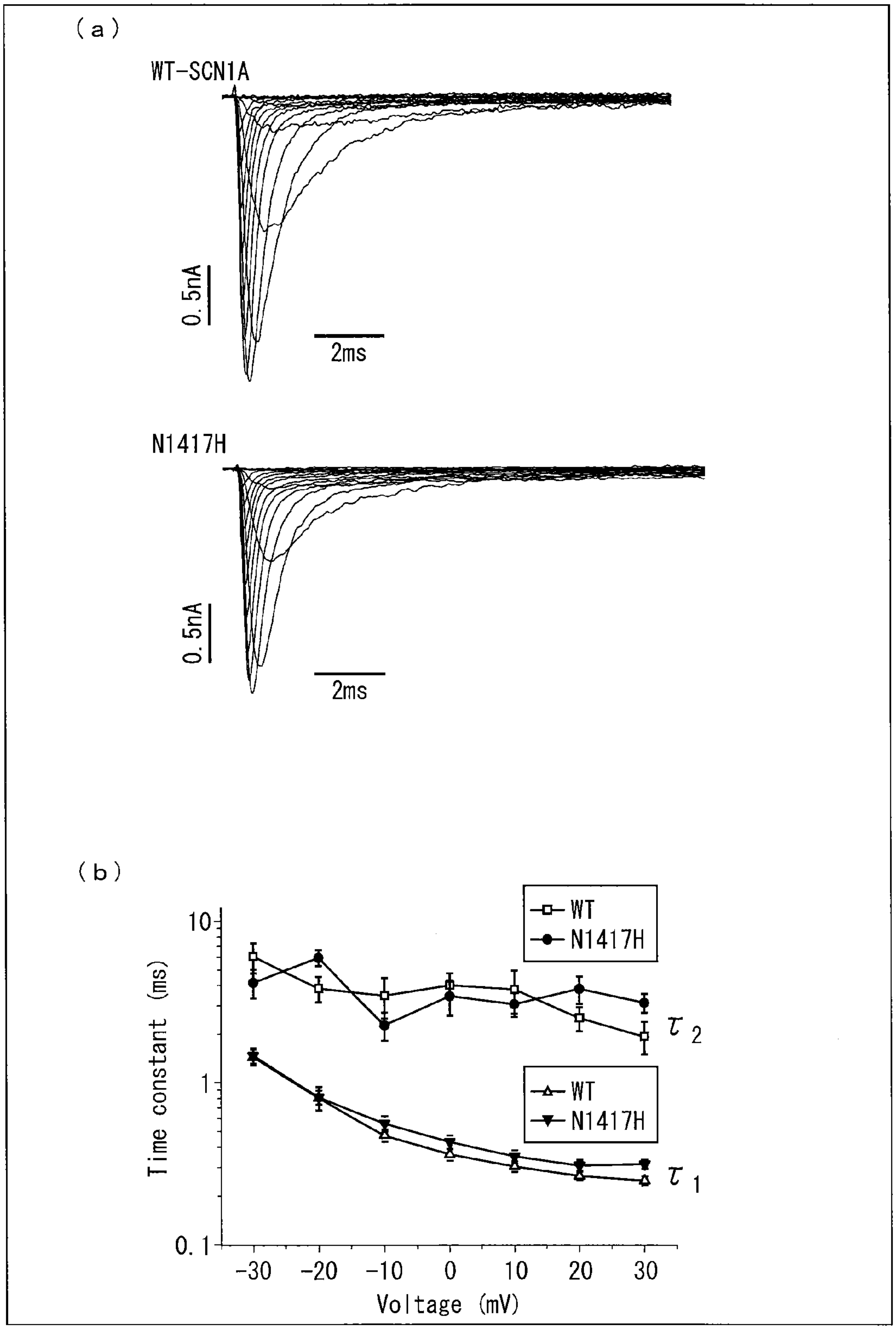
FIG. 2 is a view illustrating a result of performing function analysis of sodium ion channel, by use of patch clamping. Illustrated in (a) is a typical example of a sodium current effected by a change in potential of a normal sodium ion channel and a mutant sodium ion channel. Illustrated in (b) is a result of examining a time constant (i) at inactivation.

Described below is an embodiment of the present invention in detail. The present invention is not limited to this embodiment however, and may be carried out in modes of various modifications that are made within the described scope. Moreover, all academic literature and patent literature disclosed in the present specification are incorporated as reference. Unless mentioned otherwise, numerical ranges expressed as "A to B" denote "not less than A but not more than B".

1. Assessment Method According to the Present Invention

A method of assessing a potential for development of Dravet syndrome according to the present invention (also referred to as "assessment method according to the present invention") is a method of assessing a potential for development of Dravet syndrome in a subject, by use of a sample taken from the subject. In the present specification, the "potential for development of Dravet syndrome" includes a potential that the Dravet syndrome is already developed and a potential that the Dravet syndrome may develop in the future.

The subject is not particularly limited, and may be an individual in which Dravet syndrome has developed (individual having potential for development) or may be an individual in which the Dravet syndrome is not developed (individual having no potential for development). Out of such individuals, it is preferable that the subject is of either infants or children.

The assessment method according to the present invention, more specifically, may be of any method as long as it includes, with use of a sample taken from the subject: detecting whether or not a mutation is on α-subunit type 1 of voltage-gated sodium ion channel $Na_V1.1$; and detecting whether or not a mutation is on α-subunit type 1 of voltage-gated calcium ion channel $Ca_V2.1$. Any other specific configurations are not limited in particular.

In the embodiment, the voltage-gated sodium ion channel $Na_V1.1$ is made up of α-subunit type 1, $\beta_1$ subunit, and $\beta_2$ subunit. The $\beta_1$ subunit and the $\beta_2$ subunit are auxiliary subunits.

The α-subunit type 1 of voltage-gated sodium ion channel $Na_V1.1$ (hereinafter, referred to as "sodium ion channel α1 subunit") is for example a polypeptide that is registered as GenBank accession No. AB093548 (i.e. amino acid sequence represented by SEQ ID NO. 1). Moreover, an example of a gene that encodes the α-subunit type 1 of voltage-gated sodium ion channel $Na_V1.1$ (hereinafter, called "sodium ion channel α1 subunit gene") is, as a SCN1A gene, a polynucleotide made up of a nucleotide sequence registered as GenBank accession No. AB093548 (i.e. nucleotide sequence represented by SEQ ID NO. 2).

The voltage-gated calcium ion channel $Ca_V2.1$ is made up of α-subunit type 1, β subunit, γ subunit, and α2δ subunit.

The voltage-gated calcium ion channel $Ca_V2.1$ α-subunit type 1 (hereinafter, referred to as "calcium ion channel α1 subunit") is for example a polypeptide registered as GenBank accession No. NM 023035 (i.e. amino acid sequence represented by SEQ ID NO. 3). Moreover, an example of a gene that codes the α-subunit type 1 of voltage-gated calcium ion channel $Ca_V2.1$ (hereinafter, referred to as "calcium ion channel α1 subunit gene") is, as a CACNA1A gene, a polynucleotide made up of a nucleotide sequence registered as GenBank accession No. NM 023035 (i.e. nucleotide sequence represented by SEQ ID NO. 4).

In the present specification, for example, the term "α-subunit type 1 of voltage-gated sodium ion channel $Na_V1.1$" denotes "α-subunit type 1 protein of voltage-gated sodium ion channel $Na_V1.1$". Namely, in the present specification, unless it is clearly described as indicating a gene as like "gene encoding α-subunit type 1 of voltage-gated sodium ion channel $Na_V1.1$" or "α-subunit type 1 gene of voltage-gated sodium ion channel $Na_V1.1$", a protein is denoted. This way of description is not limited to the "α-subunit type 1 of voltage-gated sodium ion channel $Na_V1.1$", and "α-subunit type 1 of voltage-gated calcium ion channel $Ca_V2.1$" is denoted similarly thereto.

It is preferable that the assessment method according to the present invention further includes, in addition to the detecting the presence of a mutation: detecting a change in activity of the voltage-gated sodium ion channel $Na_V1.1$; and detecting a change in activity of the voltage-gated calcium ion channel $Ca_V2.1$.

The assessment method according to the present invention may include, for detecting the mutation, a step such as preprocessing of a sample that is taken from the living organism. The "preprocessing" indicates, for example, a process of extracting DNA from the sample taken from the living organism, a process of extracting RNA from the sample taken from the living organism, a process of extracting protein from the sample taken from the living organism, or like process. These preprocessing can be carried out by use of conventionally known methods.

The assessment method according to the present invention may be a method of obtaining data for assessing a potential for development of Dravet syndrome. In this case, the present invention does not include the step of determining by a doctor.

(1-1. Detecting Presence of Mutation)

In the present specification, the "detecting presence of a mutation" denotes detecting a presence of a mutation on α-subunit type 1 of voltage-gated sodium ion channel $Na_V1.1$ and detecting a presence of a mutation on α-subunit type 1 of voltage-gated calcium ion channel $Ca_V2.1$.

In the assessment method according to the present invention, the detecting of the presence of a mutation on the α-subunit type 1 of voltage-gated sodium ion channel $Na_V1.1$ may be performed prior to the detecting of the presence of a mutation on the α-subunit type 1 of voltage-gated calcium ion channel $Ca_V2.1$ or vice versa, or may be performed simultaneously.

By detecting the presence of a mutation in both the sodium ion channel α1 subunit and the calcium ion channel α1 subunit, it is possible to obtain the data that enables accurate assessment of the potential for development of Dravet syndrome.

The mutation detected by the assessment method according to the present invention may be a mutation on a nucleotide sequence of a gene, or may be a mutation on an amino acid of a protein. The "mutation on a nucleotide sequence of a gene" is not limited in particular by a specific kind of mutation as long as it is a mutation that causes a change in an amino acid sequence of a protein encoded by a gene having a mutation on its nucleotide sequence as compared to an amino acid sequence of a protein encoded by a wild-type gene. Mutations on the nucleotide sequence as described above are, for example, missense mutation (substitution of an amino acid), nonsense mutation (synthesis of an amino acid stops in an incomplete state), frameshift (a frame of an amino acid codon shifts caused by insertion or deletion of a nucleotide, which causes an amino acid sequence downstream of the mutation position to change, thereby losing its original function), splicing defect (e.g. deletion of its exon region), minority nucleotide insertion or deletion (a part of amino acids is newly added or lost however its downstream is synthesized as normal amino acid), and minor deletion of an exon region (loss of one or a plurality of exon). Variations on the nucleotide sequence as such are not limited to mutations, and may also include gene polymorphism.

Moreover, in the assessment method according to the present invention, the detection of mutation may be performed to mRNA, cDNA, and proteins obtained from these genes.

In the present specification, "gene" can be replaced by "polynucleotide", "nucleic acid" or "nucleic acid molecule".

The "polynucleotide" means a polymer of a nucleotide. Hence, the term "gene" in the present specification includes not only the double stranded DNA but also a single stranded DNA and RNA (mRNA, etc.) such as a sense strand and an antisense strand that construct the double stranded DNA.

The term "DNA" encompasses cDNA, genomic DNA and the like that can be obtained by cloning, a chemically synthesized technique or a combination of these. Namely, DNA may be a "genome" type DNA, which includes a noncoding sequence such as intron or the like that is a form included in an animal genome, or may be a cDNA obtained from mRNA with use of reverse transcriptase or polymerase, i.e. "transcription" type DNA that does not include a noncoding sequence such as intron.

Examples of the mutation on sodium ion channel α1 subunit is, more specifically, a mutation of asparagine (N) at position 1417 of the amino acid sequence of sodium ion channel α1 subunit represented by SEQ ID NO. 1, and is preferably a mutation of asparagine (N) at position 1417 to histidine (H) ("N1417H" in Table 1). This mutation is caused by, for example, a mutation of adenine (A) at position 4249 of the nucleotide sequence of sodium ion channel α1 subunit gene represented by SEQ ID NO. 2, preferably a substitution of adenine (A) at position 4249 with cytosine (C) (A4249C).

Moreover, another embodiment is a mutation of lysine (K) at position 1027 of the amino acid sequence of the sodium ion channel α1 subunit represented by SEQ ID NO. 1, preferably a mutation of lysine (K) at position 1027 to a stop codon ("K1027X" in Table 1). This mutation is caused by, for example, a mutation of adenine (A) at position 3079 of the nucleotide sequence of sodium ion channel α1 subunit gene represented by SEQ ID NO. 2, preferably a substitution of adenine (A) at position 3079 with thymine (T) (A3079T).

Yet another embodiment is a mutation of glutamine (Q) at position 1450 of the amino acid sequence of sodium ion channel α1 subunit represented by SEQ ID NO. 1, preferably a mutation of glutamine (Q) at position 1450 to arginine (R) ("Q1450R" in Table 1). This mutation is caused by, for example, a mutation of adenine (A) at position 4349 of a nucleotide sequence of sodium ion channel α1 subunit gene represented by SEQ ID NO. 2, preferably a substitution of adenine (A) at position 4349 with guanine (G) (A4349G).

Yet another embodiment is a mutation of threonine (T) at position 1082 of the amino acid sequence of sodium ion channel α1 subunit represented by SEQ ID NO. 1, preferably a mutation causing generation of a stop codon at position 1086 by frameshift ("T1082fsX1086" in Table 1). This mutation is caused by, for example, a mutation of cytosine (C) at position 3245 of a nucleotide sequence of sodium ion channel α1 subunit gene represented by SEQ ID NO. 2, preferably a deletion of cytosine (C) at position 3245 (C3245del).

Yet another embodiment is a mutation of lysine (K) at position 547 of the amino acid sequence of the sodium ion channel α1 subunit represented by SEQ ID NO. 1, preferably a mutation causing generation of a stop codon at position 570 by frameshift ("K547fsX570" in Table 1). This mutation is caused by, for example, a mutation at position 1641 of the nucleotide sequence of the sodium ion channel α1 subunit gene represented by SEQ ID NO. 2, preferably an insertion of adenine (A) into position 1641 (1641insA).

Yet another embodiment is a mutation of proline (P) at position 707 of the amino acid sequence of sodium ion channel α1 subunit represented by SEQ ID NO. 1, preferably a mutation causing generation of a stop codon at position 714 by frameshift ("P707fsX714" in Table 1). This mutation is caused by, for example, a mutation of cytosine (C) at position 2120 in the nucleotide sequence of sodium ion channel α1 subunit gene represented by SEQ ID NO. 2, preferably a deletion of cytosine (C) at position 2120 (C2120del).

Yet another embodiment is a mutation of arginine (R) at position 712 of the amino acid sequence of sodium ion channel α1 subunit represented by SEQ ID NO. 1, preferably a mutation of arginine (R) at position 712 to a stop codon ("R712X" in Table 1). This mutation is caused by, for example, a mutation of cytosine (C) at position 2134 of the nucleotide sequence of the sodium ion channel α1 subunit gene represented by SEQ ID NO. 2, preferably a substitution of cytosine (C) at position 2134 with thymine (T) (C2134T).

Yet another embodiment is a mutation of leucine (L) at position 1265 of the amino acid sequence of the sodium ion channel α1 subunit represented by SEQ ID NO. 1, preferably a mutation of leucine (L) at position 1265 to proline (P) ("L1265P" in Table 1). This mutation is caused by, for example, a mutation of thymine (T) at position 3794 of the nucleotide sequence of sodium ion channel α1 subunit gene represented by SEQ ID NO. 2, preferably a substitution of thymine (T) at position 3794 with cytosine (C) (T3794C).

Yet another embodiment is a deletion of amino acid of positions 460 to 554 of the amino acid sequence of the sodium ion channel α1 subunit represented by SEQ ID NO. 1 ("Exon10" in Table 1). This mutation is caused by, for example, a deletion of nucleotide at positions 1378 to 1662 (exon 10) of the nucleotide sequence of sodium ion channel α1 subunit gene represented by SEQ ID NO. 2.

Yet another embodiment is a mutation of arginine (R) at position 865 of the amino acid sequence of the sodium ion channel α1 subunit represented by SEQ ID NO. 1, preferably a mutation of arginine (R) at position 865 to a stop codon ("R865X" in Table 1). This mutation is caused by, for example, a mutation of cytosine (C) at position 2593 of the nucleotide sequence of the sodium ion channel α1 subunit gene represented by SEQ ID NO. 2, preferably a substitution of cytosine (C) at position 2593 with thymine (T) (C2593T).

Yet another embodiment is a mutation of arginine (R) at position 1648 of the amino acid sequence of sodium ion channel α1 subunit represented by SEQ ID NO. 1, preferably a substitution of arginine (R) at position 1648 with cysteine (C) ("R1648C" in Table 1). This mutation is caused by, for example, a mutation of cytosine (C) at position 4942 of the nucleotide sequence of sodium ion channel α1 subunit gene represented by SEQ ID NO. 2, preferably a substitution of cytosine (C) at position 4942 with thymine (T) (C4942T).

Yet another embodiment is a mutation of arginine (R) at position 931 in the amino acid sequence of sodium ion channel α1 subunit represented by SEQ ID NO. 1, preferably a substitution of arginine (R) at position 931 with cysteine (C) ("R931C" in Table 1). This mutation is caused by, for example, a mutation of cytosine (C) at position 2791 of the nucleotide sequence of sodium ion channel α1 subunit gene represented by SEQ ID NO. 2, preferably a substitution of cytosine (C) at position 2791 with thymine (T) (C2791T).

Yet another embodiment is a mutation of arginine (R) at position 501 in the amino acid sequence of sodium ion channel α1 subunit represented by SEQ ID NO. 1, preferably a mutation causing generation of a stop codon at position 543 by frameshift ("R501fsX543" in Table 1). This mutation is caused by, for example, a mutation of guanine (G) at position 1502 of the nucleotide sequence of sodium ion channel α1 subunit gene represented by SEQ ID NO. 2, preferably a deletion of guanine (G) at position 1502 (G1502del).

Yet another embodiment is a mutation of alanine (A) at position 1002 in the amino acid sequence of sodium ion channel α1 subunit represented by SEQ ID NO. 1, preferably a mutation causing generation of a stop codon at position 1009 by frameshift ("A1002fsX1009" in Table 1). This mutation is caused by, for example, a mutation of cytosine (C) at position 3006 of the nucleotide sequence of sodium ion channel α1 subunit gene represented by SEQ ID NO. 2, preferably a deletion of cytosine (C) at position 3006.

Yet another embodiment is a mutation of phenylalanine (F) at position 902 of the amino acid sequence of sodium ion channel α1 subunit represented by SEQ ID NO. 1, preferably a mutation of phenylalanine (F) at position 902 to cysteine (C) ("F902C" in Table 1). This mutation is caused by, for example, a mutation of thymine (T) at position 2705 of the nucleotide sequence of sodium ion channel α1 subunit gene represented by SEQ ID NO. 2, preferably by a substitution of thymine (T) at position 2705 with guanine (G) (T2705G).

Yet another embodiment is a mutation of glycine (G) at position 1674 of the amino acid sequence of aodium ion channel α1 subunit represented by SEQ ID NO. 1, preferably a substitution of glycine (G) at position 1674 with arginine (R) ("G1674R" in Table 1). This mutation is caused by, for example, a mutation of guanine (G) at position 5020 of the nucleotide sequence of sodium ion channel α1 subunit gene represented by SEQ ID NO. 2, preferably a substitution of guanine (G) at position 5020 with cytosine (C) (G5020C).

Yet another embodiment is a mutation of valine (V) at position 1390 of the amino acid sequence of sodium ion channel α1 subunit represented by SEQ ID NO. 1, preferably a mutation of valine (V) at position 1390 to methionine (M) ("V1390M" in Table 1). This mutation is caused by, for example, a mutation of guanine (G) at position 4168 of the nucleotide sequence of sodium ion channel α1 subunit gene represented by SEQ ID NO. 2, preferably a substitution of guanine (G) at position 4168 with adenine (A) (G4168A).

Yet another embodiment is a mutation of serine (S) at position 607 in the amino acid sequence of sodium ion channel α1 subunit represented by SEQ ID NO. 1, preferably a mutation causing generation of a stop codon at position 622 by frameshift ("S607fsX622" in Table 1). This mutation is caused by, for example, a mutation of cytosine (C) at position 1820 of the nucleotide sequence of sodium ion channel α1 subunit gene represented by SEQ ID NO. 2, preferably a deletion of cytosine (C) at position 1820 (C1820del).

Yet another embodiment is a mutation of tryptophan (W) at position 1434 of the amino acid sequence of sodium ion channel α1 subunit represented by SEQ ID NO. 1, preferably a substitution of tryptophan (W) at position 1434 with arginine (R) ("W1434R" in Table 1). This mutation is caused by a mutation of thymine (T) at position 4300 of the nucleotide sequence of sodium ion channel α1 subunit gene represented by SEQ ID NO. 2, preferably a substitution of thymine (T) at position 4300 with cytosine (C) (T4300C).

Yet another embodiment is a mutation of threonine (T) at position 1909 of the amino acid sequence of sodium ion channel α1 subunit represented by SEQ ID NO. 1, preferably a substitution of threonine (T) at position 1909 with isoleucine (I) ("T1909I" in Table 1). This mutation is caused by, for example, the mutation of cytosine (C) at position 5726 of the nucleotide sequence of sodium ion channel α1 subunit gene represented by SEQ ID NO. 2, preferably by a substitution of cytosine (C) at position 5726 with thymine (T) (C5726T).

Yet another embodiment is a mutation of phenylalanine (F) at position 1289 of the amino acid sequence of sodium ion channel α1 subunit represented by SEQ ID NO. 1, preferably a deletion of phenylalanine (F) at position 1289 ("F1289del" in Table 1). This mutation is caused by, for example, mutations of cytosine (C) at position 3867, thymine (T) at position 3868, and thymine (T) at position 3869, each in the nucleotide sequence of sodium ion channel α1 subunit gene represented by SEQ ID NO. 2, preferably a deletion of cytosine (C) at position 3867, thymine (T) at position 3868, and thymine (T) at position 3869.

Yet another embodiment is a mutation of tryptophan (W) at position 1271 of the amino acid sequence of sodium ion channel α1 subunit represented by SEQ ID NO. 1, preferably a mutation of tryptophan (W) at position 1271 to a stop codon ("W1271X" in Table 1). This mutation is caused by, for example, a mutation of guanine (G) at position 3812 of the nucleotide sequence of sodium ion channel α1 subunit gene represented by SEQ ID NO. 2, preferably by a substitution of guanine (G) at position 3812 with adenine (A) (G3812A).

Yet another embodiment is a mutation of alanine (A) at position 1429 of the amino acid sequence of sodium ion channel α1 subunit represented by SEQ ID NO. 1, preferably a mutation causing generation of a stop codon at position 1443 by frameshift ("A1429fsX1443" in Table 1). This mutation is caused by, for example, a mutation of five-nucleotide CCACA between positions 4286 to 4290 of the nucleotide sequence of sodium ion channel α1 subunit gene represented by SEQ ID NO. 2, preferably a substitution of CCACA at positions 4286 to 4290, with ATGTCC.

Moreover, another embodiment is a mutation of glycine (G) at position 1880 of the amino acid sequence of sodium ion channel α1 subunit represented by SEQ ID NO. 1, preferably a mutation causing generation of a stop codon at position 1881 by frameshift ("G1880fsX1881" in Table 1). This mutation is caused by mutation of six-nucleotide AGAGAT between positions 5640 to 5645 of the nucleotide sequence of sodium ion channel α1 subunit gene represented by SEQ ID NO. 2, preferably a substitution of six-nucleotide AGAGAT between positions 5640 to 5645 with CTAGAGTA.

Yet another embodiment is a mutation of alanine (A) at position 1685 of the amino acid sequence of sodium ion channel α1 subunit represented by SEQ ID NO. 1, preferably a substitution of alanine (A) at position 1685 with aspartic acid (D) ("A1685D" in Table 1). This mutation is caused by, for example, a mutation of cytosine (C) at position 5054 of the nucleotide sequence of sodium ion channel α1 subunit gene represented by SEQ ID NO. 2, preferably by a substitution of cytosine (C) at position 5054 with adenine (A) (C5054A).

Yet another embodiment is a mutation of arginine (R) at position 377 of the amino acid sequence of sodium ion channel α1 subunit represented by SEQ ID NO. 1, preferably a substitution of arginine (R) at position 377 with leucine (L) ("R377L" in Table 1). This mutation is caused by, for example, a mutation of guanine (G) at position 1130 of the nucleotide sequence of sodium ion channel α1 subunit gene represented by SEQ ID NO. 2, preferably by substitution of guanine (G) at position 1130 with thymine (T) (G1130T).

Yet another embodiment is a mutation of serine (S) at position 1574 of the amino acid sequence of sodium ion channel α1 subunit represented by SEQ ID NO. 1, preferably a mutation of serine (S) at position 1574 to a stop codon ("S1574X" in Table 1). This mutation is caused by, for example, a mutation of cytosine (C) at position 4721 of the nucleotide sequence of sodium ion channel α1 subunit gene represented by SEQ ID NO. 2, preferably a substitution of cytosine (C) at position 4721 with guanine (G) (C4721G).

Yet another embodiment is a mutation of glutamine (Q) at position 1277 in the amino acid sequence of the sodium ion channel α1 subunit represented by SEQ ID NO. 1, preferably a mutation of glutamine (Q) at position 1277 to a stop codon ("Q1277X" in Table 1). This mutation is caused by, for example, a mutation of cytosine (C) at position 3829 of the nucleotide sequence of sodium ion channel α1 subunit gene represented by SEQ ID NO. 2, preferably by a substitution of cytosine (C) at position 3829 with thymine (T) (C3829T).

Yet another embodiment is a mutation of glycine (G) at position 177 of the amino acid sequence of sodium ion channel α1 subunit represented by SEQ ID NO. 1, preferably a mutation of glycine (G) at position 177 to arginine (R) ("G177R" in Table 1). This mutation is caused by, for example, a mutation of guanine (G) at position 529 of the nucleotide sequence of sodium ion channel α1 subunit gene represented by SEQ ID NO. 2, preferably by a substitution of guanine (G) at position 529 with adenine (A) (G529A).

Yet another embodiment is a mutation of glutamic acid (E) at position 788 of the amino acid sequence of sodium ion channel α1 subunit represented by SEQ ID NO. 1, preferably a substitution of glutamic acid (E) at position 788 with lysine (K) ("E788K" in Table 1). This mutation is caused by, for example, a mutation of guanine (G) at position 2362 of the nucleotide sequence of sodium ion channel α1 subunit gene represented by SEQ ID NO. 2, preferably by a substitution of guanine (G) at position 2362 with adenine (A) (G2362A).

Yet another embodiment is splicing defects at positions 1429 and subsequent positions of the amino acid sequence of sodium ion channel α1 subunit represented by SEQ ID NO. 1, preferably a deletion of positions at and subsequent to 1429 ("intron 21" in Table 1). This mutation is caused by, for example, a mutation of adenine (A) at a second last position (position −2), preferably a mutation in which adenine (A) at a second last position (position −2) of the intron 21 is substituted with guanine (G) (intron 21 ag(−2)gg), out of the intron 21 present in a genomic DNA between positions 4284 and 4285 of the nucleotide sequence of sodium ion channel al subunit gene represented by SEQ ID NO. 2. Namely, the second last nucleotide sequence of the intron 21 present in the genomic DNA between positions 4284 (exon 21) and 4285 (exon 22) of the nucleotide sequence of sodium ion channel α1 subunit gene represented by SEQ ID NO. 2 is ag, and is connected to the beginning of the exon 22. Generally, since the ag of the intron 21 is a recognition sequence that is spliced, in a case in which an abnormality exists at that position, the intron is determined as still continuing, which thus causes the exon immediately after (or in its downstream) to be abnormally spliced. This makes it impossible to generate a full-length protein.

Yet another embodiment is a mutation of serine (S) at position 1574 of the amino acid sequence of sodium ion channel α1 subunit represented by SEQ ID NO. 1, preferably a mutation of serine (S) at position 1574 to a stop codon ("S1574X" in Table 1). This mutation is caused by, for example, a mutation of cytosine (C) at position 4721 of the nucleotide sequence of sodium ion channel α1 subunit gene represented by SEQ ID NO. 2, preferably a substitution of cytosine (C) at position 4721 with guanine (G).

Yet another embodiment is a mutation of valine (V) at position 212 of the amino acid sequence of sodium ion channel α1 subunit represented by SEQ ID NO. 1, preferably a substitution of valine (V) at position 212 with alanine (A) ("V212A" in Table 1). This mutation is caused by, for example, a mutation of thymine (T) at position 635 of the nucleotide sequence of sodium ion channel α1 subunit gene represented by SEQ ID NO. 2, preferably a substitution of thymine (T) at position 635 with cytosine (C) (T635C).

Yet another embodiment is a mutation of threonine (T) at position 1539 of the amino acid sequence of sodium ion channel α1 subunit represented by SEQ ID NO. 1, preferably a mutation of threonine (T) at position 1539 to proline (P) ("T1539P" in Table 1). This mutation is caused by, for example, a mutation of adenine (A) at position 4615 of the nucleotide sequence of sodium ion channel α1 subunit gene represented by SEQ ID NO. 2, preferably a substitution of adenine (A) at position 4615 with cytosine (C) (A4615C).

Yet another embodiment is a mutation of tryptophan (W) at position 738 of the amino acid sequence of sodium ion channel α1 subunit represented by SEQ ID NO. 1, preferably by mutation causing generation of a stop codon at position 746 by frameshift ("W738fsX746" in Table 1). This mutation is caused by, for example, a mutation of guanine (G) at position 2213 in the nucleotide sequence of the sodium ion channel α1 subunit gene represented by SEQ ID NO. 2, preferably a deletion of guanine (G) at position 2213 (G2213del).

Yet another embodiment is a mutation of leucine (L) at position 990 of the amino acid sequence of sodium ion channel α1 subunit represented by SEQ ID NO. 1, preferably by a mutation of leucine (L) at position 990 to phenylalanine (F) ("L990F" in Table 1). This mutation is caused by, for example, a mutation of guanine (G) at position 2970 of the nucleotide sequence of sodium ion channel α1 subunit gene represented by SEQ ID NO. 2, preferably a substitution of guanine (G) at position 2970 with thymine (T) (G2970T).

Yet another embodiment is a mutation of glycine (G) at position 163 of the amino acid sequence of sodium ion channel α1 subunit represented by SEQ ID NO. 1, preferably a mutation of glycine (G) at position 163 to glutamic acid (E) ("G163E" in Table 1). This mutation is caused by, for example, a mutation of guanine (G) at position 488 of the nucleotide sequence of sodium ion channel α1 subunit gene represented by SEQ ID NO. 2, preferably a substitution of guanine (G) at position 488 with adenine (A) (G488A).

Yet another embodiment is a mutation of alanine (A) at position 1662 of the amino acid sequence of sodium ion channel α1 subunit represented by SEQ ID NO. 1, preferably a mutation of alanine (A) at position 1662 to valine (V) ("A1662V" in Table 1). This mutation is caused by, for example, a mutation of cytosine (C) at position 4985 in the nucleotide sequence of sodium ion channel α1 subunit gene represented by SEQ ID NO. 2, preferably by a substitution of cytosine (C) at position 4985 with thymine (T) (C4985T).

Yet another embodiment is a mutation of lysine (K) at position 1057 of the amino acid sequence of sodium ion channel α1 subunit represented by SEQ ID NO. 1, preferably a mutation causing generation of a stop codon at position 1073 by frameshift ("K1057fsX1073" in Table 1). This mutation is caused by, for example, a mutation of 14 nucleotides (AGAAAGACAGTTGT) between positions 3170 to 3183 of the nucleotide sequence of sodium ion channel α1 subunit gene represented by SEQ ID NO. 2, preferably a substitution of the 14 nucleotides between the positions 3170 to 3183 with TCATTCTGTATG.

It is needless to say that the mutation on the α-subunit type 1 of the voltage-gated sodium ion channel $Na_V1.1$ is not limited to the mutations exemplified above.

Examples of mutations on a calcium ion channel α1 subunit encompass, more specifically, a mutation on methionine (M) at position 249 of an amino acid sequence of calcium ion channel α1 subunit represented by SEQ ID NO. 3, preferably a mutation on methionine (M) at position 249 to lysine (K) ("M249K" in Table 2). This mutation is caused by, for example, a mutation on thymidine (T) at position 746 of the nucleotide sequence of calcium ion channel α1 subunit gene represented by SEQ ID NO. 4, preferably a mutation on thymidine (T) at position 746 substituted with adenine (A) (T746A).

Moreover, another embodiment is a mutation on glutamic acid (E) at position 921 of the amino acid sequence of calcium ion channel α1 subunit represented by SEQ ID NO. 3, preferably a mutation on glutamic acid (E) at position 921 to aspartic acid (D) ("E921D" in Table 2). This mutation is, for example, caused by a mutation on adenine (A) at position 2762 of the nucleotide sequence of calcium ion channel α1 subunit gene represented by SEQ ID NO. 4, preferably a substitution of adenine (A) at position 2762 with cytosine (C) (A2762C).

Yet another embodiment is a mutation on glutamic acid (E) at position 996 of the amino acid sequence of calcium ion channel α1 subunit represented by SEQ ID NO. 3, preferably a mutation on glutamic acid (E) at position 996 to valine (V) ("E996V" in Table 2). This mutation is, for example, caused by a mutation on adenine (A) at position 2987 of the nucleotide sequence of the calcium ion channel α1 subunit gene represented by SEQ ID NO. 4, preferably a substitution of adenine (A) at position 2987 with thymine (T) (A2987T).

Yet another embodiment is a mutation on arginine (R) at position 1126 of the amino acid sequence of calcium ion channel α1 subunit represented by SEQ ID NO. 3, preferably a mutation on arginine (R) at position 1126 to histidine (H) ("R1126H" in Table 2). This mutation is, for example, caused by a mutation on guanine (G) at position 3377 of the nucleotide sequence of calcium ion channel α1 subunit gene represented by SEQ ID NO. 4, preferably a substitution of guanine (G) at position 3377 with adenine (A) (G3377A).

Yet another embodiment is a mutation on arginine (R) at position 2201 of the amino acid sequence of calcium ion channel α1 subunit represented by SEQ ID NO. 3, preferably a mutation on arginine (R) at position 2201 to glutamine (Q) ("R2201Q" in Table 2). This mutation is, for example, caused by mutation on guanine (G) at position 6602 of the nucleotide sequence of calcium ion channel α1 subunit gene represented by SEQ ID NO. 4, preferably by a substitution of guanine (G) at position 6602 with adenine (A) (G6602A).

Yet another embodiment is a mutation on glycine (G) at position 1108 of the amino acid sequence of calcium ion channel α1 subunit represented by SEQ ID NO. 3, preferably a mutation on glycine (G) at position 1108 to serine (S) ("G1108S" in Table 2). This mutation is, for example, caused by a mutation on guanine (G) at position 3322 of the nucleotide sequence of calcium ion channel α1 subunit gene represented by SEQ ID NO. 4, preferably a substitution of guanine (G) at position 3322 with adenine (A) (G3322A).

Yet another embodiment is a mutation on alanine (A) at position 924 of the amino acid sequence of calcium ion channel α1 subunit represented by SEQ ID NO. 3, preferably a mutation of alanine (A) at position 924 to glycine (G) ("A924G" in Table 2). This mutation is, for example, caused by a mutation on cytosine (C) at position 2771 of the nucleotide sequence of calcium ion channel α1 subunit gene represented by SEQ ID NO. 4, preferably a substitution of cytosine (C) at position 2771 with guanine (G) (C2771G).

Yet another embodiment is a mutation on glycine (G) at position 266 of the amino acid sequence of calcium ion channel α1 subunit represented by SEQ ID NO. 3, preferably a mutation on glycine (G) at position 266 to serine (S) ("G266S" in Table 2). This mutation is, for example, caused by a mutation on guanine (G) at position 796 of the nucleotide sequence of calcium ion channel α1 subunit gene represented by SEQ ID NO. 4, preferably by a substitution of guanine (G) at position 796 with adenine (A) (G796A).

Yet another embodiment is a mutation on lysine (K) at position 472 of the amino acid sequence of calcium ion channel α1 subunit represented by SEQ ID NO. 3, preferably a mutation on lysine (K) at position 472 to arginine (R) ("K472R" in Table 2). This mutation is, for example, caused by a mutation on adenine (A) at position 1415 of the nucleotide sequence of calcium ion channel α1 subunit gene represented by SEQ ID NO. 4, preferably by a substitution of adenine (A) at position 1415 with guanine (G) (A1415G).

Yet another embodiment is a deletion of an amino acid at positions 2202 to 2205 of the amino acid sequence of calcium ion channel α1 subunit represented by SEQ ID NO. 3 ("del2202-2205" in Table 2). This mutation is, for example, caused by a mutation on ACCAGGAGCGGG of positions 6605 to 6616 of the nucleotide sequence of calcium ion channel α1 subunit gene represented by SEQ ID NO. 4, preferably a deletion of ACCAGGAGCGGG at positions 6605 to 6616 (del6605-6616).

It is needless to say that the mutations related to the function abnormality of voltage-gated calcium ion channel $Ca_V2.1$ is not limited to the mutations exemplified above.

The mutations on the foregoing sodium ion channel α1 subunit and the mutations on the foregoing calcium ion channel α1 subunit are organized into Table 1 and Table 2.

TABLE 1

| Mutations on sodium ion channel a1 subunit | | | |
|---|---|---|---|
| 1289delF, | G177R, | Q1450R, | T1539P, |
| A1002fsX1009, | G1880fsX1881, | R1648C, | T1909I, |
| A1429fsX1443, | intron 21, | R377L, | V1390M, |
| A1662V, | K1027X, | R501fsX543, | V212A, |
| A1685D, | K1057fsX1073, | R712X, | W1271X, |
| E788K, | K547fsX570, | R865X, | W1434R, |
| Exon10*, | L1265P, | R931C, | W738fsX746, |
| F902C, | L990F, | S1574X, | N1417H, |
| G163E, | P707fsX714, | S607fsX622, | |
| G1674R, | Q1277X, | T1082fsX1086, | |

Exon10* exon deletion detected by MLPA

TABLE 2

| Mutations on calcium ion channel a1 subunit | | |
|---|---|---|
| A924G, | E996V, | K472R, |
| del 2202-2205, | G1108S, | R1126H, |
| E921D, | G266S, | R2201Q, |
| M249K | | |

In the assessment method according to the present invention, it is preferable that the mutation on sodium ion channel α1 subunit is, more specifically, at least one mutation shown in Table 1, and the mutation on calcium ion channel α1 subunit is, more specifically, at least one mutation shown in Table 2.

The assessment method according to the present invention is not limited in particular of how the presence of a mutation is detected for both the sodium ion channel α1 subunit and the calcium ion channel α1 subunit, and any method conventionally known may be used.

Examples of methods for detecting the presence of the mutation for both the sodium ion channel α1 subunit gene and the calcium ion channel α1 subunit gene encompass mutation detecting methods such as DNA sequencing method using PCR, SSCP method (Single strand conformation polymorphism), DHPLC method (denaturing high performance liquid chromatography); polymorphism detecting methods using real-time PCR or DNA chip; method of detecting microdeletion of exons of a gene; and Northern blotting, RT-PCR, Real-time PCR, and cDNA array, each of which detect an increase and decrease of mRNA. Moreover, when the presence of mutation is to be detected for both of sodium ion channel α1 subunit protein and calcium ion channel α1 subunit protein, a method such as Western blotting, immunostaining, protein array or the like may be used.

The following provides more specific descriptions, by separating into the following embodiments: (A) an embodiment detecting a gene mutation with use of a genomic DNA included in a sample taken from a subject, (B) an embodiment detecting a gene mutation with use of mRNA (cDNA) included in a sample taken from a subject, and (C) an embodiment detecting a protein mutation with use of a protein included in a sample taken from a subject.

(A) Embodiment Using Genomic DNA

In the embodiment detecting a gene mutation with use of a genomic DNA included in a sample taken from a subject, first, a genomic DNA is extracted from the sample taken from the subject, by a conventionally known method.

The "sample taken from the subject" is not limited in particular, and any sample from which a genomic DNA is extractable can be used. More specifically, a sample of blood, oral mucosa cells, bone marrow fluid, hair, various organs, peripheral lymphocytes, synovial cells or the like can be used. Moreover, cells taken from the subject may be cultured and a genomic DNA may be extracted from its proliferated cells.

Moreover, the extracted genomic DNA may be used upon amplification by a gene amplification method generally performed, for example, PCR (Polymerase Chain Reaction), NASBA (Nucleic acid sequence based amplification), TMA (Transcription-mediated amplification), SDA (Strand Displacement Amplification), LAMP (Loop-Mediated Isothermal Amplification), and ICAN (Isothermal and Chimeric primer-initiated Amplification of Nucleic acids).

The method of detecting the presence of mutation for both the sodium ion channel α1 subunit gene and the calcium ion channel α1 subunit gene with use of a sample including a genomic DNA prepared as such is not limited in particular, and examples encompass allele-specific oligonucleotide probe method, Oligonucleotide Ligation Assay, PCR-SSCP, PCR-CFLP, PCR-PHFA, invader method, RCA (Rolling Circle Amplification), Primer Oligo Base Extension, and like methods.

More specifically, a polynucleotide for detecting a mutation on α-subunit type 1 of the voltage-gated sodium ion channel $Na_V1.1$ and a polynucleotide for detecting a mutation on α-subunit type 1 of the voltage-gated calcium ion channel $Ca_V2.1$ are used to detect, from the genomic DNA, the presence of a mutation for both the sodium ion channel α1 subunit gene and the calcium ion channel α1 subunit gene.

The "polynucleotide for detecting a mutation on α-subunit type 1 of voltage-gated sodium ion channel $Na_V1.1$" is indicative of a polynucleotide having a nucleotide sequence complementary to a set region in a sodium ion channel α1 subunit gene (e.g. a region including an exon, or boundary region between an exon and an intron). The "polynucleotide for detecting a mutation on α-subunit type 1 of voltage-gated calcium ion channel $Ca_V2.1$" is indicative of a polynucleotide having a nucleotide sequence complementary to a set region in the calcium ion channel α1 subunit gene (e.g. a region including an exon, or a boundary region between an exon and an intron).

The "polynucleotide for detecting a mutation on α-subunit type 1 of voltage-gated sodium ion channel $Na_V1.1$" is, more specifically, a polynucleotide having a nucleotide sequence represented by any one of SEQ ID NOs.: 5, 6, and 9 to 62, for example. Moreover, the "polynucleotide for detecting a mutation on α-subunit type 1 of voltage-gated calcium ion channel $Ca_V2.1$" is, more specifically, a polynucleotide having a nucleotide sequence represented by any one of SEQ ID NOs.: 7, 8, and 63 to 143.

Two kinds of the polynucleotides may be used in combination as a primer pair, or one kind may be used as a probe. When the two kinds are used in combination as a primer pair, the polynucleotides may be used in combinations as exemplified in Examples described later.

When two kinds of the polynucleotides are used in combination as a primer pair, it is possible, for example, to amplify a set region in the gene by PCR with use of a corresponding primer pair, and thereafter, directly sequence the obtained PCR product, to detect the presence of the mutation in the gene.

Moreover, two kinds of fluorescence-labeled polynucleotides may be used as a primer pair, to amplify a set region of the gene by PCR, perform gel electrophoresis or capillary electrophoresis with the obtained PCR product, and study a strength of the signals, so as to detect the presence of a mutation in the gene.

Moreover, when one kind of the polynucleotides is to be solely used as a probe, the presence of the mutation on the gene can be detected by, for example, digesting the genomic DNA with an appropriate restriction enzyme and detecting a difference in size of the digested genomic DNA fragment by Southern blotting or the like.

As such, by detecting the presence of mutations for both the sodium ion channel α1 subunit gene and calcium ion channel α1 subunit gene with use of the genomic DNA included in the sample taken from the subject, it is possible to obtain data for assessing a potential for development of Dravet syndrome in the subject. More specifically, when a mutation is found on both the sodium ion channel α1 subunit gene and the calcium ion channel α1 subunit gene in the obtained data, it can be assessed that the subject has a high potential for development of Dravet syndrome.

The primer pair and probe used in the method of detecting the mutation may be prepared by a DNA synthesizer or the like, as in law of the art.

(B) Embodiment Using mRNA (cDNA)

In the embodiment of detecting a mutation with use of mRNA included in a sample taken from the subject, first, mRNA is extracted from a sample taken from the subject, with use of a conventionally known method.

The "sample taken from the subject" is not limited in particular, and any sample can be used as long as mRNA can be extracted therefrom and a gene that can be subjected to the detection of a mutation is expressed or is possibly expressed. The "sample taken from the subject" is preferably, for example, a peripheral blood leukemic cell, dermal fibroblast, oral mucosa cell, neuron, or muscle cell, each of a patient.

Subsequently, cDNA is prepared from the extracted mRNA by reverse transcription reaction. Furthermore, if necessary, the obtained cDNA may be amplified by a gene amplification method generally performed, for example PCR (Polymerase Chain Reaction), NASBA (Nucleic acid sequence based amplification), TMA (Transcription-mediated amplification), SDA (Strand Displacement Amplification), LAMP (Loop-Mediated Isothermal Amplification), and ICAN (Isothermal and Chimeric primer-initiated Amplification of Nucleic acids).

The method of detecting the presence of the mutation for both the sodium ion channel α1 subunit gene and calcium ion channel α1 subunit gene with use of a sample including cDNA prepared as such is not limited in particular; whether or not a gene mutation is present in a subject that is subjected to mutation detection may be detected with use of a similar method as with a case in which a gene mutation is detected with use of a genomic DNA, as described in the foregoing "(A) Embodiment using genomic DNA".

By detecting the presence of the mutation for both the sodium ion channel α1 subunit gene and calcium ion channel α1 subunit gene with use of mRNA included in the sample that is taken from the subject, it is possible to obtain data for assessing a potential for development of Dravet syndrome in the subject. More specifically, when a mutation is found in both the sodium ion channel α1 subunit gene and the calcium ion channel α1 subunit gene in the obtained data, it can be assessed that the subject has a high potential for the development of Dravet syndrome.

(C) Embodiment Using Protein

In the embodiment of detecting a mutation using protein included in the sample taken from a subject, first, protein is extracted from the sample taken from the subject with use of a conventionally known method.

The sample taken from the subject is not limited in particular, and may be any sample from which protein is extractable and in which both of sodium ion channel α1 subunit protein and calcium ion channel α1 subunit protein are expressed or is possibly expressed.

The method of detecting the presence of mutation for both the sodium ion channel α1 subunit protein and the calcium ion channel α1 subunit protein with use of the sample including the protein prepared as described above is not limited in particular, and for example an antibody which specifically recognizes just a protein having a set mutation may be prepared, to detect the mutation by ELISA or Western blotting using that antibody. In the present specification, the term "protein" may be used replaceable with "polypeptide" or "peptide".

Moreover, mutation may be detected by isolating a protein to be subjected to the mutation detection from the sample including the foregoing protein, and digesting the isolated protein with an enzyme or the like directly or if necessary, with use of a protein sequencer or a mass spectrometer. Alternatively, the mutation may be detected on the basis of an isoelectric point of the isolated protein.

As such, by detecting the presence of a mutation for both of the sodium ion channel α1 subunit protein and the calcium ion channel α1 subunit protein with use of a protein included in the sample taken from the subject, it is possible to obtain data for assessing potential for development of Dravet syndrome in the subject. More specifically, when a mutation is found on both the sodium ion channel α1 subunit protein and the calcium ion channel α1 subunit protein in the obtained data, it is possible to assess that the subject has a high potential for development of Dravet syndrome.

(1-2. Step of Detecting Change in Activity)

In the present specification, the "step of detecting change in activity" is indicative of a step of detecting whether activity of the voltage-gated sodium ion channel $Na_V1.1$ has changed and a step of detecting whether activity of the voltage-gated calcium ion channel $Ca_V2.1$ has changed.

As described in Examples later described, it is considered that the change in activity in both the voltage-gated sodium ion channel $Na_V1.1$ and the voltage-gated calcium ion channel $Ca_V2.1$, caused by the mutations on the sodium ion channel α1 subunit and on the calcium ion channel α1 subunit, is related to the development of Dravet syndrome. Hence, although the mutation on the sodium ion channel α1 subunit is not particularly limited in its position, it is preferable that the mutation is on a position that causes a change in the activity of the voltage-gated sodium ion channel $Na_V1.1$. Moreover, although the mutation on the calcium ion channel α1 subunit is not particularly limited in its position, it is preferable that the mutation is on a position that causes a change in the activity of the voltage-gated calcium ion channel $Ca_V2.1$.

Here, the activity of the voltage-gated sodium ion channel $Na_V1.1$ is, more specifically, an activity to allow transmission of sodium ion (Na+) into the cell by depending on membrane potential. The change in activity of the voltage-gated sodium ion channel $Na_V1.1$ is not limited in particular, and may be an increase of activity or may be a decrease in activity. Namely, the change is sufficiently one that shows an abnormality in the activity of the voltage-gated sodium ion channel $Na_V1.1$.

In the present specification, "the activity of the voltage-gated sodium ion channel $Na_V1.1$ is changed" indicates that an activity of a mutant voltage-gated sodium ion channel $Na_V1.1$ including the sodium ion channel α1 subunit on which the mutation is present is of a value having a statistically significant difference based on a significant test as compared to an activity of a wild-type voltage-gated sodium ion channel $Na_V1.1$, and preferably indicates that p is equal to or smaller than 0.05 by Student's t-test.

Moreover, the activity of the voltage-gated calcium ion channel $Ca_V2.1$ is, more specifically, an activity that causes transmission of calcium ion ($Ca^{2+}$) into the cell to be membrane voltage-gated. The change in function of the voltage-gated calcium ion channel $Ca_V2.1$ is not particularly limited, and may be the increase of activity or the decrease in activity. Namely, the change is sufficiently one that shows abnormality of the activity of the voltage-gated calcium ion channel $Ca_V2.1$.

In the present specification, "the activity of the voltage-gated calcium ion channel $Ca_V2.1$ is changed" indicates that the activity of a mutant voltage-gated calcium ion channel $Ca_V2.1$ including the calcium ion channel α1 subunit on which a mutation is present is of a value having a statistically significant difference based on a significant test as compared to an activity of a wild-type voltage-gated calcium ion channel $Ca_V2.1$, and preferably indicates that p is equal to or smaller than 0.05 by Student's t-test.

An example of a method of detecting that the activity of the voltage-gated sodium ion channel $Na_V1.1$ is changed by the mutation is, for example, (i) coexpressing, in a culture cell with use of a expression vector or the like, a sodium ion channel α1 subunit gene on which a mutation is present with a wild-type gene ($\beta_1$ subunit gene and $\beta_2$ subunit gene) that encodes a subunit ($\beta_1$ subunit and $\beta_2$ subunit) other than the α1 subunit, which wild-type gene makes up the voltage-gated sodium ion channel $Na_V1.1$, (ii) measuring an activity of the voltage-gated sodium ion channel $Na_V1.1$ on which a mutation is present with use of the obtained cultured cell, and (iii) comparing the activity with an activity of the wild-type voltage-gated sodium ion channel $Na_V1.1$, to confirm whether the activity of the voltage-gated sodium ion channel $Na_V1.1$ is changed. The method of measuring the activity of the voltage-gated sodium ion channel $Na_V1.1$ is not particularly limited, however it is possible to use the conventionally known patch clamping, imaging with use of a fluorescence probe, or like method.

An example of a method of detecting that the activity of the voltage-gated calcium ion channel $Ca_V2.1$ is changed by mutation is by (i) coexpressing, in a culture cell with use of an expression vector or the like, a calcium ion channel α1 subunit gene on which a mutation is present with a wild-type gene (β subunit gene, γ subunit gene, and α2δ subunit gene) that encodes a subunit (β subunit, γ subunit, and α2δ subunit) other than the α1 subunit, which wild-type gene makes up the voltage-gated calcium ion channel $Ca_V2.1$, (ii) measuring, with the obtained cultured cell, an activity of the voltage-gated calcium ion channel $Ca_V2.1$ on which the mutation is present, and (iii) comparing the activity with an activity of the wild-type voltage-gated calcium ion channel $Ca_V2.1$, to confirm whether the activity of the voltage-gated calcium ion channel $Ca_V2.1$ is changed. The method of measuring the activity of the voltage-gated calcium ion channel $Ca_V2.1$ is not limited in particular, however it is possible to use the conventionally known patch clamping, imaging using an optical probe, a calcium indicator, or a caged compound, for example.

The assessment method according to the present invention, since it includes the foregoing configuration, it is possible to obtain data for assessing a potential for development of Dravet syndrome in the subject. Hence, with the assessment method according to the present invention, it is possible to find out, with high accuracy and at an early stage, Dravet syndrome having the unfavorable prognosis, which thus allows for preparing a treatment management system by an epilepsy specialist from an earlier stage for a Dravet syndrome patient. As a result, it is possible to improve treatment intervention of the patient, reduce the mental burden on their families, and reduce the economical burden. Furthermore, it is possible to provide appropriate treatment for the patient of Dravet syndrome; this hence reduces medical fees.

2. Kit According to the Present Invention

The present invention also encompasses a kit for assessing the potential for development of Dravet syndrome, with use of the assessment method according to the present invention (hereinafter, also referred simply as "kit according to the present invention").

The kit according to the present invention is not limited in its specific configuration in particular as long as it includes at least a reagent for detecting the presence of mutation on α-subunit type 1 of the voltage-gated sodium ion channel $Na_V1.1$ and a reagent for detecting the presence of mutation on α-subunit type 1 of the voltage-gated calcium ion channel $Ca_V2.1$.

As described in "1. Assessment method according to the present invention", ways considered to detect the presence of mutation for both of α-subunit type 1 of the voltage-gated sodium ion channel $Na_V1.1$ and α-subunit type 1 of the voltage-gated calcium ion channel $Ca_V2.1$ are (A) detecting a gene mutation with use of a genomic DNA included in a sample taken from a subject, or (B) detecting a gene mutation with use of mRNA (cDNA) included in a sample taken from the subject.

Hence, in order to detect a mutation using a genomic DNA included in the sample taken from the subject or mRNA (cDNA) included in the sample taken from the subject, the kit according to the present invention includes a polynucleotide being used for determining a mutation on α-subunit type 1 of voltage-gated sodium ion channel $Na_V1.1$; and a polynucleotide being used for determining a mutation on α-subunit type 1 of voltage-gated calcium ion channel $Ca_V2.1$. Such polynucleotides can be used as, for example, a primer pair or a probe. These polynucleotides may be included solely or may be included as a combination of a plurality thereof.

The kit according to the present invention encompasses (A) a kit for detecting a mutation with use of a genomic DNA included in a sample taken from a subject and (B) a kit for detecting a mutation with use of a mRNA (cDNA) included in a sample taken from a subject. The following specifically describes the reagents included in the embodiments of the kits in (A) or (B).

(A) Kit for Detecting Mutation with Use of Genomic DNA Included in Sample Taken from Subject For example, a configuration of the sodium ion channel α1 subunit and the calcium ion channel α1 subunit may include a primer pair designed so as to allow amplification of the genomic DNA of each of the genes or a part of its region, or may include a probe designed so that one of genomic DNA of its mutant type or wild-type can be specifically detected. These polynucleotides are as described in the foregoing (A) Embodiment using genomic DNA in "1. Assessment method according to the present invention", so hence its description has been omitted here.

Furthermore, such a kit may be configured to include, in addition to the primer pair or probe, a combination of one or more reagent necessary for detecting the presence of the mutation on the gene, such as a reagent used in PCR, Southern blotting, and nucleic acid sequencing.

The reagent is selected and employed as appropriate in accordance with the detection method of the present invention, and examples thereof are dATP, dCTP, dTTP, dGTP, DNA polymerase and the like. Furthermore, the kit according to the present invention may include a suitable buffer solution and a washing solution that can be used in the PCR, Southern blotting, and nucleic acid sequencing.

(B) Kit Detecting Mutation with Use of mRNA (cDNA) Included in Sample Taken from Subject For example, a configuration of the sodium ion channel α1 subunit and the calcium ion channel α1 subunit may include a primer pair designed so as to allow amplification of the cDNA of each of the genes or a part of its region, or include a probe designed so that one of mRNA of its mutant type or wild-type can be specifically detected. These polynucleotides are as described in (B) Embodiment using mRNA (cDNA) in "1. Assessment method according to the present invention", so hence its description has been omitted here.

Furthermore, such a kit may be configured to include, in addition to the primer pair or probe, a combination of one or more reagent necessary for detecting the presence of a mutation on the gene, such as a reagent used in RT-PCR, Northern blotting, nucleic acid sequencing or the like.

The reagent is selected and employed as appropriate in accordance with the detection method of the present invention, and examples thereof are dATP, dCTP, dTTP, dGTP, DNA polymerase and the like. Furthermore, the kit according to the present invention may include a suitable buffer solution and a washing solution that can be used in RT-PCR, Northern blotting, and nucleic acid sequencing.

The kit according to the present invention may include the exemplified configuration in any combination. Furthermore, the kit may include other reagents other than the reagents exemplified above.

As described in the item "1. Assessment method according to the present invention", in order to detect the presence of mutation for both the sodium ion channel α1 subunit and the calcium ion channel α1 subunit, it is further considerable to (C) detect the mutation with use of a protein included in the sample taken from a subject.

Therefore, the kit according to the present invention may include, for example, an antibody that specifically bonds to just the wild-type or mutant protein among the proteins of the sodium ion channel α1 subunit and the calcium ion channel α1 subunit. Furthermore, the configuration may be one which, in addition to the antibody, includes one or more reagent in combination, which reagent is used for ELISA or Western blotting.

Furthermore, the kit according to the present invention may include a reagent used for measuring activity of the voltage-gated sodium ion channel $Na_V1.1$, a reagent used for measuring activity of the voltage-gated calcium ion channel $Ca_V2.1$, or the like.

With use of the kit according to the present invention as described above, it is possible to easily obtain data for assessing the potential for development of Dravet syndrome in the subject. A subject to which the kit may be applied is not particularly limited, however is preferably applied to infants or children.

3. Model Animal of Dravet Syndrome According to the Present Invention and its Production Method The present invention encompasses a model animal of Dravet syndrome, and its production method.

(3-1. Model Animal of Dravet Syndrome According to the Present Invention)

The model animal of Dravet syndrome according to the present invention has a mutation on both the sodium ion channel α1 subunit and the calcium ion channel α1 subunit. The mutation on the sodium ion channel α1 subunit and the mutation on the calcium ion channel α1 subunit are as described in the item "1. Assessment method according to the present invention" described above, so therefore specific descriptions thereof are omitted here.

It is preferable in the model animal of the Dravet syndrome that both the activity of the voltage-gated sodium ion channel $Na_V1.1$ and the activity of the voltage-gated calcium ion channel $Ca_V2.1$ are changed as compared to a wild-type animal. This change in activity is not particularly limited, and may be an increase of activity or may be a decrease in activity. The method of confirming whether or not an activity of the voltage-gated sodium ion channel $Na_V1.1$ of the model animal of Dravet syndrome according to the present invention is changed from that of a wild-type, and the method of confirming whether or not an activity of the voltage-gated calcium ion channel $Ca_V2.1$ of the model animal of Dravet syndrome according to the present invention is changed from that of a wild-type, are both not particularly limited. For example, with an individual of a model animal of Dravet syndrome according to the present invention or cells collected from the model animal of Dravet syndrome according to the present invention, confirmation may be made by measuring the activity by use of the conventionally known patch clamping, slice patching, imaging with use of fluorescence probe and like method.

The model animal of Dravet syndrome according to the present invention has the mutation on both the sodium ion channel α1 subunit and the calcium ion channel α1 subunit, so therefore develops Dravet syndrome. Such a model animal of Dravet syndrome can be used advantageously for clarification of the development mechanism of the intractable Dravet syndrome, and for development of medicament for Dravet syndrome.

In the present specification, "model animal" denotes an experiment animal used for developing a prevention method or treatment against human diseases, and more specifically is a non-human mammal such as a mouse, rat, rabbit, monkey, goat, pig, sheep, cow, or dog, and other vertebrates.

(3-2. Production Method of Model Animal of Dravet Syndrome According to the Present Invention)

A method of producing a model animal of Dravet syndrome, according to the present invention, includes: introducing a mutation on sodium ion channel α1 subunit and introducing a mutation on calcium ion channel α1 subunit.

More specifically, a mutation can be introduced on each of the genes by manipulating the gene of the model animal. Here, the "manipulating the gene of the model animal" intends to mean manipulation of a gene of a model animal by use of a conventionally known gene manipulation technique. More specifically, this encompasses all of destruction of a gene of the model animal, an introduction of a mutation to that gene, a substitution of that gene with a mutant gene, and furthermore, introduction of a foreign gene into the model animal, and crossing of model animals.

The production method according to the present invention of the model animal of Dravet syndrome may include steps other than those described above. Specific steps, materials, conditions, used devices, used equipment and the like are not limited in particular.

With the production method according to the present invention of a model animal of Dravet syndrome, it is possible to produce a model animal developed in Dravet syndrome by manipulating genes of a model animal so that a mutation is introduced into the genes of the sodium ion channel α1 subunit and the calcium ion channel α1 subunit.

4. Cells According to the Present Invention and its Production Method

The present invention also encompasses cells having a mutation on both the sodium ion channel α1 subunit and the calcium ion channel α1 subunit, and its production method.

(4-1. Cell According to the Present Invention)

The cell according to the present invention is a cell having a mutation on both the sodium ion channel α1 subunit and the calcium ion channel α1 subunit. The mutation on the sodium ion channel α1 subunit and the mutation on the calcium ion channel α1 subunit are as described in the item "1. Assessment method according to the present invention" described above, so therefore specific description thereof have been omitted here.

The cell according to the present invention intends to mean experimental culture cells having a mutation on both the sodium ion channel α1 subunit and the calcium ion channel α1 subunit. More specifically, the cell is an experimental culture cell derived from a mammal such as a human, mouse, rat, hamster, rabbit, monkey and the like, and other vertebrates.

It is preferable that with such a cell, both of activity of the voltage-gated sodium ion channel $Na_V1.1$ and activity of the voltage-gated calcium ion channel $Ca_V2.1$ are changed. This change in activity is not particularly limited, and may be an increase of activity or a decrease in activity. The method of confirming whether or not the activity of the voltage-gated sodium ion channel $Na_V1.1$ of the cell according to the present invention is changed from that of a wild-type, and a method of confirming whether or not the activity of both of the voltage-gated calcium ion channel $Ca_V2.1$ of the cell according to the present invention is changed from that of the wild-type are as described in "1. Assessment method according to the present invention" described above, so hence specific description thereof have been omitted here.

Such a cell can be used for clarification of a development mechanism of the intractable Dravet syndrome, and for the development in medicament for Dravet syndrome. For example, it is possible to suitably use this for screening of a drug for treating Dravet syndrome. Namely, this cell can also be said as a screening cell for a drug for treating Dravet syndrome. Accordingly, the present invention also encompasses a screening cell of a drug for treating Dravet syndrome (hereinafter, simply called "screening cell"), and its production method.

(4-2. Production Method of Cell According to Present Invention)

A method of producing a cell according to the present invention is a method of producing a cell that has the foregoing properties, and includes: introducing a mutation on a sodium ion channel α1 subunit; and introducing a mutation on a calcium ion channel α1 subunit. More specifically, the following three embodiments can be raised. The following three embodiments are described specifically below, however the present invention is not limited to these.

(1) Method of Using Expression Vector Etc.

This method produces a cell that expresses a mutant voltage-gated sodium ion channel $Na_V1.1$ and mutant voltage-gated calcium ion channel $Ca_V2.1$, with use of an expression vector or the like. More specifically described, in order to make a cell express the mutant voltage-gated sodium ion channel $Na_V1.1$, for example, a sodium ion channel α1 subunit gene having a mutation that causes a change in an amino acid is coexpressed, in a culture cell that serves as a host, with a wild-type gene ($\beta_1$ subunit gene and $\beta_2$ subunit gene) making up the voltage-gated sodium ion channel $Na_V1.1$, which wild-type gene encodes a subunit other than the α1 subunit ($\beta_1$ subunit and $\beta_2$ subunit), with use of an expression vector or the like. This enables the cell to express the mutant voltage-gated sodium ion channel $Na_V1.1$ that includes the mutant sodium ion channel α1 subunit.

Similarly, in order to make the cell express the mutant voltage-gated calcium ion channel $Ca_V2.1$, for example, a calcium ion channel α1 subunit gene having a mutation that causes a change in an amino acid is coexpressed, in a culture cell that serves as a host, with a wild-type gene (β subunit gene, γ subunit gene, and α2δ subunit gene) making up a voltage-gated calcium ion channel $Ca_V2.1$, which wild-type gene encodes a subunit other than the α1 subunit (β subunit, γ subunit, and α2δ subunit), with the expression vector or the like. This hence enables the cell to express a mutant voltage-gated calcium ion channel $Ca_V2.1$ that includes the mutant calcium ion channel α1 subunit.

At this time, it is preferable that the culture cell serving as a host is a cell from which no voltage-gated sodium ion channel $Na_V1.1$ and the voltage-gated calcium ion channel $Ca_V2.1$ is expressed. With use of such a cell, no effect is caused by the residing voltage-gated sodium ion channel $Na_V1.1$ and residing voltage-gated calcium ion channel $Ca_V2.1$.

(2) Method of Using Artificial Mutation Introduction

This method introduces mutation for both of the sodium ion channel α1 subunit and the calcium ion channel α1 in a culture cell expressing both the voltage-gated sodium ion channel $Na_V1.1$ and the voltage-gated calcium ion channel $Ca_V2.1$.

The method of introducing the mutation on the culture cell is not particularly limited, and a conventionally known gene manipulation technique is used in combination as appropriate.

(3) Method of Using Model Animal of Dravet Syndrome According to the Present Invention This method extracts a tissue from the model animal of Dravet syndrome according to the present invention as described above, and prepares a culture cell from that tissue. The model animal of Dravet syndrome according to the present invention is as described in "3. Model animal of Dravet syndrome according to the present invention and its production method", and so therefore specific description thereof has been omitted here. Of course, the "tissue" that is extracted is intended to mean a tissue in which both the sodium ion channel α1 subunit on which a mutation is introduced and the calcium ion channel α1 subunit on which a mutation is introduced are expressed.

This hence allows for easy production of a cell that has a mutation on both the sodium ion channel α1 subunit and the calcium ion channel α1 subunit. The kinds of tissues extracted from the model animal of Dravet syndrome is not limited in particular, and may be selected as appropriate depending on its purpose.

The method according to the present invention of producing a cell may include steps other than the steps described above. Specific steps, materials, conditions, used devices, used equipment and the like are not limited in particular.

5. Screening Method of Drug for Treating Dravet Syndrome

The model animal of Dravet syndrome according to the present invention and the cell according to the present invention can be used in development of a new treatment method and drug for treating Dravet syndrome. Hence, the present invention encompasses a screening method of a drug for treating Dravet syndrome, which screens a drug for treating Dravet syndrome (hereinafter, also called "screening method according to the present invention").

In the specification, an embodiment using a model animal of Dravet syndrome according to the present invention and an embodiment using a screening cell have been explained as embodiments of the screening method according to the present application. However, the present invention is not limited to these embodiments.

Namely, for example, the embodiment may use another model animal of Dravet syndrome instead of the model animal of Dravet syndrome according to the present invention.

(1) Case of Using Model Animal of Dravet Syndrome According to the Present Invention The method is sufficient as long as it includes administering a candidate agent to the model animal of Dravet syndrome according to the present invention, and assessing whether or not Dravet syndrome shows improvement or is cured in the model animal of Dravet syndrome to which the candidate agent is administered.

Namely, according to the screening method of the drug for treating Dravet syndrome according to the present invention, a candidate agent is administered to the model animal of Dravet syndrome, to assess whether or not that candidate agent can serve as a drug for treating Dravet syndrome in the model animal of Dravet syndrome to which the candidate agent is administered, by having the improvement or curing of Dravet syndrome serve as an indicator.

The method of assessing whether or not Dravet syndrome is improved or cured in the model animal of Dravet syndrome to which the candidate agent is administered is not limited in particular, and is sufficiently assessed by use of characteristic symptoms of Dravet syndrome as indicators. For example, it is possible to determine whether Dravet syndrome is improved or cured by comparing a control animal not having a mutation that causes an amino acid change on the sodium ion channel α1 subunit gene and the calcium ion channel α1 subunit gene (i.e. an animal not having a mutation on both of α-subunit type 1 of voltage-gated sodium ion channel $Na_V1.1$ and α-subunit type 1 of voltage-gated calcium ion channel $Ca_V2.1$) with the model animal of Dravet syndrome according to the present invention, in terms of "body temperature at convulsion onset (convulsion threshold)", "severity score", "duration of convulsion", and the like each shown in the Examples later described.

The candidate agent is not limited in particular, however it is preferable that it is a compound expectable of giving effect on the expression of voltage-gated sodium ion channel $Na_V1.1$ and/or expression of voltage-gated calcium ion channel $Ca_V2.1$, or a compound expectable of giving effect on the activity of the voltage-gated sodium ion channel $Na_V1.1$ and/or the activity of voltage-gated calcium ion channel $Ca_V2.1$ (e.g. an inhibitor or candidate substance of an inhibitor, or an agonist or a candidate substance of an agonist, each of which has effect on both the voltage-gated sodium ion channel $Na_V1.1$ and the voltage-gated calcium ion channel $Ca_V2.1$).

Moreover, the candidate agent may be an expression plasmid vector or a virus vector that includes a polynucleotide made of a sodium ion channel α1 subunit gene or a part of its nucleotide sequence. Moreover, the candidate agent may be an expression plasmid vector or a virus vector that includes a polynucleotide made of the calcium ion channel α1 subunit gene or a part of its nucleotide sequence.

The method of administering such a candidate agent to the Dravet syndrome model animal according to the present invention is not limited in particular, and a suitable method is sufficiently selected from conventionally known methods in accordance with physical properties of that candidate agent.

(2) Case of Using Screening Cell According to the Present Invention

The method at least includes administering a candidate agent to a screening cell according to the present invention, and assessing whether or not activity of voltage-gated sodium ion channel $Na_V1.1$ and/or activity of voltage-gated calcium ion channel $Ca_V2.1$ in the screening cell of a drug for treating Dravet syndrome to which the candidate agent was administered, is changed.

Namely, with the screening method according to the present embodiment, it is possible to assess whether a candidate agent can serve as a drug for treating Dravet syndrome, by administering the candidate agent to the screening cell according to the present invention, based on an indicator of whether the activity of the voltage-gated sodium ion channel $Na_V1.1$ and/or the activity of the voltage-gated calcium ion channel $Ca_V2.1$ in the screening cell to which the candidate agent is administered, is changed.

Moreover, the method of assessing, in the screening cell to which the candidate agent is administered, whether or not the activity of the voltage-gated sodium ion channel $Na_V1.1$ is changed and whether or not the activity of the voltage-gated calcium ion channel $Ca_V2.1$ is changed are not limited in particular, and the assessments are sufficiently carried out by use of an electrophysiologic measurement device, fluorescence observation device, or the like.

The candidate agent is not limited in particular, and similar substances as those described in the foregoing "(1) Case of using model animal of Dravet syndrome according to the present invention" may be used.

The method of administering such a candidate agent to a cell according to the present invention is not limited in particular, and a suitable method based on the physical properties and the like of that candidate agent is selected and used from conventionally known methods.

It is preferable in the assessment method according to the present invention that the mutation on α-subunit type 1 of the voltage-gated sodium ion channel $Na_V1.1$ is at least one of a mutation shown in Table 1, and the mutation on α-subunit type 1 of the voltage-gated calcium ion channel $Ca_V2.1$ is at least one of a mutation shown in Table 2.

It is preferable in the assessment method according to the present invention to further include:

detecting a change in activity of the voltage-gated sodium ion channel $Na_V$1.1; and detecting a change in activity of the voltage-gated calcium ion channel $Ca_V$2.1.

The present invention is not limited to the description of the embodiments above, but may be altered by a skilled person within the scope of the claims. An embodiment based on a proper combination of technical means disclosed in different embodiments is encompassed in the technical scope of the present invention.

EXAMPLES

The following describes more specifically of the present invention with use of Examples, however the present invention is not limited to the Examples.

Example 1

Identification of Risk Factors for Predicting Development of Dravet Syndrome DNA were extracted from peripheral blood of 47 Dravet syndrome patients who visited Okayama University Hospital and/or its related hospitals, and mutations on various genes were analyzed. This study was performed upon receiving approval from Okayama University, Institutional Review Board of Human Genome and Gene Analysis Research.

More specifically, a genomic DNA was extracted from peripheral blood of a patient with use of a DNA extraction kit (WB kit; Nippon gene, Tokyo, Japan), and all exons were amplified by PCR. In PCR, a reaction solution of 25 μl was used, which includes 50 ng of human genomic DNA, 20 μmol of various primers, 0.8 mM of dNTPs, 1 reaction buffer, 1.5 mM of $MgCl_2$, and 0.7 units of AmpliTaq Gold DNA polymerase (Applied Biosystems, Foster City, Calif., USA). As to the nucleotide sequence (SEQ ID NOs.: 9-62) of the primer pair used, see "Sequence of primers" described later.

An obtained PCR product was purified with use of PCR products pre-sequencing kit (Amersham Biosciences, Little Chalfont, Buckinghamshire, England). Subsequently, with use of Big Dye Terminator FS ready-reaction kit (Applied Biosystems), a sequence reaction was performed, and with use of a fluorescence sequencer (ABI PRISM3100 sequencer; Applied Biosystems), a nucleotide sequence of the obtained PCR product was determined.

First, mutation analysis was performed of SCN1A gene that encodes α-subunit type 1 (also called "α1 subunit") making up the voltage-gated sodium ion channel $Na_V$1.1, for the 47 Dravet syndrome patients. As a result, a mutation in the SCN1A gene was found in 38 patients out of the 47 Dravet syndrome patients. For the 9 patients in which no mutation was detected, a further analysis was performed on the number of gene copies of the SCN1A gene, with use of Multiplex Ligation-dependent Probe Amplification (MLPA; MRC-Holland; SALSA MLPA kit P137). As a result, a deletion of exon 10 was detected in 1 patient. The number of patients in which no mutation of the SCN1A gene was found was 8. The mutation detected in the SCN1A gene is as shown in Table 1.

Next, with use of the DNA of the 47 patients, gene analysis was performed for GABRG2 gene, CACNA1A gene, CACNB4 gene, SCN1B gene, and SCN3A gene. These genes encode proteins as follows:

GABRG2: $GABA_A$ receptor γ2 subunit gene

CACNA1A: α1 subunit of voltage-gated calcium ion channel $Ca_V$2.1

CACNB4: β4 subunit of voltage-gated calcium ion channel

SCN1B: β1 subunit of voltage-gated sodium ion channel

SCN3A: α3 subunit of voltage-gated sodium ion channel $Na_V$1.3

The nucleotide sequence (SEQ ID NOs.: 63-143) of the primer pair used for the gene analysis of the CACNA1A gene is shown in "Sequence of primers" described later.

Figure 12:
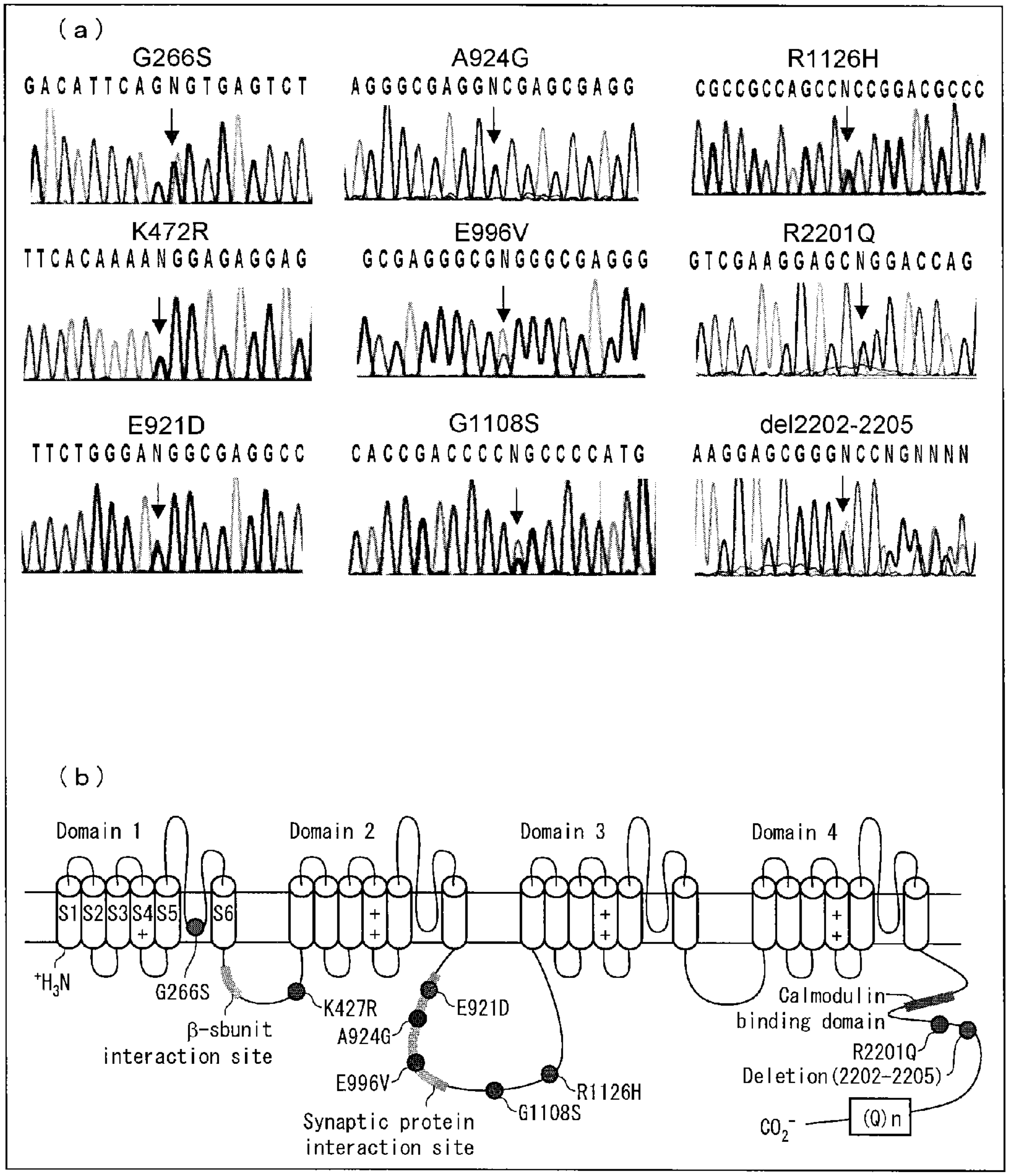
FIG. 12 is a view illustrating a result of detecting a mutation on voltage-gated calcium ion channel $Ca_V2.1$ α1 subunit. Illustrated in (a) is a result of a mutation analysis of the CACNA1A gene, and schematically illustrated in (b) is a part where a mutation was detected in the calcium ion channel α1 subunit.

As a result, various kinds of gene mutations were found in the CACNA1A gene that encodes α-subunit type 1 (also called "α1 subunit") making up the voltage-gated calcium ion channel $Ca_V$2.1 (see Table 2 and FIG. 12).

Table 3 shows the gene mutations of SCN1A and CACNA1A that were detected in the Dravet syndrome patients.

TABLE 3

| SCN1A and CACNA1A gene mutations detected in Dravet syndrome patients | | | | | |
|---|---|---|---|---|---|
| P. No. | SCN1A gene | CACNA1A gene | | | |
| 1 | G177R | G266S | | | |
| 2 | W738fsX746 | K472R | | | |
| 3 | V1390M | A924G | | | |
| 4 | V212A | E921D | E996V | | |
| 5 | R377L | E921D | E996V | | |
| 6 | Deletion of exon 10 (Exon10*) | E921D | E996V | | |
| 7 | P707fsX714 | E921D | E996V | | |
| 8 | R865X | E921D | E996V | | |
| 9 | F902C | E921D | E996V | | |
| 10 | T1082fsX1086 | E921D | E996V | | |
| 11 | Q1277X | E921D | E996V | | |
| 12 | Q1450R | E921D | E996V | | |
| 13 | A1685D | E921D | E996V | | |
| 14 | T1909I | E921D | E996V | R1126H | R2201Q |
| 15 | G163E | R1126H | R2201Q | | |
| 16 | K547fsX570 | R1126H | R2201Q | | |
| 17 | S1574X | R1126H | R2201Q | | |
| 18 | R712X | G1108S | | | |
| 19 | R1648C | G1108S | | | |
| 20 | negative | G1108S | | | |
| 21 | negative | Del2202-2205 | | | |
| 22 | R501fsX543 | negative | | | |
| 23 | S607fsX622 | negative | | | |
| 24 | E788K | negative | | | |
| 25 | R931C | negative | | | |
| 26 | R931C | negative | | | |
| 27 | L990F | negative | | | |
| 28 | A1002fsX1009 | negative | | | |
| 29 | K1027X | negative | | | |
| 30 | K1057fsX1073 | negative | | | |
| 31 | L1265P | negative | | | |
| 32 | W1271X | negative | | | |
| 33 | 1289delF | negative | | | |
| 34 | Intron 21 splicing error | negative | | | |
| 35 | A1429fsX1443 | negative | | | |
| 36 | W1434R | negative | | | |
| 37 | T1539R | negative | | | |
| 38 | S1574X | negative | | | |
| 39 | G1674R | negative | | | |
| 40 | A1662V | negative | | | |
| 41 | G1880fsX1881 | negative | | | |
| 42 | negative | negative | | | |
| 43 | negative | negative | | | |
| 44 | negative | negative | | | |
| 45 | negative | negative | | | |
| 46 | negative | negative | | | |
| 47 | negative | negative | | | |

P. No. Patient Number

Exon10* exon deletion detected by MPLA

The following mutations are mutations of the CACNA1A gene detected this time. These mutations were mutations that cause an amino acid substitution, mutations that cause no amino acid substitution, and intron mutations.

(1) Missense Mutations

G266S 1 case
K472R 1 case
E921D 11 cases
A924G 1 case
E996V 11 cases
G1108S 3 cases
R1126H 4 cases
R2201Q 4 cases (2) Deletion of Amino Acids 4 amino acid deletions (deletion 2202-2205) 1 case (3) Gene Mutation Causing No Amino Acid Change in Exon E292E (rs16006), E394E (rs2248069), 15251 (rs16010), T698T (rs16016), R1023R (rs16025), F1291F (rs16030), T1458T (new SNP or mutation), S1472S (new SNP or mutation), V1890V (rs17846921), H2225H (rs16051)

(4) Gene Mutation in Intron exon 1 upstream (rs16000), intron 1 (rs16003), intron 3 (rs17846942), intron 8 (rs2306348), intron 11 (rs10407951), intron 17 (rs16018), intron 39 (rs3816027), intron 40 (rs17846925), intron 42 (new SNP or mutation).

The missense mutations and deletion mutations detected in coding regions of the CACNA1A gene shown in the foregoing (1), and (2) are shown in Table 4.

TABLE 4

Summary of mutations detected in coding region of CACNA1A gene
Coding Region

| | Exon No. | Amino acid | Mutation type | SNP Reg. No. |
|---|---|---|---|---|
| 1 | Exon 6 | G266S | Missense | — |
| 2 | Exon 11 | K472R | Missense | — |
| 3 | Exon 19 | E921D | Missense | rs16022 |
| 4 | Exon 19 | A924G | Missense | — |
| 5 | Exon 19 | E996V | Missense | rs16023 |
| 6 | Exon 20 | G1108S | Missense | rs16027 |
| 7 | Exon 20 | R1126H | Missense | — |
| 8 | Exon 47 | R2201Q | Missense | — |
| 9 | Exon 47 | Del 2202-2205 | Deletion | — |

SNP Reg. No.: Single Nucleotide Polymorphism Registration Number

These mutations were compared and studied with a gene polymorphism (Single Nucleotide Polymorphism; SNP) database of NCBI (National Center for Biotechnology Information). As a result, it was found that 3 kinds of the mutations out of the 9 kinds of mutations were registered in the SNP database as gene polymorphism (Single Nucleotide Polymorphism; SNP).

The gene mutation shown in (3) and (4) were either a gene polymorphism registered in the SNP database, or a new gene polymorphism or mutation. The registered number in the SNP database is shown in the brackets.

Out of the SNP already reported, the mutations which caused a change in the amino acid were considered probably that although no seizure occurs just by that individual case having the CACNA1A gene SNP, but when an abnormality of SCN1A gene is simultaneously present, this is somewhat involved in the worsening of the symptom.

A comparison of patients having a mutation in either of the SCN1A gene and the CACNA1A gene or both of the SCN1A gene and CACNA1A gene, out of the 47 Dravet syndrome patients, resulted as follows.

Patients having a mutation on both SCN1A and CACNA1A: 19 cases

Patients having a mutation on just SCN1A: 20 cases

Patients having a mutation on just CACNA1A: 2 cases

Patients having no mutation on either of SCN1A or CACNA1A: 6 cases.

No reports whatsoever have been made regarding abnormalities in the CACNA1A gene of the patients of Dravet syndrome, until now. The result of the present study shows that Dravet syndrome patients highly frequently has a mutation in SCN1A, i.e. a α1 subunit gene of the voltage-gated sodium ion channel $Na_V1.1$, and in CACNA1A, i.e. a α1 subunit gene of the voltage-gated calcium ion channel $Ca_V2.1$.

A literature disclosing that a mutation on a β4 subunit of the voltage-gated calcium ion channel $Ca_V2.1$ (hereinafter, simply referred to as "calcium ion channel β4 subunit") is involved with Dravet syndrome (Iori Ohmori et al., Neurobiology of Disease 32 (2008) 349-354) describes that out of 38 patients in which a mutation was detected in the sodium ion channel α1 subunit, 1 Dravet syndrome patient had a mutation on both the sodium ion channel α1 subunit and the calcium ion channel β4 subunit.

In comparison, out of 39 patients in which a mutation was detected on the sodium ion channel α1 subunit, the patients of Dravet syndrome having a mutation on both the sodium ion channel α1 subunit and the calcium ion channel α1 subunit were 19 patients (6 patients when excluding patients having registered SNP that cause a change in an amino acid in an exon). This result shows that by detecting the mutation for both the sodium ion channel α1 subunit and the calcium ion channel α1 subunit, the detection sensitivity of Dravet syndrome patients dramatically increase as compared to detecting the mutation for both the sodium ion channel α1 subunit and the calcium ion channel β4 subunit.

In the present specification, a nucleotide number in mRNA of the SCN1A gene and an amino acid number in a protein of SCN1A were made to be in line with GenBank accession No. AB093548; methionine, encoded by the initiation codon (ATG), was numbered as the first amino acid, and the initial A of the initiation codon was numbered as the first nucleotide.

Moreover, a genome sequence of the CACNA1A gene was in line with the GenBank accession number NC_000019. The number of the nucleotide in mRNA of CACNA1A gene and the number of the amino acid in CACNA1A protein was made to be in line with the GenBank accession number NM 023035; methionine, encoded by the initiation codon (ATG), was numbered as the primacy amino acid, and the initial A of the initiation codon was numbered as the primacy nucleotide.

Example 2

Study of Gene Mutation in Benign Febrile Seizure Patient

A study was performed of a SCN1A gene and CACNA1A gene abnormality in a benign febrile seizure patient. DNA was extracted from peripheral blood of 50 patients of benign generalized epilepsy with febrile seizure plus (GEFS+), who visited Okayama University Hospital and/or its related hospitals, and mutations on various genes were analyzed. The DNA extraction, PCR amplification of the gene, and sequencing reactions were performed by the methods described above.

First, mutation analysis of voltage-gated sodium ion channel SCN1A gene was performed, which resulted in detecting gene mutation that caused amino acid changes in 6 patients. Next, mutation analysis was performed for 9 kinds of mutations of missense mutations and deletion mutations that were detected in the coding region of the CACNA1A gene, which resulted in detecting a mutation in 16 patients. Each of the mutations are shown in Table 5.

TABLE 5

SCN1A and CACNA1A gene mutations detected in benign febrile seizure

| Patient No. | SCN1A | CACNA1A | |
|---|---|---|---|
| 1 | | | |
| 2 | M1856T | | |
| 3 | | del 2202-2205 | |
| 4 | | | |
| 5 | | del 2202-2205 | |
| 6 | R1575C | | |
| 7 | | E921D | E996V |
| 8 | | E921D | E996V |
| 9 | | E921D | E996V |
| 10 | | | |
| 11 | | | |
| 12 | I1616T | | |
| 13 | | | |
| 14 | | | |
| 15 | | | |
| 16 | | | |
| 17 | | | |
| 18 | | E921D | E996V |
| 19 | | | |
| 20 | | | |
| 21 | | | |
| 22 | | E921D | E996V |
| 23 | | E921D | E996V |
| 24 | | | |
| 25 | | | |
| 26 | | E921D | E996V |
| 27 | | | |
| 28 | | E921D | E996V |
| 29 | | A924G | |
| 30 | | E921D | E996V |
| 31 | | | |
| 32 | | | |
| 33 | | E921D | E996V |
| 34 | | G1108S | |
| 35 | | | |
| 36 | I1616T | | |
| 37 | I1616T | | |
| 38 | | | |
| 39 | Y1769H | | |
| 40 | | E921D | E996V |
| 41 | | | |
| 42 | | | |
| 43 | | | |
| 44 | | | |
| 45 | | | |
| 46 | | | |
| 47 | | | |
| 48 | | E921D | E996V |
| 49 | | | |
| 50 | | | |

Out of the 50 benign epilepsy patients, it was confirmed that no patient had mutations simultaneously on both SCN1A gene and CACNA1A gene.

The following shows a result of gene mutation analysis of a total of 97 patients, of 47 malignant Dravet syndrome cases and 50 benign febrile seizure patient cases.

(1) As a result of screening patients having a mutation on the SCN1A gene among the 97 patients, 39 Dravet syndrome patients (39 cases out of 47 cases) and 6 benign epilepsy patients (6 cases out of 50 cases) were detected.

(2) As a result of screening patients having a mutation on both the SCN1A gene and CACNA1A gene out of the 97 patients, 19 Dravet syndrome patients (19 cases out of 47) were detected, and no (0) benign epilepsy patients were detected.

These results suggest that by examining both the SCN1A gene mutation and the CACNA1A gene mutation, it is possible to eliminate the false positive (benign febrile seizure patients) better than examining just the SCN1A gene mutation, and suggest a possibility of detecting the Dravet syndrome patients with higher accuracy.

Example 3

Study of Gene Mutation in a Healthy Person

To investigate whether the remaining 6 kinds of gene mutations excluding the registered 3 kinds out of the 9 kinds of missense mutations and deletion mutations detected in the coding region of the CACNA1A gene are of the gene polymorphism (SNP), gene mutation of the CACNA1A gene was similarly analyzed for DNA extracted from blood of 190 healthy persons. Results of the 9 kinds of the missense mutations and deletion mutations detected in the coding region of the CACNA1A gene are shown in Table 6. As a result, one kind of the CACNA1A gene mutation (G266S) was not detected from the healthy persons. From this result, it was found that the CACNA1A gene mutation of G266S is not an SNP, and is a novel gene mutation (gene abnormality) not found in the 190 healthy persons, which neither is in the NCBI SNP database.

TABLE 6

CACNA1A gene mutation detected in healthy persons and Dravet syndrome

| Exon | Nucleotide Substitution | Amino Acid Substitution | Dravet (n = 47) | | Control (n = 188-190) | | p-value |
|---|---|---|---|---|---|---|---|
| | | | Frequency of variants | | | | |
| 6 | A876G | G266S | 1/47 | 2.1% | 0/188 | 0% | 0.20 |
| 11 | A1415G | K472R | 1/47 | 2.1% | 1/188 | 0.53% | 0.36 |
| 19 | A2762C | E921D | 11/47 | 23.4% | 49/188 | 26.06% | 0.71 |
| 19 | C2771G | A924G | 1/47 | 2.1% | 7/190 | 3.68% | 1.00 |
| 19 | A2987T | E996V | 11/47 | 23.4% | 49/188 | 26.06% | 0.71 |
| 20 | G3322A | G1108S | 3/47 | 6.4% | 16/189 | 8.46% | 0.77 |
| 20 | G3377A | R1126H | 4/47* | 8.5% | 1/188 | 0.53% | 0.0061 |
| 47 | G6602A | R2201Q | 4/47 | 8.5% | 4/189 | 2.12% | 0.052 |

TABLE 6-continued

CACNA1A gene mutation detected in healthy persons and Dravet syndrome

| Exon | Nucleotide Substitution | Amino Acid Substitution | Dravet (n = 47) | | Control (n = 188-190) | | p-value |
|---|---|---|---|---|---|---|---|
| 47 | 6605-6616del | DQER2202-2205del | 1/47 | 2.1% | 3/190 | 1.58% | 1.00 |
| | | | Frequency of combined mutations | | | | |
| 19 | | E921D + E996V | 11/47 | 23.4% | 49/188 | 26.06% | 0.71 |
| 20 + 47 | | R1126H + R2201Q | 4/47* | 8.50% | 0/188 | 0% | 0.0014 |

As a result of studying the comparison of frequencies in which mutations occur in healthy persons and Dravet syndrome patients, it was shown that the CACNA1A gene mutation R1126H was of a larger number with Dravet syndrome in terms of statistical significance (p=0.0061), and it was found that the CACNA1A gene mutation R2201Q also had a trend having a larger number with Dravet syndrome patients (p=0.052). The patients simultaneously having both mutations of R1126H and R2201Q on the CACNA1A gene were detected significantly in just the Dravet syndrome patients (4 cases out of 47 cases), and no healthy persons were detected (p=0.0014). Examination of DNA of the parents of these four patients revealed that the two mutations of R1126H and R2201Q were simultaneously present on one chromosome, i.e. within the same CACNA1A protein molecule, and that this double mutation was inherited from the parents.

Example 4

Study of Relation Between Genotype and Symptoms

A study was performed on how the 9 kinds of missense mutations and deletion mutations detected in the coding region of CACNA1A gene give effect on the worsening of symptoms of the disease. Out of Dravet syndrome patients whose seizure symptom data is managed in detail, the seizure symptoms under the age of 1 were compared between 20 patients who have just the SCN1A gene mutation and 19 patients who have a mutation on both the SCN1A gene and the CACNA1A gene. A result thereof is shown in Table 7. Note that "GTC" in Table 7 is an abbreviation of a generalized tonic-clonic seizure, and "CPS" is an abbreviation of a complex partial seizure.

TABLE 7

Relation of symptoms under the age of 1 with genotype

| Genotype | N | Seizure onset (months) | Total no. of seizures | Total no. of prolonged (>10 min) seizures | Type of Seizures: GTC (%) | CPS (%) | Hemi-convulsion (%) | Myoclonic seizure (%) |
|---|---|---|---|---|---|---|---|---|
| SCN1A mutation + No CACNA1A variants | 20 | 5.6 ± 0.3 | 10.2 ± 1.2 | 2.4 ± 0.4 | 95 | 45 | 50 | 15 |
| SCN1A mutation + CACNA1A variants | 19 | 4.6 ± 0.4* | 10.7 ± 1.3 | 4.4 ± 0.7* | 95 | 26 | 84* | 11 |

GTC: generalized tonic-clonc seizure,

CPS: complex partial seizure

*p < 0.05

It was found that the patients having a CACNA1A variant, as compared to the patients having no CACNA1A variant, are (i) significantly quicker in seizure onset (p=0.049), (ii) significantly greater in the number of times prolonged seizures occur, which prolonged seizure is a convulsion seizure that continues for 10 or more minutes (p=0.019), and (iii) significantly higher in the frequency that a hemiconvulsion occurs (p=0.041). This indicates that when there is a variation of the CACNA1A gene including the polymorphism in addition to a SCN1A gene abnormality, there is a possibility that the symptom may worsen.

Example 5

Analysis on Functions of Mutant Voltage-Gated Calcium Ion Channel

An analysis was performed on functions of a mutant calcium ion channel and a normal (wild-type) calcium ion channel, with use of culture cells. First, cDNA of a human CACNA1A gene (SEQ ID NO.: 4) was used to prepare an expression vector having a mutant CACNA1A (double mutation of G266S; R1126H; R2201Q; deletion 2202-2205; double mutation of R1126H and R2201Q) gene. After obtaining DNA fragments including the mutated parts by PCR, regions of a normal cDNA corresponding to those fragments were substituted with those fragments, to prepare the mutant cDNA. As a control, an expression vector (pMO14X2-CACNA1A) having a normal (wild-type) CACNA1A gene was used.

Analysis was performed on functions of the mutant calcium ion channel and the normal calcium ion channel, with use of the culture cells. A α-subunit type 1 of the voltage-gated calcium ion channel $Ca_V2.1$, which is a CACNA1A gene product, had been subjected to function adjustment by the α2δ subunit and β4 subunit that similarly configure the voltage-gated calcium ion channel $Ca_V2.1$. Hence, an expression vector having a CACNA1A gene that encodes a α-subunit type 1, and an expression vector having a human CACNB4 gene (GenBank accession No. U95020) (SEQ ID NO.: 151) encoding a β4 subunit and a rabbit α2δ gene (GenBank accession No. NM_001082276) (SEQ ID NO.: 152) encoding a α2δ subunit. were coexpressed on a human renal cell HEK293 with use of a transfection reagent. Electrophysiologic properties were studied by patch clamping of a whole cell record.

More specifically, recording of a calcium ion channel current was carried out at room temperature of 22° C. to 24° C., 72 hours after transfection. With use of a multistage P-97 Flaming-Brown micropipette puller, a patch electrode was prepared from borosilicate glass.

The composition of intracellular fluid was 110 mM CsOH, 20 mM CsCl, 5 mM $MgCl_2$, 10 mM EGTA, 5 mM MgATP, 5 mM creatine-phosphate, and 10 mM HEPES. On the other hand, the composition of the used extracellular fluid was 5 mM BaCl, 150 mM TEA-Cl, 10 mM glucose, and 10 mM HEPES. The amplifier used was Axopatch200B (Axon Instruments).

Electrophysiologic properties of the mutation channel were compared with those of a normal channel, by studying voltage-gated channel activation, inactivation, recovery from inactivation, and duration current. The activation curve and the inactivation curve were analyzed by Boltzmann function, to find a half-maximal activation/inactivation ($V_{1/2}$) and a slope factor (k). The recovery curve from the inactivation was analyzed by a two exponential function. Statistics used the unpaired Student's t test. Clampfit 8.2 software and Origin-Pro 7.0 (OriginLab) were used for data analysis.

Figure 13:
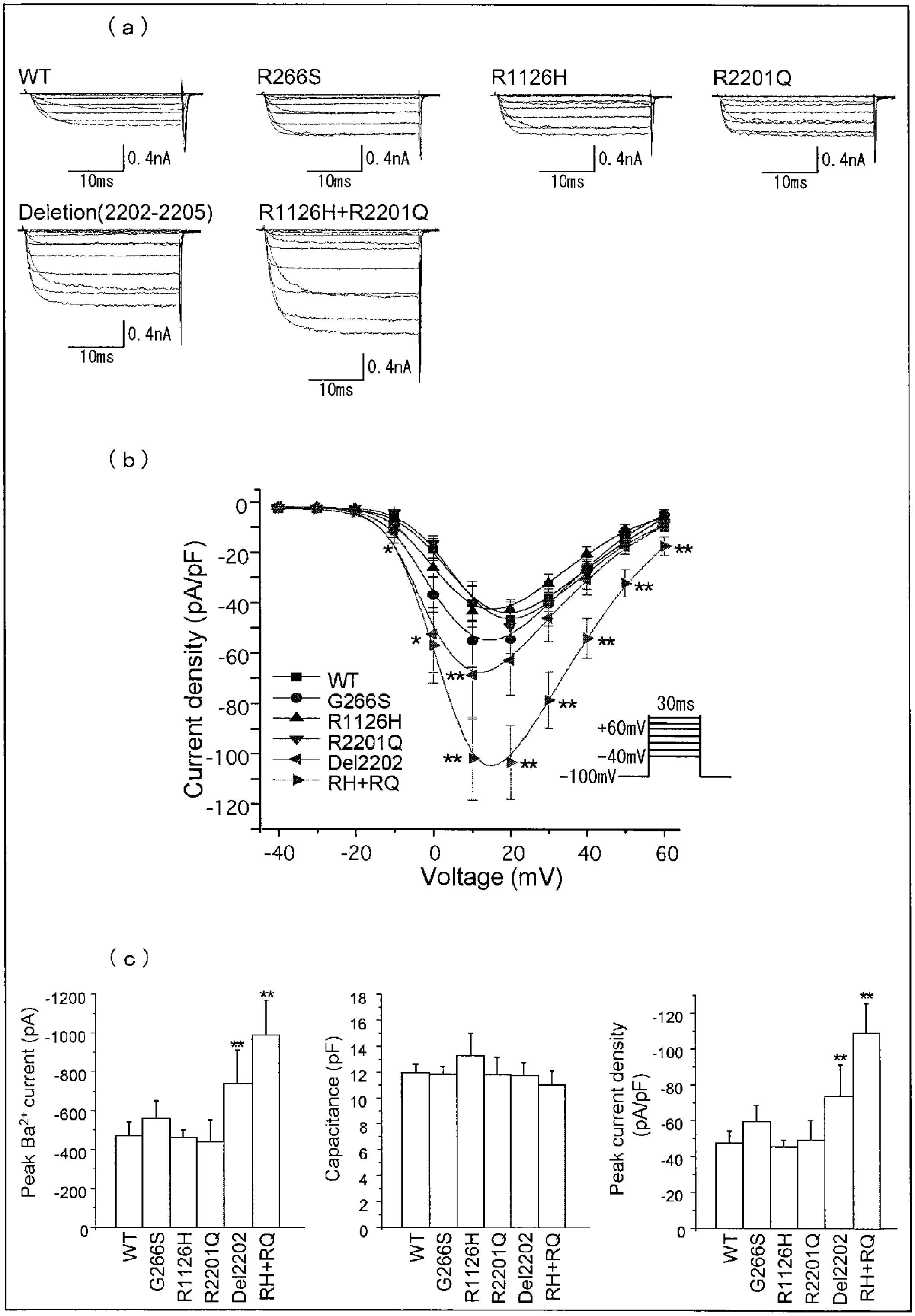
FIG. 13 is a view illustrating a result of performing function analysis of the calcium ion channel, by use of patch clamping. Illustrated in (a) is a barium current record effected by a change in potential of a normal calcium ion channel and a mutant calcium ion channel. Illustrated in (b) is a current-voltage relationship, and illustrated in (c) is peak current value (pA), a total charge (pF) and a peak current density (pA/pF).
Figure 14:
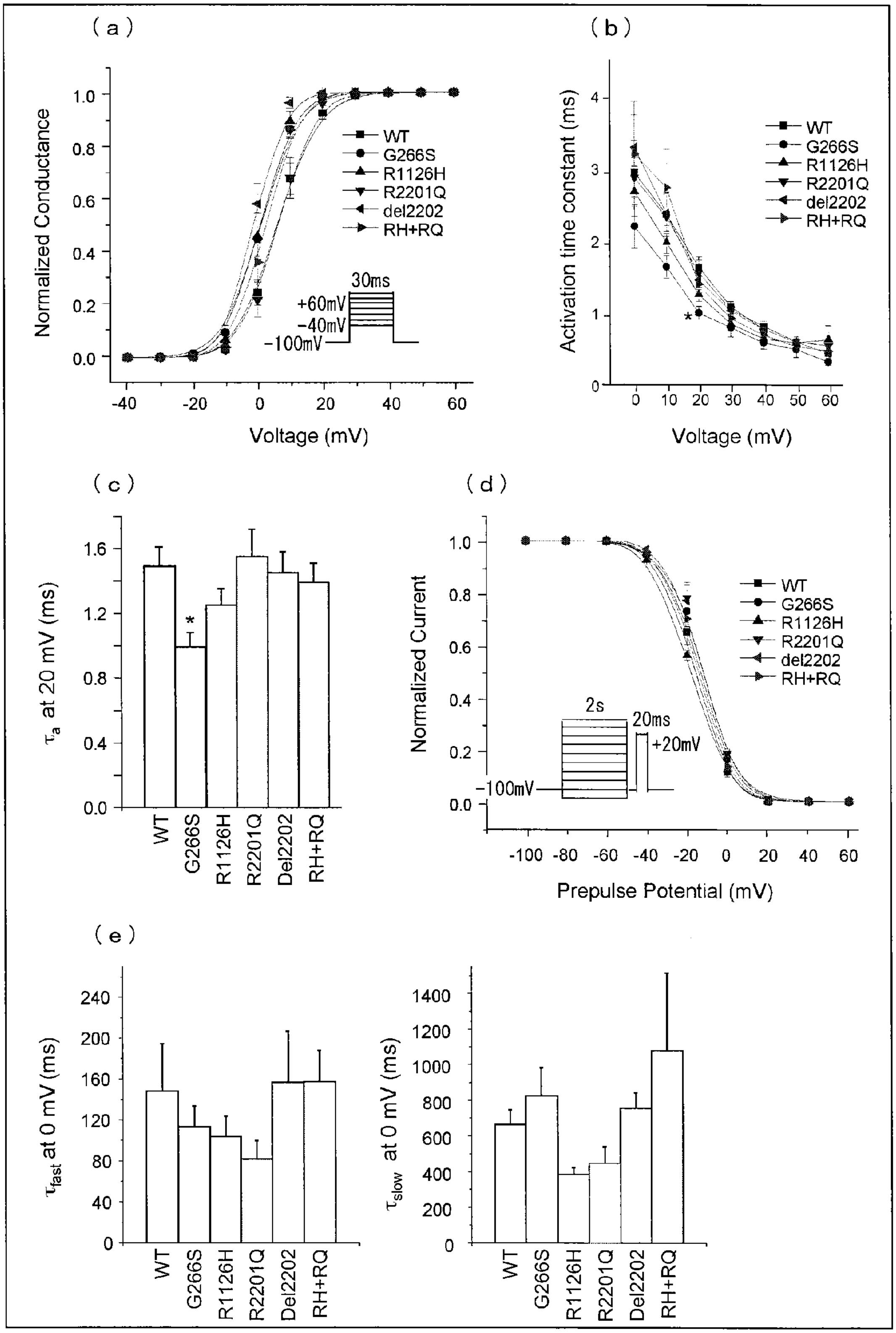
FIG. 14 is a view illustrating a result of performing function analysis of a calcium ion channel, by use of patch clamping. Illustrated in (a) is an activation curve of the calcium ion channel. Illustrated in (b) is a time constant of voltage-gated activation of the calcium ion channel. Illustrated in (c) is a time constant of voltage-gated activation at 20 mV. Illustrated in (d) is a voltage-gated inactivation curve of the calcium ion channel. Illustrated in (e) is a result of examining fast and slow inactivation time constants (i).

FIG. 13 and FIG. 14 are views illustrating results of performing function analysis of the calcium ion channel, by patch clamping. In the graphs in FIG. 13 and FIG. 14, the normal calcium ion channel is shown as "WT", and the mutant calcium ion channels are shown as "R266S", "R1126H", "R2201Q", "Del2202", and "RH+RQ". The mutation "Del2202" means the mutation "Deletion 2202-2205", and the mutation "RH+RQ" means the mutation "R1126H+R2201Q".

Illustrated in (a) of FIG. 13 is a barium current record in accordance with a change in potential of the normal calcium ion channel and the mutant calcium ion channel. Illustrated in (b) is a current-voltage relationship, and illustrated in (c) are a peak current value (pA), a total charge (pF), and a peak current density (pA/pF).

More specifically, (a) of FIG. 13 illustrates a current record of measuring barium current that is depolarized by changing a depolarizing stimulus by 10 mV each from −40 mV to +60 mV and is flowed therein. The current-voltage relationship illustrated in (b) of FIG. 13 is a graph obtained by (i) measuring a flowing barium current for every membrane potential while having a holding potential, being deeper than a resting membrane potential, as −100 mV, and a depolarizing stimulus being changed by 10 mV each from −40 mV to +60 mV, and (ii) plotting the membrane potential on a horizontal axis and a current value on a vertical axis. The view illustrated on the lower right of the graph in (b) of FIG. 13 shows that in this experiment, "the depolarizing stimulus was changed by 10 mV each from −40 mV to +60 mV for 30 ms (milliseconds), with the holding potential being −100 mV, which holding potential is deeper than the resting membrane potential".

As a result, it was found that the mutant calcium ion channel "Deletion2202-2205" and "R1126H+R2201Q" significantly increased in its flowed current amount, peak current value, and peak current density, as compared to the normal calcium ion channel.

Next, in order to specifically study the electrophysiologic properties of the calcium ion channel, a voltage-gated activity of the calcium ion channel ((a) of FIG. 14), a time constant (τ) at activation ((b) and (c) of FIG. 14), inactivation of the calcium ion channel ((d) of FIG. 14), and a time constant (τ) at inactivation ((e) FIG. 14) were measured.

The activation curve illustrated in (a) of FIG. 14 shows a barium current value flowing per membrane potential as a relative value, by having a maximum sodium current value obtained from the graph of (b) of FIG. 13 be 1, and an obtained curve was analyzed by Boltzmann function to find a half-maximal activation ($V_{1/2}$) and a slope factor (k). The view provided on the lower right of the graph in (a) of FIG. 14 represents that, in this experiment, "the depolarizing stimulus was changed by 10 mV each from −40 mV to +60 mV for 30 ms (milliseconds), with the holding potential being −100 mV, which holding potential is deeper than the resting membrane potential".

As a result of analyzing the voltage-gated activity of the calcium ion channel, it was found that (i) the mutant calcium ion channel "G266S" and "R1126H" show a significant hyperpolarization shift as compared to the normal channel, and that (ii) the mutant calcium ion channel "R1126H" and "Deletion2202-2205" significantly increased in the voltage-gated property as compared to the normal channel, by comparing the slope factor (k) (see (a) of FIG. 14 and Table 8). This means that the mutant calcium ion channel "G266S", "R1126H" and "Deletion2202-2205" are easily activated even in a low membrane potential, thereby tending to cause excess hyperexcitability of nerve cells.

Table 8 shows electrophysiologic properties of the calcium ion channel. Statistical comparison of the normal CACNA1A and the mutant CACNA1A were performed by the Student's t test. The asterisk (*) in Table 8 indicates that there is a significant difference between the normal CACNA1A and the mutant CACNA1A when a critical rate is under 5%, and the double asterisk (**) indicates that there is a significant difference between the normal CACNA1A and the mutant CACNA1A when the critical rate is under 1%.

TABLE 8

Electrophysiologic properties of calcium ion channel

| | Activation | | | Inactivation | | |
|---|---|---|---|---|---|---|
| | $V_{1/2}$ (mV) | k (mV) | n | $V_{1/2}$ (mV) | k (mV) | n |
| WT-CACNA1A | 6.3 ± 1.3 | 4.3 ± 0.2 | 16 | −16.9 ± 1.5 | −4.5 ± 0.6 | 10 |
| G266S | 1.0 ± 1.2** | 4.3 ± 0.4 | 11 | −13.8 ± 1.6 | −5.5 ± 0.3 | 10 |

TABLE 8-continued

Electrophysiologic properties of calcium ion channel

| | Activation | | | Inactivation | | |
|---|---|---|---|---|---|---|
| | $V_{1/2}$ (mV) | k (mV) | n | $V_{1/2}$ (mV) | k (mV) | n |
| R1126H | 0.4 ± 1.6** | 3.3 ± 0.3* | 10 | −18.9 ± 0.6 | −6.1 ± 0.7 | 8 |
| R2201Q | 6.4 ± 1.5 | 4.1 ± 0.2 | 8 | −13.4 ± 1.7 | −5.7 ± 0.4 | 10 |
| Deletion2202-2205 | 1.3 ± 1.4 | 3.4 ± 0.2* | 8 | −13.3 ± 1.2 | −4.7 ± 0.6 | 9 |
| R1126H + R2201Q | 2.6 ± 1.1 | 3.5 ± 0.2 | 10 | −15.2 ± 0.9 | −5.4 ± 0.1 | 10 |

$V_{1/2}$, half-maximal voltage activation and inactivation;
k, slope factor.
Statistical coparison between WT-CACNA1A and mutant channels was performed by Student's t test (*P < 0.05 and **P < 0.01 versus WT-CACNA1A).

Illustrated in (b) of FIG. 14 is a time constant of channel voltage-gated activation, that is to say, a time required for each current to reach 66.7%. Moreover, (c) of FIG. 14 illustrates a time constant of voltage-gated activation at 20 mV. From (b) and (c) of FIG. 14, it was demonstrated that the mutant calcium ion channel "G266S" was significantly small in the time constant of voltage-gated activation at 20 mV, as compared to a normal channel. Since this point is considered as that the mutant calcium ion channel "G266S" is made so as to flow a lot of current within a short depolarization, this means that there is a trend of causing hyperexcitement in the nerve cells.

Illustrated in (d) of FIG. 14 is a voltage-gated inactivation curve of the calcium ion channel, which was measured upon changing a membrane potential to activate the calcium ion channel and thereafter providing a depolarizing stimulus to measure how much barium current was flown. Note that the view illustrated on the lower left of the graph illustrated in (d) of FIG. 14 shows that, in this experiment, "the depolarizing stimulus was changed by 20 mV each from −120 mV to +60 mV for 2 s (seconds), and subsequently be changed to 20 mV, with the holding potential being −100 mV, which holding potential is deeper than the resting membrane potential".

The voltage-gated inactivation curve of the calcium ion channel showed no recognizable significant difference, in either of the mutant channel or the normal channel.

Illustrated in (e) of FIG. 14 is a result of studying an inactivation time constant (i). There are two kinds of inactivation: inactivation of a fast component and inactivation of a slow component. The "$\tau_{fast}$" in the left graph of (e) of FIG. 14 is a constant representing a time required until the inactivation of the fast component reaches 33.3%, and the "$\tau_{slow}$" in the right graph is a constant representing a time required until the inactivation of the slow component reaches 33.3%. These inactivation time constants were, more specifically, calculated by analyzing the inactivation curve with use of Clampfit 8.2 software.

As a result, there was no significant difference in the inactivation time constant between that of the normal calcium ion channel and that of the mutant calcium ion channel. Table 9 shows physiological properties of the mutant calcium ion channel. The arrow pointing upwards ↑T) in Table 9 indicates that an increase in channel activity was recognized, and the hyphen "–" indicates that no change was recognized in the channel activity.

TABLE 9

Summary of electrophysiological properties of mutant calcium ion channel

| | CACNA1A | | | | |
|---|---|---|---|---|---|
| Biophysical property | G266S | R1126H | R2201Q | Del 2202-2205 | R1126H + R2201Q |
| Peak current density | — | — | — | ↑ | ↑↑ |
| Activation $V_{1/2}$ | ↑ | ↑ | — | — | — |
| Activation slop factor | — | ↑ | — | ↑ | — |
| Activation time constants | ↑ | — | — | — | — |
| Inactivation $V_{1/2}$ | — | — | — | — | — |
| Inactivation slope factor | — | — | — | — | — |

↑, predicted gain of channel activity,
—, no predicted change in channel activity.

It was found that the mutations other than "R2201Q" in the calcium ion channel were mutations of a gain of function kind, and tends to cause excitement of the nerve cells.

Example 6

Production of Dravet Syndrome Model Rat

From the foregoing findings, it was considered that having some kind of mutation on both of SCN1A and CACNA1A is important in the development of Dravet syndrome.

Accordingly, a rat was produced which has both of the mutation on α1-subunit gene Scn1a of the voltage-gated sodium ion channel $Na_V1.1$ and the mutation on α1-subunit gene Cacna1a of the voltage-gated calcium ion channel $Ca_V2.1$, to study the worsening of symptoms (human genes are represented as SCN1A and CACNA1A, and rat genes are represented as Scn1a and Cacna1a).

More specifically, a rat having a mutation on the Scn1a gene (F344-Scn1a$^{Kyo811}$) and a rat having a mutation on the Cacna1a gene (GRY (groggy rat, Cacna1a$^{gry}$)) were used as parent rats. Each of these mice is described below.

<F344-Scn1a$^{Kyo811}$>

A rat produced by ENU mutagenesis, having a missense mutation on a α1 subunit gene (Scn1a) of the voltage-gated sodium channel $Na_V1.1$. Asparagine (N), which is an amino acid at position 1417, was mutated to histidine (H) (represented as "N1417H"). This rat served as a model animal of human generalized epilepsy febrile seizure plus (GEFS+). Background genealogy is F344/NS1c rat. This rat was provided from the Institute of Laboratory Animals, Graduate School of Medicine, Kyoto University.

<GRY (Groggy Rat, Cacna1a$^{gry}$)>

A mutant rat produced by administering methyl nitrosourea to Scl:Wistar, whose main symptoms are ataxia and absence-like seizure. This rat has an autosomal recessive mode of inheritance, and has a missense mutation on the α1-subunit of the voltage-gated calcium ion channel $Ca_V2.1$. Methionine (M), which is an amino acid at position 251, is mutated to lysine (K) (M251K). This rat was provided from the Institute of Laboratory Animals, Graduate School of Medicine, Kyoto University.

FIG. 11 is a view showing an amino acid sequence of a protein encoded by a human CACNA1A gene and an amino acid sequence of a protein encoded by a rat Cacna1a gene. The upper line of the amino acid sequence shown in FIG. 11 represents an amino acid sequence of the protein encoded by the rat Cacna1a gene (GenBank accession No. NM_012918) (SEQ ID NO.: 147), and the lower line is the amino acid sequence of the protein encoded by the human CACNA1A gene (GenBank accession No. NM_023035) (SEQ ID NO.: 3). Moreover, the squared amino acid "M" in FIG. 11 is an amino acid that is mutated from the amino acid "M" to an amino acid "K" in the human mutant CACNA1A (M249K) protein (SEQ ID NO.: 148) and the rat mutant Cacna1a (M251K) protein (SEQ ID NO.: 149).

As illustrated in FIG. 11, the mutation (M251K) on the α1 subunit of the rat voltage-gated calcium ion channel $Ca_V2.1$ corresponds to the mutation (M249K) on the α1 subunit of the human voltage-gated calcium ion channel $Ca_V2.1$.

The F344-Scn1a$^{Kyo811}$ and GRY (groggy rat, Cacna1a$^{gry}$) as described above were mated to produce a rat having each of the gene mutations.

(1. Analysis on Functions of Mutant Voltage-Gated Sodium Ion Channel)

An analysis was performed with use of culture cells, on functions of a mutant sodium ion channel and normal sodium ion channel, before tests using the rats were performed. The rat having a mutation on the Scn1a gene (F344-Scn1a$^{Kyo811}$) has asparagine (AAT), which is an amino acid at position 1417 of a protein encoded by the Scn1a gene, was changed to histidine (CAT) (N1417H). The asparagine at position 1417 is located in a pore formation region that is related to ionic permeation of sodium ion channel third domain. On this account, first, the function analysis of the mutant voltage-gated sodium ion channel included in F344-Scn1a$^{Kyo811}$ was performed.

More specifically, an expression vector having a mutant SCN1A (N1417H) gene (SEQ ID NO.: 150) including a missense mutation was prepared with use of cDNA of human SCN1A gene. As control, an expression vector having a normal (wild-type) SCN1A gene (SEQ ID NO.: 2) was prepared.

FIG. 1 is a view showing an amino acid sequence of a protein encoded by the human SCN1A gene and an amino acid sequence of a protein encoded by the rat Scn1a gene. The upper line in the amino acid sequence shown in FIG. 1 represents an amino acid sequence of a protein that is encoded by the human SCN1A gene (SEQ ID NO.: 1), and the lower line represents an amino acid sequence of a protein that is encoded by the rat Scn1a gene (SEQ ID NO.: 144). Moreover, the squared amino acid "N" in FIG. 1 is an amino acid on which a mutation from an amino acid "N" to an amino acid "H" occurs, of the human mutant SCN1A (N1417H) protein (SEQ ID NO.: 145) and the rat mutant SCN1A (N1417H) protein (SEQ ID NO.: 146).

An analysis was performed with use of culture cells, on functions of the mutant sodium ion channel and the normal sodium ion channel. The α-subunit type 1 of the voltage-gated sodium ion channel $Na_V1.1$, which is a SCN1A gene product, was adjusted in its function by $\beta_1$ subunit and $\beta_2$ subunit that similarly make up the voltage-gated sodium ion channel $Na_V1.1$. Hence, an expression vector having the SCN1A gene that encodes the α-subunit type 1 was coexpressed with an expression vector having the SCN1B gene that encodes the $\beta_1$ subunit and the SCN2B gene that encodes the $\beta_2$ subunit in a human renal cell HEK293, with use of a transfection reagent. The electrophysiologic properties were studied by patch clamping based on whole cell recording.

More specifically, recording of the sodium ion channel current was carried out at room temperature of 22° C. to 24° C., 24 hours to 48 hours after transfection. A patch electrode was prepared from borosilicate glass by use of multistage P-97 Flaming-Brown micropipette puller.

Composition of intracellular fluid was 110 mM CsF, 10 mM NaF, 20 mM CsCl, 2 mM EGTA, and 10 mM HEPES. On the other hand, the composition of extracellular fluid was 145 mM NaCl, 4 mM KCl, 1.8 mM $CaCl_2$, 1 mM $MgCl_2$, and 10 mM HEPES. Axopatch200B (Axon Instruments) was used as the amplifier.

Electrophysiologic properties of the mutation channel were compared with those of a normal channel, by studying voltage-gated channel activation, inactivation, recovery from inactivation, and duration current. The activation curve and the inactivation curve were analyzed by Boltzmann function, to find a half-maximal activation/inactivation ($V_{1/2}$) and a slope factor (k). The recovery curve from the inactivation was analyzed by a two exponential function. Durable Na current was found by a difference in the duration current when depolarized at −10 mV for 100 ms, before and after addition of 10 μM of tetrodotoxin (TTX). Statistics used were unpaired Student's t test. Clampfit 8.2 software and OriginPro 7.0 (OriginLab) were used for data analysis.

Figure 3:
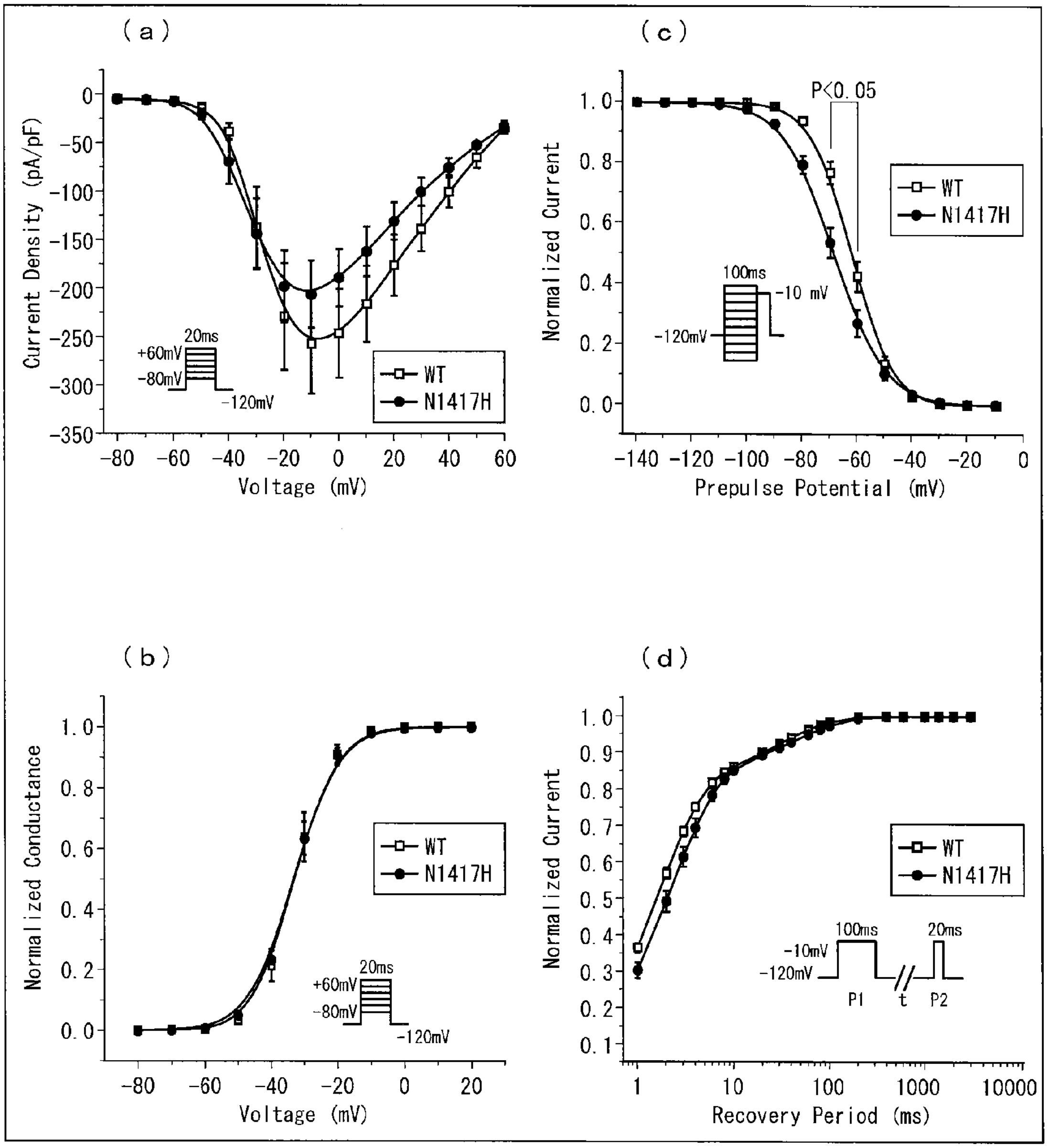
FIG. 3 is a view illustrating a result of performing function analysis of a sodium ion channel, by use of patch clamping. Illustrated in (a) is a current-voltage relationship, illustrated in (b) is an activation curve of the sodium ion channel, illustrated in (c) is an inactivation curve of the sodium ion channel, and illustrated in (d) is a recovery curve from the inactivation of the sodium ion channel.
Figure 4:
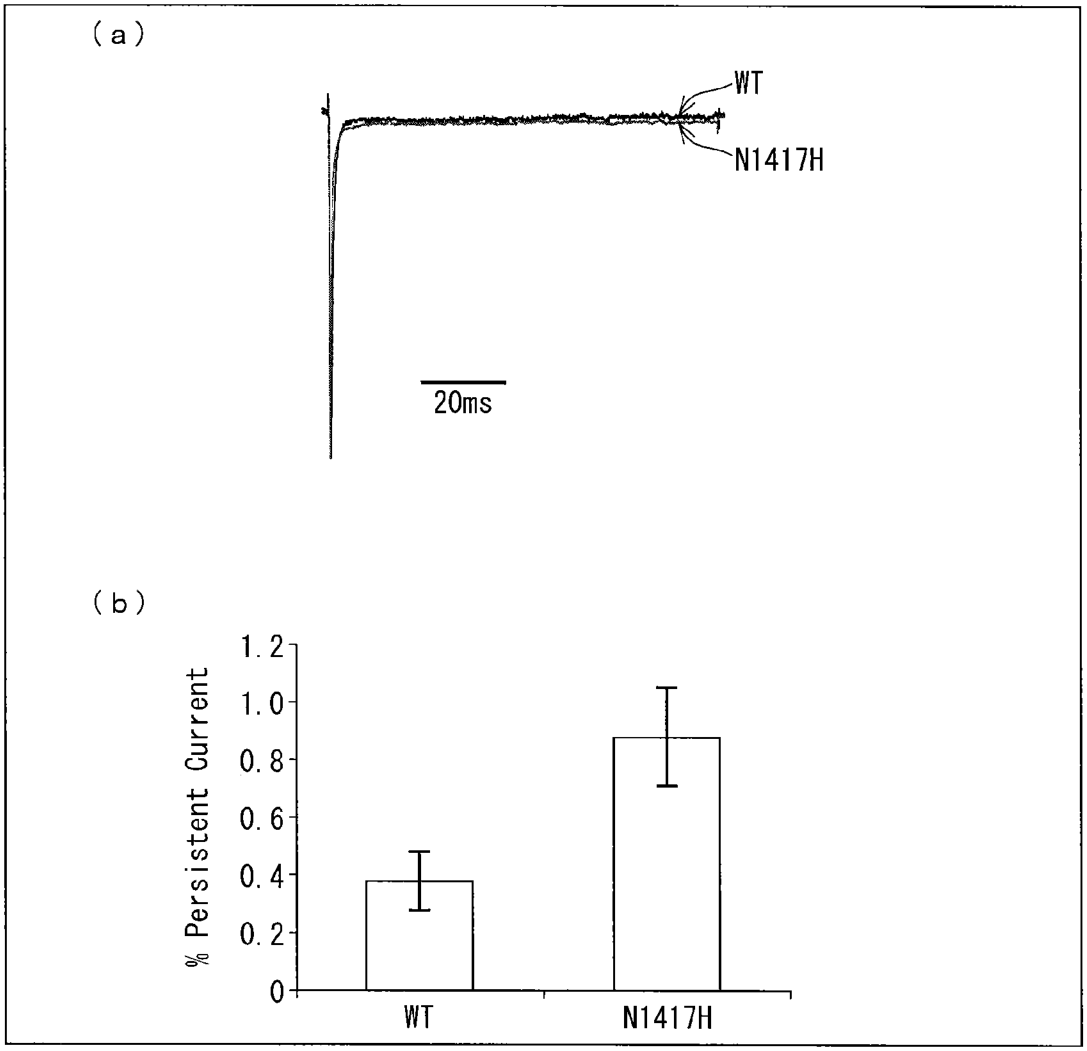
FIG. 4 is a view illustrating a result of performing function analysis of a sodium ion channel, by use of patch clamping. Illustrated in (a) is a sodium current flowing in the sodium ion channel, and illustrated in (b) is a relative value (%) of a persistent sodium current amount flowing into the sodium ion channel.

FIGS. 2 to 4 are views illustrating results of performing function analysis of the sodium ion channel by patch clamping. The graphs of FIGS. 2 to 4 show the normal sodium ion channel as "WT" or "WT-SCN1A", and show the mutant sodium ion channel as "N1417H".

Illustrated in (a) of FIG. 2 is a typical example of a sodium current in response to a change in potential of the normal sodium ion channel and the mutant sodium ion channel. More specifically, a depolarizing stimulus was changed 10 mV each from −80 mV to +60 mV for depolarization, and sodium current that flowed in was measured. As a result, both of the normal sodium ion channel and the mutant sodium ion channel function as a channel, and there was no significant difference between the two.

Illustrated in (b) of FIG. 2 is a result of studying the inactivation time constant (τ). There are two types of inactivation; an inactivation of a fast component and an inactivation of a slow component. The "τ1" in (b) of FIG. 2 is indicative of a constant indicative of a time required for the inactivation of the fast component to reach 33.3%, and the "τ2" is indicative of a constant indicative of a time required for the inactivation of the slow component to reach 33.3%. These inactivation time constants, more specifically, were calculated by analyzing the inactive curve with use of the Clampfit 8.2 software. As a result, there was no significant difference in the inactivation time constant between that of the normal sodium ion channel and that of the mutant sodium ion channel.

Next, in order to specifically study the electrophysiologic properties of the sodium ion channel, a current-voltage relationship ((a) of FIG. 3), an activation of the sodium ion channel ((b) of FIG. 3), an inactivation of the sodium ion channel ((c) of FIG. 3), and recovery from the inactivation of the sodium ion channel ((d) of FIG. 3) were measured.

More specifically, the current-voltage relationship illustrated in (a) of FIG. 3 was obtained by (i) measuring a flowing sodium current for every membrane potential while having a holding potential, being deeper than a resting membrane potential, as −120 mV, and a depolarizing stimulus being changed by 10 mV each from −80 mV to +60 mV, and (ii) plotting the membrane potential on a horizontal axis and a current value on a vertical axis. The view illustrated on the lower left of the graph in (a) of FIG. 3 shows that in this experiment, "the depolarizing stimulus was changed by 10 mV each from −80 mV to +60 mV for 20 ms (milliseconds), with the holding potential being −120 mV, which holding potential is deeper than the resting membrane potential".

The activation curve illustrated in (b) of FIG. 3 shows a sodium current value flowing per membrane potential as a relative value, by having a maximum sodium current value obtained from the graph of (a) of FIG. 3 be 1, and an obtained curve was analyzed by Boltzmann function to find a half-maximal activation ($V_{1/2}$) and a slope factor (k). The view provided on the lower right of the graph in (b) of FIG. 3 represents that in this experiment, "the depolarizing stimulus was changed by 10 mV each from −80 mV to +60 mV, for 20 ms (milliseconds), with the holding potential being −120 mV, which holding potential is deeper than the resting membrane potential".

The inactive curve illustrated in (c) of FIG. 3 was obtained by similarly changing the membrane potential to activate the channel and thereafter providing depolarizing stimulus and measuring how much the sodium current flows, to find the half-maximal inactivation ($V_{1/2}$) and the slope factor (k). Note that the view provided on the lower left of the graph of (c) of FIG. 3 represents that in this experiment, "the depolarizing stimulus was changed by 10 mV each from −140 mV to +0 mV for 100 ms (milliseconds) and subsequently changed to −10 mV, with the holding potential being −120 mV".

The recovery curve from the inactivation illustrated in (d) of FIG. 3 was obtained as follows. When a depolarizing stimulus was provided with pulse 1 (P1), the channel became inactive upon opening. When the depolarizing stimulus was returned to the original −120 mV, the sodium ion channel returned to its resting state, and upon stimulation of pulse 2 (P2), the channel opened again. The recovery time of this pulse 1 and pulse 2 were changed to obtain the recovery curve from the inactivation. This curve was analyzed by a two exponential function. It was determined whether the function of the channel was made easily excited or in the opposite was made difficult to be excited, depending on whether the recovery was quicker or slower as compared to the normal channel. The view provided on the lower right of the graph of (d) of FIG. 3 indicates that in this experiment, "a holding potential was −120 mV, −10 mV was provided for 100 ms (milliseconds) as the depolarizing stimulus and thereafter was returned to −120 mV, and after elapse of each of the times (milliseconds) shown on the x-axis, −10 mV was provided for 20 ms (milliseconds)".

As a result, no significant difference was recognized in the current-voltage relationship and the channel activation, between the normal sodium ion channel and the mutant sodium ion channel (see (a) and (b) of FIG. 3). Meanwhile, a significant test was performed regarding the channel inactivation, on a point that the normal sodium ion channel and the mutant sodium ion channel are inactivated by 50%, whereby resulted in finding that the mutant sodium ion channel had shifted significantly to the depolarization side ($p<0.05$) ((c) of FIG. 3).

As to the recovery from the channel inactivation, it was found that the recovery was significantly slow in the mutant sodium ion channel ((d) of FIG. 3). In (d) of FIG. 3, a part in which a period of recovery (Recovery period (ms)) from the inactivation was 1 ms to 8 ms corresponds to a "fast component", and a part in which the period of recovery from the inactivation was 10 ms to 100 ms corresponds to a "slow component".

More specifically, upon comparison between the normal sodium ion channel and an abnormal sodium ion channel based on a time required for the fast component in recovering from the inactivation to recover from the inactivation to 33.3%, it was found that the recovery was significantly slow for the mutant sodium ion channel (normal: $\tau_f$=1.7±0.1 ms, n=14; mutant: $\tau_f$=2.5±0.2 ms ($P<0.01$), n=12).

Similarly, upon comparison of the normal sodium ion channel with the abnormal sodium ion channel based on the time required for the slow component in recovering from the inactivation to recover from the inactivation to 33.3%, it was found that the mutant sodium ion channel was significantly slow in recovering (normal: $\tau_s$=40.3±5.3 ms, n=14; mutant: $\tau_s$=60.9±7.9 ms ($P<0.05$), n=12).

FIG. 4 shows that, even if the sodium ion channel was made inactivated after the potential was changed to activate the sodium ion channel, the baseline of the mutant sodium channel does not return back in the whole cell record, which indicates clearly that the sodium current was persistently flowing into the mutant sodium ion channel. The persistent sodium current is considered as an obstruction of an inactivation gate. From the view of (a) of FIG. 4, it was confirmed that even after the elapse of time, the inactivation was insufficient in the mutant sodium ion channel as compared to that of the normal sodium ion channel.

So as to find the persistent sodium current shown in (a) of FIG. 4, a relative value (%) was found by dividing, with a maximum current amount, a final current amount that flowed between 80 milliseconds to 100 milliseconds when a depolarizing stimulus of 100 milliseconds was given. Results thereof are shown in (b) of FIG. 4. From these results, it was found that the mutant sodium ion channel had properties that the persistent sodium current increases.

This data show that the function of the voltage-gated sodium ion channel $Na_V1.1$ became abnormal by the mutation. Namely, this means that by having the mutation, the nerve cells are easily excessively excited, that is to say, more easily causes the occurrence of a convulsion.

Literature (Satoko Tokuda et. al., BRAINRESEARCH 1133 (2007) 168-177; Kenta Tanaka et. al., Neuroscience Letters 426 (2007) 75-80) discloses that the function of the voltage-gated calcium ion channel $Ca_V2.1$ of a rat becomes abnormal due to a mutation (M251K) on the al subunit of the voltage-gated calcium ion channel $Ca_V2.1$ of the rat.

Therefore, with a rat having the mutation on both the Scn1a gene and Cacna1a gene described later, it can be considered that the functions of both the voltage-gated sodium ion channel $Na_V1.1$ and the voltage-gated calcium ion channel $Ca_V2.1$ are abnormal.

(2. Confirmation of Gene Mutation in Dravet Syndrome Model Rat)

The foregoing F344-Scn1a$^{Kyo811}$ and the GRY (groggy rat, Cacna1a$^{gry}$) were mated as parent rats (P) to produce F1 (first filial generation) rats, and these F1 rats were mated to produce F2 (second filial generation) rats. FIG. 5 is a view showing genotypes of the parent rats (P), the F1 rats and the F2 rats. As illustrated in (a) of FIG. 5, the F1 rats have the heterozygous mutation on both the Scn1a gene and the Cacna1a gene (referred to as "Scn1a mutant (hetero)+Cacna1a mutant (hetero)"). Moreover, as illustrated in (b) of FIG. 5, rats showing 9 types of genotypes were born from the F2 rats. The genotypes of each of the rats were identified by extracting a tip tissue of the tail of the rats and extracting its DNA, to perform DNA sequencing with the extracted DNA and detect its gene mutation, or by detecting a digested pattern with use of a restriction enzyme.

(Method of Confirming Gene Mutation by DNA Sequencing)

Confirmation of gene mutation by DNA sequencing was performed as follows. First, a genomic DNA was amplified with use of a primer pair that sandwiches a mutation point (a nucleotide sequence of a Scn1a amplification primer pair is represented by SEQ ID NO.: 5 and SEQ ID NO.: 6, and a nucleotide sequence of a Cacna1a amplification primer pair is represented by SEQ ID NO.: 7 and SEQ ID NO.: 8), and thereafter, an obtained PCR product was purified with use of a PCR products pre-sequencing kit (Amersham Biosciences, Little Chalfont, Buckinghamshire, England). See the item "Sequence of primers" later described for the nucleotide sequence of the used primer pairs.

Next, sequence reaction was performed with use of a Big Dye Terminator FS ready-reaction kit (Applied Biosystems), to determine a nucleotide sequence with a fluorescence sequencer (ABI PRISM3100 sequencer; Applied Biosystems).

Figure 6:
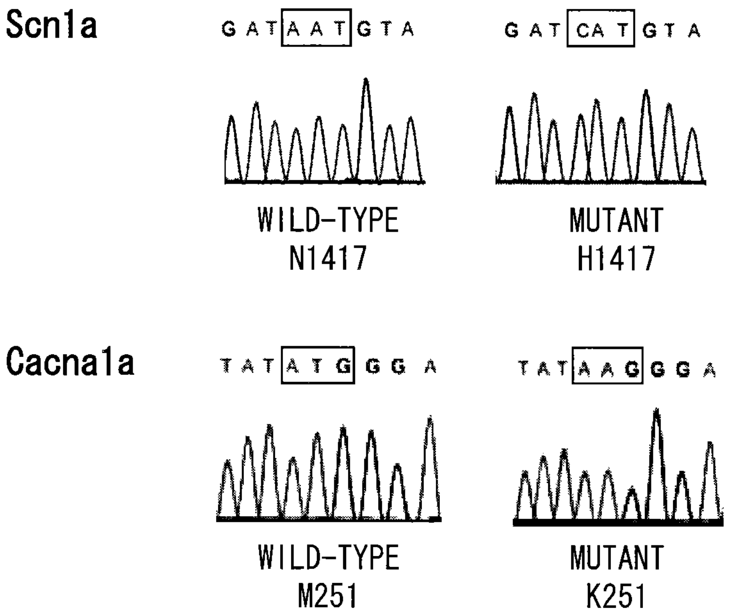
FIG. 6 is a view illustrating a method of identifying genotypes of the Scn1a gene and the Cacna1a gene of the F2 rat, by sequencing.

FIG. 6 is a view illustrating a method of identifying a genotype of the Scn1a gene and the Cacna1a gene of the F2 rats, by sequencing. As illustrated in FIG. 6, a wild-type Scn1a gene has a nucleotide at position 4249 be "A". In comparison, a mutant Scn1a gene (N1417H) has a nucleotide at position 4249 that is mutated from "A" to "C". As a result, a codon "AAT" that designates asparagine (N) being an amino acid at position 1417 in the wild-type Scn1a gene, is mutated to a codon "CAT" which designates histidine (H), in the mutant Scn1a gene (N1417H).

Moreover, the wild-type Cacna1a gene has a nucleotide at position 752 be "T". In comparison, the mutant Cacna1a gene (M251K) has a nucleotide at position 752 that is mutated from "T" to "A". As a result, a codon "ATG" that designates methionine, which is an amino acid at position 251, is mutated to a codon "AAG" that designates lysine.

(Method of Confirming Gene Mutation by Restriction Enzyme Digestion)

Figure 7:
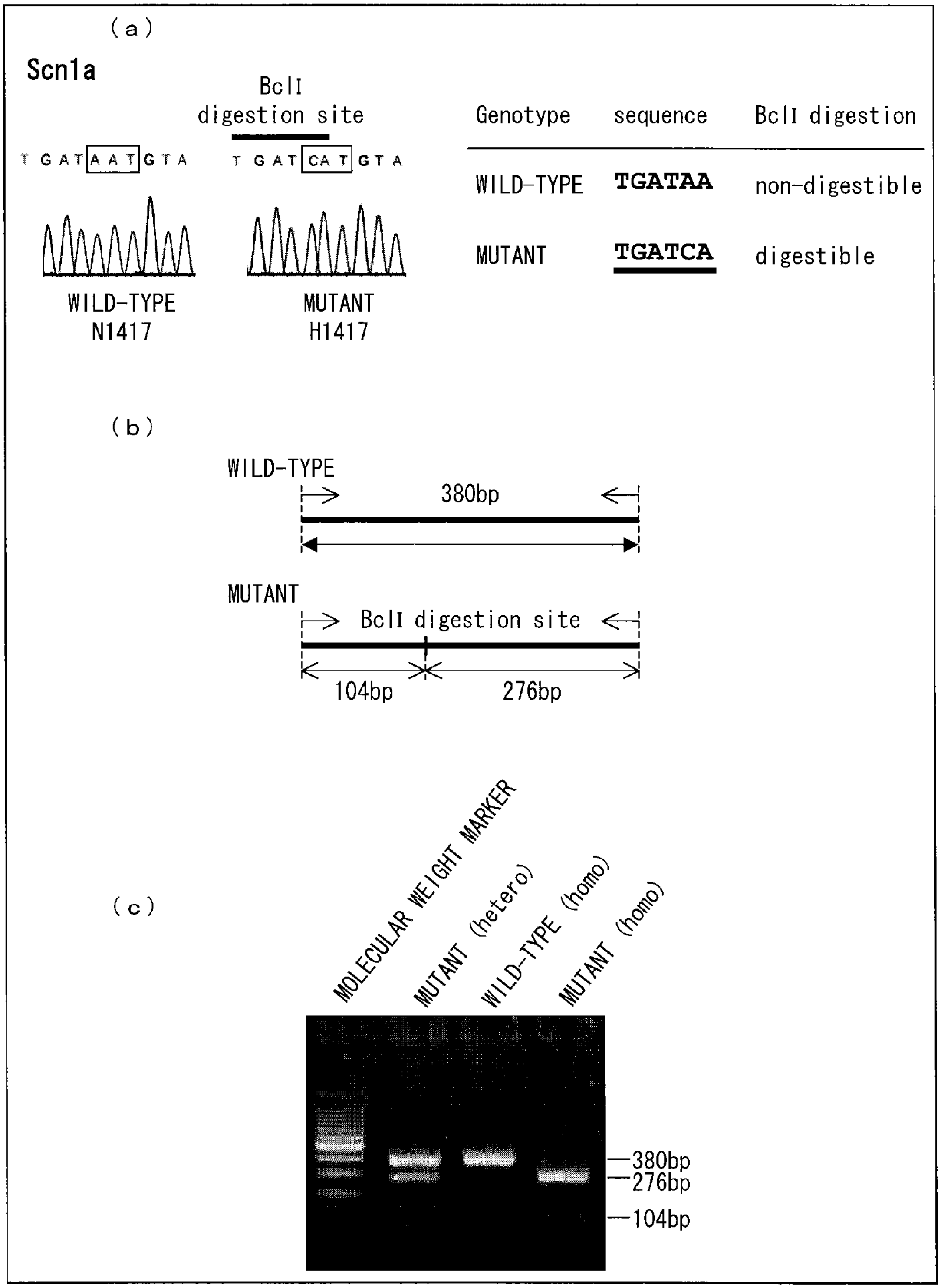
FIG. 7 is a view illustrating a method of identifying a genotype of the Scn1a gene of the F2 rat, by restriction enzyme digestion. Illustrated in (a) is a nucleotide sequence of where mutation is on a mutant Scn1a gene (N1417H), and a nucleotide sequence of a wild-type Scn1a gene corresponding to that nucleotide sequence of the mutant Scn1a gene. Illustrated in (b) is a size of a DNA fragment expected by the restriction enzyme digestion. Illustrated in (c) is a result of electrophoresis.

The method of confirming gene mutation by the restriction enzyme digestion was performed as follows. When detecting mutation in the Scn1a gene, a genomic DNA was amplified with use of a primer pair (SEQ ID NOs.: 5 and 6) that sandwich a mutation point in the Scn1a gene, and thereafter an obtained PCR product was reacted for three hours at 50° C., with use of a restriction enzyme Bc1I. Thereafter, the PCR product reacted with the restriction enzyme was subjected to electrophoresis with use of 4% agarose gel, and the size of the band was detected. FIG. 7 is a view illustrating a method of identifying the genotype of the Scn1a gene of the F2 rats, by restriction enzyme digestion.

As shown in (a) and (b) of FIG. 7, the wild-type Scn1a gene was not digested with Bc1I, so the size of the band remained as the size of the PCR product (nucleotide of 380 bp). On the other hand, the mutant Scn1a gene (N1417H) was digested with Bc1I, so two fragments (nucleotides of 276 bp and 104 bp) were detected. In a case of a heterozygous rat of the wild-type Scn1a gene and the mutant Scn1a gene (N1417H), three fragments (nucleotides of 380 bp, 276 bp, and 104 bp) were detected. Illustrated in (c) of FIG. 7 shows a result of electrophoresis.

In a case of detecting the mutation on the Cacna1a gene, a genomic DNA was amplified with use of a primer pair (SEQ ID NOs.: 7 and 8) that sandwich a mutation point of the Cacna1a gene, and thereafter, an obtained PCR product was reacted for 1 hour at 37° C. with use of a restriction enzyme PciI. Thereafter, the PCR product reacted with the restriction enzyme was subjected to electrophoresis with use of 4% agarose gel, to detect the size of a band.

Figure 8:
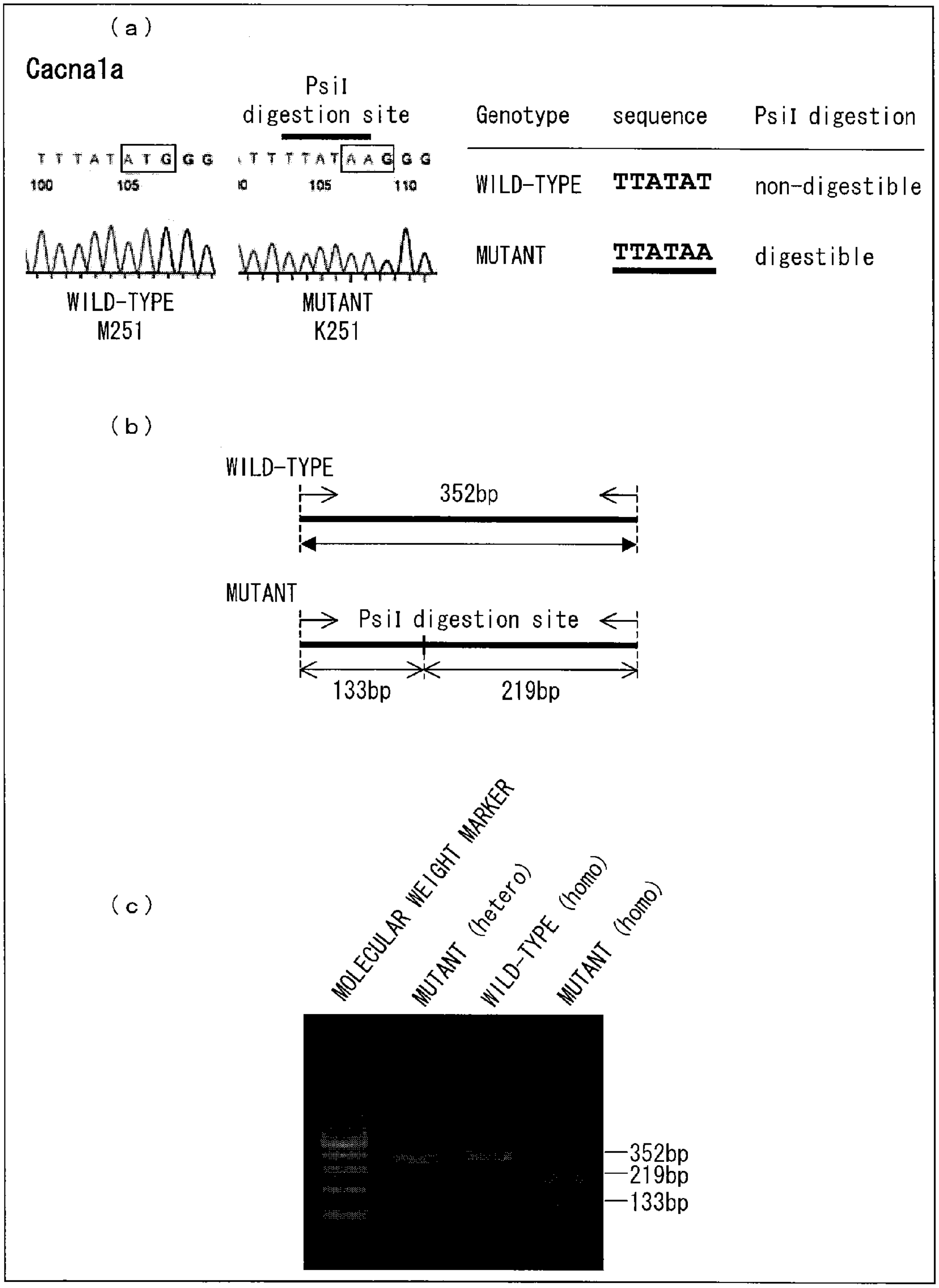
FIG. 8 is a view illustrating a method of identifying a genotype of the Cacna1a gene in a F2 rat, by restriction enzyme digestion. Illustrated in (a) is a nucleotide sequence of where a mutation is on a mutant Cacna1a gene (M251K), and a nucleotide sequence of a wild-type Cacna1a gene corresponding to that nucleotide sequence of the mutant Cacna1a gene. Illustrated in (b) is a size of a DNA fragment expected by the restriction enzyme digestion. Illustrated in (c) is a result of electrophoresis.

FIG. 8 is a view illustrating a method of identifying a genotype of the Cacna1a gene of the F2 rats, by restriction enzyme digestion. As illustrated in (a) and (b) of FIG. 8, a wild-type Cacna1a gene was not digested with PciI, so hence the size of the band remained as the size of the PCR product (nucleotide of 352 bp). On the other hand, the mutant Cacna1a gene (M251K) was digested with PciI, and thus two fragments (nucleotides of 219 bp and 133 bp) were detected. With a heterozygous rat of the wild-type Cacna1a gene and an abnormal Cacna1a gene (M251K), three fragments (nucleotides of 352 bp, 219 bp, and 133 bp) were detected. Illustrated in (c) of FIG. 8 is a result of electrophoresis.

Example 7

Analysis of Dravet Syndrome Model Rat

A study was performed on what kind of (worsening) effect was given on the seizure when a mutation on the Cacna1a gene was added to a mutation on the Scn1a gene, with use of a Dravet syndrome model rat. More specifically, comparison was made regarding symptoms when a convulsion seizure was induced by heat load, between a rat having a homozygous mutation on the Scn1a gene (referred to as "Scn1a mutant (homo)+Cacna1a wild-type (homo)") and a rat having a homozygous mutation on the Scn1a gene and a heterozygous mutation on the Cacna1a gene (referred to as "Scn1a mutant (homo)+Cacna1a mutant (hetero)").

The Scn1a mutant (homo)+Cacna1a wild-type (homo) and the Scn1a mutant (homo)+Cacna1a mutant (hetero) both have a homozygous mutation on the Scn1a gene (N1417H). Hence, comparison is made between the wild-type Cacna1a gene and the mutant Cacna1a gene (M251K), under the condition of the homozygous mutation of the Scn1a gene.

Moreover, a rat having a wild-type Scn1a gene and a wild-type Cacna1a gene (referred to as "Scn1a wild-type (homo)+Cacna1a wild-type (homo)") and a rat having a wild-type homozygous mutation on the Scn1a gene and a heterozygous mutation on the Cacna1a gene (referred to as "Scn1a wild-type (homo)+Cacna1a mutation (hetero)") were used as control. The following lists the genotypes of the rats used in the experiment. The following numbers (1) to (4) correspond to the numbers in (b) of FIG. 5.

(1) Scn1a$^{wt/wt}$Cacna1a$^{wt/wt}$ (Scn1a wild-type (homo)+Cacna1a wild-type (homo)) 14 males (2) Scn1a$^{mut/mut}$Cacna1a$^{wt/wt}$ (Scn1a mutant (homo)+Cacna1a wild-type (homo)) 7 males (3) Scn1a$^{mut/mut}$Cacna1a$^{wt/mut}$ (Scn1a mutant (homo)+Cacna1a mutant (hetero)) 17 males (4) Scn1a$^{wt/wt}$Cacna1a$^{wt/mut}$ (Scn1a wild-type (homo)+Cacna1a mutant (hetero)) 12 males.

Hot bath load (45° C.) were given on male rats of 5 weeks old of the groups (1) to (4) described above, to compare their body temperatures at a time when a convulsion is induced, their duration of the convulsion, and their severity score of the convulsion. A rectal temperature at the time when the seizure started was measured, to serve as the body temperature at the time when the convulsion was induced. The seizure severity score of the convulsion were evaluated as follows: 0=no seizure, 1=facial convulsion, 2=clonic convulsion of both arms while maintaining posture, 3=sprint or jump, 4=generalized convulsion unable to maintain posture, and 5=death caused by persistent convulsion.

Figure 9:
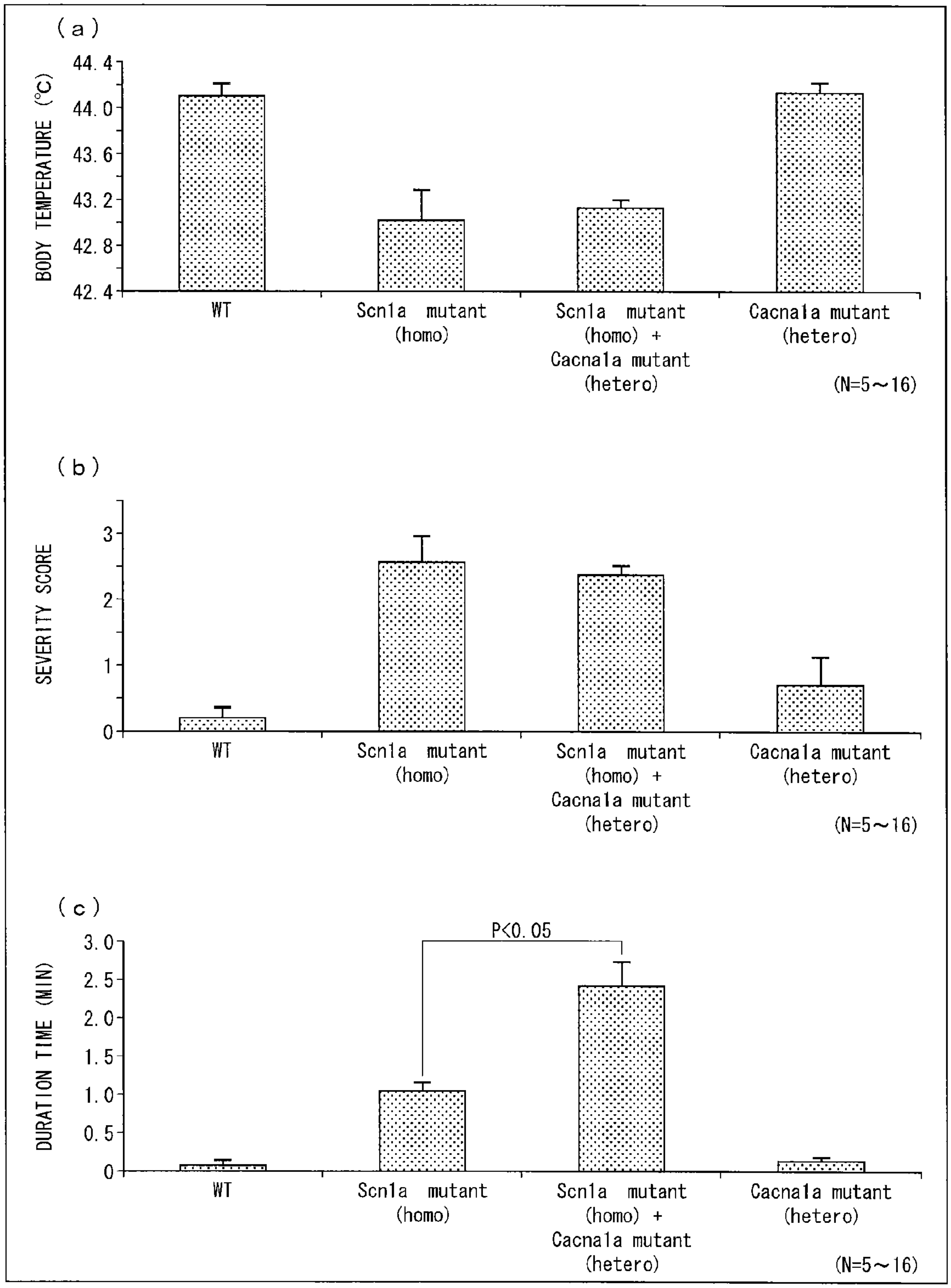
FIG. 9 is a view illustrating a result of examining an effect of a mutation on the Cacna1a gene, in a rat having a mutation on Scn1a gene. Illustrated in (a) is a body temperature at a time of convulsion onset (convulsion threshold), illustrated in (b) is a severity score, and illustrated in (c) is duration of the convulsion.

The results were as shown in FIG. 9. FIG. 9 is a view showing a result of the effect caused by the mutation on the Cacna1a gene in the Scn1a gene-mutated rat. In the graphs of (a) to (c) in FIG. 9, Scn1a$^{mut/mut}$Cacna1a$^{wt/wt}$ (the foregoing rat (2)) is shown as "Scn1a mutant (homo)". Scn1a$^{mut/mut}$Cacna1a$^{wt/mut}$ (the foregoing rat (3)) is shown as "Scn1a mutant (homo)+Cacna1a mutant (hetero)". Moreover, control Scn1a$^{wt/wt}$Cacna1a$^{wt/wt}$ (foregoing rat (1)) is shown as "WT", and control Scn1a$^{wt/wt}$Cacna1a$^{wt/mut}$ (foregoing rat (4)) is shown as "Cacna1a mutant (hetero)".

As a result of analysis, the group (3) rats (Scn1a mutant (homo)+Cacna1a mutant (hetero)) had no large difference in the body temperatures at the time of convulsion onset (convulsion threshold) ((a) of FIG. 9) and severity scores ((b) of FIG. 9), from those of the group (2) rats (Scn1a mutant (homo)+Cacna1a wild-type (homo)). However, it was found that the duration of the convulsion ((c) of FIG. 9) became significantly long. This result demonstrates that the mutation of the Cacna1a gene relates to the worsening of the symptoms of convulsion.

Figure 10:
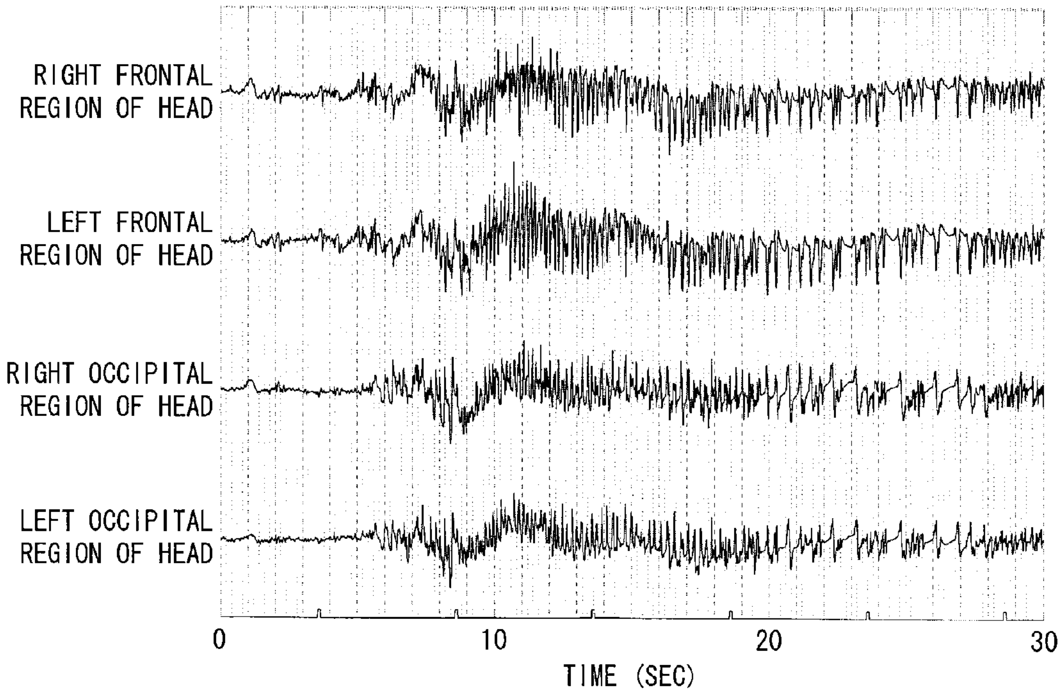
FIG. 10 is a view illustrating a part of an electroencephalogram at a time of seizure of a rat in group (3) (Scn1a mutant (homo)+Cacna1a mutant (hetero)).

Furthermore, FIG. 10 shows a part of an electroencephalogram during a seizure of a group (3) rat (Scn1a mutant (homo)+Cacna1a mutant (hetero)). It was considered from this result that a rat having a mutation on the Scn1a gene and the Cacna1a gene could serve as a model rat of the intractable Dravet syndrome. The model rat is expected to be usefully used in the future for clarification of the onset mechanism of the intractable Dravet syndrome, development of medicament for Dravet syndrome, and like uses.

Moreover, these results are considered as supporting the gene analysis data of Example 1, that a variation of the CACNA1A gene was detected in addition to a mutation on the SCN1A gene, in a patient of Dravet syndrome which is an intractable epilepsy. Namely, the method according to the present invention of obtaining data for assessing the potential for development of Dravet syndrome can be said as a technique supported by the gene analysis results of the Examples, a mutant channel function analysis result, and animal experiment results.

CONCLUSION

The present invention was developed based on a molecular foundation of development of the intractable Dravet syndrome; the assessment method according to the present invention can be said as useful as an early detection method of Dravet syndrome patients. By use of the assessment method according to the present invention, it is possible to find Dravet syndrome, which has an unfavorable prognosis, in high accuracy and at an early stage. This allows for an epilepsy specialist to prepare a treatment management system for the patient of Dravet syndrome from an early stage. As a result, this leads to improvement in therapeutic intervention of the patient, reduction of mental load on the family, and reduction of economical burden. Moreover, it is possible to carry out appropriate treatment to the Dravet syndrome patient, so therefore is considered as contributive to the reduction of medical fees.

Furthermore, with use of the kit according to the present invention, it is possible to easily detect the mutation for both the SCN1A gene and CACNA1A gene. Consequently, the kit according to the present invention is useful for a general pediatrician to distinguish a patient of Dravet syndrome who requires treatment by a specialist out of the benign febrile epilepsies, during the initial stage of the disease under the age of one.

By use of the assessment method and the kit according to the present invention, it is possible to detect with high accuracy a patient of Dravet syndrome at the point in time of under the age of one, which was difficult to detect until now. Moreover, by examining gene abnormalities upon sending the blood taken to an examination center, it is possible to detect Dravet syndrome patients in high accuracy even for a remote personal hospital or the like.

Moreover, the model animal and cell according to the present invention may be usefully used in the clarification of an onset mechanism of the intractable Dravet syndrome, the development of medicament for Dravet syndrome, and like uses.

<Primer Sequences>

Table 10 shows a nucleotide sequence of a primer pair used for amplifying the Scn1a gene and amplifying the Cacna1a gene.

TABLE 10

| | | |
|---|---|---|
| Scn1a amplification | Sense primer: 5'-TGA CTT TTC TTT CTC TCC GTT TG-3' | SEQ ID NO.: 5 |
| | Antisense primer: 5'-TGG CTG CAA TAA TCA CTT TGT T-3' | SEQ ID NO.: 6 |
| Cacna1a amplification | Sense primer: 5'- TCT CTG TCT CCC CAG GTT TAC-3' | SEQ ID NO: 7 |
| | Antisense primer: 5'-GTG GCT AAC ACA CAG CTT TGC-3' | SEQ ID NO.: 8 |

Tables 11 and 12 show nucleotide sequences of primer pairs used for detecting SCN1A gene genomes.

TABLE 11

| | | |
|---|---|---|
| Exon 1 amplification | Sense primer: 5'-tcatggcacagttcctgtatc-3' | SEQ ID NO.: 9 |
| | Antisense primer: 5'-gcagtaggcaattagcagcaa-3' | SEQ ID NO.: 10 |
| Exon 2 amplification | Sense primer: 5'-tggggcactttagaaattgtg-3' | SEQ ID NO.: 11 |
| | Antisense primer: 5'-tgacaaagatgcaaaatgagag-3' | SEQ ID NO.: 12 |
| Exon 3 amplification | Sense primer: 5'-gcagtttgggcttttcaatg-3' | SEQ ID NO.: 13 |
| | Antisense primer: 5'-tgagcattgtcctcttgctg-3' | SEQ ID NO.: 14 |
| Exon 4 amplification | Sense primer: 5'-agggctacgtttcatttgtatg-3' | SEQ ID NO.: 15 |
| | Antisense primer: 5'-tgtgctaaattgaaatccagag-3' | SEQ ID NO.: 16 |
| Exon 5 amplification | Sense primer: 5'-CAGCTCTTCGCACTTTCAGA-3' | SEQ ID NO.: 17 |
| | Antisense primer: 5'-TCAAGCAGAGAAGGATGCTGA-3' | SEQ ID NO.: 18 |
| Exon 6 amplification | Sense primer: 5'-agcgttgcaaacattcttgg-3' | SEQ ID NO.: 19 |
| | Antisense primer: 5'-gggatatccagcccctcaag-3' | SEQ ID NO.: 20 |
| Exon 7 amplification | Sense primer: 5'-gacaaatacttgtgcctttgaatg-3' | SEQ ID NO.: 21 |
| | Antisense primer: 5'-acataatctcatactttatcaaaaacc-3' | SEQ ID NO.: 22 |

TABLE 11-continued

| | | |
|---|---|---|
| Exon 8 amplification | Sense primer: 5'-gaaatggaggtgttgaaaatgc-3' | SEQ ID NO.: 23 |
| | Antisense primer: 5'-aatccttggcatcactctgc-3' | SEQ ID NO.: 24 |
| Exon 9 amplification | Sense primer: 5'-agtacagggtgctatgaccaac-3' | SEQ ID NO.: 25 |
| | Antisense primer: 5'-tcctcatacaaccacctgctc-3' | SEQ ID NO.: 26 |
| Exon 10 amplification | Sense primer: 5'-tctccaaaagccttcattagg-3' | SEQ ID NO.: 27 |
| | Antisense primer: 5'-ttctaattctccccctctctcc-3' | SEQ ID NO.: 28 |
| Exon 11 amplification | Sense primer: 5'-tcctcattctttaatcccaagg-3' | SEQ ID NO.: 29 |
| | Antisense primer: 5'-gccgttctgtagaaacactgg-3' | SEQ ID NO.: 30 |
| Exon 12 amplification | Sense primer: 5'-gtcagaaatatctgccatcacc-3' | SEQ ID NO.: 31 |
| | Antisense primer: 5'-gaatgcactattcccaactcac-3' | SEQID NO.: 32 |
| Exon 13 amplification | Sense primer: 5'-tgggctctatgtgtgtgtctg-3' | SEQ ID NO.: 33 |
| | Antisense primer: 5'-ggaagcatgaaggatggttg-3' | SEQ ID NO.: 34 |
| Exon 14 amplification | Sense primer: 5'-tacttcgcgtttccacaagg-3' | SEQ ID NO.: 35 |
| | Antisense primer: 5'-gctatgcaagaaccctgattg-3' | SEQ ID NO.: 36 |

TABLE 12

| | | |
|---|---|---|
| Exon 15 amplification | Sense primer: 5'-atgagcctgagcggttagg-3' | SEQ ID NO.: 37 |
| | Antisense primer: 5'-atacatgtgccatgctggtg-3' | SEQ ID NO.: 38 |
| Exon 16 amplification | Sense primer: 5'-tgctgtggtgtttccttctc-3' | SEQ ID NO.: 39 |
| | Antisense primer: 5'-tgtattcataccttcccacacc-3' | SEQ ID NO.: 40 |
| Exon 17 amplification | Sense primer: 5'-aaaagggttagcacagacaatg-3' | SEQ ID NO.: 41 |
| | Antisense primer: 5'-attgggcagatataatcaaagc-3' | SEQ ID NO.: 42 |
| Exon 18 amplification | Sense primer: 5'-cacacagctgatgaatgtgc-3' | SEQ ID NO.: 43 |
| | Antisense primer: 5'-tgaagggctacactttctgg-3' | SEQ ID NO.: 44 |
| Exon 19 amplification | Sense primer: 5'-tctgccctcctattccaatg-3' | SEQ ID NO.: 45 |
| | Antisense primer: 5'-gcccttgtcttccagaaatg-3' | SEQ ID NO.: 46 |
| Exon 20 amplification | Sense primer: 5'-aaaaattacatcctttacatcaaactg-3' | SEQ ID NO.: 47 |
| | Antisense primer: 5'-ttttgcatgcatagattttcc-3' | SEQ ID NO.: 48 |
| Exon 21 amplification | Sense primer: 5'-tgaaccttgcttttacatatcc-3' | SEQ ID NO.: 49 |
| | Antisense primer: 5'-acccatctgggctcataaac-3' | SEQ ID NO.: 50 |
| Exon 22 amplification | Sense primer: 5'-tgtcttggtccaaaatctgtg-3' | SEQ ID NO.: 51 |
| | Antisense primer: 5'-ttggtcgtttatgctttattcg-3' | SEQ ID NO.: 52 |

TABLE 12-continued

| | | |
|---|---|---|
| Exon 23 amplification | Sense primer: 5'-ccctaaaggccaatttcagg-3' | SEQ ID NO.: 53 |
| | Antisense primer: 5'-atttggcagagaaaacactcc-3' | SEQ ID NO.: 54 |
| Exon 24 amplification | Sense primer: 5'-gagatttgggggtgtttgtc-3' | SEQ ID NO.: 55 |
| | Antisense primer: 5'-ggattgtaatggggtgcttc-3' | SEQ ID NO.: 56 |
| Exon 25 amplification | Sense primer: 5'-caaaaatcagggccaatgac-3' | SEQ ID NO.: 57 |
| | Antisense primer: 5'-tgattgctgggatgatcttg-3' | SEQ ID NO.: 58 |
| Exon 26(1) amplification | Sense primer: 5'-aggactctgaaccttaccttgg-3' | SEQ ID NO.: 59 |
| | Antisense primer: 5'-ccatgaatcgctcttccatc-3' | SEQ ID NO.: 60 |
| Exon 26(2) amplification | Sense primer: 5'-tgtgggaacccatctgttg-3' | SEQ ID NO.: 61 |
| | Antisense primer: 5'-gtttgctgacaaggggtcac-3' | SEQ ID NO.: 62 |

Tables 13 and 14 show nucleotide sequences of primer pairs used for detecting the CACNA1A gene genome. In Tables 13 and 14, for example, E1F indicates an Exon 1 amplification sense primer, and E1Rv indicates an Exon 1 amplification antisense primer.

TABLE 13

| | | |
|---|---|---|
| Exon 1 amplification | CACNA1A-E1F: 5'-tctccgcagtcgtagctccag-3' | SEQ ID NO.: 63 |
| | CACNA1A-E1Rv: 5'-agagattctttcacactcctcc-3' | SEQ ID NO.: 64 |
| Exon 2 amplification | CACNA1A-E2F: 5'-tttagaagtcacctgatctggg-3' | SEQ ID NO.: 65 |
| | CACNA1A-E2Rv: 5'-gacagagcgagactctggttca-3' | SEQ ID NO.: 66 |
| Exon 3 amplification | CACNA1A-E3F: 5'-gacaagagaactctgcaagagg-3' | SEQ ID NO.: 67 |
| | CACNA1A-E3Rv: 5'-atacagctgagacatggaggtg-3' | SEQ ID NO.: 68 |
| Exon 4 amplification | CACNA1A-E4F: 5'-tttatcccgtgaggcaggtactg-3' | SEQ ID NO.: 69 |
| | CACNA1A-E4Rv: 5'-cctcctgagatgctctgcatag-3' | SEQ ID NO.: 70 |
| Exon 5 amplification | CACNA1A-E5F: 5'-tgtggtgcttccttcaccattg-3' | SEQ ID NO.: 71 |
| | CACNA1A-E5Rv: 5'-cagaggctatttcactcactgc-3' | SEQ ID NO.: 72 |
| Exon 6 amplification | CACNA1A-E6F: 5'-ccccaaagccaaacattgatctc-3' | SEQ ID NO.: 73 |
| | CACNA1A-E6Rv: 5'-actctgattgtccacacacactg-3' | SEQ ID NO.: 74 |
| Exon 7 amplification | CACNA1A-E7F: 5'-cagaaaacgttcctccatttccc-3' | SEQ ID NO.: 75 |
| | CACNA1A-E7Rv: 5'-aagcttcaatggcctctacttgg-3' | SEQ ID NO.: 76 |
| Exon 8 amplification | CACNA1A-E8F: 5'-gccatactctggcttttctatgc-3' | SEQ ID NO.: 77 |
| | CACNA1A-E8Rv: 5'-cgtgatgtcagatcctggcttc-3' | SEQ ID NO.: 78 |
| Exon 9 amplification | CACNA1A-E9F: 5'-gttggctattgctactgttgcg-3' | SEQ ID NO.: 79 |
| | CACNA1A-E9Rv: 5'-gatccttagaaccagtcacctg-3' | SEQ ID NO.: 80 |

TABLE 13-continued

| | | |
|---|---|---|
| Exon 10 amplification | CACNA1A-E10F: 5'-tgatagtgccaccttgaacctc-3' | SEQ ID NO.: 81 |
| | CACNA1A-E10Rv: 5'-tgatgtaatctgcccaggacac-3' | SEQ ID NO.: 82 |
| Exon 11 amplification | CACNA1A-E11F: 5'-ctgcaacagagaactatcagcc-3' | SEQ ID NO.: 83 |
| | CACNA1A-E11Rv: 5'-aagagaagtggaaaaagggtgtg-3' | SEQ ID NO.: 84 |
| Exon 12 amplification | CACNA1A-E12F: 5'-gtagttctagcatgttggaggc-3' | SEQ ID NO.: 85 |
| | CACNA1A-E12Rv: 5'-atctgtcattccaggcaagagc-3' | SEQ ID NO.: 86 |
| Exon 13~15 amplification | CACNA1A-E13F: 5'-atggatgaatgaggggtcaag-3' | SEQ ID NO.: 87 |
| | CACNA1A-E15Rv: 5'-agcaggcactttcatctgtgac-3' | SEQ ID NO.: 88 |
| Exon 13~15 amplification | CACNA1A-E13F2: 5'-tccatttggagggaggagtttg-3' | SEQ ID NO.: 89 |
| | CACNA1A-E15Rv: 5'-agcaggcactttcatctgtgac-3' | SEQ ID NO.: 88 |
| Exon 14~15 amplification | CACNA1A-E14F: 5'-cctccagaaagttgggaaagtg-3' | SEQ ID NO.: 90 |
| | CACNA1A-E15Rv: 5'-agcaggcactttcatctgtgac-3' | SEQ ID NO.: 88 |
| Exon 16~17 amplification | CACNA1A-E16F: 5'-aaggagaagccaacacggagtc-3' | SEQ ID NO.: 91 |
| | CACNA1A-E17Rv: 5'-ggtggtaactttgccagagaaac-3' | SEQ ID NO.: 92 |
| Exon 18 amplification | CACNA1A-E18F: 5'-agcaggtacccattccaattgg-3' | SEQ ID NO.: 93 |
| | CACNA1A-E18Rv: 5'-aatctgtgcctgggatagtgtg-3' | SEQ ID NO.: 94 |
| Exon 19 amplification (1) | CACNA1A-E19F: 5'-cctgactcagatgctcacagac-3' | SEQ ID NO.: 95 |
| | CACNA1A-E19Rv: 5'-acacagcacgtgctactttggc-3' | SEQ ID NO.: 96 |
| Exon 19 amplification (2) | CACNA1A-E19F2: 5'-gaggacttcctcaggaaacag-3' | SEQ ID NO.: 97 |
| | CACNA1A-E19Rv: 5'-acacagcacgtgctactttggc-3' | SEQ ID NO.: 96 |
| Exon 20 amplification | CACNA1A-E20F: 5'-agatggaatcttagctaggatcc-3' | SEQ ID NO.: 98 |
| | CACNA1A-E20Rv: 5'-aattatctcactgaaccctccac-3' | SEQ ID NO.: 99 |
| Exon 21 amplification | CACNA1A-E21F: 5'-agaaatgtcagccgcttcttgc-3' | SEQ ID NO.: 100 |
| | CACNA1A-E21Rv: 5'-ggtggtcaacactcactcattg-3' | SEQ ID NO.: 101 |
| Exon 22 amplification | CACNA1A-E22F: 5'-tttgttgtgtaggaggccttgg-3' | SEQ ID NO.: 102 |
| | CACNA1A-E22Rv: 5'-aacatcccaccctacctatgag-3' | SEQ ID NO.: 103 |

TABLE 14

| | | |
|---|---|---|
| Exon 23 amplification | CACNA1A-E23F: 5'-cctgcgcaactgtatatagcag-3' | SEQ ID NO.: 104 |
| | CACNA1A-E23Rv: 5'-ctcaacctcctgatctcaagtg-3' | SEQ ID NO.: 105 |
| Exon 24 amplification | CACNA1A-E24F: 5'-cccaaagtttggatctaagagcc-3' | SEQ ID NO.: 106 |
| | CACNA1A-E24Rv: 5'-aaagccatcgaagctcttcctg-3' | SEQ ID NO.: 107 |

TABLE 14-continued

| | | |
|---|---|---|
| Exon 25 amplification | CACNA1A-E25F: 5'-caggtgaaatggaccactcttc-3' | SEQ ID NO.: 108 |
| | CACNA1A-E25Rv: 5'-tccttgagcagtgtacaacctg-3' | SEQ ID NO.: 109 |
| Exon 26 amplification | CACNA1A-E26F: 5'-gaatgccaggattgagtccaac-3' | SEQ ID NO.: 110 |
| | CACNA1A-E26Rv: 5'-gaatgtgctggaaagtggagac-3' | SEQ ID NO.: 111 |
| Exon 27 amplification | CACNA1A-E27F: 5'-cactgcttcccaagcagtctag-3' | SEQ ID NO.: 112 |
| | CACNA1A-E27Rv: 5'-attacaggcgtgagccaccatg-3' | SEQ ID NO.: 113 |
| Exon 28 amplification | CACNA1A-E28F: 5'-tttccctctgttcctgttctgc-3' | SEQ ID NO.: 114 |
| | CACNA1A-E28Rv: 5'-ttcggttgggacaatgcttctg-3' | SEQ ID NO.: 115 |
| Exon 29 amplification | CACNA1A-E29F: 5'-ctcaagcaactgtagctgttgg-3' | SEQ ID NO.: 116 |
| | CACNA1A-E29Rv: 5'-ttatcagggtagaggcaggaac-3' | SEQ ID NO.: 117 |
| Exon 30 amplification | CACNA1A-E30F: 5'-gtgaaaagaagagcctagtccg-3' | SEQ ID NO.: 118 |
| | CACNA1A-E30Rv: 5'-atggtaacactcacaggttgg-3' | SEQ ID NO.: 119 |
| Exon 31 amplification | CACNA1A-E31F: 5'-gcccttcgaacaaccataactg-3' | SEQ ID NO.: 120 |
| | CACNA1A-E31Rv: 5'-cctacagccaagctttggttac-3' | SEQ ID NO.: 121 |
| Exon 32 amplification | CACNA1A-E32F: 5'-cccattggtttttggcactgg-3' | SEQ ID NO.: 122 |
| | CACNA1A-E32Rv: 5'-ggacagacagacagaggagag-3' | SEQ ID NO.: 123 |
| Exon 33~35 amplification | CACNA1A-E33F: 5'-tgttggttggcttcatgtaggg-3' | SEQ ID NO.: 124 |
| | CACNA1A-E35Rv: 5'-cagaattatcagagcaggtccc-3' | SEQ ID NO.: 125 |
| Exon 36 amplification | CACNA1A-E36F: 5'-tctcagctcccagtaaaaggag-3' | SEQ ID NO.: 126 |
| | CACNA1A-E36Rv: 5'-caacagtgctgagtttgagacg-3' | SEQ ID NO.: 127 |
| Exon 37 amplification | CACNA1A-E37F: 5'-ggcctctgtgtacatgtctttg-3' | SEQ ID NO.: 128 |
| | CACNA1A-E37Rv: 5'-gggtatgcaagggtgatgattc-3' | SEQ ID NO.: 129 |
| Exon 38 amplification | CACNA1A-E38F: 5'-tgtttctccccacctctcttc-3' | SEQ ID NO.: 130 |
| | CACNA1A-E38Rv: 5'-aaaaaaacccagtgcctggacg-3' | SEQ ID NO.: 131 |
| Exon 39 amplification | CACNA1A-E39F: 5'-agaaactgagtactgggacagg-3' | SEQ ID NO.: 132 |
| | CACNA1A-E39Rv: 5'-ggaagagtgaatgaagatccgg-3' | SEQ ID NO.: 133 |
| Exon 40~41 amplification | CACNA1A-E40F: 5'-aaagattggggtctcgttctcg-3' | SEQ ID NO.: 134 |
| | CACNA1A-E41Rv: 5'-ccctcatattccagttggttcc-3' | SEQ ID NO.: 135 |
| Exon 42~44 amplification | CACNA1A-E42F: 5'-gtgtgtgtgtgtgtatactggg-3' | SEQ ID NO.: 136 |
| | CACNA1A-E44Rv: 5'-cagactgcttcagagactgaag-3' | SEQ ID NO.: 137 |
| Exon 45 amplification | CACNA1A-E45F: 5'-ccgatttctcttgatgccagtg-3' | SEQ ID NO.: 138 |
| | CACNA1A-E45Rv: 5'-agggtgcgattgccaaagaaag-3' | SEQ ID NO.: 139 |

TABLE 14-continued

| | | |
|---|---|---|
| Exon 46~47 amplification | CACNA1A-E46F: 5'-acccagagccctgattgatcag-3' | SEQ ID NO.: 140 |
| | CACNA1A-E47Rv: 5'-ttggatggggtatccccttctc-3' | SEQ ID NO.: 141 |
| Exon 48 amplification | CACNA1A-E48F: 5'-tctcttcctcccaatcccgtg-3' | SEQ ID NO.: 142 |
| | CACNA1A-E48Rv: 5'-tgcccaggagggtctcttttg-3' | SEQ ID NO.: 143 |

INDUSTRIAL APPLICABILITY

As described above, by detecting the presence of a mutation on both α-subunit type 1 of voltage-gated sodium ion channel $Na_V1.1$ and α-subunit type 1 of voltage-gated calcium ion channel $Ca_V2.1$, it is possible to obtain data for assessing a potential for development of Dravet syndrome of a subject who has not yet been subjected to onset of Dravet syndrome, with high accuracy. Hence, it is possible to distinguish a patient of Dravet syndrome that requires treatment by a specialist, out of benign febrile seizure patents, at an initial stage of disease under the age of one. Hence, it is possible to use not only in the field of diagnosis medical treatment such as medical devices, diagnosis kits and the like, but broadly in the health science and medical field industry.

Moreover, in the present invention, by introducing a mutation on both of α-subunit type 1 of voltage-gated sodium ion channel $Na_V1.1$ and α-subunit type 1 of voltage-gated calcium ion channel $Ca_V2.1$, it is possible to produce a model animal of Dravet syndrome. Such a model animal of Dravet syndrome can be used for development of medicament and treatment methods of Dravet syndrome. Hence, the present invention can be widely used in the industry of life science fields including the pharmaceutical field.

The invention claimed is:

1. A model animal of Dravet syndrome, having a mutation on both α-subunit type 1 of voltage-gated sodium ion channel $Na_V1.1$ (Nav1.1α1) and α-subunit type 1 of voltage-gated calcium ion channel $Ca_V2.1$ (Cav2.1α1), wherein the mutation on the Nav1.1α1 is selected from the group consisting of A1685D, F902C, deletion of Exon 10, G163E, G177R, K547fsX570, P707fsX714, Q1277X, Q1450R, R1648C, R377L, R712X, R865X, S1574X, T1082fsX1086, T1909I, V1390M, V212A, and W738fsX746, and the mutation on the Cav2.1α1 is selected from the group consisting of A924G, E921D, E996V, G1108S, G266S, K472R, R1126H and R2201Q, wherein in the case that the mutation on the Nav1.1α1 is G177R, the mutation on the Cav2.1α1 is G266S, in the case that the mutation on the Nav1.1α1 is W738fsX746, the mutation on the Cav2.1α1 is K472R, in the case that the mutation on the Nav1.1α1 is V1390M, the mutation on the Cav2.1α1 is A924G, in the case that the mutation on the Nav1.1α1 is selected from the group consisting of A1685D, F902C, deletion of Exon 10, P707fsX714, Q1277X, Q1450R, R377L, R865X, T1082fsX1086 and V212A, the mutation on the Cav2.1α1 is at least one of E921D and E996V, in the case that the mutation on the Nav1.1α1 is T1909I, the mutation of Cav2.1α1 is at least one of E921D, E996V, R1126H and R2201Q, in the case that the mutation on the Nav1.1α1 is selected from the group consisting of G163E, K547fsX570 and S1574X, the mutation on the Cav2.1α1 is at least one of R1126H and R2201Q, and in the case that the mutation on the Nav1.1α1 is selected from the group consisting of R712X and R1648C, the mutation on the Cav2.1α1 is G1108S.

2. The model animal according to claim 1, wherein the mutation on the Nav1.1α1 is selected from the group consisting of V212A, R377L, deletion of exon 10, P707fsX714, R865X, F902C, T1082fsX1086, Q1277X, Q1450R, A1685D, and wherein the mutation on the Cav2.1α1 is either E921D or E996V.

3. The model animal according to claim 1, wherein the mutation on the Nav1.1α1 is T1909I, and wherein the mutation on the Cav2.1α1 is selected form the group consisting of E921D, E996V, R1126H, and R2201Q.

4. The method according to claim 1, wherein the mutation on the Nav1.1α1 is selected from the group consisting of G163E, K547fsX570, and S1574X, and wherein the mutation on the Cav2.1α1 is either R1126H or R2201Q.

5. A method of producing a model animal of Dravet syndrome as set forth in claim 1, the method comprising:

introducing a mutation on a α-subunit type 1 of the voltage-gated sodium ion channel $Na_V1.1$ (Nav1.1α1); and introducing a mutation on a α-subunit type 1 of the voltage-gated calcium ion channel $Ca_V2.1$ (Cav2.1α1), wherein the mutation on the Nav1.1α1 is selected from the group consisting of A1685D, F902C, deletion of Exon 10, G163E, G177R, K547fsX570, P707fsX714, Q1277X, Q1450R, R1648C, R377L, R712X, R865X, S1574X, T1082fsX1086, T1909I, V1390M, V212A, and W738fsX746, and the mutation on the Nav1.1α1 is selected from the group consisting of A924G, E921D, E996V, G1108S, G266S, K472R, R1126H and R2201Q, wherein in the case that the mutation on the Nav1.1α1 is G177R, the mutation on the Cav2.1α1 is G266S, in the case that the mutation on the Nav1.1α1 is W738fsX746, the mutation on the Cav2.1α1 is K472R, in the case that the mutation on the Nav1.1α1 is V1390M, the mutation on the Cav2.1α1 is A924G, in the case that the mutation on the Nav1.1α1 is selected from the group consisting of A1685D, F902C, deletion of Exon 10, P707fsX714, Q1277X, Q1450R, R377L, R865X, T1082fsX1086 and V212A, the mutation on the Cav2.1α1 is at least one of E921D and E996V, in the case that the mutation on the Nav1.1α1 is T1909I, the mutation of Cav2.1α1 is at least one of E921D, E996V, R1126H and R2201Q, in the case that the mutation on the Nav1.1α1 is selected from the group consisting of G163E, K547fsX570 and S1574X, the mutation on the Cav2.1α1 is at least one of R1126H and R2201Q, and in the case that the mutation on the Nav1.1α1 is selected from the group consisting of R712X and R1648C, the mutation on the Cav2.1α1 is G1108S.

6. The method according to claim 5, wherein the mutation on the Nav1.1α1 is selected from the group consisting of V212A, R377L, deletion of exon 10, P707fsX714, R865X, F902C, T1082fsX1086, Q1277X, Q1450R, A1685D, and wherein the mutation on the Cav2.1α1 is either E921D or E996V.

7. The method according to claim 5, wherein the mutation on the Nav1.1α1 is T1909I, and wherein the mutation on the Cav2.1α1 is selected form the group consisting of E921D, E996V, R1126H, and R2201Q.

8. The method according to claim 5, wherein the mutation on the Nav1.1α1 is selected from the group consisting of G163E, K547fsX570, and S1574X, and wherein the mutation on the Cav2.1α1 is either R1126H or R2201Q.

9. A screening method of a drug for treating Dravet syndrome, the method comprising:

administering a candidate agent to the model animal of Dravet syndrome as set forth in claim 1; and assessing whether or not the administering of the candidate agent has made Dravet syndrome improve or cure in the model animal of Dravet syndrome.

* * * * *

SEQUENCE LISTING

```
<160> NUMBER OF SEQ ID NOS: 152

<210> SEQ ID NO 1
<211> LENGTH: 2009
<212> TYPE: PRT
<213> ORGANISM: Homo sapiens

<400> SEQUENCE: 1

Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
```

-continued

```
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Gln Ala Ala Thr Ala
    450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
        515                 520                 525

Ile Arg Arg Lys Gly Phe Arg Phe Ser Ile Glu Gly Asn Arg Leu Thr
    530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
        595                 600                 605

Phe Val Pro Arg Arg His Gly Glu Arg Arg Asn Ser Asn Leu Ser Gln
    610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
            660                 665                 670
```

-continued

```
Ile Asp Lys Pro Ala Thr Asp Asp Asn Gly Thr Thr Thr Glu Thr Glu
        675                 680                 685

Met Arg Lys Arg Arg Ser Ser Ser Phe His Val Ser Met Asp Phe Leu
    690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
            740                 745                 750

Tyr Trp Leu Lys Val Lys His Val Val Asn Leu Val Val Met Asp Pro
        755                 760                 765

Phe Val Asp Leu Ala Ile Thr Ile Cys Ile Val Leu Asn Thr Leu Phe
    770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
            820                 825                 830

Asn Ile Phe Asp Gly Phe Ile Val Thr Leu Ser Leu Val Glu Leu Gly
        835                 840                 845

Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
            900                 905                 910

Gly Lys Ser Tyr Lys Asp Cys Val Cys Lys Ile Ala Ser Asp Cys Gln
        915                 920                 925

Leu Pro Arg Trp His Met Asn Asp Phe Phe His Ser Phe Leu Ile Val
    930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
            980                 985                 990

Ser Ser Phe Ser Ala Asp Asn Leu  Ala Ala Thr Asp Asp  Asp Asn Glu
        995                 1000                 1005

Met Asn  Asn Leu Gln Ile Ala  Val Asp Arg Met His  Lys Gly Val
    1010                 1015                 1020

Ala Tyr  Val Lys Arg Lys Ile  Tyr Glu Phe Ile Gln  Gln Ser Phe
    1025                 1030                 1035

Ile Arg  Lys Gln Lys Ile Leu  Asp Glu Ile Lys Pro  Leu Asp Asp
    1040                 1045                 1050

Leu Asn  Asn Lys Lys Asp Ser  Cys Met Ser Asn His  Thr Thr Glu
    1055                 1060                 1065

Ile Gly  Lys Asp Leu Asp Tyr  Leu Lys Asp Val Asn  Gly Thr Thr
    1070                 1075                 1080
```

-continued

```
Ser Gly  Ile Gly Thr Gly Ser  Ser Val Glu Lys Tyr  Ile Ile Asp
    1085                 1090                 1095

Glu Ser  Asp Tyr Met Ser Phe  Ile Asn Asn Pro Ser  Leu Thr Val
    1100                 1105                 1110

Thr Val  Pro Ile Ala Val Gly  Glu Ser Asp Phe Glu  Asn Leu Asn
    1115                 1120                 1125

Thr Glu  Asp Phe Ser Ser Glu  Ser Asp Leu Glu Glu  Ser Lys Glu
    1130                 1135                 1140

Lys Leu  Asn Glu Ser Ser Ser  Ser Ser Glu Gly Ser  Thr Val Asp
    1145                 1150                 1155

Ile Gly  Ala Pro Val Glu Glu  Gln Pro Val Val Glu  Pro Glu Glu
    1160                 1165                 1170

Thr Leu  Glu Pro Glu Ala Cys  Phe Thr Glu Gly Cys  Val Gln Arg
    1175                 1180                 1185

Phe Lys  Cys Cys Gln Ile Asn  Val Glu Glu Gly Arg  Gly Lys Gln
    1190                 1195                 1200

Trp Trp  Asn Leu Arg Arg Thr  Cys Phe Arg Ile Val  Glu His Asn
    1205                 1210                 1215

Trp Phe  Glu Thr Phe Ile Val  Phe Met Ile Leu Leu  Ser Ser Gly
    1220                 1225                 1230

Ala Leu  Ala Phe Glu Asp Ile  Tyr Ile Asp Gln Arg  Lys Thr Ile
    1235                 1240                 1245

Lys Thr  Met Leu Glu Tyr Ala  Asp Lys Val Phe Thr  Tyr Ile Phe
    1250                 1255                 1260

Ile Leu  Glu Met Leu Leu Lys  Trp Val Ala Tyr Gly  Tyr Gln Thr
    1265                 1270                 1275

Tyr Phe  Thr Asn Ala Trp Cys  Trp Leu Asp Phe Leu  Ile Val Asp
    1280                 1285                 1290

Val Ser  Leu Val Ser Leu Thr  Ala Asn Ala Leu Gly  Tyr Ser Glu
    1295                 1300                 1305

Leu Gly  Ala Ile Lys Ser Leu  Arg Thr Leu Arg Ala  Leu Arg Pro
    1310                 1315                 1320

Leu Arg  Ala Leu Ser Arg Phe  Glu Gly Met Arg Val  Val Val Asn
    1325                 1330                 1335

Ala Leu  Leu Gly Ala Ile Pro  Ser Ile Met Asn Val  Leu Leu Val
    1340                 1345                 1350

Cys Leu  Ile Phe Trp Leu Ile  Phe Ser Ile Met Gly  Val Asn Leu
    1355                 1360                 1365

Phe Ala  Gly Lys Phe Tyr His  Cys Ile Asn Thr Thr  Thr Gly Asp
    1370                 1375                 1380

Arg Phe  Asp Ile Glu Asp Val  Asn Asn His Thr Asp  Cys Leu Lys
    1385                 1390                 1395

Leu Ile  Glu Arg Asn Glu Thr  Ala Arg Trp Lys Asn  Val Lys Val
    1400                 1405                 1410

Asn Phe  Asp Asn Val Gly Phe  Gly Tyr Leu Ser Leu  Leu Gln Val
    1415                 1420                 1425

Ala Thr  Phe Lys Gly Trp Met  Asp Ile Met Tyr Ala  Ala Val Asp
    1430                 1435                 1440

Ser Arg  Asn Val Glu Leu Gln  Pro Lys Tyr Glu Glu  Ser Leu Tyr
    1445                 1450                 1455

Met Tyr  Leu Tyr Phe Val Ile  Phe Ile Ile Phe Gly  Ser Phe Phe
    1460                 1465                 1470

Thr Leu  Asn Leu Phe Ile Gly  Val Ile Ile Asp Asn  Phe Asn Gln
```

```
    1475                1480                1485

Gln Lys  Lys Lys Phe Gly Gly  Gln Asp Ile Phe Met  Thr Glu Glu
    1490                1495                1500

Gln Lys  Lys Tyr Tyr Asn Ala  Met Lys Lys Leu Gly  Ser Lys Lys
    1505                1510                1515

Pro Gln  Lys Pro Ile Pro Arg  Pro Gly Asn Lys Phe  Gln Gly Met
    1520                1525                1530

Val Phe  Asp Phe Val Thr Arg  Gln Val Phe Asp Ile  Ser Ile Met
    1535                1540                1545

Ile Leu  Ile Cys Leu Asn Met  Val Thr Met Met Val  Glu Thr Asp
    1550                1555                1560

Asp Gln  Ser Glu Tyr Val Thr  Thr Ile Leu Ser Arg  Ile Asn Leu
    1565                1570                1575

Val Phe  Ile Val Leu Phe Thr  Gly Glu Cys Val Leu  Lys Leu Ile
    1580                1585                1590

Ser Leu  Arg His Tyr Tyr Phe  Thr Ile Gly Trp Asn  Ile Phe Asp
    1595                1600                1605

Phe Val  Val Val Ile Leu Ser  Ile Val Gly Met Phe  Leu Ala Glu
    1610                1615                1620

Leu Ile  Glu Lys Tyr Phe Val  Ser Pro Thr Leu Phe  Arg Val Ile
    1625                1630                1635

Arg Leu  Ala Arg Ile Gly Arg  Ile Leu Arg Leu Ile  Lys Gly Ala
    1640                1645                1650

Lys Gly  Ile Arg Thr Leu Leu  Phe Ala Leu Met Met  Ser Leu Pro
    1655                1660                1665

Ala Leu  Phe Asn Ile Gly Leu  Leu Leu Phe Leu Val  Met Phe Ile
    1670                1675                1680

Tyr Ala  Ile Phe Gly Met Ser  Asn Phe Ala Tyr Val  Lys Arg Glu
    1685                1690                1695

Val Gly  Ile Asp Asp Met Phe  Asn Phe Glu Thr Phe  Gly Asn Ser
    1700                1705                1710

Met Ile  Cys Leu Phe Gln Ile  Thr Thr Ser Ala Gly  Trp Asp Gly
    1715                1720                1725

Leu Leu  Ala Pro Ile Leu Asn  Ser Lys Pro Pro Asp  Cys Asp Pro
    1730                1735                1740

Asn Lys  Val Asn Pro Gly Ser  Ser Val Lys Gly Asp  Cys Gly Asn
    1745                1750                1755

Pro Ser  Val Gly Ile Phe Phe  Phe Val Ser Tyr Ile  Ile Ile Ser
    1760                1765                1770

Phe Leu  Val Val Val Asn Met  Tyr Ile Ala Val Ile  Leu Glu Asn
    1775                1780                1785

Phe Ser  Val Ala Thr Glu Glu  Ser Ala Glu Pro Leu  Ser Glu Asp
    1790                1795                1800

Asp Phe  Glu Met Phe Tyr Glu  Val Trp Glu Lys Phe  Asp Pro Asp
    1805                1810                1815

Ala Thr  Gln Phe Met Glu Phe  Glu Lys Leu Ser Gln  Phe Ala Ala
    1820                1825                1830

Ala Leu  Glu Pro Pro Leu Asn  Leu Pro Gln Pro Asn  Lys Leu Gln
    1835                1840                1845

Leu Ile  Ala Met Asp Leu Pro  Met Val Ser Gly Asp  Arg Ile His
    1850                1855                1860

Cys Leu  Asp Ile Leu Phe Ala  Phe Thr Lys Arg Val  Leu Gly Glu
    1865                1870                1875
```

Ser Gly Glu Met Asp Ala Leu Arg Ile Gln Met Glu Glu Arg Phe
1880 1885 1890

Met Ala Ser Asn Pro Ser Lys Val Ser Tyr Gln Pro Ile Thr Thr
1895 1900 1905

Thr Leu Lys Arg Lys Gln Glu Glu Val Ser Ala Val Ile Ile Gln
1910 1915 1920

Arg Ala Tyr Arg Arg His Leu Leu Lys Arg Thr Val Lys Gln Ala
1925 1930 1935

Ser Phe Thr Tyr Asn Lys Asn Lys Ile Lys Gly Gly Ala Asn Leu
1940 1945 1950

Leu Ile Lys Glu Asp Met Ile Ile Asp Arg Ile Asn Glu Asn Ser
1955 1960 1965

Ile Thr Glu Lys Thr Asp Leu Thr Met Ser Thr Ala Ala Cys Pro
1970 1975 1980

Pro Ser Tyr Asp Arg Val Thr Lys Pro Ile Val Glu Lys His Glu
1985 1990 1995

Gln Glu Gly Lys Asp Glu Lys Ala Lys Gly Lys
2000 2005

<210> SEQ ID NO 2
<211> LENGTH: 6030
<212> TYPE: DNA
<213> ORGANISM: Homo sapiens

<400> SEQUENCE: 2
atggagcaaa cagtgcttgt accaccagga cctgacagct tcaacttctt caccagagaa 60
tctcttgcgg ctattgaaag acgcattgca gaagaaaagg caaagaatcc caaaccagac 120
aaaaaagatg acgacgaaaa tggcccaaag ccaaatagtg acttggaagc tggaaagaac 180
cttccattta tttatggaga cattcctcca gagatggtgt cagagcccct ggaggacctg 240
gacccctact atatcaataa gaaaactttt atagtattga ataaagggaa ggccatcttc 300
cggttcagtg ccacctctgc cctgtacatt ttaactccct tcaatcctct taggaaaata 360
gctattaaga ttttggtaca ttcattattc agcatgctaa ttatgtgcac tattttgaca 420
aactgtgtgt ttatgacaat gagtaaccct cctgattgga caaagaatgt agaatacacc 480
ttcacaggaa tatatacttt tgaatcactt ataaaaatta ttgcaagggg attctgttta 540
gaagatttta ctttccttcg ggatccatgg aactggctcg atttcactgt cattacattt 600
gcgtacgtca cagagtttgt ggacctgggc aatgtctcgg cattgagaac attcagagtt 660
ctccgagcat tgaagacgat ttcagtcatt ccaggcctga aaaccattgt gggagccctg 720
atccagtctg tgaagaagct ctcagatgta atgatcctga ctgtgttctg tctgagcgta 780
tttgctctaa ttgggctgca gctgttcatg ggcaacctga ggaataaatg tatacaatgg 840
cctcccacca atgcttcctt ggaggaacat agtatagaaa agaatataac tgtgaattat 900
aatggtacac ttataaatga aactgtcttt gagtttgact ggaagtcata tattcaagat 960
tcaagatatc attatttcct ggagggtttt ttagatgcac tactatgtgg aaatagctct 1020
gatgcaggcc aatgtccaga gggatatatg tgtgtgaaag ctggtagaaa tcccaattat 1080
ggctacacaa gctttgatac cttcagttgg gctttttttgt ccttgtttcg actaatgact 1140
caggacttct gggaaaatct ttatcaactg acattacgtg ctgctgggaa aacgtacatg 1200 atatttttg tattggtcat tttcttgggc tcattctacc taataaattt gatcctggct 1260
gtggtggcca tggcctacga ggaacagaat caggccacct tggaagaagc agaacagaaa 1320

-continued

```
gaggccgaat ttcagcagat gattgaacag cttaaaaagc aacaggaggc agctcagcag   1380
gcagcaacgg caactgcctc agaacattcc agagagccca gtgcagcagg caggctctca   1440
gacagctcat ctgaagcctc taagttgagt tccaagagtg ctaaggaaag aagaaatcgg   1500
aggaagaaaa gaaaacagaa agagcagtct ggtggggaag agaaagatga ggatgaattc   1560
caaaaatctg aatctgagga cagcatcagg aggaaaggtt ttcgcttctc cattgaaggg   1620
aaccgattga catatgaaaa gaggtactcc tccccacacc agtctttgtt gagcatccgt   1680
ggctccctat tttcaccaag gcgaaatagc agaacaagcc ttttcagctt tagagggcga   1740
gcaaaggatg tgggatctga gaacgacttc gcagatgatg agcacagcac ctttgaggat   1800
aacgagagcc gtagagattc cttgtttgtg ccccgacgac acggagagag acgcaacagc   1860
aacctgagtc agaccagtag gtcatcccgg atgctggcag tgtttccagc gaatgggaag   1920
atgcacagca ctgtggattg caatggtgtg gtttccttgg ttggtggacc ttcagttcct   1980
acatcgcctg ttggacagct tctgccagag gtgataatag ataagccagc tactgatgac   2040
aatggaacaa ccactgaaac tgaaatgaga aagagaaggt caagttcttt ccacgtttcc   2100
atggactttc tagaagatcc ttcccaaagg caacgagcaa tgagtatagc cagcattcta   2160
acaaatacag tagaagaact tgaagaatcc aggcagaaat gcccaccctg ttggtataaa   2220
ttttccaaca tattcttaat ctgggactgt tctccatatt ggttaaaagt gaaacatgtt   2280
gtcaacctgg ttgtgatgga cccatttgtt gacctggcca tcaccatctg tattgtctta   2340
aatactcttt tcatggccat ggagcactat ccaatgacgg accatttcaa taatgtgctt   2400
acagtaggaa acttggtttt cactgggatc tttacagcag aaatgtttct gaaaattatt   2460
gccatggatc cttactatta tttccaagaa ggctggaata tctttgacgg ttttattgtg   2520
acgcttagcc tggtagaact tggactcgcc aatgtggaag gattatctgt tctccgttca   2580
tttcgattgc tgcgagtttt caagttggca aaatcttggc caacgttaaa tatgctaata   2640
aagatcatcg gcaattccgt gggggctctg ggaaatttaa ccctcgtctt ggccatcatc   2700
gtcttcattt ttgccgtggt cggcatgcag ctctttggta aaagctacaa agattgtgtc   2760
tgcaagatcg ccagtgattg tcaactccca cgctggcaca tgaatgactt cttccactcc   2820
ttcctgattg tgttccgcgt gctgtgtggg gagtggatag agaccatgtg ggactgtatg   2880
gaggttgctg gtcaagccat gtgccttact gtcttcatga tggtcatggt gattggaaac   2940
ctagtggtcc tgaatctctt tctggccttg cttctgagct catttagtgc agacaacctt   3000
gcagccactg atgatgataa tgaaatgaat aatctccaaa ttgctgtgga taggatgcac   3060
aaaggagtag cttatgtgaa aagaaaaata tatgaattta ttcaacagtc cttcattagg   3120
aaacaaaaga ttttagatga aattaaacca cttgatgatc taaacaacaa gaaagacagt   3180
tgtatgtcca atcatacaac agaaattggg aaagatcttg actatcttaa agatgtaaat   3240
ggaactacaa gtggtatagg aactggcagc agtgttgaaa aatacattat tgatgaaagt   3300
gattacatgt cattcataaa caaccccagt cttactgtga ctgtaccaat tgctgtagga   3360
gaatctgact ttgaaaattt aaacacggaa gactttagta gtgaatcgga tctggaagaa   3420
agcaaagaga aactgaatga aagcagtagc tcatcagaag gtagcactgt ggacatcggc   3480
gcacctgtag aagaacagcc cgtagtggaa cctgaagaaa ctcttgaacc agaagcttgt   3540
ttcactgaag gctgtgtaca aagattcaag tgttgtcaaa tcaatgtgga agaaggcaga   3600
ggaaaacaat ggtggaacct gagaaggacg tgtttccgaa tagttgaaca taactggttt   3660
```

-continued

```
gagaccttca ttgttttcat gattctcctt agtagtggtg ctctggcatt tgaagatata   3720
tatattgatc agcgaaagac gattaagacg atgttggaat atgctgacaa ggttttcact   3780
tacattttca ttctggaaat gcttctaaaa tgggtggcat atggctatca aacatatttc   3840
accaatgcct ggtgttggct ggacttctta attgttgatg tttcattggt cagtttaaca   3900
gcaaatgcct tgggttactc agaacttgga gccatcaaat ctctcaggac actaagagct   3960
ctgagacctc taagagcctt atctcgattt gaagggatga gggtggttgt gaatgccctt   4020
ttaggagcaa ttccatccat catgaatgtg cttctggttt gtcttatatt ctggctaatt   4080
ttcagcatca tgggcgtaaa tttgtttgct ggcaaattct accactgtat taacaccaca   4140
actggtgaca ggtttgacat cgaagacgtg aataatcata ctgattgcct aaaactaata   4200
gaaagaaatg agactgctcg atggaaaaat gtgaaagtaa actttgataa tgtaggattt   4260
gggtatctct ctttgcttca agttgccaca ttcaaaggat ggatggatat aatgtatgca   4320
gcagttgatt ccagaaatgt ggaactccag cctaagtatg aagaaagtct gtacatgtat   4380
ctttactttg ttattttcat catctttggg tccttcttca ccttgaacct gtttattggt   4440
gtcatcatag ataatttcaa ccagcagaaa aagaagtttg gaggtcaaga catctttatg   4500
acagaagaac agaagaaata ctataatgca atgaaaaaat taggatcgaa aaaaccgcaa   4560
aagcctatac ctcgaccagg aaacaaattt caaggaatgg tctttgactt cgtaaccaga   4620
caagtttttg acataagcat catgattctc atctgtctta acatggtcac aatgatggtg   4680
gaaacagatg accagagtga atatgtgact accattttgt cacgcatcaa tctggtgttc   4740
attgtgctat ttactggaga gtgtgtactg aaactcatct ctctacgcca ttattatttt   4800
accattggat ggaatatttt tgattttgtg gttgtcattc tctccattgt aggtatgttt   4860
cttgccgagc tgatagaaaa gtatttcgtg tcccctaccc tgttccgagt gatccgtctt   4920
gctaggattg gccgaatcct acgtctgatc aaaggagcaa aggggatccg cacgctgctc   4980
tttgctttga tgatgtccct tcctgcgttg tttaacatcg gcctcctact cttcctagtc   5040
atgttcatct acgccatctt tgggatgtcc aactttgcct atgttaagag ggaagttggg   5100
atcgatgaca tgttcaactt tgagaccttt ggcaacagca tgatctgcct attccaaatt   5160
acaacctctg ctggctggga tggattgcta gcacccattc tcaacagtaa gccacccgac   5220
tgtgacccta ataaagttaa ccctggaagc tcagttaagg gagactgtgg gaacccatct   5280
gttggaattt tcttttttgt cagttacatc atcatatcct tcctggttgt ggtgaacatg   5340
tacatcgcgg tcatcctgga gaacttcagt gttgctactg aagaaagtgc agagcctctg   5400
agtgaggatg actttgagat gttctatgag gtttgggaga agtttgatcc cgatgcaact   5460
cagttcatgg aatttgaaaa attatctcag tttgcagctg cgcttgaacc gcctctcaat   5520
ctgccacaac caaacaaact ccagctcatt gccatggatt tgcccatggt gagtggtgac   5580
cggatccact gtcttgatat cttatttgct tttacaaagc gggttctagg agagagtgga   5640
gagatggatg ctctacgaat acagatggaa gagcgattca tggcttccaa tccttccaag   5700
gtctcctatc agccaatcac tactacttta aaacgaaaac aagaggaagt atctgctgtc   5760
attattcagc gtgcttacag acgccacctt ttaaagcgaa ctgtaaaaca agcttccttt   5820
acgtacaata aaaacaaaat caaaggtggg gctaatcttc ttataaaaga agacatgata   5880
attgacagaa taaatgaaaa ctctattaca gaaaaaactg atctgaccat gtccactgca   5940
gcttgtccac cttcctatga ccgggtgaca aagccaattg tggaaaaaca tgagcaagaa   6000
ggcaaagatg aaaaagccaa agggaaataa                                    6030
```

<210> SEQ ID NO 3
<211> LENGTH: 2512
<212> TYPE: PRT
<213> ORGANISM: Homo sapiens

<400> SEQUENCE: 3

```
Met Ala Arg Phe Gly Asp Glu Met Pro Ala Arg Tyr Gly Gly Gly Gly
1               5                   10                  15

Ser Gly Ala Ala Ala Gly Val Val Val Gly Ser Gly Gly Gly Arg Gly
            20                  25                  30

Ala Gly Gly Ser Arg Gln Gly Gly Gln Pro Gly Ala Gln Arg Met Tyr
        35                  40                  45

Lys Gln Ser Met Ala Gln Arg Ala Arg Thr Met Ala Leu Tyr Asn Pro
    50                  55                  60

Ile Pro Val Arg Gln Asn Cys Leu Thr Val Asn Arg Ser Leu Phe Leu
65                  70                  75                  80

Phe Ser Glu Asp Asn Val Val Arg Lys Tyr Ala Lys Lys Ile Thr Glu
                85                  90                  95

Trp Pro Pro Phe Glu Tyr Met Ile Leu Ala Thr Ile Ile Ala Asn Cys
            100                 105                 110

Ile Val Leu Ala Leu Glu Gln His Leu Pro Asp Asp Asp Lys Thr Pro
        115                 120                 125

Met Ser Glu Arg Leu Asp Asp Thr Glu Pro Tyr Phe Ile Gly Ile Phe
    130                 135                 140

Cys Phe Glu Ala Gly Ile Lys Ile Ile Ala Leu Gly Phe Ala Phe His
145                 150                 155                 160

Lys Gly Ser Tyr Leu Arg Asn Gly Trp Asn Val Met Asp Phe Val Val
                165                 170                 175

Val Leu Thr Gly Ile Leu Ala Thr Val Gly Thr Glu Phe Asp Leu Arg
            180                 185                 190

Thr Leu Arg Ala Val Arg Val Leu Arg Pro Leu Lys Leu Val Ser Gly
        195                 200                 205

Ile Pro Ser Leu Gln Val Val Leu Lys Ser Ile Met Lys Ala Met Ile
    210                 215                 220

Pro Leu Leu Gln Ile Gly Leu Leu Leu Phe Phe Ala Ile Leu Ile Phe
225                 230                 235                 240

Ala Ile Ile Gly Leu Glu Phe Tyr Met Gly Lys Phe His Thr Thr Cys
                245                 250                 255

Phe Glu Glu Gly Thr Asp Asp Ile Gln Gly Glu Ser Pro Ala Pro Cys
            260                 265                 270

Gly Thr Glu Glu Pro Ala Arg Thr Cys Pro Asn Gly Thr Lys Cys Gln
        275                 280                 285

Pro Tyr Trp Glu Gly Pro Asn Asn Gly Ile Thr Gln Phe Asp Asn Ile
    290                 295                 300

Leu Phe Ala Val Leu Thr Val Phe Gln Cys Ile Thr Met Glu Gly Trp
305                 310                 315                 320

Thr Asp Leu Leu Tyr Asn Ser Asn Asp Ala Ser Gly Asn Thr Trp Asn
                325                 330                 335

Trp Leu Tyr Phe Ile Pro Leu Ile Ile Ile Gly Ser Phe Phe Met Leu
            340                 345                 350

Asn Leu Val Leu Gly Val Leu Ser Gly Glu Phe Ala Lys Glu Arg Glu
        355                 360                 365

Arg Val Glu Asn Arg Arg Ala Phe Leu Lys Leu Arg Arg Gln Gln Gln
```

-continued

```
    370                 375                 380

Ile Glu Arg Glu Leu Asn Gly Tyr Met Glu Trp Ile Ser Lys Ala Glu
385                 390                 395                 400

Glu Val Ile Leu Ala Glu Asp Glu Thr Asp Gly Glu Gln Arg His Pro
                405                 410                 415

Phe Asp Gly Ala Leu Arg Arg Thr Thr Ile Lys Lys Ser Lys Thr Asp
            420                 425                 430

Leu Leu Asn Pro Glu Glu Ala Glu Asp Gln Leu Ala Asp Ile Ala Ser
        435                 440                 445

Val Gly Ser Pro Phe Ala Arg Ala Ser Ile Lys Ser Ala Lys Leu Glu
    450                 455                 460

Asn Ser Thr Phe Phe His Lys Lys Glu Arg Arg Met Arg Phe Tyr Ile
465                 470                 475                 480

Arg Arg Met Val Lys Thr Gln Ala Phe Tyr Trp Thr Val Leu Ser Leu
                485                 490                 495

Val Ala Leu Asn Thr Leu Cys Val Ala Ile Val His Tyr Asn Gln Pro
            500                 505                 510

Glu Trp Leu Ser Asp Phe Leu Tyr Tyr Ala Glu Phe Ile Phe Leu Gly
        515                 520                 525

Leu Phe Met Ser Glu Met Phe Ile Lys Met Tyr Gly Leu Gly Thr Arg
    530                 535                 540

Pro Tyr Phe His Ser Ser Phe Asn Cys Phe Asp Cys Gly Val Ile Ile
545                 550                 555                 560

Gly Ser Ile Phe Glu Val Ile Trp Ala Val Ile Lys Pro Gly Thr Ser
                565                 570                 575

Phe Gly Ile Ser Val Leu Arg Ala Leu Arg Leu Leu Arg Ile Phe Lys
            580                 585                 590

Val Thr Lys Tyr Trp Ala Ser Leu Arg Asn Leu Val Val Ser Leu Leu
        595                 600                 605

Asn Ser Met Lys Ser Ile Ile Ser Leu Leu Phe Leu Leu Phe Leu Phe
    610                 615                 620

Ile Val Val Phe Ala Leu Leu Gly Met Gln Leu Phe Gly Gly Gln Phe
625                 630                 635                 640

Asn Phe Asp Glu Gly Thr Pro Pro Thr Asn Phe Asp Thr Phe Pro Ala
                645                 650                 655

Ala Ile Met Thr Val Phe Gln Ile Leu Thr Gly Glu Asp Trp Asn Glu
            660                 665                 670

Val Met Tyr Asp Gly Ile Lys Ser Gln Gly Gly Val Gln Gly Gly Met
        675                 680                 685

Val Phe Ser Ile Tyr Phe Ile Val Leu Thr Leu Phe Gly Asn Tyr Thr
    690                 695                 700

Leu Leu Asn Val Phe Leu Ala Ile Ala Val Asp Asn Leu Ala Asn Ala
705                 710                 715                 720

Gln Glu Leu Thr Lys Val Glu Ala Asp Glu Gln Glu Glu Glu Glu Ala
                725                 730                 735

Ala Asn Gln Lys Leu Ala Leu Gln Lys Ala Lys Glu Val Ala Glu Val
            740                 745                 750

Ser Pro Leu Ser Ala Ala Asn Met Ser Ile Ala Val Lys Glu Gln Gln
        755                 760                 765

Lys Asn Gln Lys Pro Ala Lys Ser Val Trp Glu Gln Arg Thr Ser Glu
    770                 775                 780

Met Arg Lys Gln Asn Leu Leu Ala Ser Arg Glu Ala Leu Tyr Asn Glu
785                 790                 795                 800
```

-continued

```
Met Asp Pro Asp Glu Arg Trp Lys Ala Ala Tyr Thr Arg His Leu Arg
                805                 810                 815

Pro Asp Met Lys Thr His Leu Asp Arg Pro Leu Val Val Asp Pro Gln
            820                 825                 830

Glu Asn Arg Asn Asn Asn Thr Asn Lys Ser Arg Ala Ala Glu Pro Thr
        835                 840                 845

Val Asp Gln Arg Leu Gly Gln Gln Arg Ala Glu Asp Phe Leu Arg Lys
    850                 855                 860

Gln Ala Arg Tyr His Asp Arg Ala Arg Asp Pro Ser Gly Ser Ala Gly
865                 870                 875                 880

Leu Asp Ala Arg Arg Pro Trp Ala Gly Ser Gln Glu Ala Glu Leu Ser
                885                 890                 895

Arg Glu Gly Pro Tyr Gly Arg Glu Ser Asp His His Ala Arg Glu Gly
            900                 905                 910

Ser Leu Glu Gln Pro Gly Phe Trp Glu Gly Glu Ala Glu Arg Gly Lys
        915                 920                 925

Ala Gly Asp Pro His Arg Arg His Val His Arg Gln Gly Gly Ser Arg
    930                 935                 940

Glu Ser Arg Ser Gly Ser Pro Arg Thr Gly Ala Asp Gly Glu His Arg
945                 950                 955                 960

Arg His Arg Ala His Arg Arg Pro Gly Glu Glu Gly Pro Glu Asp Lys
                965                 970                 975

Ala Glu Arg Arg Ala Arg His Arg Glu Gly Ser Arg Pro Ala Arg Gly
            980                 985                 990

Gly Glu Gly Glu Gly Glu Gly Pro  Asp Gly Gly Glu Arg  Arg Arg Arg
        995                 1000                1005

His Arg  His Gly Ala Pro Ala  Thr Tyr Glu Gly Asp  Ala Arg Arg
    1010                1015                1020

Glu Asp  Lys Glu Arg Arg His  Arg Arg Arg Lys Glu  Asn Gln Gly
    1025                1030                1035

Ser Gly  Val Pro Val Ser Gly  Pro Asn Leu Ser Thr  Thr Arg Pro
    1040                1045                1050

Ile Gln  Gln Asp Leu Gly Arg  Gln Asp Pro Pro Leu  Ala Glu Asp
    1055                1060                1065

Ile Asp  Asn Met Lys Asn Asn  Lys Leu Ala Thr Ala  Glu Ser Ala
    1070                1075                1080

Ala Pro  His Gly Ser Leu Gly  His Ala Gly Leu Pro  Gln Ser Pro
    1085                1090                1095

Ala Lys  Met Gly Asn Ser Thr  Asp Pro Gly Pro Met  Leu Ala Ile
    1100                1105                1110

Pro Ala  Met Ala Thr Asn Pro  Gln Asn Ala Ala Ser  Arg Arg Thr
    1115                1120                1125

Pro Asn  Asn Pro Gly Asn Pro  Ser Asn Pro Gly Pro  Pro Lys Thr
    1130                1135                1140

Pro Glu  Asn Ser Leu Ile Val  Thr Asn Pro Ser Gly  Thr Gln Thr
    1145                1150                1155

Asn Ser  Ala Lys Thr Ala Arg  Lys Pro Asp His Thr  Thr Val Asp
    1160                1165                1170

Ile Pro  Pro Ala Cys Pro Pro  Pro Leu Asn His Thr  Val Val Gln
    1175                1180                1185

Val Asn  Lys Asn Ala Asn Pro  Asp Pro Leu Pro Lys  Lys Glu Glu
    1190                1195                1200
```

-continued

```
Glu Lys  Lys Glu Glu Glu Glu  Asp Asp Arg Gly Glu  Asp Gly Pro
    1205                 1210                 1215

Lys Pro  Met Pro Pro Tyr Ser  Ser Met Phe Ile Leu  Ser Thr Thr
    1220                 1225                 1230

Asn Pro  Leu Arg Arg Leu Cys  His Tyr Ile Leu Asn  Leu Arg Tyr
    1235                 1240                 1245

Phe Glu  Met Cys Ile Leu Met  Val Ile Ala Met Ser  Ser Ile Ala
    1250                 1255                 1260

Leu Ala  Ala Glu Asp Pro Val  Gln Pro Asn Ala Pro  Arg Asn Asn
    1265                 1270                 1275

Val Leu  Arg Tyr Phe Asp Tyr  Val Phe Thr Gly Val  Phe Thr Phe
    1280                 1285                 1290

Glu Met  Val Ile Lys Met Ile  Asp Leu Gly Leu Val  Leu His Gln
    1295                 1300                 1305

Gly Ala  Tyr Phe Arg Asp Leu  Trp Asn Ile Leu Asp  Phe Ile Val
    1310                 1315                 1320

Val Ser  Gly Ala Leu Val Ala  Phe Ala Phe Thr Gly  Asn Ser Lys
    1325                 1330                 1335

Gly Lys  Asp Ile Asn Thr Ile  Lys Ser Leu Arg Val  Leu Arg Val
    1340                 1345                 1350

Leu Arg  Pro Leu Lys Thr Ile  Lys Arg Leu Pro Lys  Leu Lys Ala
    1355                 1360                 1365

Val Phe  Asp Cys Val Val Asn  Ser Leu Lys Asn Val  Phe Asn Ile
    1370                 1375                 1380

Leu Ile  Val Tyr Met Leu Phe  Met Phe Ile Phe Ala  Val Val Ala
    1385                 1390                 1395

Val Gln  Leu Phe Lys Gly Lys  Phe Phe His Cys Thr  Asp Glu Ser
    1400                 1405                 1410

Lys Glu  Phe Glu Lys Asp Cys  Arg Gly Lys Tyr Leu  Leu Tyr Glu
    1415                 1420                 1425

Lys Asn  Glu Val Lys Ala Arg  Asp Arg Glu Trp Lys  Lys Tyr Glu
    1430                 1435                 1440

Phe His  Tyr Asp Asn Val Leu  Trp Ala Leu Leu Thr  Leu Phe Thr
    1445                 1450                 1455

Val Ser  Thr Gly Glu Gly Trp  Pro Gln Val Leu Lys  His Ser Val
    1460                 1465                 1470

Asp Ala  Thr Phe Glu Asn Gln  Gly Pro Ser Pro Gly  Tyr Arg Met
    1475                 1480                 1485

Glu Met  Ser Ile Phe Tyr Val  Val Tyr Phe Val Val  Phe Pro Phe
    1490                 1495                 1500

Phe Phe  Val Asn Ile Phe Val  Ala Leu Ile Ile Ile  Thr Phe Gln
    1505                 1510                 1515

Glu Gln  Gly Asp Lys Met Met  Glu Glu Tyr Ser Leu  Glu Lys Asn
    1520                 1525                 1530

Glu Arg  Ala Cys Ile Asp Phe  Ala Ile Ser Ala Lys  Pro Leu Thr
    1535                 1540                 1545

Arg His  Met Pro Gln Asn Lys  Gln Ser Phe Gln Tyr  Arg Met Trp
    1550                 1555                 1560

Gln Phe  Val Val Ser Pro Pro  Phe Glu Tyr Thr Ile  Met Ala Met
    1565                 1570                 1575

Ile Ala  Leu Asn Thr Ile Val  Leu Met Met Lys Phe  Tyr Gly Ala
    1580                 1585                 1590

Ser Val  Ala Tyr Glu Asn Ala  Leu Arg Val Phe Asn  Ile Val Phe
```

-continued

```
    1595                1600                1605

Thr Ser  Leu Phe Ser Leu Glu  Cys Val Leu Lys Val  Met Ala Phe
    1610                1615                1620

Gly Ile  Leu Asn Tyr Phe Arg  Asp Ala Trp Asn Ile  Phe Asp Phe
    1625                1630                1635

Val Thr  Val Leu Gly Ser Ile  Thr Asp Ile Leu Val  Thr Glu Phe
    1640                1645                1650

Gly Asn  Pro Asn Asn Phe Ile  Asn Leu Ser Phe Leu  Arg Leu Phe
    1655                1660                1665

Arg Ala  Ala Arg Leu Ile Lys  Leu Leu Arg Gln Gly  Tyr Thr Ile
    1670                1675                1680

Arg Ile  Leu Leu Trp Thr Phe  Val Gln Ser Phe Lys  Ala Leu Pro
    1685                1690                1695

Tyr Val  Cys Leu Leu Ile Ala  Met Leu Phe Phe Ile  Tyr Ala Ile
    1700                1705                1710

Ile Gly  Met Gln Val Phe Gly  Asn Ile Gly Ile Asp  Val Glu Asp
    1715                1720                1725

Glu Asp  Ser Asp Glu Asp Glu  Phe Gln Ile Thr Glu  His Asn Asn
    1730                1735                1740

Phe Arg  Thr Phe Phe Gln Ala  Leu Met Leu Leu Phe  Arg Ser Ala
    1745                1750                1755

Thr Gly  Glu Ala Trp His Asn  Ile Met Leu Ser Cys  Leu Ser Gly
    1760                1765                1770

Lys Pro  Cys Asp Lys Asn Ser  Gly Ile Leu Thr Arg  Glu Cys Gly
    1775                1780                1785

Asn Glu  Phe Ala Tyr Phe Tyr  Phe Val Ser Phe Ile  Phe Leu Cys
    1790                1795                1800

Ser Phe  Leu Met Leu Asn Leu  Phe Val Ala Val Ile  Met Asp Asn
    1805                1810                1815

Phe Glu  Tyr Leu Thr Arg Asp  Ser Ser Ile Leu Gly  Pro His His
    1820                1825                1830

Leu Asp  Glu Tyr Val Arg Val  Trp Ala Glu Tyr Asp  Pro Ala Ala
    1835                1840                1845

Trp Gly  Arg Met Pro Tyr Leu  Asp Met Tyr Gln Met  Leu Arg His
    1850                1855                1860

Met Ser  Pro Pro Leu Gly Leu  Gly Lys Lys Cys Pro  Ala Arg Val
    1865                1870                1875

Ala Tyr  Lys Arg Leu Leu Arg  Met Asp Leu Pro Val  Ala Asp Asp
    1880                1885                1890

Asn Thr  Val His Phe Asn Ser  Thr Leu Met Ala Leu  Ile Arg Thr
    1895                1900                1905

Ala Leu  Asp Ile Lys Ile Ala  Lys Gly Gly Ala Asp  Lys Gln Gln
    1910                1915                1920

Met Asp  Ala Glu Leu Arg Lys  Glu Met Met Ala Ile  Trp Pro Asn
    1925                1930                1935

Leu Ser  Gln Lys Thr Leu Asp  Leu Leu Val Thr Pro  His Lys Ser
    1940                1945                1950

Thr Asp  Leu Thr Val Gly Lys  Ile Tyr Ala Ala Met  Met Ile Met
    1955                1960                1965

Glu Tyr  Tyr Arg Gln Ser Lys  Ala Lys Lys Leu Gln  Ala Met Arg
    1970                1975                1980

Glu Glu  Gln Asp Arg Thr Pro  Leu Met Phe Gln Arg  Met Glu Pro
    1985                1990                1995
```

-continued

```
Pro Ser  Pro Thr Gln Glu Gly  Gly Pro Gly Gln Asn  Ala Leu Pro
    2000                 2005                 2010

Ser Thr  Gln Leu Asp Pro Gly  Gly Ala Leu Met Ala  His Glu Ser
    2015                 2020                 2025

Gly Leu  Lys Glu Ser Pro Ser  Trp Val Thr Gln Arg  Ala Gln Glu
    2030                 2035                 2040

Met Phe  Gln Lys Thr Gly Thr  Trp Ser Pro Glu Gln  Gly Pro Pro
    2045                 2050                 2055

Thr Asp  Met Pro Asn Ser Gln  Pro Asn Ser Gln Ser  Val Glu Met
    2060                 2065                 2070

Arg Glu  Met Gly Arg Asp Gly  Tyr Ser Asp Ser Glu  His Tyr Leu
    2075                 2080                 2085

Pro Met  Glu Gly Gln Gly Arg  Ala Ala Ser Met Pro  Arg Leu Pro
    2090                 2095                 2100

Ala Glu  Asn Gln Arg Arg Arg  Gly Arg Pro Arg Gly  Asn Asn Leu
    2105                 2110                 2115

Ser Thr  Ile Ser Asp Thr Ser  Pro Met Lys Arg Ser  Ala Ser Val
    2120                 2125                 2130

Leu Gly  Pro Lys Ala Arg Arg  Leu Asp Asp Tyr Ser  Leu Glu Arg
    2135                 2140                 2145

Val Pro  Pro Glu Glu Asn Gln  Arg His His Gln Arg  Arg Arg Asp
    2150                 2155                 2160

Arg Ser  His Arg Ala Ser Glu  Arg Ser Leu Gly Arg  Tyr Thr Asp
    2165                 2170                 2175

Val Asp  Thr Gly Leu Gly Thr  Asp Leu Ser Met Thr  Thr Gln Ser
    2180                 2185                 2190

Gly Asp  Leu Pro Ser Lys Glu  Arg Asp Gln Glu Arg  Gly Arg Pro
    2195                 2200                 2205

Lys Asp  Arg Lys His Arg Gln  His His His His His  His His His
    2210                 2215                 2220

His His  Pro Pro Pro Pro Asp  Lys Asp Arg Tyr Ala  Gln Glu Arg
    2225                 2230                 2235

Pro Asp  His Gly Arg Ala Arg  Ala Arg Asp Gln Arg  Trp Ser Arg
    2240                 2245                 2250

Ser Pro  Ser Glu Gly Arg Glu  His Met Ala His Arg  Gln Gly Ser
    2255                 2260                 2265

Ser Ser  Val Ser Gly Ser Pro  Ala Pro Ser Thr Ser  Gly Thr Ser
    2270                 2275                 2280

Thr Pro  Arg Arg Gly Arg Arg  Gln Leu Pro Gln Thr  Pro Ser Thr
    2285                 2290                 2295

Pro Arg  Pro His Val Ser Tyr  Ser Pro Val Ile Arg  Lys Ala Gly
    2300                 2305                 2310

Gly Ser  Gly Pro Pro Gln Gln  Gln Gln Gln Gln Gln  Gln Gln Gln
    2315                 2320                 2325

Gln Gln  Gln Ala Val Ala Arg  Pro Gly Arg Ala Ala  Thr Ser Gly
    2330                 2335                 2340

Pro Arg  Arg Tyr Pro Gly Pro  Thr Ala Glu Pro Leu  Ala Gly Asp
    2345                 2350                 2355

Arg Pro  Pro Thr Gly Gly His  Ser Ser Gly Arg Ser  Pro Arg Met
    2360                 2365                 2370

Glu Arg  Arg Val Pro Gly Pro  Ala Arg Ser Glu Ser  Pro Arg Ala
    2375                 2380                 2385
```

-continued

```
Cys Arg  His Gly Gly Ala Arg  Trp Pro Ala Ser Gly  Pro His Val
    2390                 2395                 2400

Ser Glu  Gly Pro Pro Gly Pro  Arg His His Gly Tyr  Tyr Arg Gly
    2405                 2410                 2415

Ser Asp  Tyr Asp Glu Ala Asp  Gly Pro Gly Ser Gly  Gly Gly Glu
    2420                 2425                 2430

Glu Ala  Met Ala Gly Ala Tyr  Asp Ala Pro Pro Pro  Val Arg His
    2435                 2440                 2445

Ala Ser  Ser Gly Ala Thr Gly  Arg Ser Pro Arg Thr  Pro Arg Ala
    2450                 2455                 2460

Ser Gly  Pro Ala Cys Ala Ser  Pro Ser Arg His Gly  Arg Arg Leu
    2465                 2470                 2475

Pro Asn  Gly Tyr Tyr Pro Ala  His Gly Leu Ala Arg  Pro Arg Gly
    2480                 2485                 2490

Pro Gly  Ser Arg Lys Gly Leu  His Glu Pro Tyr Ser  Glu Ser Asp
    2495                 2500                 2505

Asp Asp  Trp Cys
    2510
```

<210> SEQ ID NO 4
<211> LENGTH: 7539
<212> TYPE: DNA
<213> ORGANISM: Homo sapiens

<400> SEQUENCE: 4

```
atggcccgct tcggagacga gatgccggcc cgctacgggg gaggaggctc cggggcagcc     60

gccggggtgg tcgtgggcag cggaggcggg cgaggagccg ggggcagccg gcagggcggg    120

cagcccgggg cgcaaaggat gtacaagcag tcaatggcgc agagagcgcg gaccatggca    180

ctctacaacc ccatccccgt ccgacagaac tgcctcacgg ttaaccggtc tctcttcctc    240

ttcagcgaag acaacgtggt gagaaaatac gccaaaaaga tcaccgaatg gcctcccttt    300

gaatatatga ttttagccac catcatagcg aattgcatcg tcctcgcact ggagcagcat    360

ctgcctgatg atgacaagac cccgatgtct gaacggctgg atgacacaga accatacttc    420

attggaattt tttgtttcga ggctggaatt aaaatcattg cccttgggtt tgccttccac    480

aaaggctcct acttgaggaa tggctggaat gtcatggact ttgtggtggt gctaacgggc    540

atcttggcga cagttgggac ggagtttgac ctacggacgc tgagggcagt tcgagtgctg    600

cggccgctca agctggtgtc tggaatccca agtttacaag tcgtcctgaa gtcgatcatg    660

aaggcgatga tccctttgct gcagatcggc ctcctcctat tttttgcaat ccttattttt    720

gcaatcatag ggttagaatt ttatatggga aaatttcata ccacctgctt tgaagagggg    780

acagatgaca ttcagggtga gtctccggct ccatgtggga cagaagagcc cgcccgcacc    840

tgccccaatg ggaccaaatg tcagccctac tgggaagggc ccaacaacgg gatcactcag    900

ttcgacaaca tcctgtttgc agtgctgact gttttccagt gcataaccat ggaagggtgg    960

actgatctcc tctacaatag caacgatgcc tcagggaaca cttggaactg gttgtacttc   1020

atcccccctca tcatcatcgg ctcctttttt atgctgaacc ttgtgctggg tgtgctgtca   1080

ggggagtttg ccaaagaaag ggaacgggtg gagaaccggc gggcttttct gaagctgagg   1140

cggcaacaac agattgaacg tgagctcaat gggtacatgg agtggatctc aaaagcagaa   1200

gaggtgatcc tcgccgagga tgaaactgac ggggagcaga ggcatccctt tgatggagct   1260

ctgcggagaa ccaccataaa gaaaagcaag acagatttgc tcaaccccga agaggctgag   1320
```

-continued

```
gatcagctgg ctgatatagc ctctgtgggt tctcccttcg cccgagccag cattaaaagt   1380
gccaagctgg agaactcgac ctttttttcac aaaaaggaga ggaggatgcg tttctacatc   1440
cgccgcatgg tcaaaactca ggccttctac tggactgtac tcagtttggt agctctcaac   1500
acgctgtgtg ttgctattgt tcactacaac cagcccgagt ggctctccga cttcctttac   1560
tatgcagaat tcattttctt aggactcttt atgtccgaaa tgtttataaa aatgtacggg   1620
cttgggacgc ggccttactt ccactcttcc ttcaactgct ttgactgtgg ggttatcatt   1680
gggagcatct tcgaggtcat ctgggctgtc ataaaacctg gcacatcctt tggaatcagc   1740
gtgttacgag ccctcaggtt attgcgtatt ttcaaagtca caaagtactg ggcatctctc   1800
agaaacctgg tcgtctctct cctcaactcc atgaagtcca tcatcagcct gttgtttctc   1860
cttttcctgt tcattgtcgt cttcgccctt ttgggaatgc aactcttcgg cggccagttt   1920
aatttcgatg aagggactcc tcccaccaac ttcgatactt ttccagcagc aataatgacg   1980
gtgtttcaga tcctgacggg cgaagactgg aacgaggtca tgtacgacgg gatcaagtct   2040
caggggggcg tgcagggcgg catggtgttc tccatctatt tcattgtact gacgctcttt   2100
gggaactaca ccctcctgaa tgtgttcttg gccatcgctg tggacaatct ggccaacgcc   2160
caggagctca ccaaggtgga ggcggacgag caagaggaag aagaagcagc gaaccagaaa   2220
cttgccctac agaaagccaa ggaggtggca gaagtgagtc ctctgtccgc ggccaacatg   2280
tctatagctg tgaaagagca acagaagaat caaaagccag ccaagtccgt gtgggagcag   2340
cggaccagtg agatgcgaaa gcagaacttg ctggccagcc gggaggccct gtataacgaa   2400
atggacccgg acgagcgctg gaaggctgcc tacacgcggc acctgcggcc agacatgaag   2460
acgcacttgg accggccgct ggtggtggac ccgcaggaga accgcaacaa caacaccaac   2520
aagagccggg cggccgagcc caccgtggac cagcgcctcg gccagcagcg cgccgaggac   2580
ttcctcagga aacaggcccg ctaccacgat cgggcccggg accccagcgg ctcggcgggc   2640
ctggacgcac ggaggccctg ggcgggaagc caggaggccg agctgagccg ggagggaccc   2700
tacggccgcg agtcggacca ccacgcccgg gagggcagcc tggagcaacc cgggttctgg   2760
gagggcgagg ccgagcgagg caaggccggg gacccccacc ggaggcacgt gcaccggcag   2820
gggggcagca gggagagccg cagcgggtcc ccgcgcacgg gcgcggacgg ggagcatcga   2880
cgtcatcgcg cgcaccgcag gcccggggag gagggtccgg aggacaaggc ggagcggagg   2940
gcgcggcacc gcgagggcag ccggccggcc cggggcggcg agggcgaggg cgagggcccc   3000
gacgggggcg agcgcaggag aaggcaccgg catggcgctc cagccacgta cgagggggac   3060
gcgcggaggg aggacaagga gcggaggcat cggaggagga aagagaacca gggctccggg   3120
gtccctgtgt cgggccccaa cctgtcaacc acccggccaa tccagcagga cctgggccgc   3180
caagacccac ccctggcaga ggatattgac aacatgaaga acaacaagct ggccaccgcg   3240
gagtcggccg ctccccacgg cagccttggc cacgccggcc tgccccagag cccagccaag   3300
atgggaaaca gcaccgaccc cggccccatg ctggccatcc ctgccatggc caccaacccc   3360
cagaacgccg ccagccgccg gacgcccaac aacccgggga acccatccaa tcccggcccc   3420
cccaagaccc ccgagaatag ccttatcgtc accaacccca gcggcaccca gaccaattca   3480
gctaagactg ccaggaaacc cgaccacacc acagtggaca tccccccagc ctgcccaccc   3540
cccctcaacc acaccgtcgt acaagtgaac aaaaacgcca acccagaccc actgccaaaa   3600
aaagaggaag agaagaagga ggaggaggaa gacgaccgtg gggaagacgg ccctaagcca   3660
atgcctccct atagctccat gttcatcctg tccacgacca accccccttcg ccgcctgtgc   3720
```

-continued

```
cattacatcc tgaacctgcg ctactttgag atgtgcatcc tcatggtcat tgccatgagc   3780
agcatcgccc tggccgccga ggaccctgtg cagcccaacg cacctcggaa caacgtgctg   3840
cgatactttg actacgtttt tacaggcgtc tttacctttg agatggtgat caagatgatt   3900
gacctggggc tcgtcctgca tcagggtgcc tacttccgtg acctctggaa tattctcgac   3960
ttcatagtgg tcagtggggc cctggtagcc tttgccttca ctggcaatag caaaggaaaa   4020
gacatcaaca cgattaaatc cctccgagtc ctccgggtgc tacgacctct taaaaccatc   4080
aagcggctgc caaagctcaa ggctgtgttt gactgtgtgg tgaactcact taaaaacgtc   4140
ttcaacatcc tcatcgtcta catgctattc atgttcatct tcgccgtggt ggctgtgcag   4200
ctcttcaagg ggaaattctt ccactgcact gacgagtcca aagagtttga gaaagattgt   4260
cgaggcaaat acctcctcta cgagaagaat gaggtgaagg cgcgagaccg ggagtggaag   4320
aagtatgaat tccattacga caatgtgctg tgggctctgc tgaccctctt caccgtgtcc   4380
acgggagaag gctggccaca ggtcctcaag cattcggtgg acgccacctt tgagaaccag   4440
ggccccagcc ccgggtaccg catggagatg tccattttct acgtcgtcta ctttgtggtg   4500
ttccccttct tctttgtcaa tatctttgtg gccttgatca tcatcacctt ccaggagcaa   4560
ggggacaaga tgatggagga atacagcctg gagaaaaatg agagggcctg cattgatttc   4620
gccatcagcg ccaagccgct gacccgacac atgccgcaga acaagcagag cttccagtac   4680
cgcatgtggc agttcgtggt gtctccgcct ttcgagtaca cgatcatggc catgatcgcc   4740
ctcaacacca tcgtgcttat gatgaagttc tatggggctt ctgttgctta tgaaaatgcc   4800
ctgcgggtgt tcaacatcgt cttcacctcc ctcttctctc tggaatgtgt gctgaaagtc   4860
atggcttttg ggattctgaa ttatttccgc gatgcctgga acatcttcga ctttgtgact   4920
gttctgggca gcatcaccga tatcctcgtg actgagtttg ggaatccgaa taacttcatc   4980
aacctgagct ttctccgcct cttccgagct gcccggctca tcaaacttct ccgtcagggt   5040
tacaccatcc gcattcttct ctggaccttt gtgcagtcct tcaaggccct gccttatgtc   5100
tgtctgctga tcgccatgct cttcttcatc tatgccatca ttgggatgca ggtgtttggt   5160
aacattggca tcgacgtgga ggacgaggac agtgatgaag atgagttcca aatcactgag   5220
cacaataact tccggacctt cttccaggcc ctcatgcttc tcttccggag tgccaccggg   5280
gaagcttggc acaacatcat gctttcctgc ctcagcggga aaccgtgtga taagaactct   5340
ggcatcctga ctcgagagtg tggcaatgaa tttgcttatt tttactttgt ttccttcatc   5400
ttcctctgct cgtttctgat gctgaatctc tttgtcgccg tcatcatgga caactttgag   5460
tacctcaccc gagactcctc catcctgggc ccccaccacc tggatgagta cgtgcgtgtc   5520
tgggccgagt atgaccccgc agcttggggc cgcatgcctt acctggacat gtatcagatg   5580
ctgagacaca tgtctccgcc cctgggtctg gggaagaagt gtccggccag agtggcttac   5640
aagcggcttc tgcggatgga cctgcccgtc gcagatgaca acaccgtcca cttcaattcc   5700
accctcatgg ctctgatccg cacagccctg gacatcaaga ttgccaaggg aggagccgac   5760
aaacagcaga tggacgctga gctgcggaag gagatgatgg cgatttggcc caatctgtcc   5820
cagaagacgc tagacctgct ggtcacacct cacaagtcca cggacctcac cgtggggaag   5880
atctacgcag ccatgatgat catggagtac taccggcaga gcaaggccaa gaagctgcag   5940
gccatgcgcg aggagcagga ccggacaccc ctcatgttcc agcgcatgga gcccccgtcc   6000
ccaacgcagg aagggggacc tggccagaac gccctcccct ccacccagct ggacccagga   6060
```

ggagccctga tggctcacga aagcggcctc aaggagagcc cgtcctgggt gacccagcgt 6120
gcccaggaga tgttccagaa gacgggcaca tggagtccgg aacaaggccc ccctaccgac 6180
atgcccaaca gccagcctaa ctctcagtcc gtggagatgc gagagatggg cagagatggc 6240
tactccgaca gcgagcacta cctccccatg gaaggccagg gccgggctgc ctccatgccc 6300
cgcctccctg cagagaacca gaggagaagg ggccggccac gtgggaataa cctcagtacc 6360
atctcagaca ccagccccat gaagcgttca gcctccgtgc tgggccccaa ggcccgacgc 6420
ctggacgatt actcgctgga gcgggtcccg cccgaggaga accagcggca ccaccagcgg 6480
cgccgcgacc gcagccaccg cgcctctgag cgctccctgg gccgctacac cgatgtggac 6540
acaggcttgg ggacagacct gagcatgacc acccaatccg gggacctgcc gtcgaaggag 6600
cgggaccagg agcggggccg gcccaaggat cggaagcatc gacagcacca ccaccaccac 6660
caccaccacc accatccccc gccccccgac aaggaccgct atgcccagga acggccggac 6720
cacggccggg cacgggctcg ggaccagcgc tggtcccgct cgcccagcga gggccgagag 6780
cacatggcgc accggcaggg cagtagttcc gtaagtggaa gcccagcccc ctcaacatct 6840
ggtaccagca ctccgcggcg gggccgccgc cagctccccc agacccccctc cacccccccgg 6900 ccacacgtgt cctattcccc tgtgatccgt aaggccggcg gctcggggcc cccgcagcag 6960
cagcagcagc agcagcagca gcagcagcag caggcggtgg ccaggccggg ccgggcggcc 7020
accagcggcc ctcggaggta cccaggcccc acggccgagc ctctggccgg agatcggccg 7080
cccacggggg gccacagcag cggccgctcg cccaggatgg agaggcgggt cccaggcccg 7140
gcccggagcg agtcccccag ggcctgtcga cacggcgggg cccggtggcc ggcatctggc 7200
ccgcacgtgt ccgaggggcc cccgggtccc cggcaccatg gctactaccg gggctccgac 7260
tacgacgagg ccgatggccc gggcagcggg ggcggcgagg aggccatggc cggggcctac 7320
gacgcgccac cccccgtacg acacgcgtcc tcgggcgcca ccgggcgctc gcccaggact 7380
ccccgggcct cgggcccggc ctgcgcctcg ccttctcggc acggccggcg actccccaac 7440
ggctactacc cggcgcacgg actggccagg ccccgcgggc cgggctccag gaagggcctg 7500
cacgaaccct acagcgagag tgacgatgat tggtgctaa 7539

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 5
tgacttttct ttctctccgt ttg 23

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 6
tggctgcaat aatcactttg tt 22

<210> SEQ ID NO 7
<211> LENGTH: 21

<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 7
tctctgtctc cccaggttta c 21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 8
gtggctaaca cacagctttg c 21

<210> SEQ ID NO 9
<211> LENGTH: 21
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 9
tcatggcaca gttcctgtat c 21

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 10
gcagtaggca attagcagca a 21

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 11
tggggcactt tagaaattgt g 21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 12
tgacaaagat gcaaaatgag ag 22

<210> SEQ ID NO 13
<211> LENGTH: 20
<212> TYPE: DNA

-continued

```
<213> ORGANISM: Artificial Sequence
<220> FEATURE:
<223> OTHER INFORMATION: Description of Artificial Sequence: Synthesized
      Oligonucleotide

<400> SEQUENCE: 13

gcagtttggg cttttcaatg                                                20


<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 14

tgagcattgt cctcttgctg                                                20


<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 15

agggctacgt ttcatttgta tg                                             22


<210> SEQ ID NO 16
<211> LENGTH: 22
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 16

tgtgctaaat tgaaatccag ag                                             22


<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 17

cagctcttcg cactttcaga                                                20


<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 18

tcaagcagag aaggatgctg a                                              21


<210> SEQ ID NO 19
<211> LENGTH: 20
<212> TYPE: DNA
<213> ORGANISM: Artificial Sequence
```

<220> FEATURE:
<223> OTHER INFORMATION: Description of Artificial Sequence: Synthesized
Oligonucleotide

<400> SEQUENCE: 19
agcgttgcaa acattcttgg 20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 20
gggatatcca gcccctcaag 20

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 21
gacaaatact tgtgcctttg aatg 24

<210> SEQ ID NO 22
<211> LENGTH: 27
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 22
acataatctc atactttatc aaaaacc 27

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 23
gaaatggagg tgttgaaaat gc 22

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 24
aatccttggc atcactctgc 20

<210> SEQ ID NO 25
<211> LENGTH: 22
<212> TYPE: DNA
<213> ORGANISM: Artificial Sequence
<220> FEATURE:

-continued

<223> OTHER INFORMATION: Description of Artificial Sequence: Synthesized
      Oligonucleotide

<400> SEQUENCE: 25
agtacagggt gctatgacca ac 22

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 26
tcctcataca accacctgct c 21

<210> SEQ ID NO 27
<211> LENGTH: 21
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 27
tctccaaaag ccttcattag g 21

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 28
ttctaattct ccccctctct cc 22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 29
tcctcattct ttaatcccaa gg 22

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 30
gccgttctgt agaaacactg g 21

<210> SEQ ID NO 31
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 31
gtcagaaata tctgccatca cc 22

<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 32
gaatgcacta ttcccaactc ac 22

<210> SEQ ID NO 33
<211> LENGTH: 21
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 33
tgggctctat gtgtgtgtct g 21

<210> SEQ ID NO 34
<211> LENGTH: 20
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 34
ggaagcatga aggatggttg 20

<210> SEQ ID NO 35
<211> LENGTH: 20
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 35
tacttcgcgt ttccacaagg 20

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 36
gctatgcaag aaccctgatt g 21

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 37
atgagcctga gacggttagg 20

<210> SEQ ID NO 38
<211> LENGTH: 20
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 38
atacatgtgc catgctggtg 20

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 39
tgctgtggtg tttccttctc 20

<210> SEQ ID NO 40
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 40
tgtattcata ccttcccaca cc 22

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 41
aaaagggtta gcacagacaa tg 22

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 42
attgggcaga tataatcaaa gc 22

<210> SEQ ID NO 43
<211> LENGTH: 20
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 43
cacacagctg atgaatgtgc 20

<210> SEQ ID NO 44
<211> LENGTH: 20
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 44
tgaagggcta cactttctgg 20

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 45
tctgccctcc tattccaatg 20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 46
gcccttgtct tccagaaatg 20

<210> SEQ ID NO 47
<211> LENGTH: 27
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 47
aaaaattaca tcctttacat caaactg 27

<210> SEQ ID NO 48
<211> LENGTH: 21
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 48
ttttgcatgc atagattttc c 21

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 49
tgaaccttgc ttttacatat cc 22

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 50
acccatctgg gctcataaac 20

<210> SEQ ID NO 51
<211> LENGTH: 21
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 51
tgtcttggtc caaaatctgt g 21

<210> SEQ ID NO 52
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 52
ttggtcgttt atgctttatt cg 22

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 53
ccctaaaggc caatttcagg 20

<210> SEQ ID NO 54
<211> LENGTH: 21
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 54
atttggcaga gaaaacactc c 21

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 55
gagatttggg ggtgtttgtc 20

<210> SEQ ID NO 56
<211> LENGTH: 20
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 56
ggattgtaat ggggtgcttc 20

<210> SEQ ID NO 57
<211> LENGTH: 20
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 57
caaaaatcag ggccaatgac 20

<210> SEQ ID NO 58
<211> LENGTH: 20
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 58
tgattgctgg gatgatcttg 20

<210> SEQ ID NO 59
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 59
aggactctga accttacctt gg 22

<210> SEQ ID NO 60
<211> LENGTH: 20
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 60
ccatgaatcg ctcttccatc 20

<210> SEQ ID NO 61
<211> LENGTH: 19
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 61
tgtgggaacc catctgttg 19

<210> SEQ ID NO 62
<211> LENGTH: 20
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 62
gtttgctgac aaggggtcac 20

<210> SEQ ID NO 63
<211> LENGTH: 21
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 63
tctccgcagt cgtagctcca g 21

<210> SEQ ID NO 64
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 64
agagattctt tcacactcct cc 22

<210> SEQ ID NO 65
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 65
tttagaagtc acctgatctg gg 22

<210> SEQ ID NO 66
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 66
gacagagcga gactctggtt ca 22

<210> SEQ ID NO 67
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 67
gacaagagaa ctctgcaaga gg 22

-continued

<210> SEQ ID NO 68
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 68
atacagctga gacatggagg tg 22

<210> SEQ ID NO 69
<211> LENGTH: 23
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 69
tttatcccgt gaggcaggta ctg 23

<210> SEQ ID NO 70
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 70
cctcctgaga tgctctgcat ag 22

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 71
tgtggtgctt ccttcaccat tg 22

<210> SEQ ID NO 72
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 72
cagaggctat ttcactcact gc 22

<210> SEQ ID NO 73
<211> LENGTH: 23
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 73
ccccaaagcc aaacattgat ctc 23

-continued

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 74
actctgattg tccacacaca ctg 23

<210> SEQ ID NO 75
<211> LENGTH: 23
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 75
cagaaaacgt tcctccattt ccc 23

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 76
aagcttcaat ggcctctact tgg 23

<210> SEQ ID NO 77
<211> LENGTH: 23
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 77
gccatactct ggcttttcta tgc 23

<210> SEQ ID NO 78
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 78
cgtgatgtca gatcctggct tc 22

<210> SEQ ID NO 79
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 79
gttggctatt gctactgttg cg 22

<210> SEQ ID NO 80

<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 80
gatccttaga accagtcacc tg 22

<210> SEQ ID NO 81
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 81
tgatagtgcc accttgaacc tc 22

<210> SEQ ID NO 82
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 82
tgatgtaatc tgcccaggac ac 22

<210> SEQ ID NO 83
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 83
ctgcaacaga gaactatcag cc 22

<210> SEQ ID NO 84
<211> LENGTH: 23
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 84
aagagaagtg gaaaaagggt gtg 23

<210> SEQ ID NO 85
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 85
gtagttctag catgttggag gc 22

<210> SEQ ID NO 86
<211> LENGTH: 22

<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 86
atctgtcatt ccaggcaaga gc 22

<210> SEQ ID NO 87
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 87
atggatgaat gagggggtca ag 22

<210> SEQ ID NO 88
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 88
agcaggcact ttcatctgtg ac 22

<210> SEQ ID NO 89
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 89
tccatttgga gggaggagtt tg 22

<210> SEQ ID NO 90
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 90
cctccagaaa gttgggaaag tg 22

<210> SEQ ID NO 91
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 91
aaggagaagc caacacggag tc 22

<210> SEQ ID NO 92
<211> LENGTH: 23
<212> TYPE: DNA

<213> ORGANISM: Artificial Sequence
<220> FEATURE:
<223> OTHER INFORMATION: Description of Artificial Sequence: Synthesized
Oligonucleotide

<400> SEQUENCE: 92
ggtggtaact ttgccagaga aac 23

<210> SEQ ID NO 93
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 93
agcaggtacc cattccaatt gg 22

<210> SEQ ID NO 94
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 94
aatctgtgcc tgggatagtg tg 22

<210> SEQ ID NO 95
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 95
cctgactcag atgctcacag ac 22

<210> SEQ ID NO 96
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 96
acacagcacg tgctactttg gc 22

<210> SEQ ID NO 97
<211> LENGTH: 21
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 97
gaggacttcc tcaggaaaca g 21

<210> SEQ ID NO 98
<211> LENGTH: 23
<212> TYPE: DNA
<213> ORGANISM: Artificial Sequence

```
<220> FEATURE:
<223> OTHER INFORMATION: Description of Artificial Sequence: Synthesized
      Oligonucleotide

<400> SEQUENCE: 98

agatggaatc ttagctagga tcc                                          23


<210> SEQ ID NO 99
<211> LENGTH: 23
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 99

aattatctca ctgaaccctc cac                                          23


<210> SEQ ID NO 100
<211> LENGTH: 22
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 100

agaaatgtca gccgcttctt gc                                           22


<210> SEQ ID NO 101
<211> LENGTH: 22
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 101

ggtggtcaac actcactcat tg                                           22


<210> SEQ ID NO 102
<211> LENGTH: 22
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 102

tttgttgtgt aggaggcctt gg                                           22


<210> SEQ ID NO 103
<211> LENGTH: 22
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 103

aacatcccac cctacctatg ag                                           22


<210> SEQ ID NO 104
<211> LENGTH: 22
<212> TYPE: DNA
<213> ORGANISM: Artificial Sequence
<220> FEATURE:
```

<223> OTHER INFORMATION: Description of Artificial Sequence: Synthesized
      Oligonucleotide

<400> SEQUENCE: 104
cctgcgcaac tgtatatagc ag 22

<210> SEQ ID NO 105
<211> LENGTH: 22
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 105
ctcaacctcc tgatctcaag tg 22

<210> SEQ ID NO 106
<211> LENGTH: 23
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 106
cccaaagttt ggatctaaga gcc 23

<210> SEQ ID NO 107
<211> LENGTH: 22
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 107
aaagccatcg aagctcttcc tg 22

<210> SEQ ID NO 108
<211> LENGTH: 22
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 108
caggtgaaat ggaccactct tc 22

<210> SEQ ID NO 109
<211> LENGTH: 22
<212> TYPE: DNA
<213> ORGANISM: Artificial Sequence
<220> FEATURE:
<223> OTHER INFORMATION: Description of Artificial Sequence: Synthesized
      Oligonucleotide

<400> SEQUENCE: 109
tccttgagca gtgtacaacc tg 22

<210> SEQ ID NO 110
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 110
gaatgccagg attgagtcca ac 22

<210> SEQ ID NO 111
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 111
gaatgtgctg gaaagtggag ac 22

<210> SEQ ID NO 112
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 112
cactgcttcc caagcagtct ag 22

<210> SEQ ID NO 113
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 113
attacaggcg tgagccacca tg 22

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 114
tttccctctg ttcctgttct gc 22

<210> SEQ ID NO 115
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 115
ttcggttggg acaatgcttc tg 22

<210> SEQ ID NO 116
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 116
ctcaagcaac tgtagctgtt gg 22

<210> SEQ ID NO 117
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 117
ttatcagggt agaggcagga ac 22

<210> SEQ ID NO 118
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 118
gtgaaaagaa gagcctagtc cg 22

<210> SEQ ID NO 119
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 119
atggtaacac tcacaggttg gg 22

<210> SEQ ID NO 120
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 120
gcccttcgaa caaccataac tg 22

<210> SEQ ID NO 121
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 121
cctacagcca agctttggtt ac 22

<210> SEQ ID NO 122
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 122
cccattggtt ttttggcact gg 22

<210> SEQ ID NO 123
<211> LENGTH: 21
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 123
ggacagacag acagaggaga g 21

<210> SEQ ID NO 124
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 124
tgttggttgg cttcatgtag gg 22

<210> SEQ ID NO 125
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 125
cagaattatc agagcaggtc cc 22

<210> SEQ ID NO 126
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 126
tctcagctcc cagtaaaagg ag 22

<210> SEQ ID NO 127
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 127
caacagtgct gagtttgaga cg 22

<210> SEQ ID NO 128
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 128
ggcctctgtg tacatgtctt tg 22

<210> SEQ ID NO 129
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 129
gggtatgcaa gggtgatgat tc 22

<210> SEQ ID NO 130
<211> LENGTH: 21
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 130
tgtttctccc cacctctctt c 21

<210> SEQ ID NO 131
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 131
aaaaaaaccc agtgcctgga cg 22

<210> SEQ ID NO 132
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 132
agaaactgag tactgggaca gg 22

<210> SEQ ID NO 133
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 133
ggaagagtga atgaagatcc gg 22

<210> SEQ ID NO 134
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 134
aaagattggg gtctcgttct cg 22

<210> SEQ ID NO 135
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 135
ccctcatatt ccagttggtt cc 22

<210> SEQ ID NO 136
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 136
gtgtgtgtgt gtgtatactg gg 22

<210> SEQ ID NO 137
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 137
cagactgctt cagagactga ag 22

<210> SEQ ID NO 138
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 138
ccgatttctc ttgatgccag tg 22

<210> SEQ ID NO 139
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 139
agggtgcgat tgccaaagaa ag 22

<210> SEQ ID NO 140
<211> LENGTH: 22
<212> TYPE: DNA
<213> ORGANISM: Artificial Sequence
<220> FEATURE:
<223> OTHER INFORMATION: Description of Artificial Sequence: Synthesized
Oligonucleotide

<400> SEQUENCE: 140
acccagagcc ctgattgatc ag 22

-continued

<210> SEQ ID NO 141
<211> LENGTH: 22
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 141
ttggatgggg tatccccttc tc 22

<210> SEQ ID NO 142
<211> LENGTH: 21
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 142
tctcttcctc ccaatcccgt g 21

<210> SEQ ID NO 143
<211> LENGTH: 21
<212> TYPE: DNA
<213> ORGANISM: Artificial Sequence
<220> FEATURE:
<223> OTHER INFORMATION: Description of Artificial Sequence: Synthesized Oligonucleotide

<400> SEQUENCE: 143
tgcccaggag ggtctctttt g 21

<210> SEQ ID NO 144
<211> LENGTH: 2009
<212> TYPE: PRT
<213> ORGANISM: Rattus norvegicus

<400> SEQUENCE: 144

```
Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
```

-continued

```
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Val Gln Trp Pro Pro Thr Asn Ala Ser Leu Glu
        275                 280                 285

Glu His Ser Ile Glu Lys Asn Val Thr Thr Asp Tyr Asn Gly Thr Leu
    290                 295                 300

Val Asn Glu Thr Val Phe Glu Phe Asp Trp Lys Ser Tyr Ile Gln Asp
305                 310                 315                 320

Ser Arg Tyr His Tyr Phe Leu Glu Gly Val Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Leu
        435                 440                 445

Glu Gln Leu Lys Lys Gln Gln Glu Ala Ala Gln Gln Ala Ala Ala Ala
    450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Asp Asp Glu Phe His Lys Ser Glu Ser Glu Asp Ser
        515                 520                 525

Ile Arg Arg Lys Gly Phe Arg Phe Ser Ile Glu Gly Asn Arg Leu Thr
    530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590
```

```
Asp Glu His Ser Thr Phe Glu Asp Asn Glu Ser Arg Arg Asp Ser Leu
        595                 600                 605

Phe Val Pro Arg Arg His Gly Glu Arg Arg Asn Ser Asn Leu Ser Gln
    610                 615                 620

Thr Ser Arg Ser Ser Arg Met Leu Ala Gly Leu Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
            660                 665                 670

Ile Asp Lys Pro Ala Thr Asp Asp Asn Gly Thr Thr Thr Glu Thr Glu
        675                 680                 685

Met Arg Lys Arg Arg Ser Ser Ser Phe His Val Ser Met Asp Phe Leu
    690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
            740                 745                 750

Tyr Trp Leu Lys Val Lys His Ile Val Asn Leu Val Val Met Asp Pro
        755                 760                 765

Phe Val Asp Leu Ala Ile Thr Ile Cys Ile Val Leu Asn Thr Leu Phe
    770                 775                 780

Met Ala Met Glu His Tyr Pro Met Thr Glu His Phe Asn His Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
            820                 825                 830

Asn Ile Phe Asp Gly Phe Ile Val Thr Leu Ser Leu Val Glu Leu Gly
        835                 840                 845

Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
            900                 905                 910

Gly Lys Ser Tyr Lys Asp Cys Val Cys Lys Ile Ala Thr Asp Cys Lys
        915                 920                 925

Leu Pro Arg Trp His Met Asn Asp Phe Phe His Ser Phe Leu Ile Val
    930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Arg Asn Leu Val Val Leu Asn Leu Phe Leu Ala Leu Leu Leu
            980                 985                 990

Ser Ser Phe Ser Ala Asp Asn Leu  Ala Ala Thr Asp Asp  Asp Asn Glu
        995                 1000                 1005
```

```
Met Asn  Asn Leu Gln Ile Ala  Val Asp Arg Met His  Lys Gly Val
    1010                 1015                 1020

Ala Tyr  Val Lys Arg Lys Ile  Tyr Glu Phe Ile Gln  Gln Ser Phe
    1025                 1030                 1035

Val Arg  Lys Gln Lys Ile Leu  Asp Glu Ile Lys Pro  Leu Asp Asp
    1040                 1045                 1050

Leu Asn  Asn Arg Lys Asp Asn  Cys Thr Ser Asn His  Thr Thr Glu
    1055                 1060                 1065

Ile Gly  Lys Asp Leu Asp Cys  Leu Lys Asp Val Asn  Gly Thr Thr
    1070                 1075                 1080

Ser Gly  Ile Gly Thr Gly Ser  Ser Val Glu Lys Tyr  Ile Ile Asp
    1085                 1090                 1095

Glu Ser  Asp Tyr Met Ser Phe  Ile Asn Asn Pro Ser  Leu Thr Val
    1100                 1105                 1110

Thr Val  Pro Ile Ala Val Gly  Glu Ser Asp Phe Glu  Asn Leu Asn
    1115                 1120                 1125

Thr Glu  Asp Phe Ser Ser Glu  Ser Asp Leu Glu Glu  Ser Lys Glu
    1130                 1135                 1140

Lys Leu  Asn Glu Ser Ser Ser  Ser Ser Glu Gly Ser  Thr Val Asp
    1145                 1150                 1155

Ile Gly  Ala Pro Ala Glu Glu  Gln Pro Val Met Glu  Pro Glu Glu
    1160                 1165                 1170

Thr Leu  Glu Pro Glu Ala Cys  Phe Thr Glu Gly Cys  Val Gln Arg
    1175                 1180                 1185

Phe Lys  Cys Cys Gln Ile Ser  Val Glu Glu Gly Arg  Gly Lys Gln
    1190                 1195                 1200

Trp Trp  Asn Leu Arg Arg Thr  Cys Phe Arg Ile Val  Glu His Asn
    1205                 1210                 1215

Trp Phe  Glu Thr Phe Ile Val  Phe Met Ile Leu Leu  Ser Ser Gly
    1220                 1225                 1230

Ala Leu  Ala Phe Glu Asp Ile  Tyr Ile Asp Gln Arg  Lys Thr Ile
    1235                 1240                 1245

Lys Thr  Met Leu Glu Tyr Ala  Asp Lys Val Phe Thr  Tyr Ile Phe
    1250                 1255                 1260

Ile Leu  Glu Met Leu Leu Lys  Trp Val Ala Tyr Gly  Tyr Gln Thr
    1265                 1270                 1275

Tyr Phe  Thr Asn Ala Trp Cys  Trp Leu Asp Phe Leu  Ile Val Asp
    1280                 1285                 1290

Val Ser  Leu Val Ser Leu Thr  Ala Asn Ala Leu Gly  Tyr Ser Glu
    1295                 1300                 1305

Leu Gly  Ala Ile Lys Ser Leu  Arg Thr Leu Arg Ala  Leu Arg Pro
    1310                 1315                 1320

Leu Arg  Ala Leu Ser Arg Phe  Glu Gly Met Arg Val  Val Val Asn
    1325                 1330                 1335

Ala Leu  Leu Gly Ala Ile Pro  Ser Ile Met Asn Val  Leu Leu Val
    1340                 1345                 1350

Cys Leu  Ile Phe Trp Leu Ile  Phe Ser Ile Met Gly  Val Asn Leu
    1355                 1360                 1365

Phe Ala  Gly Lys Phe Tyr His  Cys Val Asn Thr Thr  Thr Gly Asp
    1370                 1375                 1380

Thr Phe  Glu Ile Thr Glu Val  Asn Asn His Ser Asp  Cys Leu Lys
    1385                 1390                 1395

Leu Ile  Glu Arg Asn Glu Thr  Ala Arg Trp Lys Asn  Val Lys Val
```

```
    1400                1405                1410

Asn Phe Asp Asn Val Gly Phe Gly Tyr Leu Ser Leu Leu Gln Val
    1415                1420                1425

Ala Thr Phe Lys Gly Trp Met Asp Ile Met Tyr Ala Ala Val Asp
    1430                1435                1440

Ser Arg Asn Val Glu Leu Gln Pro Lys Tyr Glu Glu Ser Leu Tyr
    1445                1450                1455

Met Tyr Leu Tyr Phe Val Ile Phe Ile Ile Phe Gly Ser Phe Phe
    1460                1465                1470

Thr Leu Asn Leu Phe Ile Gly Val Ile Ile Asp Asn Phe Asn Gln
    1475                1480                1485

Gln Lys Lys Lys Phe Gly Gly Gln Asp Ile Phe Met Thr Glu Glu
    1490                1495                1500

Gln Lys Lys Tyr Tyr Asn Ala Met Lys Lys Leu Gly Ser Lys Lys
    1505                1510                1515

Pro Gln Lys Pro Ile Pro Arg Pro Gly Asn Lys Phe Gln Gly Met
    1520                1525                1530

Val Phe Asp Phe Val Thr Arg Gln Val Phe Asp Ile Ser Ile Met
    1535                1540                1545

Ile Leu Ile Cys Leu Asn Met Val Thr Met Met Val Glu Thr Asp
    1550                1555                1560

Asp Gln Ser Asp Tyr Val Thr Ser Ile Leu Ser Arg Ile Asn Leu
    1565                1570                1575

Val Phe Ile Val Leu Phe Thr Gly Glu Cys Val Leu Lys Leu Ile
    1580                1585                1590

Ser Leu Arg His Tyr Tyr Phe Thr Ile Gly Trp Asn Ile Phe Asp
    1595                1600                1605

Phe Val Val Val Ile Leu Ser Ile Val Gly Met Phe Leu Ala Glu
    1610                1615                1620

Leu Ile Glu Lys Tyr Phe Val Ser Pro Thr Leu Phe Arg Val Ile
    1625                1630                1635

Arg Leu Ala Arg Ile Gly Arg Ile Leu Arg Leu Ile Lys Gly Ala
    1640                1645                1650

Lys Gly Ile Arg Thr Leu Leu Phe Ala Leu Met Met Ser Leu Pro
    1655                1660                1665

Ala Leu Phe Asn Ile Gly Leu Leu Leu Phe Leu Val Met Phe Ile
    1670                1675                1680

Tyr Ala Ile Phe Gly Met Ser Asn Phe Ala Tyr Val Lys Arg Glu
    1685                1690                1695

Val Gly Ile Asp Asp Met Phe Asn Phe Glu Thr Phe Gly Asn Ser
    1700                1705                1710

Met Ile Cys Leu Phe Gln Ile Thr Thr Ser Ala Gly Trp Asp Gly
    1715                1720                1725

Leu Leu Ala Pro Ile Leu Asn Ser Lys Pro Pro Asp Cys Asp Pro
    1730                1735                1740

Asn Lys Val Asn Pro Gly Ser Ser Val Lys Gly Asp Cys Gly Asn
    1745                1750                1755

Pro Ser Val Gly Ile Phe Phe Phe Val Ser Tyr Ile Ile Ile Ser
    1760                1765                1770

Phe Leu Val Val Val Asn Met Tyr Ile Ala Val Ile Leu Glu Asn
    1775                1780                1785

Phe Ser Val Ala Thr Glu Glu Ser Ala Glu Pro Leu Ser Glu Asp
    1790                1795                1800
```

Asp Phe Glu Met Phe Tyr Glu Val Trp Glu Lys Phe Asp Pro Asp
1805 1810 1815

Ala Thr Gln Phe Met Glu Phe Glu Lys Leu Ser Gln Phe Ala Ala
1820 1825 1830

Ala Leu Glu Pro Pro Leu Asn Leu Pro Gln Pro Asn Lys Leu Gln
1835 1840 1845

Leu Ile Ala Met Asp Leu Pro Met Val Ser Gly Asp Arg Ile His
1850 1855 1860

Cys Leu Asp Ile Leu Phe Ala Phe Thr Lys Arg Val Leu Gly Glu
1865 1870 1875

Ser Gly Glu Met Asp Ala Leu Arg Ile Gln Met Glu Glu Arg Phe
1880 1885 1890

Met Ala Ser Asn Pro Ser Lys Val Ser Tyr Gln Pro Ile Thr Thr
1895 1900 1905

Thr Leu Lys Arg Lys Gln Glu Glu Val Ser Ala Val Ile Ile Gln
1910 1915 1920

Arg Ala Tyr Arg Arg His Leu Leu Lys Arg Thr Val Lys Gln Ala
1925 1930 1935

Ser Phe Thr Tyr Asn Lys Asn Lys Leu Lys Gly Gly Ala Asn Leu
1940 1945 1950

Leu Val Lys Glu Asp Met Ile Ile Asp Arg Ile Asn Glu Asn Ser
1955 1960 1965

Ile Thr Glu Lys Thr Asp Leu Thr Met Ser Thr Ala Ala Cys Pro
1970 1975 1980

Pro Ser Tyr Asp Arg Val Thr Lys Pro Ile Val Glu Lys His Glu
1985 1990 1995

Gln Glu Gly Lys Asp Glu Lys Ala Lys Gly Lys
2000 2005

<210> SEQ ID NO 145
<211> LENGTH: 2009
<212> TYPE: PRT
<213> ORGANISM: Homo sapiens

<400> SEQUENCE: 145

Met Glu Gln Thr Val Leu Val Pro Pro Gly Pro Asp Ser Phe Asn Phe
1 5 10 15

Phe Thr Arg Glu Ser Leu Ala Ala Ile Glu Arg Arg Ile Ala Glu Glu
20 25 30

Lys Ala Lys Asn Pro Lys Pro Asp Lys Lys Asp Asp Asp Glu Asn Gly
35 40 45

Pro Lys Pro Asn Ser Asp Leu Glu Ala Gly Lys Asn Leu Pro Phe Ile
50 55 60

Tyr Gly Asp Ile Pro Pro Glu Met Val Ser Glu Pro Leu Glu Asp Leu
65 70 75 80

Asp Pro Tyr Tyr Ile Asn Lys Lys Thr Phe Ile Val Leu Asn Lys Gly
85 90 95

Lys Ala Ile Phe Arg Phe Ser Ala Thr Ser Ala Leu Tyr Ile Leu Thr
100 105 110

Pro Phe Asn Pro Leu Arg Lys Ile Ala Ile Lys Ile Leu Val His Ser
115 120 125

Leu Phe Ser Met Leu Ile Met Cys Thr Ile Leu Thr Asn Cys Val Phe
130 135 140

Met Thr Met Ser Asn Pro Pro Asp Trp Thr Lys Asn Val Glu Tyr Thr

-continued

```
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Gln Ala Ala Thr Ala
    450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
        515                 520                 525

Ile Arg Arg Lys Gly Phe Arg Phe Ser Ile Glu Gly Asn Arg Leu Thr
    530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575
```

-continued

```
Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
        595                 600                 605

Phe Val Pro Arg Arg His Gly Glu Arg Arg Asn Ser Asn Leu Ser Gln
    610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
            660                 665                 670

Ile Asp Lys Pro Ala Thr Asp Asp Asn Gly Thr Thr Thr Glu Thr Glu
        675                 680                 685

Met Arg Lys Arg Arg Ser Ser Ser Phe His Val Ser Met Asp Phe Leu
    690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
            740                 745                 750

Tyr Trp Leu Lys Val Lys His Val Val Asn Leu Val Val Met Asp Pro
        755                 760                 765

Phe Val Asp Leu Ala Ile Thr Ile Cys Ile Val Leu Asn Thr Leu Phe
    770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
            820                 825                 830

Asn Ile Phe Asp Gly Phe Ile Val Thr Leu Ser Leu Val Glu Leu Gly
        835                 840                 845

Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
            900                 905                 910

Gly Lys Ser Tyr Lys Asp Cys Val Cys Lys Ile Ala Ser Asp Cys Gln
        915                 920                 925

Leu Pro Arg Trp His Met Asn Asp Phe Phe His Ser Phe Leu Ile Val
    930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
            980                 985                 990
```

```
Ser Ser Phe Ser Ala Asp Asn Leu  Ala Ala Thr Asp Asp  Asp Asn Glu
        995                 1000                1005

Met Asn  Asn Leu Gln Ile Ala  Val Asp Arg Met His  Lys Gly Val
    1010                 1015                 1020

Ala Tyr  Val Lys Arg Lys Ile  Tyr Glu Phe Ile Gln  Gln Ser Phe
    1025                 1030                 1035

Ile Arg  Lys Gln Lys Ile Leu  Asp Glu Ile Lys Pro  Leu Asp Asp
    1040                 1045                 1050

Leu Asn  Asn Lys Lys Asp Ser  Cys Met Ser Asn His  Thr Thr Glu
    1055                 1060                 1065

Ile Gly  Lys Asp Leu Asp Tyr  Leu Lys Asp Val Asn  Gly Thr Thr
    1070                 1075                 1080

Ser Gly  Ile Gly Thr Gly Ser  Ser Val Glu Lys Tyr  Ile Ile Asp
    1085                 1090                 1095

Glu Ser  Asp Tyr Met Ser Phe  Ile Asn Asn Pro Ser  Leu Thr Val
    1100                 1105                 1110

Thr Val  Pro Ile Ala Val Gly  Glu Ser Asp Phe Glu  Asn Leu Asn
    1115                 1120                 1125

Thr Glu  Asp Phe Ser Ser Glu  Ser Asp Leu Glu Glu  Ser Lys Glu
    1130                 1135                 1140

Lys Leu  Asn Glu Ser Ser Ser  Ser Ser Glu Gly Ser  Thr Val Asp
    1145                 1150                 1155

Ile Gly  Ala Pro Val Glu Glu  Gln Pro Val Val Glu  Pro Glu Glu
    1160                 1165                 1170

Thr Leu  Glu Pro Glu Ala Cys  Phe Thr Glu Gly Cys  Val Gln Arg
    1175                 1180                 1185

Phe Lys  Cys Cys Gln Ile Asn  Val Glu Glu Gly Arg  Gly Lys Gln
    1190                 1195                 1200

Trp Trp  Asn Leu Arg Arg Thr  Cys Phe Arg Ile Val  Glu His Asn
    1205                 1210                 1215

Trp Phe  Glu Thr Phe Ile Val  Phe Met Ile Leu Leu  Ser Ser Gly
    1220                 1225                 1230

Ala Leu  Ala Phe Glu Asp Ile  Tyr Ile Asp Gln Arg  Lys Thr Ile
    1235                 1240                 1245

Lys Thr  Met Leu Glu Tyr Ala  Asp Lys Val Phe Thr  Tyr Ile Phe
    1250                 1255                 1260

Ile Leu  Glu Met Leu Leu Lys  Trp Val Ala Tyr Gly  Tyr Gln Thr
    1265                 1270                 1275

Tyr Phe  Thr Asn Ala Trp Cys  Trp Leu Asp Phe Leu  Ile Val Asp
    1280                 1285                 1290

Val Ser  Leu Val Ser Leu Thr  Ala Asn Ala Leu Gly  Tyr Ser Glu
    1295                 1300                 1305

Leu Gly  Ala Ile Lys Ser Leu  Arg Thr Leu Arg Ala  Leu Arg Pro
    1310                 1315                 1320

Leu Arg  Ala Leu Ser Arg Phe  Glu Gly Met Arg Val  Val Val Asn
    1325                 1330                 1335

Ala Leu  Leu Gly Ala Ile Pro  Ser Ile Met Asn Val  Leu Leu Val
    1340                 1345                 1350

Cys Leu  Ile Phe Trp Leu Ile  Phe Ser Ile Met Gly  Val Asn Leu
    1355                 1360                 1365

Phe Ala  Gly Lys Phe Tyr His  Cys Ile Asn Thr Thr  Thr Gly Asp
    1370                 1375                 1380

Arg Phe  Asp Ile Glu Asp Val  Asn Asn His Thr Asp  Cys Leu Lys
```

```
    1385                1390                1395

Leu Ile  Glu Arg Asn Glu Thr  Ala Arg Trp Lys Asn  Val Lys Val
    1400                1405                1410

Asn Phe  Asp His Val Gly Phe  Gly Tyr Leu Ser Leu  Leu Gln Val
    1415                1420                1425

Ala Thr  Phe Lys Gly Trp Met  Asp Ile Met Tyr Ala  Ala Val Asp
    1430                1435                1440

Ser Arg  Asn Val Glu Leu Gln  Pro Lys Tyr Glu Glu  Ser Leu Tyr
    1445                1450                1455

Met Tyr  Leu Tyr Phe Val Ile  Phe Ile Ile Phe Gly  Ser Phe Phe
    1460                1465                1470

Thr Leu  Asn Leu Phe Ile Gly  Val Ile Ile Asp Asn  Phe Asn Gln
    1475                1480                1485

Gln Lys  Lys Lys Phe Gly Gly  Gln Asp Ile Phe Met  Thr Glu Glu
    1490                1495                1500

Gln Lys  Lys Tyr Tyr Asn Ala  Met Lys Lys Leu Gly  Ser Lys Lys
    1505                1510                1515

Pro Gln  Lys Pro Ile Pro Arg  Pro Gly Asn Lys Phe  Gln Gly Met
    1520                1525                1530

Val Phe  Asp Phe Val Thr Arg  Gln Val Phe Asp Ile  Ser Ile Met
    1535                1540                1545

Ile Leu  Ile Cys Leu Asn Met  Val Thr Met Met Val  Glu Thr Asp
    1550                1555                1560

Asp Gln  Ser Glu Tyr Val Thr  Thr Ile Leu Ser Arg  Ile Asn Leu
    1565                1570                1575

Val Phe  Ile Val Leu Phe Thr  Gly Glu Cys Val Leu  Lys Leu Ile
    1580                1585                1590

Ser Leu  Arg His Tyr Tyr Phe  Thr Ile Gly Trp Asn  Ile Phe Asp
    1595                1600                1605

Phe Val  Val Val Ile Leu Ser  Ile Val Gly Met Phe  Leu Ala Glu
    1610                1615                1620

Leu Ile  Glu Lys Tyr Phe Val  Ser Pro Thr Leu Phe  Arg Val Ile
    1625                1630                1635

Arg Leu  Ala Arg Ile Gly Arg  Ile Leu Arg Leu Ile  Lys Gly Ala
    1640                1645                1650

Lys Gly  Ile Arg Thr Leu Leu  Phe Ala Leu Met Met  Ser Leu Pro
    1655                1660                1665

Ala Leu  Phe Asn Ile Gly Leu  Leu Leu Phe Leu Val  Met Phe Ile
    1670                1675                1680

Tyr Ala  Ile Phe Gly Met Ser  Asn Phe Ala Tyr Val  Lys Arg Glu
    1685                1690                1695

Val Gly  Ile Asp Asp Met Phe  Asn Phe Glu Thr Phe  Gly Asn Ser
    1700                1705                1710

Met Ile  Cys Leu Phe Gln Ile  Thr Thr Ser Ala Gly  Trp Asp Gly
    1715                1720                1725

Leu Leu  Ala Pro Ile Leu Asn  Ser Lys Pro Pro Asp  Cys Asp Pro
    1730                1735                1740

Asn Lys  Val Asn Pro Gly Ser  Ser Val Lys Gly Asp  Cys Gly Asn
    1745                1750                1755

Pro Ser  Val Gly Ile Phe Phe  Phe Val Ser Tyr Ile  Ile Ile Ser
    1760                1765                1770

Phe Leu  Val Val Val Asn Met  Tyr Ile Ala Val Ile  Leu Glu Asn
    1775                1780                1785
```

```
Phe Ser  Val Ala Thr Glu Glu  Ser Ala Glu Pro Leu  Ser Glu Asp
    1790                 1795                 1800

Asp Phe  Glu Met Phe Tyr Glu  Val Trp Glu Lys Phe  Asp Pro Asp
    1805                 1810                 1815

Ala Thr  Gln Phe Met Glu Phe  Glu Lys Leu Ser Gln  Phe Ala Ala
    1820                 1825                 1830

Ala Leu  Glu Pro Pro Leu Asn  Leu Pro Gln Pro Asn  Lys Leu Gln
    1835                 1840                 1845

Leu Ile  Ala Met Asp Leu Pro  Met Val Ser Gly Asp  Arg Ile His
    1850                 1855                 1860

Cys Leu  Asp Ile Leu Phe Ala  Phe Thr Lys Arg Val  Leu Gly Glu
    1865                 1870                 1875

Ser Gly  Glu Met Asp Ala Leu  Arg Ile Gln Met Glu  Glu Arg Phe
    1880                 1885                 1890

Met Ala  Ser Asn Pro Ser Lys  Val Ser Tyr Gln Pro  Ile Thr Thr
    1895                 1900                 1905

Thr Leu  Lys Arg Lys Gln Glu  Glu Val Ser Ala Val  Ile Ile Gln
    1910                 1915                 1920

Arg Ala  Tyr Arg Arg His Leu  Leu Lys Arg Thr Val  Lys Gln Ala
    1925                 1930                 1935

Ser Phe  Thr Tyr Asn Lys Asn  Lys Ile Lys Gly Gly  Ala Asn Leu
    1940                 1945                 1950

Leu Ile  Lys Glu Asp Met Ile  Ile Asp Arg Ile Asn  Glu Asn Ser
    1955                 1960                 1965

Ile Thr  Glu Lys Thr Asp Leu  Thr Met Ser Thr Ala  Ala Cys Pro
    1970                 1975                 1980

Pro Ser  Tyr Asp Arg Val Thr  Lys Pro Ile Val Glu  Lys His Glu
    1985                 1990                 1995

Gln Glu  Gly Lys Asp Glu Lys  Ala Lys Gly Lys
    2000                 2005
```

<210> SEQ ID NO 146
<211> LENGTH: 2009
<212> TYPE: PRT
<213> ORGANISM: Rattus norvegicus

<400> SEQUENCE: 146

```
Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
```

-continued

```
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Val Gln Trp Pro Pro Thr Asn Ala Ser Leu Glu
        275                 280                 285

Glu His Ser Ile Glu Lys Asn Val Thr Thr Asp Tyr Asn Gly Thr Leu
    290                 295                 300

Val Asn Glu Thr Val Phe Glu Phe Asp Trp Lys Ser Tyr Ile Gln Asp
305                 310                 315                 320

Ser Arg Tyr His Tyr Phe Leu Glu Gly Val Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415

Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Leu
        435                 440                 445

Glu Gln Leu Lys Lys Gln Gln Glu Ala Ala Gln Gln Ala Ala Ala Ala
    450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Asp Asp Glu Phe His Lys Ser Glu Ser Glu Asp Ser
        515                 520                 525

Ile Arg Arg Lys Gly Phe Arg Phe Ser Ile Glu Gly Asn Arg Leu Thr
    530                 535                 540

Tyr Glu Lys Arg Tyr Ser Ser Pro His Gln Ser Leu Leu Ser Ile Arg
545                 550                 555                 560
```

```
Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
        595                 600                 605

Phe Val Pro Arg Arg His Gly Glu Arg Arg Asn Ser Asn Leu Ser Gln
    610                 615                 620

Thr Ser Arg Ser Ser Arg Met Leu Ala Gly Leu Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
            660                 665                 670

Ile Asp Lys Pro Ala Thr Asp Asp Asn Gly Thr Thr Thr Glu Thr Glu
        675                 680                 685

Met Arg Lys Arg Arg Ser Ser Ser Phe His Val Ser Met Asp Phe Leu
    690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
            740                 745                 750

Tyr Trp Leu Lys Val Lys His Ile Val Asn Leu Val Val Met Asp Pro
        755                 760                 765

Phe Val Asp Leu Ala Ile Thr Ile Cys Ile Val Leu Asn Thr Leu Phe
    770                 775                 780

Met Ala Met Glu His Tyr Pro Met Thr Glu His Phe Asn His Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
            820                 825                 830

Asn Ile Phe Asp Gly Phe Ile Val Thr Leu Ser Leu Val Glu Leu Gly
        835                 840                 845

Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
            900                 905                 910

Gly Lys Ser Tyr Lys Asp Cys Val Cys Lys Ile Ala Thr Asp Cys Lys
        915                 920                 925

Leu Pro Arg Trp His Met Asn Asp Phe Phe His Ser Phe Leu Ile Val
    930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975
```

-continued

```
Val Ile Arg Asn Leu Val Val Leu Asn Leu Phe Leu Ala Leu Leu Leu
            980                 985                 990

Ser Ser Phe Ser Ala Asp Asn Leu  Ala Ala Thr Asp Asp  Asp Asn Glu
        995                 1000                 1005

Met Asn  Asn Leu Gln Ile Ala  Val Asp Arg Met His  Lys Gly Val
    1010                 1015                 1020

Ala Tyr  Val Lys Arg Lys Ile  Tyr Glu Phe Ile Gln  Gln Ser Phe
    1025                 1030                 1035

Val Arg  Lys Gln Lys Ile Leu  Asp Glu Ile Lys Pro  Leu Asp Asp
    1040                 1045                 1050

Leu Asn  Asn Arg Lys Asp Asn  Cys Thr Ser Asn His  Thr Thr Glu
    1055                 1060                 1065

Ile Gly  Lys Asp Leu Asp Cys  Leu Lys Asp Val Asn  Gly Thr Thr
    1070                 1075                 1080

Ser Gly  Ile Gly Thr Gly Ser  Ser Val Glu Lys Tyr  Ile Ile Asp
    1085                 1090                 1095

Glu Ser  Asp Tyr Met Ser Phe  Ile Asn Asn Pro Ser  Leu Thr Val
    1100                 1105                 1110

Thr Val  Pro Ile Ala Val Gly  Glu Ser Asp Phe Glu  Asn Leu Asn
    1115                 1120                 1125

Thr Glu  Asp Phe Ser Ser Glu  Ser Asp Leu Glu Glu  Ser Lys Glu
    1130                 1135                 1140

Lys Leu  Asn Glu Ser Ser Ser  Ser Ser Glu Gly Ser  Thr Val Asp
    1145                 1150                 1155

Ile Gly  Ala Pro Ala Glu Glu  Gln Pro Val Met Glu  Pro Glu Glu
    1160                 1165                 1170

Thr Leu  Glu Pro Glu Ala Cys  Phe Thr Glu Gly Cys  Val Gln Arg
    1175                 1180                 1185

Phe Lys  Cys Cys Gln Ile Ser  Val Glu Glu Gly Arg  Gly Lys Gln
    1190                 1195                 1200

Trp Trp  Asn Leu Arg Arg Thr  Cys Phe Arg Ile Val  Glu His Asn
    1205                 1210                 1215

Trp Phe  Glu Thr Phe Ile Val  Phe Met Ile Leu Leu  Ser Ser Gly
    1220                 1225                 1230

Ala Leu  Ala Phe Glu Asp Ile  Tyr Ile Asp Gln Arg  Lys Thr Ile
    1235                 1240                 1245

Lys Thr  Met Leu Glu Tyr Ala  Asp Lys Val Phe Thr  Tyr Ile Phe
    1250                 1255                 1260

Ile Leu  Glu Met Leu Leu Lys  Trp Val Ala Tyr Gly  Tyr Gln Thr
    1265                 1270                 1275

Tyr Phe  Thr Asn Ala Trp Cys  Trp Leu Asp Phe Leu  Ile Val Asp
    1280                 1285                 1290

Val Ser  Leu Val Ser Leu Thr  Ala Asn Ala Leu Gly  Tyr Ser Glu
    1295                 1300                 1305

Leu Gly  Ala Ile Lys Ser Leu  Arg Thr Leu Arg Ala  Leu Arg Pro
    1310                 1315                 1320

Leu Arg  Ala Leu Ser Arg Phe  Glu Gly Met Arg Val  Val Val Asn
    1325                 1330                 1335

Ala Leu  Leu Gly Ala Ile Pro  Ser Ile Met Asn Val  Leu Leu Val
    1340                 1345                 1350

Cys Leu  Ile Phe Trp Leu Ile  Phe Ser Ile Met Gly  Val Asn Leu
    1355                 1360                 1365

Phe Ala  Gly Lys Phe Tyr His  Cys Val Asn Thr Thr  Thr Gly Asp
```

-continued

```
    1370                1375                1380

Thr Phe  Glu Ile Thr Glu Val  Asn Asn His Ser Asp  Cys Leu Lys
    1385                1390                1395

Leu Ile  Glu Arg Asn Glu Thr  Ala Arg Trp Lys Asn  Val Lys Val
    1400                1405                1410

Asn Phe  Asp His Val Gly Phe  Gly Tyr Leu Ser Leu  Leu Gln Val
    1415                1420                1425

Ala Thr  Phe Lys Gly Trp Met  Asp Ile Met Tyr Ala  Ala Val Asp
    1430                1435                1440

Ser Arg  Asn Val Glu Leu Gln  Pro Lys Tyr Glu Glu  Ser Leu Tyr
    1445                1450                1455

Met Tyr  Leu Tyr Phe Val Ile  Phe Ile Ile Phe Gly  Ser Phe Phe
    1460                1465                1470

Thr Leu  Asn Leu Phe Ile Gly  Val Ile Ile Asp Asn  Phe Asn Gln
    1475                1480                1485

Gln Lys  Lys Lys Phe Gly Gly  Gln Asp Ile Phe Met  Thr Glu Glu
    1490                1495                1500

Gln Lys  Lys Tyr Tyr Asn Ala  Met Lys Lys Leu Gly  Ser Lys Lys
    1505                1510                1515

Pro Gln  Lys Pro Ile Pro Arg  Pro Gly Asn Lys Phe  Gln Gly Met
    1520                1525                1530

Val Phe  Asp Phe Val Thr Arg  Gln Val Phe Asp Ile  Ser Ile Met
    1535                1540                1545

Ile Leu  Ile Cys Leu Asn Met  Val Thr Met Met Val  Glu Thr Asp
    1550                1555                1560

Asp Gln  Ser Asp Tyr Val Thr  Ser Ile Leu Ser Arg  Ile Asn Leu
    1565                1570                1575

Val Phe  Ile Val Leu Phe Thr  Gly Glu Cys Val Leu  Lys Leu Ile
    1580                1585                1590

Ser Leu  Arg His Tyr Tyr Phe  Thr Ile Gly Trp Asn  Ile Phe Asp
    1595                1600                1605

Phe Val  Val Val Ile Leu Ser  Ile Val Gly Met Phe  Leu Ala Glu
    1610                1615                1620

Leu Ile  Glu Lys Tyr Phe Val  Ser Pro Thr Leu Phe  Arg Val Ile
    1625                1630                1635

Arg Leu  Ala Arg Ile Gly Arg  Ile Leu Arg Leu Ile  Lys Gly Ala
    1640                1645                1650

Lys Gly  Ile Arg Thr Leu Leu  Phe Ala Leu Met Met  Ser Leu Pro
    1655                1660                1665

Ala Leu  Phe Asn Ile Gly Leu  Leu Leu Phe Leu Val  Met Phe Ile
    1670                1675                1680

Tyr Ala  Ile Phe Gly Met Ser  Asn Phe Ala Tyr Val  Lys Arg Glu
    1685                1690                1695

Val Gly  Ile Asp Asp Met Phe  Asn Phe Glu Thr Phe  Gly Asn Ser
    1700                1705                1710

Met Ile  Cys Leu Phe Gln Ile  Thr Thr Ser Ala Gly  Trp Asp Gly
    1715                1720                1725

Leu Leu  Ala Pro Ile Leu Asn  Ser Lys Pro Pro Asp  Cys Asp Pro
    1730                1735                1740

Asn Lys  Val Asn Pro Gly Ser  Ser Val Lys Gly Asp  Cys Gly Asn
    1745                1750                1755

Pro Ser  Val Gly Ile Phe Phe  Phe Val Ser Tyr Ile  Ile Ile Ser
    1760                1765                1770
```

```
Phe Leu  Val Val Val Asn Met  Tyr Ile Ala Val Ile  Leu Glu Asn
    1775                 1780                 1785

Phe Ser  Val Ala Thr Glu Glu  Ser Ala Glu Pro Leu  Ser Glu Asp
    1790                 1795                 1800

Asp Phe  Glu Met Phe Tyr Glu  Val Trp Glu Lys Phe  Asp Pro Asp
    1805                 1810                 1815

Ala Thr  Gln Phe Met Glu Phe  Glu Lys Leu Ser Gln  Phe Ala Ala
    1820                 1825                 1830

Ala Leu  Glu Pro Pro Leu Asn  Leu Pro Gln Pro Asn  Lys Leu Gln
    1835                 1840                 1845

Leu Ile  Ala Met Asp Leu Pro  Met Val Ser Gly Asp  Arg Ile His
    1850                 1855                 1860

Cys Leu  Asp Ile Leu Phe Ala  Phe Thr Lys Arg Val  Leu Gly Glu
    1865                 1870                 1875

Ser Gly  Glu Met Asp Ala Leu  Arg Ile Gln Met Glu  Glu Arg Phe
    1880                 1885                 1890

Met Ala  Ser Asn Pro Ser Lys  Val Ser Tyr Gln Pro  Ile Thr Thr
    1895                 1900                 1905

Thr Leu  Lys Arg Lys Gln Glu  Glu Val Ser Ala Val  Ile Ile Gln
    1910                 1915                 1920

Arg Ala  Tyr Arg Arg His Leu  Leu Lys Arg Thr Val  Lys Gln Ala
    1925                 1930                 1935

Ser Phe  Thr Tyr Asn Lys Asn  Lys Leu Lys Gly Gly  Ala Asn Leu
    1940                 1945                 1950

Leu Val  Lys Glu Asp Met Ile  Ile Asp Arg Ile Asn  Glu Asn Ser
    1955                 1960                 1965

Ile Thr  Glu Lys Thr Asp Leu  Thr Met Ser Thr Ala  Ala Cys Pro
    1970                 1975                 1980

Pro Ser  Tyr Asp Arg Val Thr  Lys Pro Ile Val Glu  Lys His Glu
    1985                 1990                 1995

Gln Glu  Gly Lys Asp Glu Lys  Ala Lys Gly Lys
    2000                 2005


<210> SEQ ID NO 147
<211> LENGTH: 2368
<212> TYPE: PRT
<213> ORGANISM: Rattus norvegicus

<400> SEQUENCE: 147

Met Ala Arg Phe Gly Asp Glu Met Pro Gly Arg Tyr Gly Ala Gly Gly
1               5                   10                  15

Gly Gly Ser Gly Pro Ala Ala Gly Val Val Val Gly Ala Ala Gly Gly
            20                  25                  30

Arg Gly Ala Gly Gly Ser Arg Gln Gly Gly Gln Pro Gly Ala Gln Arg
        35                  40                  45

Met Tyr Lys Gln Ser Met Ala Gln Arg Ala Arg Thr Met Ala Leu Tyr
    50                  55                  60

Asn Pro Ile Pro Val Arg Gln Asn Cys Leu Thr Val Asn Arg Ser Leu
65                  70                  75                  80

Phe Leu Phe Ser Glu Asp Asn Val Val Arg Lys Tyr Ala Lys Lys Ile
                85                  90                  95

Thr Glu Trp Pro Pro Phe Glu Tyr Met Ile Leu Ala Thr Ile Ile Ala
            100                 105                 110

Asn Cys Ile Val Leu Ala Leu Glu Gln His Leu Pro Asp Asp Asp Lys
```

```
        115                 120                 125

Thr Pro Met Ser Glu Arg Leu Asp Asp Thr Glu Pro Tyr Phe Ile Gly
    130                 135                 140

Ile Phe Cys Phe Glu Ala Gly Ile Lys Ile Val Ala Leu Gly Phe Ala
145                 150                 155                 160

Phe His Lys Gly Ser Tyr Leu Arg Asn Gly Trp Asn Val Met Asp Phe
                165                 170                 175

Val Val Val Leu Thr Gly Ile Leu Ala Thr Val Gly Thr Glu Phe Asp
            180                 185                 190

Leu Arg Thr Leu Arg Ala Val Arg Val Leu Arg Pro Leu Lys Leu Val
        195                 200                 205

Ser Gly Ile Pro Ser Leu Gln Val Val Leu Lys Ser Ile Met Lys Ala
    210                 215                 220

Met Ile Pro Leu Leu Gln Ile Gly Leu Leu Leu Phe Phe Ala Ile Leu
225                 230                 235                 240

Ile Phe Ala Ile Ile Gly Leu Glu Phe Tyr Met Gly Lys Phe His Thr
                245                 250                 255

Thr Cys Phe Glu Glu Gly Thr Asp Asp Ile Gln Gly Glu Ser Pro Ala
            260                 265                 270

Pro Cys Gly Thr Glu Glu Pro Ala Arg Thr Cys Pro Asn Gly Thr Lys
        275                 280                 285

Cys Gln Pro Tyr Trp Glu Gly Pro Asn Asn Gly Ile Thr Gln Phe Asp
    290                 295                 300

Asn Ile Leu Phe Ala Val Leu Thr Val Phe Gln Cys Ile Thr Met Glu
305                 310                 315                 320

Gly Trp Thr Asp Leu Leu Tyr Asn Ser Asn Asp Ala Ser Gly Asn Thr
                325                 330                 335

Trp Asn Trp Leu Tyr Phe Ile Pro Leu Ile Ile Ile Gly Ser Phe Phe
            340                 345                 350

Met Leu Asn Leu Val Leu Gly Val Leu Ser Gly Glu Phe Ala Lys Glu
        355                 360                 365

Arg Glu Arg Val Glu Asn Arg Arg Ala Phe Leu Lys Leu Arg Arg Gln
    370                 375                 380

Gln Gln Ile Glu Arg Glu Leu Asn Gly Tyr Met Glu Trp Ile Ser Lys
385                 390                 395                 400

Ala Glu Glu Val Ile Leu Ala Glu Asp Glu Thr Asp Val Glu Gln Arg
                405                 410                 415

His Pro Phe Asp Gly Ala Leu Arg Arg Ala Thr Leu Lys Lys Ser Lys
            420                 425                 430

Thr Asp Leu Leu Asn Pro Glu Glu Ala Glu Asp Gln Leu Ala Asp Ile
        435                 440                 445

Ala Ser Val Gly Ser Pro Phe Ala Arg Ala Ser Ile Lys Ser Ala Lys
    450                 455                 460

Leu Glu Asn Ser Thr Phe Phe His Lys Lys Glu Arg Arg Met Arg Phe
465                 470                 475                 480

Tyr Ile Arg Arg Met Val Lys Thr Gln Ala Phe Tyr Trp Thr Val Leu
                485                 490                 495

Ser Leu Val Ala Leu Asn Thr Leu Trp Leu Ala Ile Val His Tyr Asn
            500                 505                 510

Gln Pro Glu Trp Leu Ser Asp Phe Leu Tyr Tyr Ala Glu Phe Ile Phe
        515                 520                 525

Leu Gly Leu Phe Met Ser Glu Met Phe Ile Lys Met Tyr Gly Leu Gly
    530                 535                 540
```

```
Thr Arg Pro Tyr Phe His Ser Ser Phe Asn Cys Phe Asp Cys Gly Val
545                 550                 555                 560

Ile Ile Gly Ser Ile Phe Glu Val Ile Trp Ala Val Ile Lys Pro Gly
                565                 570                 575

Thr Ser Phe Gly Ile Ser Val Leu Arg Ala Leu Arg Leu Leu Arg Ile
            580                 585                 590

Phe Lys Val Thr Lys Tyr Trp Ala Ser Leu Arg Asn Leu Val Val Ser
        595                 600                 605

Leu Leu Asn Ser Met Lys Ser Ile Ile Ser Leu Leu Phe Leu Leu Phe
    610                 615                 620

Leu Phe Ile Val Val Phe Ala Leu Leu Gly Met Gln Leu Phe Gly Gly
625                 630                 635                 640

Gln Phe Asn Phe Asp Glu Gly Thr Pro Pro Thr Asn Phe Asp Thr Phe
                645                 650                 655

Pro Ala Ala Ile Met Thr Val Phe Gln Ile Leu Thr Gly Glu Asp Trp
            660                 665                 670

Asn Glu Val Met Tyr Asp Glu Ile Lys Ser Gln Gly Gly Val Gln Gly
        675                 680                 685

Gly Met Val Phe Ser Ile Tyr Phe Ile Val Leu Thr Leu Phe Gly Asn
    690                 695                 700

Tyr Thr Leu Leu Asn Val Phe Leu Ala Ile Ala Val Asp Asn Leu Ala
705                 710                 715                 720

Asn Ala Gln Glu Leu Thr Lys Asp Glu Gln Glu Glu Glu Glu Ala Ala
                725                 730                 735

Asn Gln Lys Leu Ala Leu Gln Lys Ala Lys Glu Val Ala Glu Val Ser
            740                 745                 750

Pro Leu Ser Ala Ala Asn Met Ser Ile Ala Val Lys Glu Gln Gln Lys
        755                 760                 765

Asn Gln Lys Pro Ala Lys Ser Val Trp Glu Gln Arg Thr Ser Glu Met
    770                 775                 780

Arg Lys Gln Asn Leu Leu Ala Ser Arg Glu Ala Leu Tyr Gly Asp Ala
785                 790                 795                 800

Ala Glu Arg Trp Pro Thr Thr Tyr Ala Arg Pro Leu Arg Pro Asp Val
                805                 810                 815

Lys Thr His Leu Asp Arg Pro Leu Val Val Asp Pro Gln Glu Asn Arg
            820                 825                 830

Asn Asn Asn Thr Asn Lys Ser Arg Ala Pro Glu Ala Leu Arg Gln Thr
        835                 840                 845

Ala Arg Pro Arg Glu Ser Ala Arg Asp Pro Asp Ala Arg Arg Ala Trp
    850                 855                 860

Pro Ser Ser Pro Glu Arg Ala Pro Gly Arg Glu Gly Pro Tyr Gly Arg
865                 870                 875                 880

Glu Ser Glu Pro Gln Gln Arg Glu His Ala Pro Pro Arg Glu His Val
                885                 890                 895

Pro Trp Asp Ala Asp Pro Glu Arg Ala Lys Ala Gly Asp Ala Pro Arg
            900                 905                 910

Arg His Thr His Arg Pro Val Ala Glu Gly Glu Pro Arg Arg His Arg
        915                 920                 925

Ala Arg Arg Arg Pro Gly Asp Glu Pro Asp Asp Arg Pro Glu Arg Arg
    930                 935                 940

Pro Arg Pro Arg Asp Ala Thr Arg Pro Ala Arg Ala Ala Asp Gly Glu
945                 950                 955                 960
```

-continued

```
Gly Asp Asp Gly Glu Arg Lys Arg Arg His Arg His Gly Pro Pro Ala
                965                 970                 975

His Asp Asp Arg Glu Arg Arg His Arg Arg Arg Lys Glu Ser Gln Gly
            980                 985                 990

Ser Gly Val Pro Met Ser Gly Pro  Asn Leu Ser Thr Thr  Arg Pro Ile
        995                 1000                 1005

Gln Gln  Asp Leu Gly Arg Gln  Asp Leu Pro Leu Ala  Glu Asp Leu
    1010                 1015                 1020

Asp Asn  Met Lys Asn Asn Lys  Leu Ala Thr Gly Glu  Pro Ala Ser
    1025                 1030                 1035

Pro His  Asp Ser Leu Gly His  Ser Gly Leu Pro Pro  Ser Pro Ala
    1040                 1045                 1050

Lys Ile  Gly Asn Ser Thr Asn  Pro Gly Pro Ala Leu  Ala Thr Asn
    1055                 1060                 1065

Pro Gln  Asn Ala Ala Ser Arg  Arg Thr Pro Asn Asn  Pro Gly Asn
    1070                 1075                 1080

Pro Ser  Asn Pro Gly Pro Pro  Lys Thr Pro Glu Asn  Ser Leu Ile
    1085                 1090                 1095

Val Thr  Asn Pro Ser Ser Thr  Gln Pro Asn Ser Ala  Lys Thr Ala
    1100                 1105                 1110

Arg Lys  Pro Glu His Met Ala  Val Glu Ile Pro Pro  Ala Cys Pro
    1115                 1120                 1125

Pro Leu  Asn His Thr Val Val  Gln Val Asn Lys Asn  Ala Asn Pro
    1130                 1135                 1140

Asp Pro  Leu Pro Lys Lys Glu  Glu Glu Lys Lys Glu  Glu Glu Glu
    1145                 1150                 1155

Ala Asp  Pro Gly Glu Asp Gly  Pro Lys Pro Met Pro  Pro Tyr Ser
    1160                 1165                 1170

Ser Met  Phe Ile Leu Ser Thr  Thr Asn Pro Leu Arg  Arg Leu Cys
    1175                 1180                 1185

His Tyr  Ile Leu Asn Leu Arg  Tyr Phe Glu Met Cys  Ile Leu Met
    1190                 1195                 1200

Val Ile  Ala Met Ser Ser Ile  Ala Leu Ala Ala Glu  Asp Pro Val
    1205                 1210                 1215

Gln Pro  Asn Ala Pro Arg Asn  Asn Val Leu Arg Tyr  Phe Asp Tyr
    1220                 1225                 1230

Val Phe  Thr Gly Val Phe Thr  Phe Glu Met Val Ile  Lys Met Ile
    1235                 1240                 1245

Asp Leu  Gly Leu Val Leu His  Gln Gly Ala Tyr Phe  Arg Asp Leu
    1250                 1255                 1260

Trp Asn  Ile Leu Asp Phe Ile  Val Val Ser Gly Ala  Leu Val Ala
    1265                 1270                 1275

Phe Ala  Phe Thr Gly Asn Ser  Lys Gly Lys Asp Ile  Asn Thr Ile
    1280                 1285                 1290

Lys Ser  Leu Arg Val Leu Arg  Val Leu Arg Pro Leu  Lys Thr Ile
    1295                 1300                 1305

Lys Arg  Leu Pro Lys Leu Lys  Ala Val Phe Asp Cys  Val Val Asn
    1310                 1315                 1320

Ser Leu  Lys Asn Val Phe Asn  Ile Leu Ile Val Tyr  Met Leu Phe
    1325                 1330                 1335

Met Phe  Ile Phe Ala Val Val  Ala Val Gln Leu Phe  Lys Gly Lys
    1340                 1345                 1350

Phe Phe  His Cys Thr Asp Glu  Ser Lys Glu Phe Glu  Arg Asp Cys
```

```
    1355                1360                1365

Arg Gly  Lys Tyr Leu Leu Tyr  Glu Lys Asn Glu Val  Lys Ala Arg
    1370                1375                1380

Asp Arg  Glu Trp Lys Lys Tyr  Asp Phe His Tyr Asp  Asn Val Leu
    1385                1390                1395

Trp Ala  Leu Leu Thr Leu Phe  Thr Val Ser Thr Gly  Glu Gly Trp
    1400                1405                1410

Pro Gln  Val Leu Lys His Ser  Val Asp Ala Thr Phe  Glu Asn Gln
    1415                1420                1425

Gly Pro  Ser Pro Gly Tyr Arg  Met Glu Met Ser Ile  Phe Tyr Val
    1430                1435                1440

Val Tyr  Phe Val Val Phe Pro  Phe Phe Phe Val Asn  Ile Phe Val
    1445                1450                1455

Ala Leu  Ile Ile Ile Thr Phe  Gln Glu Gln Gly Asp  Lys Met Met
    1460                1465                1470

Glu Glu  Tyr Ser Leu Glu Lys  Asn Glu Arg Ala Cys  Ile Asp Phe
    1475                1480                1485

Ala Ile  Ser Ala Lys Pro Leu  Thr Arg His Met Pro  Gln Asn Lys
    1490                1495                1500

Gln Ser  Phe Gln Tyr Arg Met  Trp Gln Phe Val Val  Ser Pro Pro
    1505                1510                1515

Phe Glu  Tyr Thr Ile Met Ala  Met Ile Ala Leu Asn  Thr Ile Val
    1520                1525                1530

Leu Met  Met Lys Phe Tyr Gly  Ala Ser Val Ala Tyr  Glu Asn Ala
    1535                1540                1545

Leu Arg  Val Phe Asn Ile Val  Phe Thr Ser Leu Phe  Ser Leu Glu
    1550                1555                1560

Cys Val  Leu Lys Val Met Ala  Phe Gly Ile Leu Asn  Tyr Phe Arg
    1565                1570                1575

Asp Ala  Trp Asn Ile Phe Asp  Phe Val Thr Val Leu  Gly Ser Ile
    1580                1585                1590

Thr Asp  Ile Leu Val Thr Glu  Phe Gly Asn Asn Phe  Ile Asn Leu
    1595                1600                1605

Ser Phe  Leu Arg Leu Phe Arg  Ala Ala Arg Leu Ile  Lys Leu Leu
    1610                1615                1620

Arg Gln  Gly Tyr Thr Ile Arg  Ile Leu Leu Trp Thr  Phe Val Gln
    1625                1630                1635

Ser Phe  Lys Ala Leu Pro Tyr  Val Cys Leu Leu Ile  Ala Met Leu
    1640                1645                1650

Phe Phe  Ile Tyr Ala Ile Ile  Gly Met Gln Val Phe  Gly Asn Ile
    1655                1660                1665

Gly Ile  Asp Gly Glu Asp Glu  Asp Ser Asp Glu Asp  Glu Phe Gln
    1670                1675                1680

Ile Thr  Glu His Asn Asn Phe  Arg Thr Phe Phe Gln  Ala Leu Met
    1685                1690                1695

Leu Leu  Phe Arg Ser Ala Thr  Gly Glu Ala Trp His  Asn Ile Met
    1700                1705                1710

Leu Ser  Cys Leu Ser Gly Lys  Pro Cys Asp Lys Asn  Ser Gly Ile
    1715                1720                1725

Gln Lys  Pro Glu Cys Gly Asn  Glu Phe Ala Tyr Phe  Tyr Phe Val
    1730                1735                1740

Ser Phe  Ile Phe Leu Cys Ser  Phe Leu Met Leu Asn  Leu Phe Val
    1745                1750                1755
```

Ala Val Ile Met Asp Asn Phe Glu Tyr Leu Thr Arg Asp Ser Ser
1760 1765 1770

Ile Leu Gly Pro His His Leu Asp Glu Tyr Val Arg Val Trp Ala
1775 1780 1785

Glu Tyr Asp Pro Ala Ala Cys Gly Arg Ile His Tyr Lys Asp Met
1790 1795 1800

Tyr Ser Leu Leu Arg Val Ile Ser Pro Pro Leu Gly Leu Gly Lys
1805 1810 1815

Lys Cys Pro His Arg Val Ala Cys Lys Arg Leu Leu Arg Met Asp
1820 1825 1830

Leu Pro Val Ala Asp Asp Asn Thr Val His Phe Asn Ser Thr Leu
1835 1840 1845

Met Ala Leu Ile Arg Thr Ala Leu Asp Ile Lys Ile Ala Lys Gly
1850 1855 1860

Gly Ala Asp Lys Gln Gln Met Asp Ala Glu Leu Arg Lys Glu Met
1865 1870 1875

Met Ala Ile Trp Pro Asn Leu Ser Gln Lys Thr Leu Asp Leu Leu
1880 1885 1890

Val Thr Pro His Lys Ser Thr Asp Leu Thr Val Gly Lys Ile Tyr
1895 1900 1905

Ala Ala Met Met Ile Met Glu Tyr Tyr Arg Gln Ser Lys Ala Lys
1910 1915 1920

Lys Leu Gln Ala Met Arg Glu Glu Gln Asn Arg Thr Pro Leu Met
1925 1930 1935

Phe Gln Arg Met Glu Pro Pro Ser Pro Thr Gln Glu Gly Gly Pro
1940 1945 1950

Ser Gln Asn Ala Leu Pro Ser Thr Gln Leu Asp Pro Gly Gly Gly
1955 1960 1965

Leu Met Ala Gln Glu Ser Ser Met Lys Glu Ser Pro Ser Trp Val
1970 1975 1980

Thr Gln Arg Ala Gln Glu Met Phe Gln Lys Thr Gly Thr Trp Ser
1985 1990 1995

Pro Glu Arg Gly Pro Pro Ile Asp Met Pro Asn Ser Gln Pro Asn
2000 2005 2010

Ser Gln Ser Val Glu Met Arg Glu Met Gly Thr Asp Gly Tyr Ser
2015 2020 2025

Asp Ser Glu His Tyr Leu Pro Met Glu Gly Gln Thr Arg Ala Ala
2030 2035 2040

Ser Met Pro Arg Leu Pro Ala Glu Asn Gln Arg Arg Arg Gly Arg
2045 2050 2055

Pro Arg Gly Asn Asn Leu Ser Thr Ile Ser Asp Thr Ser Pro Met
2060 2065 2070

Lys Arg Ser Ala Ser Val Leu Gly Pro Lys Ala Arg Arg Leu Asp
2075 2080 2085

Asp Tyr Ser Leu Glu Arg Val Pro Pro Glu Glu Asn Gln Arg Tyr
2090 2095 2100

His Gln Arg Arg Arg Asp Arg Gly His Arg Thr Ser Glu Arg Ser
2105 2110 2115

Leu Gly Arg Tyr Thr Asp Val Asp Thr Gly Leu Gly Thr Asp Leu
2120 2125 2130

Ser Met Thr Thr Gln Ser Gly Asp Leu Pro Ser Lys Asp Arg Asp
2135 2140 2145

-continued

```
Gln Asp  Arg Gly Arg Pro Lys  Asp Arg Lys His Arg  Pro His His
    2150                 2155                 2160

His His  His His His His His  His Pro Pro Ala Pro  Asp Arg Glu
    2165                 2170                 2175

Arg Tyr  Ala Gln Glu Arg Pro  Asp Thr Gly Arg Ala  Arg Ala Arg
    2180                 2185                 2190

Glu Gln  Arg Trp Ser Arg Ser  Pro Ser Glu Gly Arg  Glu His Ala
    2195                 2200                 2205

Thr His  Arg Gln Gly Ser Ser  Ser Val Ser Gly Ser  Pro Ala Pro
    2210                 2215                 2220

Ser Thr  Ser Gly Thr Ser Thr  Pro Arg Arg Gly Arg  Arg Gln Leu
    2225                 2230                 2235

Pro Gln  Thr Pro Cys Thr Pro  Arg Pro Leu Val Ser  Tyr Ser Pro
    2240                 2245                 2250

Ala Pro  Arg Arg Pro Ala Ala  Arg Arg Met Ala Gly  Pro Pro Ala
    2255                 2260                 2265

Pro Pro  Gly Gly Ser Pro Arg  Gly Cys Arg Arg Ala  Pro Arg Trp
    2270                 2275                 2280

Pro Ala  His Ala Pro Glu Gly  Pro Arg Pro Arg Gly  Ala Asp Tyr
    2285                 2290                 2295

Thr Glu  Pro Asp Ser Pro Arg  Glu Pro Pro Gly Gly  Ala His Glu
    2300                 2305                 2310

Pro Ala  Pro Arg Ser Pro Arg  Thr Pro Arg Ala Ala  Gly Cys Ala
    2315                 2320                 2325

Ser Pro  Arg His Gly Arg Arg  Leu Pro Asn Gly Tyr  Tyr Ala Gly
    2330                 2335                 2340

His Gly  Ala Pro Arg Pro Arg  Thr Ala Arg Arg Gly  Ala His Asp
    2345                 2350                 2355

Ala Tyr  Ser Glu Ser Glu Asp  Asp Trp Cys
    2360                 2365


<210> SEQ ID NO 148
<211> LENGTH: 2512
<212> TYPE: PRT
<213> ORGANISM: Homo sapiens

<400> SEQUENCE: 148

Met Ala Arg Phe Gly Asp Glu Met Pro Ala Arg Tyr Gly Gly Gly Gly
1               5                   10                  15

Ser Gly Ala Ala Ala Gly Val Val Val Gly Ser Gly Gly Gly Arg Gly
            20                  25                  30

Ala Gly Gly Ser Arg Gln Gly Gly Gln Pro Gly Ala Gln Arg Met Tyr
        35                  40                  45

Lys Gln Ser Met Ala Gln Arg Ala Arg Thr Met Ala Leu Tyr Asn Pro
    50                  55                  60

Ile Pro Val Arg Gln Asn Cys Leu Thr Val Asn Arg Ser Leu Phe Leu
65                  70                  75                  80

Phe Ser Glu Asp Asn Val Val Arg Lys Tyr Ala Lys Lys Ile Thr Glu
                85                  90                  95

Trp Pro Pro Phe Glu Tyr Met Ile Leu Ala Thr Ile Ile Ala Asn Cys
            100                 105                 110

Ile Val Leu Ala Leu Glu Gln His Leu Pro Asp Asp Asp Lys Thr Pro
        115                 120                 125

Met Ser Glu Arg Leu Asp Asp Thr Glu Pro Tyr Phe Ile Gly Ile Phe
    130                 135                 140
```

-continued

```
Cys Phe Glu Ala Gly Ile Lys Ile Ile Ala Leu Gly Phe Ala Phe His
145                 150                 155                 160

Lys Gly Ser Tyr Leu Arg Asn Gly Trp Asn Val Met Asp Phe Val Val
                165                 170                 175

Val Leu Thr Gly Ile Leu Ala Thr Val Gly Thr Glu Phe Asp Leu Arg
            180                 185                 190

Thr Leu Arg Ala Val Arg Val Leu Arg Pro Leu Lys Leu Val Ser Gly
        195                 200                 205

Ile Pro Ser Leu Gln Val Val Leu Lys Ser Ile Met Lys Ala Met Ile
    210                 215                 220

Pro Leu Leu Gln Ile Gly Leu Leu Leu Phe Phe Ala Ile Leu Ile Phe
225                 230                 235                 240

Ala Ile Ile Gly Leu Glu Phe Tyr Lys Gly Lys Phe His Thr Thr Cys
                245                 250                 255

Phe Glu Glu Gly Thr Asp Asp Ile Gln Gly Glu Ser Pro Ala Pro Cys
            260                 265                 270

Gly Thr Glu Glu Pro Ala Arg Thr Cys Pro Asn Gly Thr Lys Cys Gln
        275                 280                 285

Pro Tyr Trp Glu Gly Pro Asn Asn Gly Ile Thr Gln Phe Asp Asn Ile
    290                 295                 300

Leu Phe Ala Val Leu Thr Val Phe Gln Cys Ile Thr Met Glu Gly Trp
305                 310                 315                 320

Thr Asp Leu Leu Tyr Asn Ser Asn Asp Ala Ser Gly Asn Thr Trp Asn
                325                 330                 335

Trp Leu Tyr Phe Ile Pro Leu Ile Ile Ile Gly Ser Phe Phe Met Leu
            340                 345                 350

Asn Leu Val Leu Gly Val Leu Ser Gly Glu Phe Ala Lys Glu Arg Glu
        355                 360                 365

Arg Val Glu Asn Arg Arg Ala Phe Leu Lys Leu Arg Arg Gln Gln Gln
    370                 375                 380

Ile Glu Arg Glu Leu Asn Gly Tyr Met Glu Trp Ile Ser Lys Ala Glu
385                 390                 395                 400

Glu Val Ile Leu Ala Glu Asp Glu Thr Asp Gly Glu Gln Arg His Pro
                405                 410                 415

Phe Asp Gly Ala Leu Arg Arg Thr Thr Ile Lys Lys Ser Lys Thr Asp
            420                 425                 430

Leu Leu Asn Pro Glu Glu Ala Glu Asp Gln Leu Ala Asp Ile Ala Ser
        435                 440                 445

Val Gly Ser Pro Phe Ala Arg Ala Ser Ile Lys Ser Ala Lys Leu Glu
    450                 455                 460

Asn Ser Thr Phe Phe His Lys Lys Glu Arg Arg Met Arg Phe Tyr Ile
465                 470                 475                 480

Arg Arg Met Val Lys Thr Gln Ala Phe Tyr Trp Thr Val Leu Ser Leu
                485                 490                 495

Val Ala Leu Asn Thr Leu Cys Val Ala Ile Val His Tyr Asn Gln Pro
            500                 505                 510

Glu Trp Leu Ser Asp Phe Leu Tyr Tyr Ala Glu Phe Ile Phe Leu Gly
        515                 520                 525

Leu Phe Met Ser Glu Met Phe Ile Lys Met Tyr Gly Leu Gly Thr Arg
    530                 535                 540

Pro Tyr Phe His Ser Ser Phe Asn Cys Phe Asp Cys Gly Val Ile Ile
545                 550                 555                 560
```

```
Gly Ser Ile Phe Glu Val Ile Trp Ala Val Ile Lys Pro Gly Thr Ser
                565                 570                 575

Phe Gly Ile Ser Val Leu Arg Ala Leu Arg Leu Leu Arg Ile Phe Lys
            580                 585                 590

Val Thr Lys Tyr Trp Ala Ser Leu Arg Asn Leu Val Val Ser Leu Leu
        595                 600                 605

Asn Ser Met Lys Ser Ile Ile Ser Leu Leu Phe Leu Leu Phe Leu Phe
    610                 615                 620

Ile Val Val Phe Ala Leu Leu Gly Met Gln Leu Phe Gly Gly Gln Phe
625                 630                 635                 640

Asn Phe Asp Glu Gly Thr Pro Pro Thr Asn Phe Asp Thr Phe Pro Ala
                645                 650                 655

Ala Ile Met Thr Val Phe Gln Ile Leu Thr Gly Glu Asp Trp Asn Glu
            660                 665                 670

Val Met Tyr Asp Gly Ile Lys Ser Gln Gly Gly Val Gln Gly Gly Met
        675                 680                 685

Val Phe Ser Ile Tyr Phe Ile Val Leu Thr Leu Phe Gly Asn Tyr Thr
    690                 695                 700

Leu Leu Asn Val Phe Leu Ala Ile Ala Val Asp Asn Leu Ala Asn Ala
705                 710                 715                 720

Gln Glu Leu Thr Lys Val Glu Ala Asp Glu Gln Glu Glu Glu Glu Ala
                725                 730                 735

Ala Asn Gln Lys Leu Ala Leu Gln Lys Ala Lys Glu Val Ala Glu Val
            740                 745                 750

Ser Pro Leu Ser Ala Ala Asn Met Ser Ile Ala Val Lys Glu Gln Gln
        755                 760                 765

Lys Asn Gln Lys Pro Ala Lys Ser Val Trp Glu Gln Arg Thr Ser Glu
    770                 775                 780

Met Arg Lys Gln Asn Leu Leu Ala Ser Arg Glu Ala Leu Tyr Asn Glu
785                 790                 795                 800

Met Asp Pro Asp Glu Arg Trp Lys Ala Ala Tyr Thr Arg His Leu Arg
                805                 810                 815

Pro Asp Met Lys Thr His Leu Asp Arg Pro Leu Val Val Asp Pro Gln
            820                 825                 830

Glu Asn Arg Asn Asn Asn Thr Asn Lys Ser Arg Ala Ala Glu Pro Thr
        835                 840                 845

Val Asp Gln Arg Leu Gly Gln Gln Arg Ala Glu Asp Phe Leu Arg Lys
    850                 855                 860

Gln Ala Arg Tyr His Asp Arg Ala Arg Asp Pro Ser Gly Ser Ala Gly
865                 870                 875                 880

Leu Asp Ala Arg Arg Pro Trp Ala Gly Ser Gln Glu Ala Glu Leu Ser
                885                 890                 895

Arg Glu Gly Pro Tyr Gly Arg Glu Ser Asp His His Ala Arg Glu Gly
            900                 905                 910

Ser Leu Glu Gln Pro Gly Phe Trp Glu Gly Glu Ala Glu Arg Gly Lys
        915                 920                 925

Ala Gly Asp Pro His Arg Arg His Val His Arg Gln Gly Gly Ser Arg
    930                 935                 940

Glu Ser Arg Ser Gly Ser Pro Arg Thr Gly Ala Asp Gly Glu His Arg
945                 950                 955                 960

Arg His Arg Ala His Arg Arg Pro Gly Glu Glu Gly Pro Glu Asp Lys
                965                 970                 975

Ala Glu Arg Arg Ala Arg His Arg Glu Gly Ser Arg Pro Ala Arg Gly
```

```
            980                 985                 990

Gly Glu Gly Glu Gly Glu Gly Pro  Asp Gly Gly Glu Arg  Arg Arg Arg
        995                 1000                1005

His Arg  His Gly Ala Pro Ala  Thr Tyr Glu Gly Asp  Ala Arg Arg
    1010                 1015                 1020

Glu Asp  Lys Glu Arg Arg His  Arg Arg Arg Lys Glu  Asn Gln Gly
    1025                 1030                 1035

Ser Gly  Val Pro Val Ser Gly  Pro Asn Leu Ser Thr  Thr Arg Pro
    1040                 1045                 1050

Ile Gln  Gln Asp Leu Gly Arg  Gln Asp Pro Pro Leu  Ala Glu Asp
    1055                 1060                 1065

Ile Asp  Asn Met Lys Asn Asn  Lys Leu Ala Thr Ala  Glu Ser Ala
    1070                 1075                 1080

Ala Pro  His Gly Ser Leu Gly  His Ala Gly Leu Pro  Gln Ser Pro
    1085                 1090                 1095

Ala Lys  Met Gly Asn Ser Thr  Asp Pro Gly Pro Met  Leu Ala Ile
    1100                 1105                 1110

Pro Ala  Met Ala Thr Asn Pro  Gln Asn Ala Ala Ser  Arg Arg Thr
    1115                 1120                 1125

Pro Asn  Asn Pro Gly Asn Pro  Ser Asn Pro Gly Pro  Pro Lys Thr
    1130                 1135                 1140

Pro Glu  Asn Ser Leu Ile Val  Thr Asn Pro Ser Gly  Thr Gln Thr
    1145                 1150                 1155

Asn Ser  Ala Lys Thr Ala Arg  Lys Pro Asp His Thr  Thr Val Asp
    1160                 1165                 1170

Ile Pro  Pro Ala Cys Pro Pro  Pro Leu Asn His Thr  Val Val Gln
    1175                 1180                 1185

Val Asn  Lys Asn Ala Asn Pro  Asp Pro Leu Pro Lys  Lys Glu Glu
    1190                 1195                 1200

Glu Lys  Lys Glu Glu Glu Glu  Asp Asp Arg Gly Glu  Asp Gly Pro
    1205                 1210                 1215

Lys Pro  Met Pro Pro Tyr Ser  Ser Met Phe Ile Leu  Ser Thr Thr
    1220                 1225                 1230

Asn Pro  Leu Arg Arg Leu Cys  His Tyr Ile Leu Asn  Leu Arg Tyr
    1235                 1240                 1245

Phe Glu  Met Cys Ile Leu Met  Val Ile Ala Met Ser  Ser Ile Ala
    1250                 1255                 1260

Leu Ala  Ala Glu Asp Pro Val  Gln Pro Asn Ala Pro  Arg Asn Asn
    1265                 1270                 1275

Val Leu  Arg Tyr Phe Asp Tyr  Val Phe Thr Gly Val  Phe Thr Phe
    1280                 1285                 1290

Glu Met  Val Ile Lys Met Ile  Asp Leu Gly Leu Val  Leu His Gln
    1295                 1300                 1305

Gly Ala  Tyr Phe Arg Asp Leu  Trp Asn Ile Leu Asp  Phe Ile Val
    1310                 1315                 1320

Val Ser  Gly Ala Leu Val Ala  Phe Ala Phe Thr Gly  Asn Ser Lys
    1325                 1330                 1335

Gly Lys  Asp Ile Asn Thr Ile  Lys Ser Leu Arg Val  Leu Arg Val
    1340                 1345                 1350

Leu Arg  Pro Leu Lys Thr Ile  Lys Arg Leu Pro Lys  Leu Lys Ala
    1355                 1360                 1365

Val Phe  Asp Cys Val Val Asn  Ser Leu Lys Asn Val  Phe Asn Ile
    1370                 1375                 1380
```

```
Leu Ile  Val Tyr Met Leu Phe  Met Phe Ile Phe Ala  Val Val Ala
    1385                 1390                 1395

Val Gln  Leu Phe Lys Gly Lys  Phe Phe His Cys Thr  Asp Glu Ser
    1400                 1405                 1410

Lys Glu  Phe Glu Lys Asp Cys  Arg Gly Lys Tyr Leu  Leu Tyr Glu
    1415                 1420                 1425

Lys Asn  Glu Val Lys Ala Arg  Asp Arg Glu Trp Lys  Lys Tyr Glu
    1430                 1435                 1440

Phe His  Tyr Asp Asn Val Leu  Trp Ala Leu Leu Thr  Leu Phe Thr
    1445                 1450                 1455

Val Ser  Thr Gly Glu Gly Trp  Pro Gln Val Leu Lys  His Ser Val
    1460                 1465                 1470

Asp Ala  Thr Phe Glu Asn Gln  Gly Pro Ser Pro Gly  Tyr Arg Met
    1475                 1480                 1485

Glu Met  Ser Ile Phe Tyr Val  Val Tyr Phe Val Val  Phe Pro Phe
    1490                 1495                 1500

Phe Phe  Val Asn Ile Phe Val  Ala Leu Ile Ile Ile  Thr Phe Gln
    1505                 1510                 1515

Glu Gln  Gly Asp Lys Met Met  Glu Glu Tyr Ser Leu  Glu Lys Asn
    1520                 1525                 1530

Glu Arg  Ala Cys Ile Asp Phe  Ala Ile Ser Ala Lys  Pro Leu Thr
    1535                 1540                 1545

Arg His  Met Pro Gln Asn Lys  Gln Ser Phe Gln Tyr  Arg Met Trp
    1550                 1555                 1560

Gln Phe  Val Val Ser Pro Pro  Phe Glu Tyr Thr Ile  Met Ala Met
    1565                 1570                 1575

Ile Ala  Leu Asn Thr Ile Val  Leu Met Met Lys Phe  Tyr Gly Ala
    1580                 1585                 1590

Ser Val  Ala Tyr Glu Asn Ala  Leu Arg Val Phe Asn  Ile Val Phe
    1595                 1600                 1605

Thr Ser  Leu Phe Ser Leu Glu  Cys Val Leu Lys Val  Met Ala Phe
    1610                 1615                 1620

Gly Ile  Leu Asn Tyr Phe Arg  Asp Ala Trp Asn Ile  Phe Asp Phe
    1625                 1630                 1635

Val Thr  Val Leu Gly Ser Ile  Thr Asp Ile Leu Val  Thr Glu Phe
    1640                 1645                 1650

Gly Asn  Pro Asn Asn Phe Ile  Asn Leu Ser Phe Leu  Arg Leu Phe
    1655                 1660                 1665

Arg Ala  Ala Arg Leu Ile Lys  Leu Leu Arg Gln Gly  Tyr Thr Ile
    1670                 1675                 1680

Arg Ile  Leu Leu Trp Thr Phe  Val Gln Ser Phe Lys  Ala Leu Pro
    1685                 1690                 1695

Tyr Val  Cys Leu Leu Ile Ala  Met Leu Phe Phe Ile  Tyr Ala Ile
    1700                 1705                 1710

Ile Gly  Met Gln Val Phe Gly  Asn Ile Gly Ile Asp  Val Glu Asp
    1715                 1720                 1725

Glu Asp  Ser Asp Glu Asp Glu  Phe Gln Ile Thr Glu  His Asn Asn
    1730                 1735                 1740

Phe Arg  Thr Phe Phe Gln Ala  Leu Met Leu Leu Phe  Arg Ser Ala
    1745                 1750                 1755

Thr Gly  Glu Ala Trp His Asn  Ile Met Leu Ser Cys  Leu Ser Gly
    1760                 1765                 1770
```

```
Lys Pro  Cys Asp Lys Asn Ser  Gly Ile Leu Thr Arg  Glu Cys Gly
    1775                 1780                 1785

Asn Glu  Phe Ala Tyr Phe Tyr  Phe Val Ser Phe Ile  Phe Leu Cys
    1790                 1795                 1800

Ser Phe  Leu Met Leu Asn Leu  Phe Val Ala Val Ile  Met Asp Asn
    1805                 1810                 1815

Phe Glu  Tyr Leu Thr Arg Asp  Ser Ser Ile Leu Gly  Pro His His
    1820                 1825                 1830

Leu Asp  Glu Tyr Val Arg Val  Trp Ala Glu Tyr Asp  Pro Ala Ala
    1835                 1840                 1845

Trp Gly  Arg Met Pro Tyr Leu  Asp Met Tyr Gln Met  Leu Arg His
    1850                 1855                 1860

Met Ser  Pro Pro Leu Gly Leu  Gly Lys Lys Cys Pro  Ala Arg Val
    1865                 1870                 1875

Ala Tyr  Lys Arg Leu Leu Arg  Met Asp Leu Pro Val  Ala Asp Asp
    1880                 1885                 1890

Asn Thr  Val His Phe Asn Ser  Thr Leu Met Ala Leu  Ile Arg Thr
    1895                 1900                 1905

Ala Leu  Asp Ile Lys Ile Ala  Lys Gly Gly Ala Asp  Lys Gln Gln
    1910                 1915                 1920

Met Asp  Ala Glu Leu Arg Lys  Glu Met Met Ala Ile  Trp Pro Asn
    1925                 1930                 1935

Leu Ser  Gln Lys Thr Leu Asp  Leu Leu Val Thr Pro  His Lys Ser
    1940                 1945                 1950

Thr Asp  Leu Thr Val Gly Lys  Ile Tyr Ala Ala Met  Met Ile Met
    1955                 1960                 1965

Glu Tyr  Tyr Arg Gln Ser Lys  Ala Lys Lys Leu Gln  Ala Met Arg
    1970                 1975                 1980

Glu Glu  Gln Asp Arg Thr Pro  Leu Met Phe Gln Arg  Met Glu Pro
    1985                 1990                 1995

Pro Ser  Pro Thr Gln Glu Gly  Gly Pro Gly Gln Asn  Ala Leu Pro
    2000                 2005                 2010

Ser Thr  Gln Leu Asp Pro Gly  Gly Ala Leu Met Ala  His Glu Ser
    2015                 2020                 2025

Gly Leu  Lys Glu Ser Pro Ser  Trp Val Thr Gln Arg  Ala Gln Glu
    2030                 2035                 2040

Met Phe  Gln Lys Thr Gly Thr  Trp Ser Pro Glu Gln  Gly Pro Pro
    2045                 2050                 2055

Thr Asp  Met Pro Asn Ser Gln  Pro Asn Ser Gln Ser  Val Glu Met
    2060                 2065                 2070

Arg Glu  Met Gly Arg Asp Gly  Tyr Ser Asp Ser Glu  His Tyr Leu
    2075                 2080                 2085

Pro Met  Glu Gly Gln Gly Arg  Ala Ala Ser Met Pro  Arg Leu Pro
    2090                 2095                 2100

Ala Glu  Asn Gln Arg Arg Arg  Gly Arg Pro Arg Gly  Asn Asn Leu
    2105                 2110                 2115

Ser Thr  Ile Ser Asp Thr Ser  Pro Met Lys Arg Ser  Ala Ser Val
    2120                 2125                 2130

Leu Gly  Pro Lys Ala Arg Arg  Leu Asp Asp Tyr Ser  Leu Glu Arg
    2135                 2140                 2145

Val Pro  Pro Glu Glu Asn Gln  Arg His His Gln Arg  Arg Arg Asp
    2150                 2155                 2160

Arg Ser  His Arg Ala Ser Glu  Arg Ser Leu Gly Arg  Tyr Thr Asp
```

```
    2165                2170                2175

Val Asp  Thr Gly Leu Gly Thr  Asp Leu Ser Met Thr  Thr Gln Ser
    2180                2185                2190

Gly Asp  Leu Pro Ser Lys Glu  Arg Asp Gln Glu Arg  Gly Arg Pro
    2195                2200                2205

Lys Asp  Arg Lys His Arg Gln  His His His His His  His His His
    2210                2215                2220

His His  Pro Pro Pro Pro Asp  Lys Asp Arg Tyr Ala  Gln Glu Arg
    2225                2230                2235

Pro Asp  His Gly Arg Ala Arg  Ala Arg Asp Gln Arg  Trp Ser Arg
    2240                2245                2250

Ser Pro  Ser Glu Gly Arg Glu  His Met Ala His Arg  Gln Gly Ser
    2255                2260                2265

Ser Ser  Val Ser Gly Ser Pro  Ala Pro Ser Thr Ser  Gly Thr Ser
    2270                2275                2280

Thr Pro  Arg Arg Gly Arg Arg  Gln Leu Pro Gln Thr  Pro Ser Thr
    2285                2290                2295

Pro Arg  Pro His Val Ser Tyr  Ser Pro Val Ile Arg  Lys Ala Gly
    2300                2305                2310

Gly Ser  Gly Pro Pro Gln Gln  Gln Gln Gln Gln Gln  Gln Gln Gln
    2315                2320                2325

Gln Gln  Gln Ala Val Ala Arg  Pro Gly Arg Ala Ala  Thr Ser Gly
    2330                2335                2340

Pro Arg  Arg Tyr Pro Gly Pro  Thr Ala Glu Pro Leu  Ala Gly Asp
    2345                2350                2355

Arg Pro  Pro Thr Gly Gly His  Ser Ser Gly Arg Ser  Pro Arg Met
    2360                2365                2370

Glu Arg  Arg Val Pro Gly Pro  Ala Arg Ser Glu Ser  Pro Arg Ala
    2375                2380                2385

Cys Arg  His Gly Gly Ala Arg  Trp Pro Ala Ser Gly  Pro His Val
    2390                2395                2400

Ser Glu  Gly Pro Pro Gly Pro  Arg His His Gly Tyr  Tyr Arg Gly
    2405                2410                2415

Ser Asp  Tyr Asp Glu Ala Asp  Gly Pro Gly Ser Gly  Gly Gly Glu
    2420                2425                2430

Glu Ala  Met Ala Gly Ala Tyr  Asp Ala Pro Pro Pro  Val Arg His
    2435                2440                2445

Ala Ser  Ser Gly Ala Thr Gly  Arg Ser Pro Arg Thr  Pro Arg Ala
    2450                2455                2460

Ser Gly  Pro Ala Cys Ala Ser  Pro Ser Arg His Gly  Arg Arg Leu
    2465                2470                2475

Pro Asn  Gly Tyr Tyr Pro Ala  His Gly Leu Ala Arg  Pro Arg Gly
    2480                2485                2490

Pro Gly  Ser Arg Lys Gly Leu  His Glu Pro Tyr Ser  Glu Ser Asp
    2495                2500                2505

Asp Asp  Trp Cys
    2510
```

<210> SEQ ID NO 149
<211> LENGTH: 2368
<212> TYPE: PRT
<213> ORGANISM: Rattus norvegicus

<400> SEQUENCE: 149

```
Met Ala Arg Phe Gly Asp Glu Met Pro Gly Arg Tyr Gly Ala Gly Gly
1               5                   10                  15

Gly Gly Ser Gly Pro Ala Ala Gly Val Val Val Gly Ala Ala Gly Gly
            20                  25                  30

Arg Gly Ala Gly Gly Ser Arg Gln Gly Gly Gln Pro Gly Ala Gln Arg
        35                  40                  45

Met Tyr Lys Gln Ser Met Ala Gln Arg Ala Arg Thr Met Ala Leu Tyr
    50                  55                  60

Asn Pro Ile Pro Val Arg Gln Asn Cys Leu Thr Val Asn Arg Ser Leu
65                  70                  75                  80

Phe Leu Phe Ser Glu Asp Asn Val Val Arg Lys Tyr Ala Lys Lys Ile
                85                  90                  95

Thr Glu Trp Pro Pro Phe Glu Tyr Met Ile Leu Ala Thr Ile Ile Ala
            100                 105                 110

Asn Cys Ile Val Leu Ala Leu Glu Gln His Leu Pro Asp Asp Asp Lys
        115                 120                 125

Thr Pro Met Ser Glu Arg Leu Asp Asp Thr Glu Pro Tyr Phe Ile Gly
    130                 135                 140

Ile Phe Cys Phe Glu Ala Gly Ile Lys Ile Val Ala Leu Gly Phe Ala
145                 150                 155                 160

Phe His Lys Gly Ser Tyr Leu Arg Asn Gly Trp Asn Val Met Asp Phe
                165                 170                 175

Val Val Val Leu Thr Gly Ile Leu Ala Thr Val Gly Thr Glu Phe Asp
            180                 185                 190

Leu Arg Thr Leu Arg Ala Val Arg Val Leu Arg Pro Leu Lys Leu Val
        195                 200                 205

Ser Gly Ile Pro Ser Leu Gln Val Val Leu Lys Ser Ile Met Lys Ala
    210                 215                 220

Met Ile Pro Leu Leu Gln Ile Gly Leu Leu Leu Phe Phe Ala Ile Leu
225                 230                 235                 240

Ile Phe Ala Ile Ile Gly Leu Glu Phe Tyr Lys Gly Lys Phe His Thr
                245                 250                 255

Thr Cys Phe Glu Glu Gly Thr Asp Asp Ile Gln Gly Glu Ser Pro Ala
            260                 265                 270

Pro Cys Gly Thr Glu Glu Pro Ala Arg Thr Cys Pro Asn Gly Thr Lys
        275                 280                 285

Cys Gln Pro Tyr Trp Glu Gly Pro Asn Asn Gly Ile Thr Gln Phe Asp
    290                 295                 300

Asn Ile Leu Phe Ala Val Leu Thr Val Phe Gln Cys Ile Thr Met Glu
305                 310                 315                 320

Gly Trp Thr Asp Leu Leu Tyr Asn Ser Asn Asp Ala Ser Gly Asn Thr
                325                 330                 335

Trp Asn Trp Leu Tyr Phe Ile Pro Leu Ile Ile Ile Gly Ser Phe Phe
            340                 345                 350

Met Leu Asn Leu Val Leu Gly Val Leu Ser Gly Glu Phe Ala Lys Glu
        355                 360                 365

Arg Glu Arg Val Glu Asn Arg Arg Ala Phe Leu Lys Leu Arg Arg Gln
    370                 375                 380

Gln Gln Ile Glu Arg Glu Leu Asn Gly Tyr Met Glu Trp Ile Ser Lys
385                 390                 395                 400

Ala Glu Glu Val Ile Leu Ala Glu Asp Glu Thr Asp Val Glu Gln Arg
                405                 410                 415

His Pro Phe Asp Gly Ala Leu Arg Arg Ala Thr Leu Lys Lys Ser Lys
```

```
            420                 425                 430

Thr Asp Leu Leu Asn Pro Glu Glu Ala Glu Asp Gln Leu Ala Asp Ile
        435                 440                 445

Ala Ser Val Gly Ser Pro Phe Ala Arg Ala Ser Ile Lys Ser Ala Lys
    450                 455                 460

Leu Glu Asn Ser Thr Phe Phe His Lys Lys Glu Arg Arg Met Arg Phe
465                 470                 475                 480

Tyr Ile Arg Arg Met Val Lys Thr Gln Ala Phe Tyr Trp Thr Val Leu
                485                 490                 495

Ser Leu Val Ala Leu Asn Thr Leu Trp Leu Ala Ile Val His Tyr Asn
            500                 505                 510

Gln Pro Glu Trp Leu Ser Asp Phe Leu Tyr Tyr Ala Glu Phe Ile Phe
        515                 520                 525

Leu Gly Leu Phe Met Ser Glu Met Phe Ile Lys Met Tyr Gly Leu Gly
    530                 535                 540

Thr Arg Pro Tyr Phe His Ser Ser Phe Asn Cys Phe Asp Cys Gly Val
545                 550                 555                 560

Ile Ile Gly Ser Ile Phe Glu Val Ile Trp Ala Val Ile Lys Pro Gly
                565                 570                 575

Thr Ser Phe Gly Ile Ser Val Leu Arg Ala Leu Arg Leu Leu Arg Ile
            580                 585                 590

Phe Lys Val Thr Lys Tyr Trp Ala Ser Leu Arg Asn Leu Val Val Ser
        595                 600                 605

Leu Leu Asn Ser Met Lys Ser Ile Ile Ser Leu Leu Phe Leu Leu Phe
    610                 615                 620

Leu Phe Ile Val Val Phe Ala Leu Leu Gly Met Gln Leu Phe Gly Gly
625                 630                 635                 640

Gln Phe Asn Phe Asp Glu Gly Thr Pro Pro Thr Asn Phe Asp Thr Phe
                645                 650                 655

Pro Ala Ala Ile Met Thr Val Phe Gln Ile Leu Thr Gly Glu Asp Trp
            660                 665                 670

Asn Glu Val Met Tyr Asp Glu Ile Lys Ser Gln Gly Gly Val Gln Gly
        675                 680                 685

Gly Met Val Phe Ser Ile Tyr Phe Ile Val Leu Thr Leu Phe Gly Asn
    690                 695                 700

Tyr Thr Leu Leu Asn Val Phe Leu Ala Ile Ala Val Asp Asn Leu Ala
705                 710                 715                 720

Asn Ala Gln Glu Leu Thr Lys Asp Glu Gln Glu Glu Glu Glu Ala Ala
                725                 730                 735

Asn Gln Lys Leu Ala Leu Gln Lys Ala Lys Glu Val Ala Glu Val Ser
            740                 745                 750

Pro Leu Ser Ala Ala Asn Met Ser Ile Ala Val Lys Glu Gln Gln Lys
        755                 760                 765

Asn Gln Lys Pro Ala Lys Ser Val Trp Glu Gln Arg Thr Ser Glu Met
    770                 775                 780

Arg Lys Gln Asn Leu Leu Ala Ser Arg Glu Ala Leu Tyr Gly Asp Ala
785                 790                 795                 800

Ala Glu Arg Trp Pro Thr Thr Tyr Ala Arg Pro Leu Arg Pro Asp Val
                805                 810                 815

Lys Thr His Leu Asp Arg Pro Leu Val Val Asp Pro Gln Glu Asn Arg
            820                 825                 830

Asn Asn Asn Thr Asn Lys Ser Arg Ala Pro Glu Ala Leu Arg Gln Thr
        835                 840                 845
```

```
Ala Arg Pro Arg Glu Ser Ala Arg Asp Pro Asp Ala Arg Arg Ala Trp
    850                 855                 860

Pro Ser Ser Pro Glu Arg Ala Pro Gly Arg Glu Gly Pro Tyr Gly Arg
865                 870                 875                 880

Glu Ser Glu Pro Gln Gln Arg Glu His Ala Pro Pro Arg Glu His Val
                885                 890                 895

Pro Trp Asp Ala Asp Pro Glu Arg Ala Lys Ala Gly Asp Ala Pro Arg
            900                 905                 910

Arg His Thr His Arg Pro Val Ala Glu Gly Glu Pro Arg Arg His Arg
        915                 920                 925

Ala Arg Arg Arg Pro Gly Asp Glu Pro Asp Asp Arg Pro Glu Arg Arg
    930                 935                 940

Pro Arg Pro Arg Asp Ala Thr Arg Pro Ala Arg Ala Ala Asp Gly Glu
945                 950                 955                 960

Gly Asp Asp Gly Glu Arg Lys Arg Arg His Arg His Gly Pro Pro Ala
                965                 970                 975

His Asp Asp Arg Glu Arg Arg His Arg Arg Arg Lys Glu Ser Gln Gly
            980                 985                 990

Ser Gly Val Pro Met Ser Gly Pro  Asn Leu Ser Thr Thr  Arg Pro Ile
        995                 1000                1005

Gln Gln  Asp Leu Gly Arg Gln  Asp Leu Pro Leu Ala  Glu Asp Leu
    1010                 1015                 1020

Asp Asn  Met Lys Asn Asn Lys  Leu Ala Thr Gly Glu  Pro Ala Ser
    1025                 1030                 1035

Pro His  Asp Ser Leu Gly His  Ser Gly Leu Pro Pro  Ser Pro Ala
    1040                 1045                 1050

Lys Ile  Gly Asn Ser Thr Asn  Pro Gly Pro Ala Leu  Ala Thr Asn
    1055                 1060                 1065

Pro Gln  Asn Ala Ala Ser Arg  Arg Thr Pro Asn Asn  Pro Gly Asn
    1070                 1075                 1080

Pro Ser  Asn Pro Gly Pro Pro  Lys Thr Pro Glu Asn  Ser Leu Ile
    1085                 1090                 1095

Val Thr  Asn Pro Ser Ser Thr  Gln Pro Asn Ser Ala  Lys Thr Ala
    1100                 1105                 1110

Arg Lys  Pro Glu His Met Ala  Val Glu Ile Pro Pro  Ala Cys Pro
    1115                 1120                 1125

Pro Leu  Asn His Thr Val Val  Gln Val Asn Lys Asn  Ala Asn Pro
    1130                 1135                 1140

Asp Pro  Leu Pro Lys Lys Glu  Glu Glu Lys Lys Glu  Glu Glu Glu
    1145                 1150                 1155

Ala Asp  Pro Gly Glu Asp Gly  Pro Lys Pro Met Pro  Pro Tyr Ser
    1160                 1165                 1170

Ser Met  Phe Ile Leu Ser Thr  Thr Asn Pro Leu Arg  Arg Leu Cys
    1175                 1180                 1185

His Tyr  Ile Leu Asn Leu Arg  Tyr Phe Glu Met Cys  Ile Leu Met
    1190                 1195                 1200

Val Ile  Ala Met Ser Ser Ile  Ala Leu Ala Ala Glu  Asp Pro Val
    1205                 1210                 1215

Gln Pro  Asn Ala Pro Arg Asn  Asn Val Leu Arg Tyr  Phe Asp Tyr
    1220                 1225                 1230

Val Phe  Thr Gly Val Phe Thr  Phe Glu Met Val Ile  Lys Met Ile
    1235                 1240                 1245
```

-continued

```
Asp Leu  Gly Leu Val Leu His  Gln Gly Ala Tyr Phe  Arg Asp Leu
    1250                 1255                 1260

Trp Asn  Ile Leu Asp Phe Ile  Val Val Ser Gly Ala  Leu Val Ala
    1265                 1270                 1275

Phe Ala  Phe Thr Gly Asn Ser  Lys Gly Lys Asp Ile  Asn Thr Ile
    1280                 1285                 1290

Lys Ser  Leu Arg Val Leu Arg  Val Leu Arg Pro Leu  Lys Thr Ile
    1295                 1300                 1305

Lys Arg  Leu Pro Lys Leu Lys  Ala Val Phe Asp Cys  Val Val Asn
    1310                 1315                 1320

Ser Leu  Lys Asn Val Phe Asn  Ile Leu Ile Val Tyr  Met Leu Phe
    1325                 1330                 1335

Met Phe  Ile Phe Ala Val Val  Ala Val Gln Leu Phe  Lys Gly Lys
    1340                 1345                 1350

Phe Phe  His Cys Thr Asp Glu  Ser Lys Glu Phe Glu  Arg Asp Cys
    1355                 1360                 1365

Arg Gly  Lys Tyr Leu Leu Tyr  Glu Lys Asn Glu Val  Lys Ala Arg
    1370                 1375                 1380

Asp Arg  Glu Trp Lys Lys Tyr  Asp Phe His Tyr Asp  Asn Val Leu
    1385                 1390                 1395

Trp Ala  Leu Leu Thr Leu Phe  Thr Val Ser Thr Gly  Glu Gly Trp
    1400                 1405                 1410

Pro Gln  Val Leu Lys His Ser  Val Asp Ala Thr Phe  Glu Asn Gln
    1415                 1420                 1425

Gly Pro  Ser Pro Gly Tyr Arg  Met Glu Met Ser Ile  Phe Tyr Val
    1430                 1435                 1440

Val Tyr  Phe Val Val Phe Pro  Phe Phe Phe Val Asn  Ile Phe Val
    1445                 1450                 1455

Ala Leu  Ile Ile Ile Thr Phe  Gln Glu Gln Gly Asp  Lys Met Met
    1460                 1465                 1470

Glu Glu  Tyr Ser Leu Glu Lys  Asn Glu Arg Ala Cys  Ile Asp Phe
    1475                 1480                 1485

Ala Ile  Ser Ala Lys Pro Leu  Thr Arg His Met Pro  Gln Asn Lys
    1490                 1495                 1500

Gln Ser  Phe Gln Tyr Arg Met  Trp Gln Phe Val Val  Ser Pro Pro
    1505                 1510                 1515

Phe Glu  Tyr Thr Ile Met Ala  Met Ile Ala Leu Asn  Thr Ile Val
    1520                 1525                 1530

Leu Met  Met Lys Phe Tyr Gly  Ala Ser Val Ala Tyr  Glu Asn Ala
    1535                 1540                 1545

Leu Arg  Val Phe Asn Ile Val  Phe Thr Ser Leu Phe  Ser Leu Glu
    1550                 1555                 1560

Cys Val  Leu Lys Val Met Ala  Phe Gly Ile Leu Asn  Tyr Phe Arg
    1565                 1570                 1575

Asp Ala  Trp Asn Ile Phe Asp  Phe Val Thr Val Leu  Gly Ser Ile
    1580                 1585                 1590

Thr Asp  Ile Leu Val Thr Glu  Phe Gly Asn Asn Phe  Ile Asn Leu
    1595                 1600                 1605

Ser Phe  Leu Arg Leu Phe Arg  Ala Ala Arg Leu Ile  Lys Leu Leu
    1610                 1615                 1620

Arg Gln  Gly Tyr Thr Ile Arg  Ile Leu Leu Trp Thr  Phe Val Gln
    1625                 1630                 1635

Ser Phe  Lys Ala Leu Pro Tyr  Val Cys Leu Leu Ile  Ala Met Leu
```

```
    1640                1645                1650

Phe Phe  Ile Tyr Ala Ile Ile  Gly Met Gln Val Phe  Gly Asn Ile
    1655                1660                1665

Gly Ile  Asp Gly Glu Asp Glu  Asp Ser Asp Glu Asp  Glu Phe Gln
    1670                1675                1680

Ile Thr  Glu His Asn Asn Phe  Arg Thr Phe Phe Gln  Ala Leu Met
    1685                1690                1695

Leu Leu  Phe Arg Ser Ala Thr  Gly Glu Ala Trp His  Asn Ile Met
    1700                1705                1710

Leu Ser  Cys Leu Ser Gly Lys  Pro Cys Asp Lys Asn  Ser Gly Ile
    1715                1720                1725

Gln Lys  Pro Glu Cys Gly Asn  Glu Phe Ala Tyr Phe  Tyr Phe Val
    1730                1735                1740

Ser Phe  Ile Phe Leu Cys Ser  Phe Leu Met Leu Asn  Leu Phe Val
    1745                1750                1755

Ala Val  Ile Met Asp Asn Phe  Glu Tyr Leu Thr Arg  Asp Ser Ser
    1760                1765                1770

Ile Leu  Gly Pro His His Leu  Asp Glu Tyr Val Arg  Val Trp Ala
    1775                1780                1785

Glu Tyr  Asp Pro Ala Ala Cys  Gly Arg Ile His Tyr  Lys Asp Met
    1790                1795                1800

Tyr Ser  Leu Leu Arg Val Ile  Ser Pro Pro Leu Gly  Leu Gly Lys
    1805                1810                1815

Lys Cys  Pro His Arg Val Ala  Cys Lys Arg Leu Leu  Arg Met Asp
    1820                1825                1830

Leu Pro  Val Ala Asp Asp Asn  Thr Val His Phe Asn  Ser Thr Leu
    1835                1840                1845

Met Ala  Leu Ile Arg Thr Ala  Leu Asp Ile Lys Ile  Ala Lys Gly
    1850                1855                1860

Gly Ala  Asp Lys Gln Gln Met  Asp Ala Glu Leu Arg  Lys Glu Met
    1865                1870                1875

Met Ala  Ile Trp Pro Asn Leu  Ser Gln Lys Thr Leu  Asp Leu Leu
    1880                1885                1890

Val Thr  Pro His Lys Ser Thr  Asp Leu Thr Val Gly  Lys Ile Tyr
    1895                1900                1905

Ala Ala  Met Met Ile Met Glu  Tyr Tyr Arg Gln Ser  Lys Ala Lys
    1910                1915                1920

Lys Leu  Gln Ala Met Arg Glu  Glu Gln Asn Arg Thr  Pro Leu Met
    1925                1930                1935

Phe Gln  Arg Met Glu Pro Pro  Ser Pro Thr Gln Glu  Gly Gly Pro
    1940                1945                1950

Ser Gln  Asn Ala Leu Pro Ser  Thr Gln Leu Asp Pro  Gly Gly Gly
    1955                1960                1965

Leu Met  Ala Gln Glu Ser Ser  Met Lys Glu Ser Pro  Ser Trp Val
    1970                1975                1980

Thr Gln  Arg Ala Gln Glu Met  Phe Gln Lys Thr Gly  Thr Trp Ser
    1985                1990                1995

Pro Glu  Arg Gly Pro Pro Ile  Asp Met Pro Asn Ser  Gln Pro Asn
    2000                2005                2010

Ser Gln  Ser Val Glu Met Arg  Glu Met Gly Thr Asp  Gly Tyr Ser
    2015                2020                2025

Asp Ser  Glu His Tyr Leu Pro  Met Glu Gly Gln Thr  Arg Ala Ala
    2030                2035                2040
```

```
Ser Met  Pro Arg Leu Pro Ala  Glu Asn Gln Arg Arg  Arg Gly Arg
    2045                 2050                 2055

Pro Arg  Gly Asn Asn Leu Ser  Thr Ile Ser Asp Thr  Ser Pro Met
    2060                 2065                 2070

Lys Arg  Ser Ala Ser Val Leu  Gly Pro Lys Ala Arg  Arg Leu Asp
    2075                 2080                 2085

Asp Tyr  Ser Leu Glu Arg Val  Pro Pro Glu Glu Asn  Gln Arg Tyr
    2090                 2095                 2100

His Gln  Arg Arg Arg Asp Arg  Gly His Arg Thr Ser  Glu Arg Ser
    2105                 2110                 2115

Leu Gly  Arg Tyr Thr Asp Val  Asp Thr Gly Leu Gly  Thr Asp Leu
    2120                 2125                 2130

Ser Met  Thr Thr Gln Ser Gly  Asp Leu Pro Ser Lys  Asp Arg Asp
    2135                 2140                 2145

Gln Asp  Arg Gly Arg Pro Lys  Asp Arg Lys His Arg  Pro His His
    2150                 2155                 2160

His His  His His His His His  His Pro Pro Ala Pro  Asp Arg Glu
    2165                 2170                 2175

Arg Tyr  Ala Gln Glu Arg Pro  Asp Thr Gly Arg Ala  Arg Ala Arg
    2180                 2185                 2190

Glu Gln  Arg Trp Ser Arg Ser  Pro Ser Glu Gly Arg  Glu His Ala
    2195                 2200                 2205

Thr His  Arg Gln Gly Ser Ser  Ser Val Ser Gly Ser  Pro Ala Pro
    2210                 2215                 2220

Ser Thr  Ser Gly Thr Ser Thr  Pro Arg Arg Gly Arg  Arg Gln Leu
    2225                 2230                 2235

Pro Gln  Thr Pro Cys Thr Pro  Arg Pro Leu Val Ser  Tyr Ser Pro
    2240                 2245                 2250

Ala Pro  Arg Arg Pro Ala Ala  Arg Arg Met Ala Gly  Pro Pro Ala
    2255                 2260                 2265

Pro Pro  Gly Gly Ser Pro Arg  Gly Cys Arg Arg Ala  Pro Arg Trp
    2270                 2275                 2280

Pro Ala  His Ala Pro Glu Gly  Pro Arg Pro Arg Gly  Ala Asp Tyr
    2285                 2290                 2295

Thr Glu  Pro Asp Ser Pro Arg  Glu Pro Pro Gly Gly  Ala His Glu
    2300                 2305                 2310

Pro Ala  Pro Arg Ser Pro Arg  Thr Pro Arg Ala Ala  Gly Cys Ala
    2315                 2320                 2325

Ser Pro  Arg His Gly Arg Arg  Leu Pro Asn Gly Tyr  Tyr Ala Gly
    2330                 2335                 2340

His Gly  Ala Pro Arg Pro Arg  Thr Ala Arg Arg Gly  Ala His Asp
    2345                 2350                 2355

Ala Tyr  Ser Glu Ser Glu Asp  Asp Trp Cys
    2360                 2365
```

<210> SEQ ID NO 150
<211> LENGTH: 6030
<212> TYPE: DNA
<213> ORGANISM: Homo sapiens

<400> SEQUENCE: 150

```
atggagcaaa cagtgcttgt accaccagga cctgacagct tcaacttctt caccagagaa     60

tctcttgcgg ctattgaaag acgcattgca gaagaaaagg caaagaatcc caaaccagac    120
```

-continued

```
aaaaaagatg acgacgaaaa tggcccaaag ccaaatagtg acttggaagc tggaaagaac    180
cttccattta tttatggaga cattcctcca gagatggtgt cagagcccct ggaggacctg    240
gacccctact atatcaataa gaaaactttt atagtattga ataaagggaa ggccatcttc    300
cggttcagtg ccacctctgc cctgtacatt ttaactccct tcaatcctct taggaaaata    360
gctattaaga ttttggtaca ttcattattc agcatgctaa ttatgtgcac tattttgaca    420
aactgtgtgt ttatgacaat gagtaaccct cctgattgga caaagaatgt agaatacacc    480
ttcacaggaa tatatacttt tgaatcactt ataaaaatta ttgcaagggg attctgttta    540
gaagatttta ctttccttcg ggatccatgg aactggctcg atttcactgt cattacattt    600
gcgtacgtca cagagtttgt ggacctgggc aatgtctcgg cattgagaac attcagagtt    660
ctccgagcat tgaagacgat ttcagtcatt ccaggcctga aaccattgt gggagccctg    720
atccagtctg tgaagaagct ctcagatgta atgatcctga ctgtgttctg tctgagcgta    780
tttgctctaa ttgggctgca gctgttcatg ggcaacctga ggaataaatg tatacaatgg    840
cctcccacca atgcttcctt ggaggaacat agtatagaaa agaatataac tgtgaattat    900
aatggtacac ttataaatga aactgtcttt gagtttgact ggaagtcata tattcaagat    960
tcaagatatc attatttcct ggagggtttt ttagatgcac tactatgtgg aaatagctct   1020
gatgcaggcc aatgtccaga gggatatatg tgtgtgaaag ctggtagaaa tcccaattat   1080
ggctacacaa gctttgatac cttcagttgg gcttttttgt ccttgtttcg actaatgact   1140
caggacttct gggaaaatct ttatcaactg acattacgtg ctgctgggaa aacgtacatg   1200
atattttttg tattggtcat tttcttgggc tcattctacc taataaattt gatcctggct   1260
gtggtggcca tggcctacga ggaacagaat caggccacct tggaagaagc agaacagaaa   1320
gaggccgaat ttcagcagat gattgaacag cttaaaaagc aacaggaggc agctcagcag   1380
gcagcaacgg caactgcctc agaacattcc agagagccca gtgcagcagg caggctctca   1440
gacagctcat ctgaagcctc taagttgagt tccaagagtg ctaaggaaag aagaaatcgg   1500
aggaagaaaa gaaaacagaa agagcagtct ggtggggaag agaaagatga ggatgaattc   1560
caaaaatctg aatctgagga cagcatcagg aggaaaggtt ttcgcttctc cattgaaggg   1620
aaccgattga catatgaaaa gaggtactcc tccccacacc agtctttgtt gagcatccgt   1680
ggctccctat tttcaccaag gcgaaatagc agaacaagcc ttttcagctt tagagggcga   1740
gcaaaggatg tgggatctga gaacgacttc gcagatgatg agcacagcac ctttgaggat   1800
aacgagagcc gtagagattc cttgtttgtg ccccgacgac acggagagag acgcaacagc   1860
aacctgagtc agaccagtag gtcatcccgg atgctggcag tgtttccagc gaatgggaag   1920
atgcacagca ctgtggattg caatggtgtg gtttccttgg ttggtggacc ttcagttcct   1980
acatcgcctg ttggacagct tctgccagag gtgataatag ataagccagc tactgatgac   2040
aatggaacaa ccactgaaac tgaaatgaga aagagaaggt caagttcttt ccacgtttcc   2100
atggactttc tagaagatcc ttcccaaagg caacgagcaa tgagtatagc cagcattcta   2160
acaaatacag tagaagaact tgaagaatcc aggcagaaat gcccaccctg ttggtataaa   2220
ttttccaaca tattcttaat ctgggactgt tctccatatt ggttaaaagt gaaacatgtt   2280
gtcaacctgg ttgtgatgga cccatttgtt gacctggcca tcaccatctg tattgtctta   2340
aatactcttt tcatggccat ggagcactat ccaatgacgg accatttcaa taatgtgctt   2400
acagtaggaa acttggtttt cactgggatc tttacagcag aaatgtttct gaaaattatt   2460
gccatggatc cttactatta tttccaagaa ggctggaata tctttgacgg ttttattgtg   2520
```

-continued

```
acgcttagcc tggtagaact tggactcgcc aatgtggaag gattatctgt tctccgttca   2580
tttcgattgc tgcgagtttt caagttggca aaatcttggc caacgttaaa tatgctaata   2640
aagatcatcg gcaattccgt gggggctctg ggaaatttaa ccctcgtctt ggccatcatc   2700
gtcttcattt ttgccgtggt cggcatgcag ctctttggta aaagctacaa agattgtgtc   2760
tgcaagatcg ccagtgattg tcaactccca cgctggcaca tgaatgactt cttccactcc   2820
ttcctgattg tgttccgcgt gctgtgtggg gagtggatag agaccatgtg ggactgtatg   2880
gaggttgctg gtcaagccat gtgccttact gtcttcatga tggtcatggt gattggaaac   2940
ctagtggtcc tgaatctctt tctggccttg cttctgagct catttagtgc agacaacctt   3000
gcagccactg atgatgataa tgaaatgaat aatctccaaa ttgctgtgga taggatgcac   3060
aaaggagtag cttatgtgaa aagaaaaata tatgaattta ttcaacagtc cttcattagg   3120
aaacaaaaga ttttagatga aattaaacca cttgatgatc taaacaacaa gaaagacagt   3180
tgtatgtcca atcatacaac agaaattggg aaagatcttg actatcttaa agatgtaaat   3240
ggaactacaa gtggtatagg aactggcagc agtgttgaaa aatacattat tgatgaaagt   3300
gattacatgt cattcataaa caaccccagt cttactgtga ctgtaccaat tgctgtagga   3360
gaatctgact ttgaaaattt aaacacggaa gactttagta gtgaatcgga tctggaagaa   3420
agcaaagaga aactgaatga aagcagtagc tcatcagaag gtagcactgt ggacatcggc   3480
gcacctgtag aagaacagcc cgtagtggaa cctgaagaaa ctcttgaacc agaagcttgt   3540
ttcactgaag gctgtgtaca aagattcaag tgttgtcaaa tcaatgtgga agaaggcaga   3600
ggaaaacaat ggtggaacct gagaaggacg tgtttccgaa tagttgaaca taactggttt   3660
gagaccttca ttgttttcat gattctcctt agtagtggtg ctctggcatt tgaagatata   3720
tatattgatc agcgaaagac gattaagacg atgttggaat atgctgacaa ggttttcact   3780
tacattttca ttctggaaat gcttctaaaa tgggtggcat atggctatca aacatatttc   3840
accaatgcct ggtgttggct ggacttctta attgttgatg tttcattggt cagtttaaca   3900
gcaaatgcct tgggttactc agaacttgga gccatcaaat ctctcaggac actaagagct   3960
ctgagacctc taagagcctt atctcgattt gaagggatga gggtggttgt gaatgccctt   4020
ttaggagcaa ttccatccat catgaatgtg cttctggttt gtcttatatt ctggctaatt   4080
ttcagcatca tgggcgtaaa tttgtttgct ggcaaattct accactgtat taacaccaca   4140
actggtgaca ggtttgacat cgaagacgtg aataatcata ctgattgcct aaaactaata   4200
gaaagaaatg agactgctcg atggaaaaat gtgaaagtaa actttgatca tgtaggattt   4260
gggtatctct ctttgcttca agttgccaca ttcaaaggat ggatggatat aatgtatgca   4320
gcagttgatt ccagaaatgt ggaactccag cctaagtatg aagaaagtct gtacatgtat   4380
ctttactttg ttattttcat catctttggg tccttcttca ccttgaacct gtttattggt   4440
gtcatcatag ataatttcaa ccagcagaaa aagaagtttg gaggtcaaga catctttatg   4500
acagaagaac agaagaaata ctataatgca atgaaaaaat taggatcgaa aaaaccgcaa   4560
aagcctatac ctcgaccagg aaacaaattt caaggaatgg tctttgactt cgtaaccaga   4620
caagtttttg acataagcat catgattctc atctgtctta acatggtcac aatgatggtg   4680
gaaacagatg accagagtga atatgtgact accattttgt cacgcatcaa tctggtgttc   4740
attgtgctat ttactggaga gtgtgtactg aaactcatct ctctacgcca ttattatttt   4800
accattggat ggaatatttt tgattttgtg gttgtcattc tctccattgt aggtatgttt   4860
```

```
cttgccgagc tgatagaaaa gtatttcgtg tcccctaccc tgttccgagt gatccgtctt   4920
gctaggattg gccgaatcct acgtctgatc aaaggagcaa aggggatccg cacgctgctc   4980
tttgctttga tgatgtccct tcctgcgttg tttaacatcg gcctcctact cttcctagtc   5040
atgttcatct acgccatctt tgggatgtcc aactttgcct atgttaagag ggaagttggg   5100
atcgatgaca tgttcaactt tgagaccttt ggcaacagca tgatctgcct attccaaatt   5160
acaacctctg ctggctggga tggattgcta gcacccattc tcaacagtaa gccacccgac   5220
tgtgacccta ataaagttaa ccctggaagc tcagttaagg gagactgtgg gaacccatct   5280
gttggaattt tctttttgt cagttacatc atcatatcct tcctggttgt ggtgaacatg   5340
tacatcgcgg tcatcctgga gaacttcagt gttgctactg aagaaagtgc agagcctctg   5400
agtgaggatg actttgagat gttctatgag gtttgggaga agtttgatcc cgatgcaact   5460
cagttcatgg aatttgaaaa attatctcag tttgcagctg cgcttgaacc gcctctcaat   5520
ctgccacaac caaacaaact ccagctcatt gccatggatt tgcccatggt gagtggtgac   5580
cggatccact gtcttgatat cttatttgct tttacaaagc gggttctagg agagagtgga   5640
gagatggatg ctctacgaat acagatggaa gagcgattca tggcttccaa tccttccaag   5700
gtctcctatc agccaatcac tactacttta aaacgaaaac aagaggaagt atctgctgtc   5760
attattcagc gtgcttacag acgccacctt ttaaagcgaa ctgtaaaaca agcttccttt   5820
acgtacaata aaaacaaaat caaaggtggg gctaatcttc ttataaaaga agacatgata   5880
attgacagaa taaatgaaaa ctctattaca gaaaaaactg atctgaccat gtccactgca   5940
gcttgtccac cttcctatga ccgggtgaca aagccaattg tggaaaaaca tgagcaagaa   6000
ggcaaagatg aaaaagccaa agggaaataa                                    6030
```

<210> SEQ ID NO 151
<211> LENGTH: 1563
<212> TYPE: DNA
<213> ORGANISM: Homo sapiens

<400> SEQUENCE: 151

```
atgtcctcct cctcctacgc caagaacggg accgcggacg ggccgcactc ccccacctcg     60
caggtggccc gaggcaccac aacccggagg agcaggttga aaagatccga tggcagcacc    120
acttcgacca gcttcatcct cagacagggt tcagcggatt cctacacaag caggccgtct    180
gactccgatg tctctttgga agaggaccgg gaagcaattc gacaggagag agaacagcaa    240
gcagctatcc agcttgagag agcaaagtcc aaacctgtag catttgccgt gaagacaaat    300
gtgagctact gcggcgccct ggacgaggat gtgcctgttc caagcacagc tatctccttt    360
gatgctaaag actttctaca tattaaagag aaatataaca atgattggtg gataggaagg    420
ctggtgaaag agggctgtga aattggcttc attccaagtc cactcagatt ggagaacata    480
cggatccagc aagaacaaaa aagaggacgt tttcacggag ggaaatcaag tggaaattct    540
tcttcaagtc ttggagaaat ggtatctggg acattccgag caactcccac atcaacagca    600
aaacagaagc aaaaagtgac ggagcacatt cctccttacg atgttgtacc gtcaatgcgt    660
ccggtggtgt tagtggggcc gtcactgaaa ggttacgagg taacagacat gatgcagaaa    720
gccctctttg attccctgaa gcacaggttt gatgggagga tttcaataac gagagtgaca    780
gctgacattt ctcttgctaa gaggtctgtc ctaaataatc ccagcaagag agcaataatt    840
gaacgttcga acacccggtc cagcttagcg gaagtacaaa gtgaaattga aagaatcttt    900
gagttggcaa gatctttgca actggttgtt cttgatgcag acaccatcaa tcacccagca    960
```

caactlataa agacttcctt agcaccaatt attgttcatg taaaagtctc atctccaaag 1020
gttttacagc ggttgattaa atctagagga aagtcacaaa gtaaacactt gaatgttcaa 1080
ctggtggcag ctgataaact tgcacaatgc cccccagaaa tgtttgatgt tatattggat 1140
gaaaatcagc ttgaggatgc atgtgaacat ctaggggagt acctggaggc gtactggcgt 1200
gccacccaca caaccagtag cacacccatg accccgctgc tgggaaggaa tttgggctcc 1260
acggcactct caccatatcc cacagcaatt tctgggttac agagtcagcg aatgaggcac 1320
agcaaccact ccacagagaa ctctccaatt gaaagacgaa gtctaatgac ctctgatgaa 1380
aattatcaca atgaaagggc tcggaagagt aggaaccgct tgtcttccag ttctcagcat 1440
agccgagatc attaccctct tgtggaagaa gattaccctg actcatacca ggacacttac 1500
aaaccccata ggaaccgagg atcacctggg ggatatagcc atgactcccg acataggctt 1560
tga 1563

<210> SEQ ID NO 152
<211> LENGTH: 3321
<212> TYPE: DNA
<213> ORGANISM: Oryctolagus cuniculus

<400> SEQUENCE: 152
atggctgcgg gccgcccgct ggcctggacg ctgacacttt ggcaggcgtg gctgatcctg 60
atcgggccct cgtcggagga gccgttccct tcagccgtca ctatcaagtc atgggtggat 120
aagatgcaag aagacctggt cacactggca aaaacagcaa gtggagtcca tcagcttgtt 180
gatatttatg agaaatatca agatttgtat actgtggaac caaataatgc acgtcagctg 240
gtggaaattg cagccagaga cattgagaag cttctcagca acagatctaa agccctggtg 300
cgcctggctt tggaagcaga gaaagttcaa gcagcccacc aatggaggga agattttgca 360
agcaatgaag ttgtctacta taacgcgaag gatgatcttg atcctgaaaa aaatgacagt 420
gaaccaggca gccagaggat caaacctgtt ttcattgacg atgctaactt tagaagacaa 480
gtatcctatc agcacgcagc tgtccatatc cccactgaca tctatgaagg atcgacaatc 540
gtgttaaacg aactcaactg gacaagtgcc ttagatgacg ttttcaaaaa aaatcgagag 600
gaagaccctt cactgttgtg gcaggtgttt ggcagtgcca ctggcctggc ccggtattac 660
ccagcttctc catgggttga taatagccga accccaaaca agattgatct ttatgatgta 720
cgcagaagac catggtacat ccaaggtgct gcatccccta aagatatgct tattctggtg 780
gatgtgagtg gaagcgttag tggactgaca ctcaaactca tccggacatc cgtctccgaa 840
atgttggaaa ccctctcaga tgatgatttt gtgaacgtgg cttcatttaa cagcaatgct 900
caggatgtaa gctgctttca gcaccttgtc caagcaaatg taagaaataa gaaagtgttg 960
aaagatgcag tgaataatat cacagcaaaa ggaatcacag attataagaa gggctttagt 1020
tttgcttttg agcagctgct taattataat gtatccagag ccaactgcaa taagattatc 1080
atgttgttca cggacggagg agaagagaga gcccaggaga tatttgccaa atacaataaa 1140
gacaagaaag tacgtgtatt cacattctca gttggccaac ataattacga cagaggacct 1200
attcagtgga tggcttgcga aaataaaggt tattattatg aaattccatc cattggagcc 1260
ataagaatta atactcagga atacctagat gttctgggaa gaccgatggt tttagcagga 1320
gacaaagcta agcaagtcca atggacaaat gtgtacctgg atgcactgga actgggactt 1380
gtcattactg gaactcttcc ggtcttcaac ataactggcc aatttgaaaa taagacaaac 1440

-continued

```
ttaaagaacc agctgattct tggagtgatg ggagttgatg tgtctttgga agatattaaa   1500
agactgacac cacgttttac actctgcccc aatggctact attttgcaat tgatcctaat   1560
ggttatgtgt tattacatcc aaatcttcag ccaaagccta ttggtgtagg tataccaaca   1620
attaatttga gaaaaaggag acccaatgtt cagaacccca aatctcagga gccagtgaca   1680
ttggatttcc tcgatgcaga gttggagaat gacattaaag tggagattcg aaataaaatg   1740
atcgatggag aaagtggaga aaaaacattc agaactctgg ttaaatctca agatgagaga   1800
tatattgaca aaggaaacag gacatacacg tggactcctg tcaacggcac agattatagc   1860
agtttggcct tggtattacc aacctacagt ttttactata taaaagccaa aatagaagag   1920
acaataactc aggccagata ttcagaaaca ctgaaaccgg ataattttga agaatctggc   1980
tacacattcc tagcaccaag agattactgc agtgacctta aaccttcaga taataacact   2040
gaatttcttt taaatttcaa tgagtttatt gatagaaaaa ctccaaacaa cccatcctgt   2100
aatacagact tgattaatag agtcttgctg gatgcaggct ttacaaatga acttgttcaa   2160
aattactgga gtaagcagaa gaatatcaag ggagtgaaag cacggtttgt tgtgactgat   2220
ggtgggatta ccagagttta tcccaaagag gctggagaaa attggcagga aaacccagag   2280
acatatgaag acagcttcta taaaaggagc ctcgataatg ataactacgt tttcactgct   2340
ccctacttta acaaaagtgg acctggggcc tatgagtcag gcattatggt aagcaaagct   2400
gtagaaatat atatccaagg aaaacttctt aaacctgcag ttgttggaat taaaattgat   2460
gtaaattctt ggatagagaa tttcaccaaa acttcaatca gggatccgtg tgctggtcca   2520
gtttgtgact gcaaacgaaa cagtgatgta atggattgtg tgattctaga tgacggtggg   2580
tttcttttga tggccaacca tgatgattat accaatcaga ttggaagatt ctttggagag   2640
attgatccaa gcttgatgag acacctggtc aatatatcag tttatgcctt taacaaatct   2700
tatgattatc agtcggtgtg tgaacctggt gctgcgccaa agcagggagc agggcaccgc   2760
tcggcttatg tgccatcaat agcagacata ctgcagattg gatggtgggc cactgctgct   2820
gcctggtcta ttcttcagca gtttctgttg agtttgactt ttccacggct ccttgaggca   2880
gctgatatgg aggatgacga cttcactgcc tccatgtcaa agcagagctg catcactgag   2940
caaacccagt atttcttcga taatgacagc aaatcgttca gtggggtatt agactgtggg   3000
aattgttcca gaatctttca tgtagaaaag ctcatgaaca ccaatttaat attcataatg   3060
gtagagagca aggggacatg tccctgtgac acacggctgc tcatacaagc agagcaaact   3120
tctgatggac cagatccttg tgatatggtt aagcaaccca gatatcgaaa agggccagat   3180
gtctgctttg acaacaatgt cctggaggat tatactgact gcggtggggt ctctggatta   3240
aatccttccc tgtggtccat catcgggata cagtttgtac tgctttggct ggtttctggc   3300
agcagacact gcctgttatg a                                             3321
```